United States Patent
Yen et al.

(10) Patent No.: US 12,180,473 B2
(45) Date of Patent: Dec. 31, 2024

(54) CHIMERIC RNA-DRIVEN GENOMIC REARRANGEMENT IN MAMMALIAN CELLS

(71) Applicant: Baylor College of Medicine, Houston, TX (US)

(72) Inventors: Laising Yen, Houston, TX (US); Sachin Kumar Gupta, Houston, TX (US); Jocelyn Duen-Ya Jea, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 937 days.

(21) Appl. No.: 17/047,924

(22) PCT Filed: Apr. 16, 2019

(86) PCT No.: PCT/US2019/027672
§ 371 (c)(1),
(2) Date: Oct. 15, 2020

(87) PCT Pub. No.: WO2019/204302
PCT Pub. Date: Oct. 24, 2019

(65) Prior Publication Data
US 2021/0238592 A1 Aug. 5, 2021

Related U.S. Application Data

(60) Provisional application No. 62/658,358, filed on Apr. 16, 2018.

(51) Int. Cl.
*C12N 15/113* (2010.01)
*C12N 15/90* (2006.01)

(52) U.S. Cl.
CPC ............ *C12N 15/113* (2013.01); *C12N 15/90* (2013.01); *C12N 2310/11* (2013.01)

(58) Field of Classification Search
CPC .. C12N 15/113; C12N 15/90; C12N 2310/11; C12N 15/102
See application file for complete search history.

(56) References Cited

U.S. PATENT DOCUMENTS

| | | | |
|---|---|---|---|
| 2015/0110861 A1 | 4/2015 | Tolentino et al. | |
| 2016/0340743 A1 | 11/2016 | Yen et al. | |
| 2017/0240924 A1* | 8/2017 | Luo | A61K 38/1761 |

FOREIGN PATENT DOCUMENTS

| | | |
|---|---|---|
| WO | 2012/149522 A1 | 11/2012 |
| WO | 2015/103057 A1 | 7/2015 |

OTHER PUBLICATIONS

Nowacki et al. RNA-mediated epigenetic programming of a genome-rearrangement pathway, 2008, Nature, 451, 153-158 (Year: 2008).*

(Continued)

*Primary Examiner* — Ram R Shukla
*Assistant Examiner* — Keyur A Vyas
(74) *Attorney, Agent, or Firm* — Norton Rose Fulbright US LLP

(57) ABSTRACT

Embodiments of the disclosure include methods and compositions in which two inter-chromosomal or intra-chromosomal genomic DNA regions are rearranged upon exposure of the genomic DNA to a chimeric RNA that produces fusion of the two regions. The chimeric RNA hybridizes to the two different parts of the genomic DNA and forms a DNA/RNA hybrid in a sequence-specific manner, thereby facilitating genomic rearrangement. In particular embodiments this mechanism is utilized to produce directed gene fusion in targeted genomic DNA regions.

16 Claims, 79 Drawing Sheets
Specification includes a Sequence Listing.

3-way junction stem formation

(56) References Cited

OTHER PUBLICATIONS

Li et al. Chimeric RNAs and their implications in cancer, 2017, Current Op. in Genetics and Development, 48: 36-43 (Year: 2017).*
Inusa et al., Sickle Cell Disease—genetics, pathophysiology, clinical presentation and treatment, 2019, International J of Neonatal Screening, 5, 20 (p. 1-15) (Year: 2019).*
Zaphirpoulos, Trans-splicing in higher eukaryotes; implications for cancer development, 2011, Frontiers in Genetics, 2, 1-4 (Year: 2011).*
Pathak and Bordoni, Genetics, Chromosomes, www.ncbi.nlm.nih.gov/books/NBK557784/, updated Apr. 2023, accessed Aug. 3, 2023, (Year: 2023).*
Gupta, S. et al. RNA-Mediated Genomic Arrangements In Mammalian Cells. PNAS. Dec. 11, 2018, vol. 115, No. 52, pp. E12295-E12304, doi:10.1073/pnas.1814704115; published online on Jun. 16, 2017.
Chwalenia, Katarzyna et al: "Chimeric RNAs in cancer and normal physiology", Wiley Interdisciplinary Reviews: RNA, vol. 8, No. 6, Jun. 7, 2017 (Jun. 7, 2017), p. e1427.
Li, Zi et al: "Chimeric RNAs and their implications in cancer", Current Opinion in Genetics & Development., vol. 48, Feb. 1, 2018 (Feb. 1, 2018).
Zaphiropoulos, Peter G.: "Trans-splicing in Higher Eukaryotes: Implications for Cancer Development?", Frontiers in Genetics, vol. 2, Jun. 23, 2011 (Jun. 23, 2011).

* cited by examiner

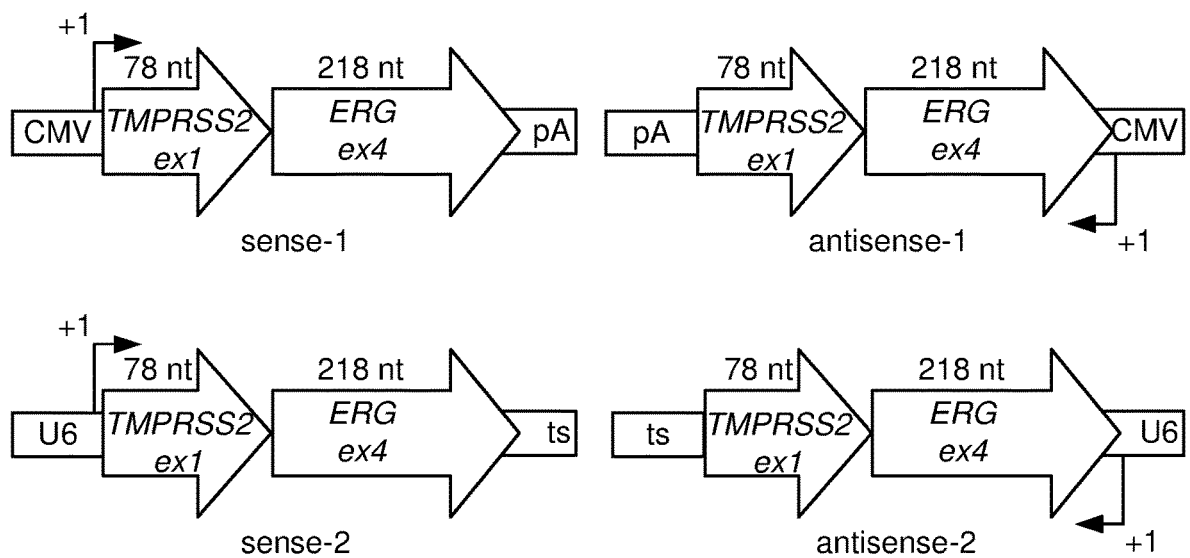
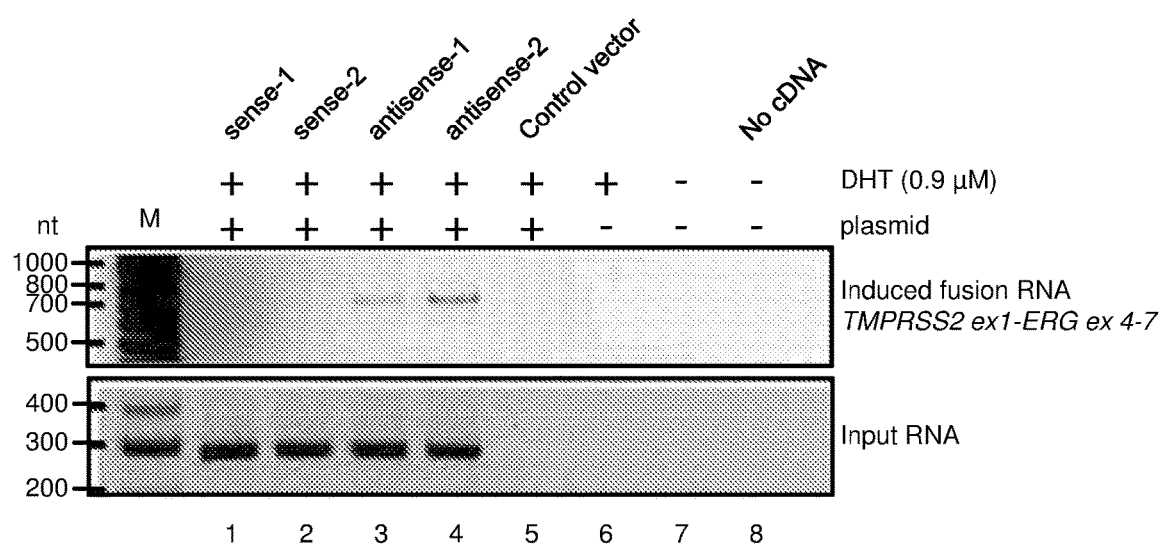
FIG. 1A

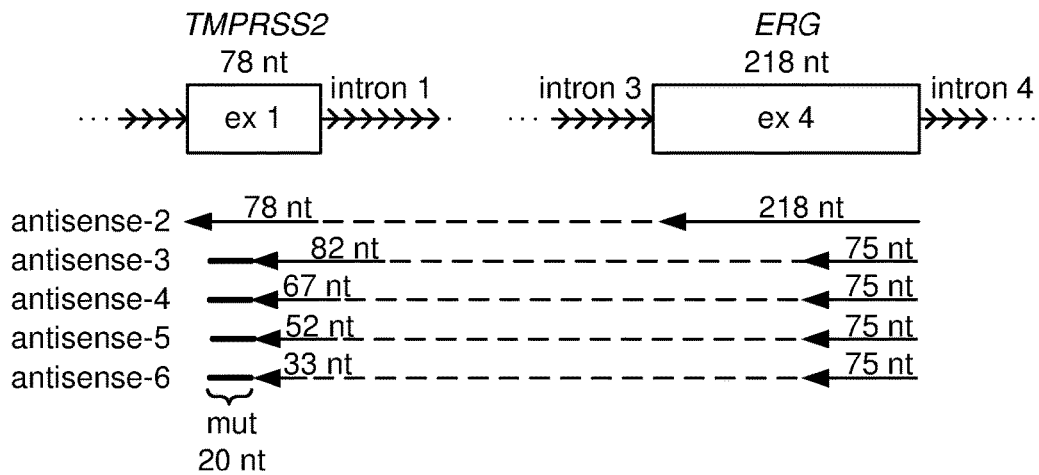
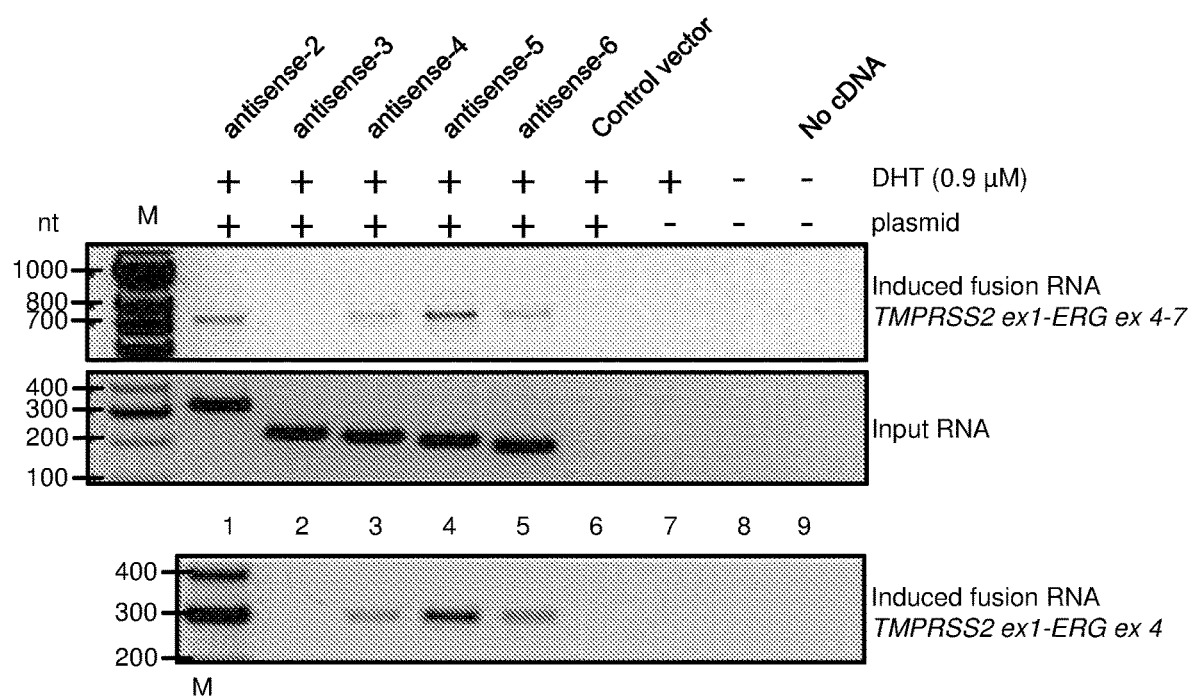
FIG. 1B

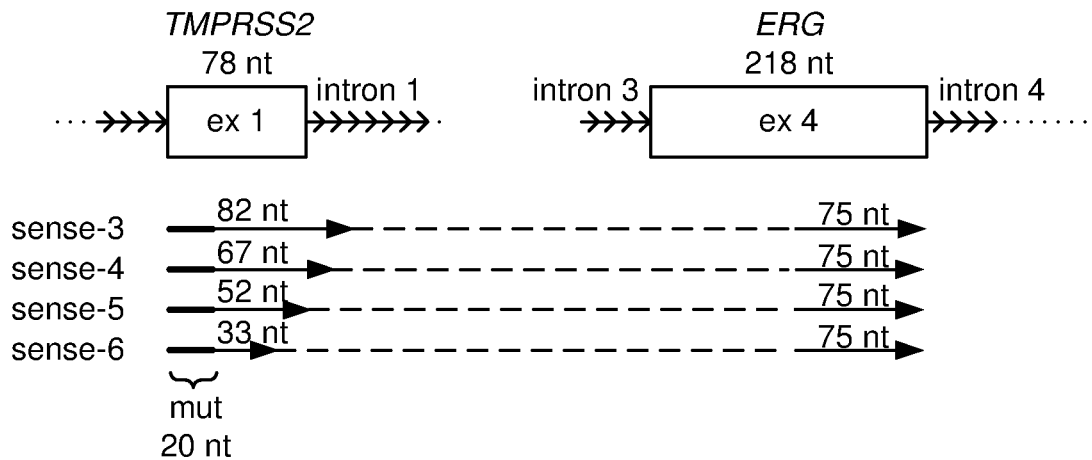
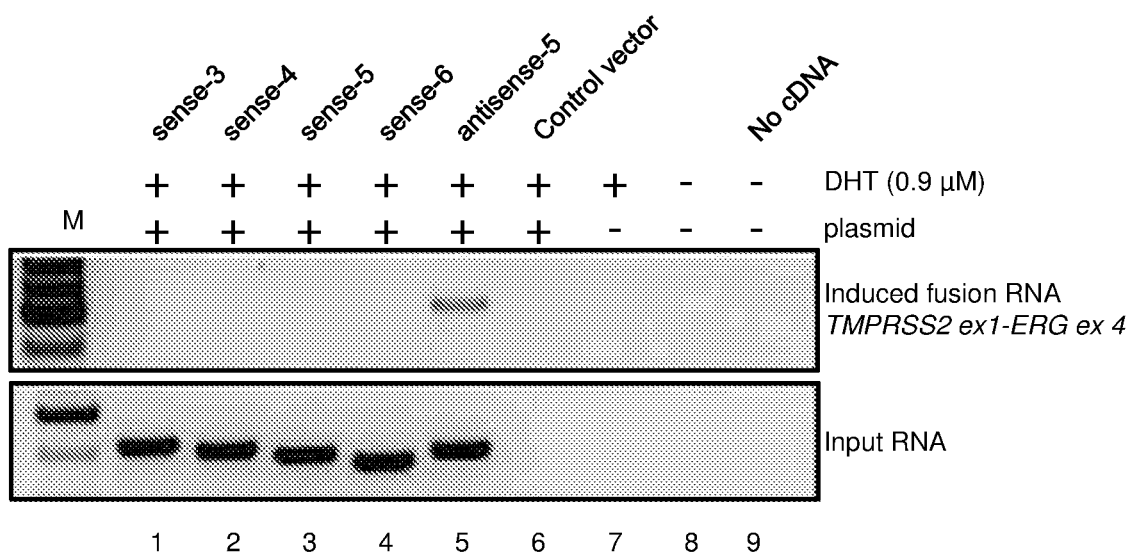
FIG. 1C

|  | Untransfected LNCaP cells | Enriched LNCaP population |
|---|---|---|
| Total No. of imaged cells | 620 | 3301 |
| No. of cells positive for fusion genes | 0 | 30 |
| % | 0 | 0.91 |

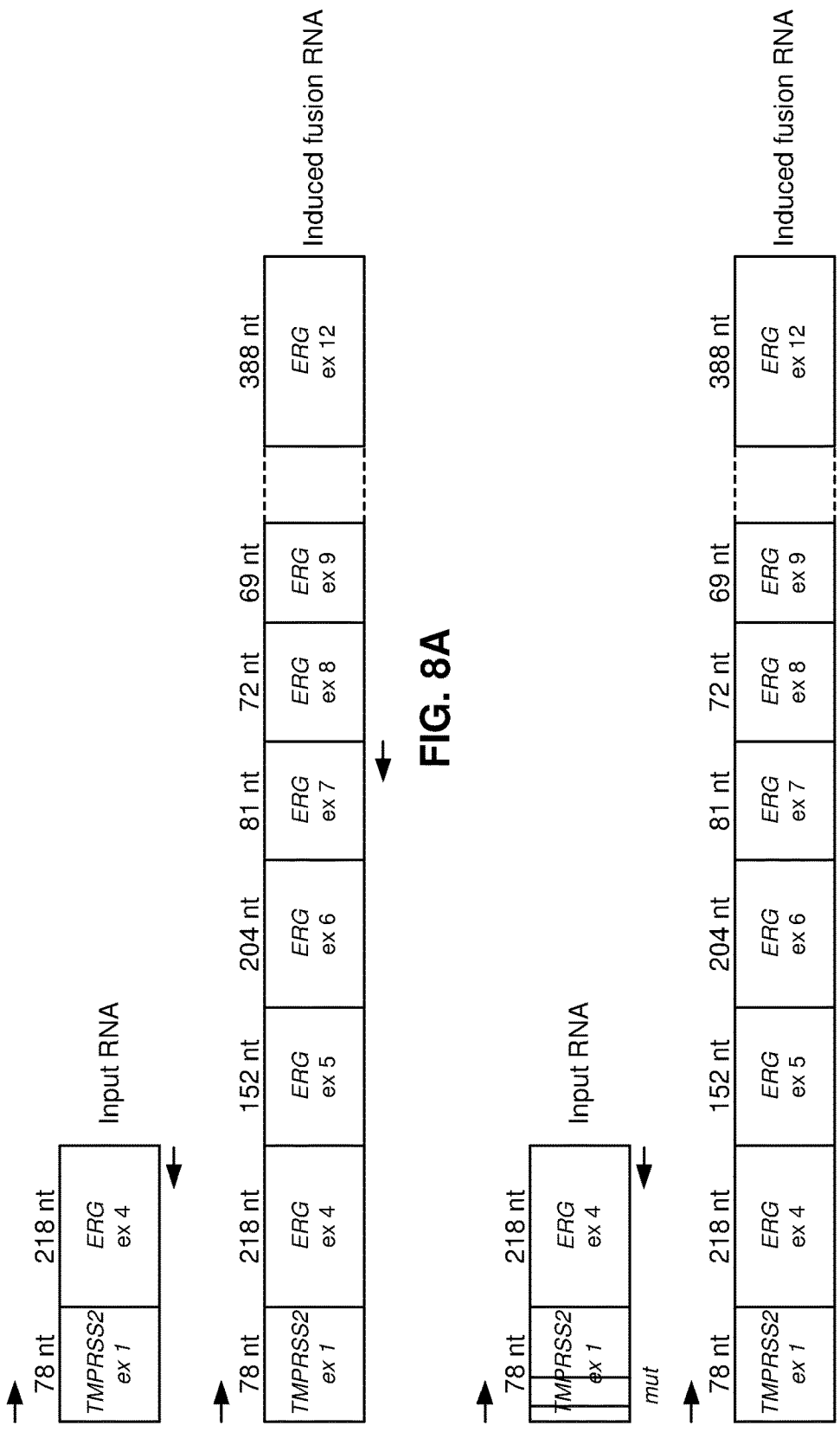

Digested DNA fragments

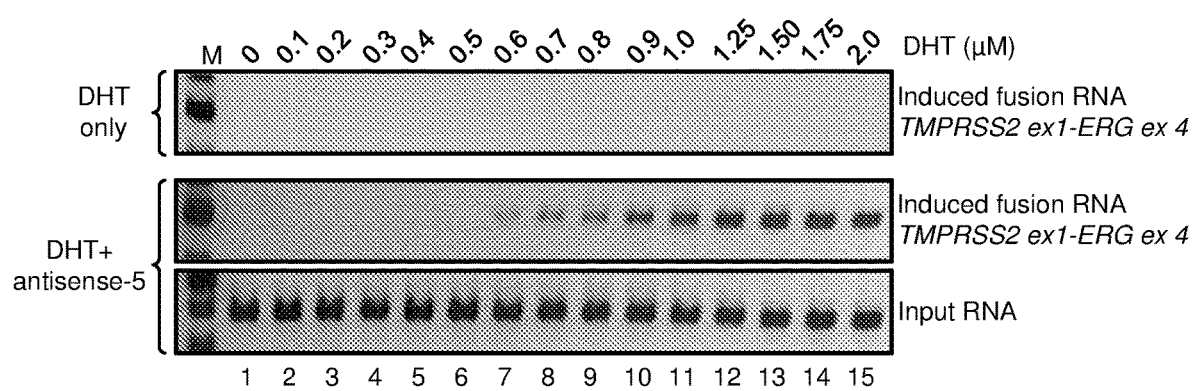
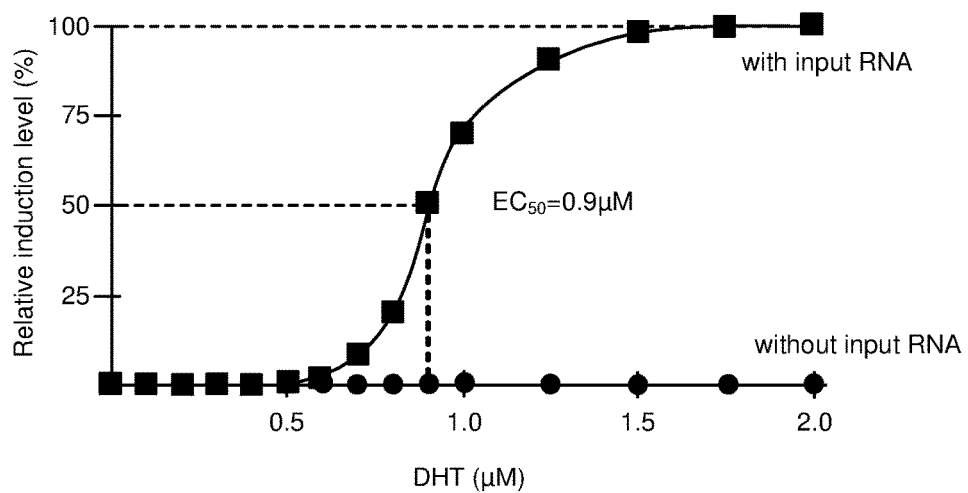
FIG. 12

Stem A  
TMPRSS2 5'- GGGTCCGG GC TGGGGAGGGAACC GGG GC GC TGGGACC -3'  
ERG     3'- CAGTATCA CG GACCCTCCCTG_GCC AGTAGACA GAA -5'

Stem B  
TMPRSS2 5'- GGCTC GGGGTCCG GC TGGGGAGGG GAACCTG GGGC GCCTG -3'  
ERG     3'- CGGTG GGGGAGCA CG CGACCCCTCC CTTGGAC CCCG ATACAC -5'

Stem C  
TMPRSS2 5'- TTT GGGGAGGAGGA CTGGGAGTGCTG TC GGTTGGCTTCTT -3'  
ERG     3'- ACTAAAAATACTGA GACCCTCACGAC TG GGAGTTTTGGATT -5'

Stem D  
TMPRSS2 5'- TCCCGG GGT GCTGGGAGAGTGCTGGG GC CC GGACCC CT -3'  
ERG     3'- GACCTA CCA CGAGACCCTCTCACGACCC TG GT CCTGG GA -5'

Stem E  
TMPRSS2 5'- GTTGA CGG CA TCTCCA TTT GT TAG CTATTATTG TT TAA CTG TTT CAC AA -3'  
ERG     3'- ATGTT GTT TG GAC GGT AAA CA ATCGATAATAAC TT ACA ATA GAT -5'

Stem F  
TMPRSS2 5'- TCAAGTGCTC CA GTCTG CAG TGG CGCTCTG CT CGAG CA -3'  
ERG     3'- CAACGGGTCC GA CTCAG GTC ACG GTACTAGAG CT GAGC GT -5'

Stem G  
TMPRSS2 5'- ACAGAGAA TTT GCTGA ATTTCA AGTTCA CT GGT GATGA -3'  
ERG     3'- CAGAGAGACG AAA ATCGAT TAAAAGT AGTCCA G AGT GAGAGT -5'

FIG. 14

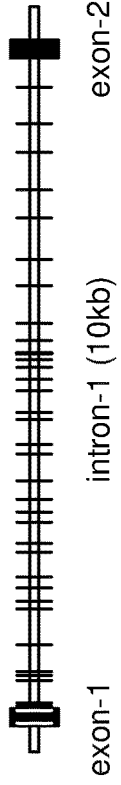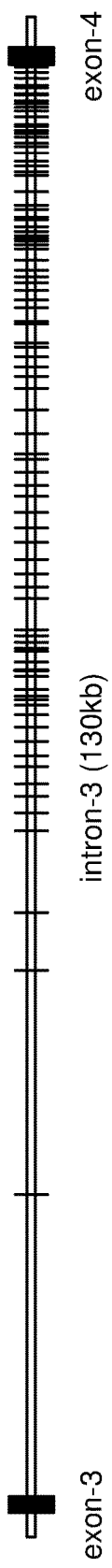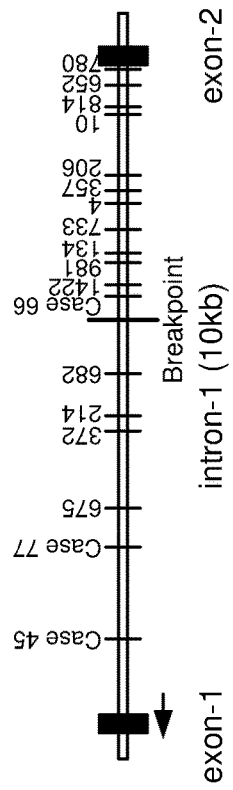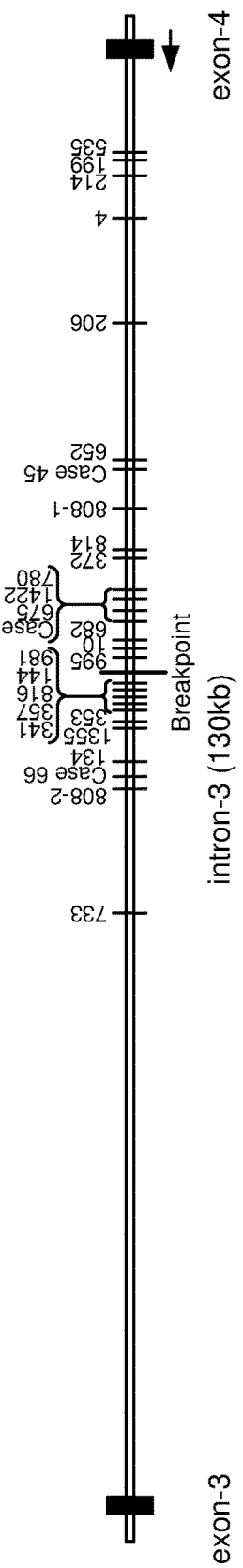
FIG. 19A
FIG. 19B

| STEMS | TMPRSS2 (-strand) | ETV (-strand) | Tm |
|---|---|---|---|
| TMPRSS2-ETV1 stem A | chr21:41507672-41507697 | chr7:13988013-13988040 | 72°C |
| TMPRSS2-ETV1 stem B | chr21:41506698-41506713 | chr7:13988054-13988069 | 46°C |
| TMPRSS2-ETV1 stem C | chr21:41506649-41506661 | chr7:13988373-13988385 | 42°C |
| TMPRSS2-ETV1 stem D | chr21:41506584-41506594 | chr7:13988732-13988742 | 36°C |
| TMPRSS2-ETV1 stem E | chr21:41505067-41505077 | chr7:13988373-13988383 | 38°C |
| TMPRSS2-ETV1 stem F | chr21:41505211-41505223 | chr7:13987620-13987632 | 34°C |
| TMPRSS2-ETV1 stem G | chr21:41498215-41498225 | chr7:13986643-13986753 | 26°C |
| TMPRSS2-ETV1 stem H | chr21:41498359-41498369 | chr7:13986021-13987031 | 26°C |
| EXONS | | | |
| TMPRSS2 exon-1 | chr21:41508081-41508158 | | |
| TMPRSS2 exon-2 | chr21:41498119-41498189 | | |
| ETV1 exon-2 | | chr7:13989090-13989139 | |
| ETV1 exon-3 | | chr7:13988140-13988173 | |
| ETV1 exon-4 | | chr7:13986638-13986685 | |

**Locations of 23 forward primers in *TMPRSS2* intron-1**
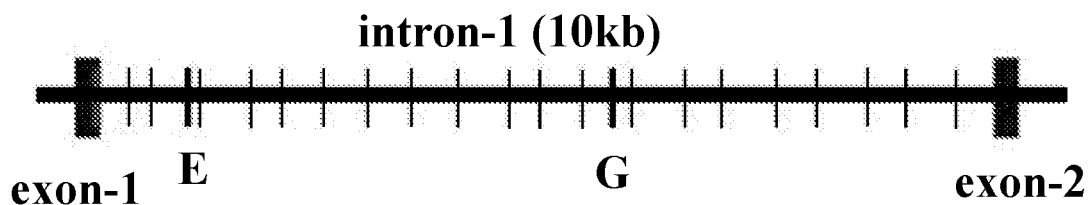
**Locations of 7 reverse primers in *ETV1* intron-2**
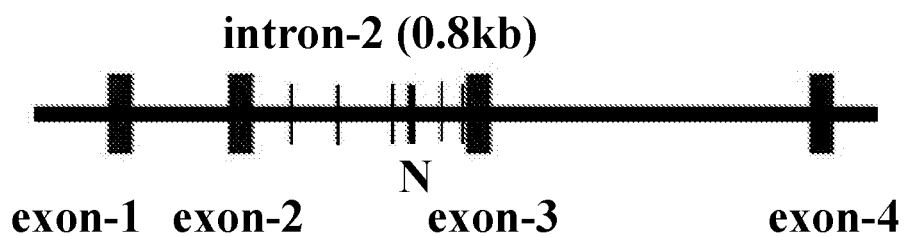
FIG. 22

Stem B- Size of Bulge
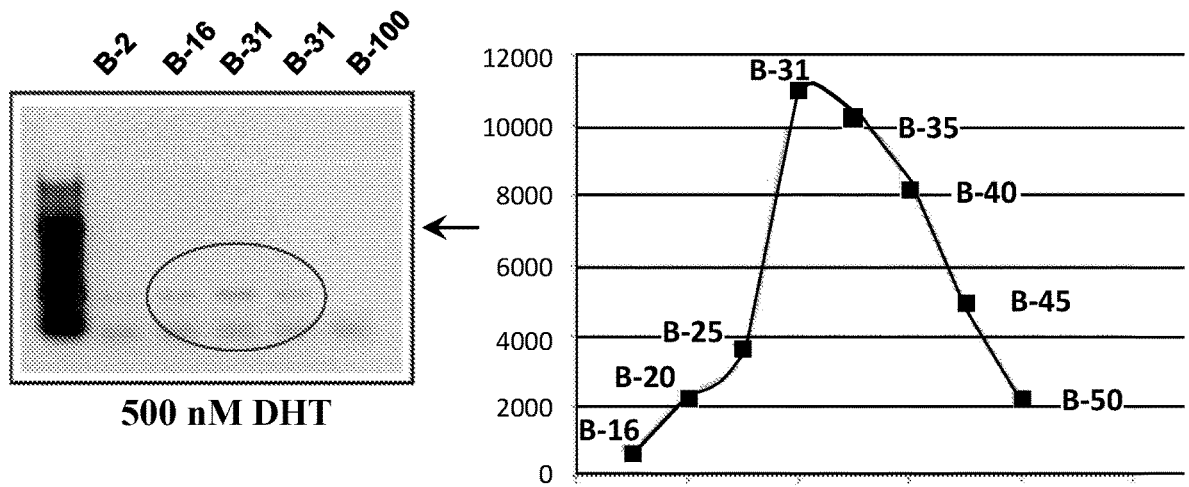
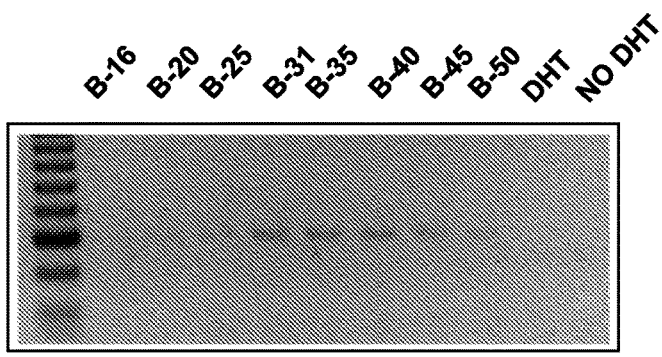
FIG. 25

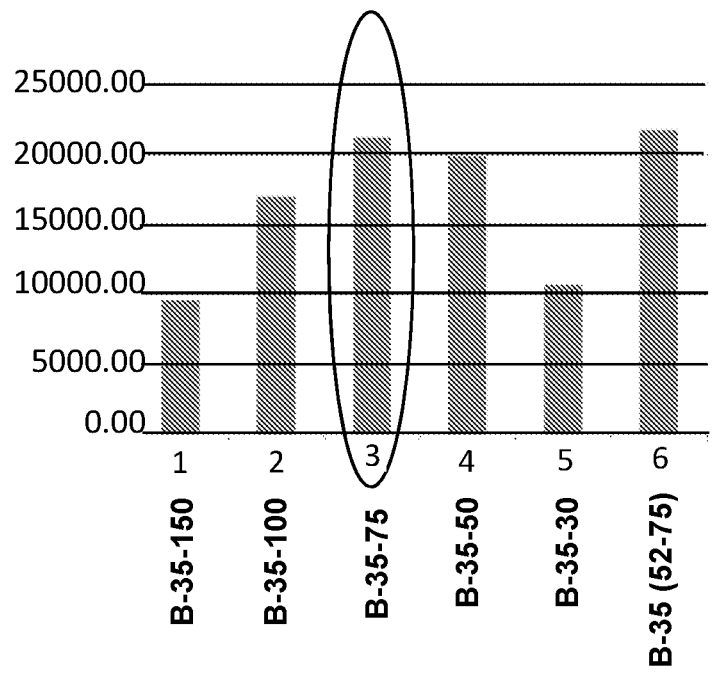
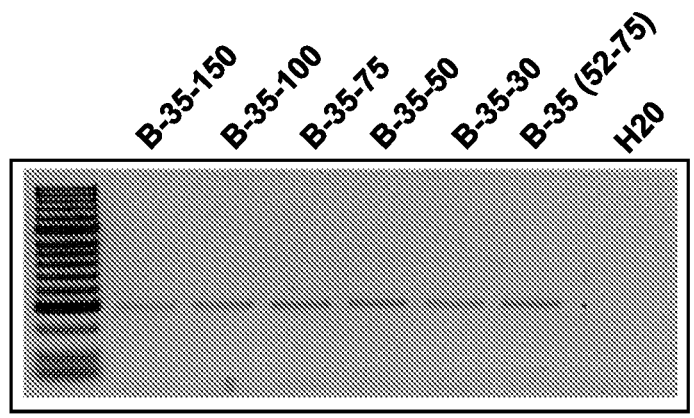
FIG. 30

Stem C
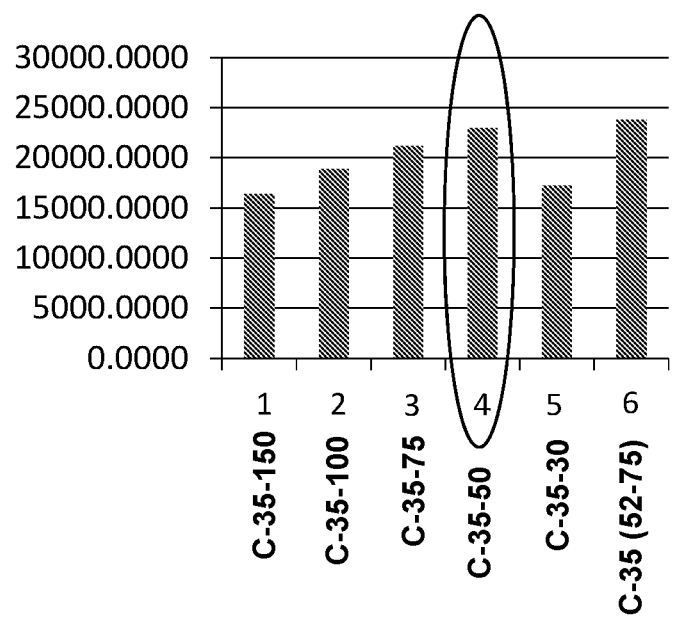
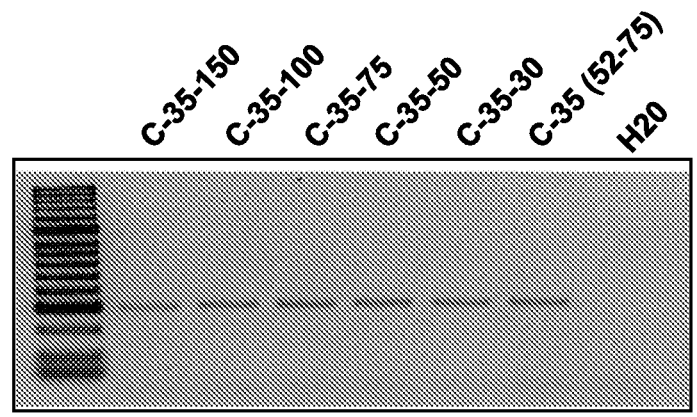
FIG. 31 stem D
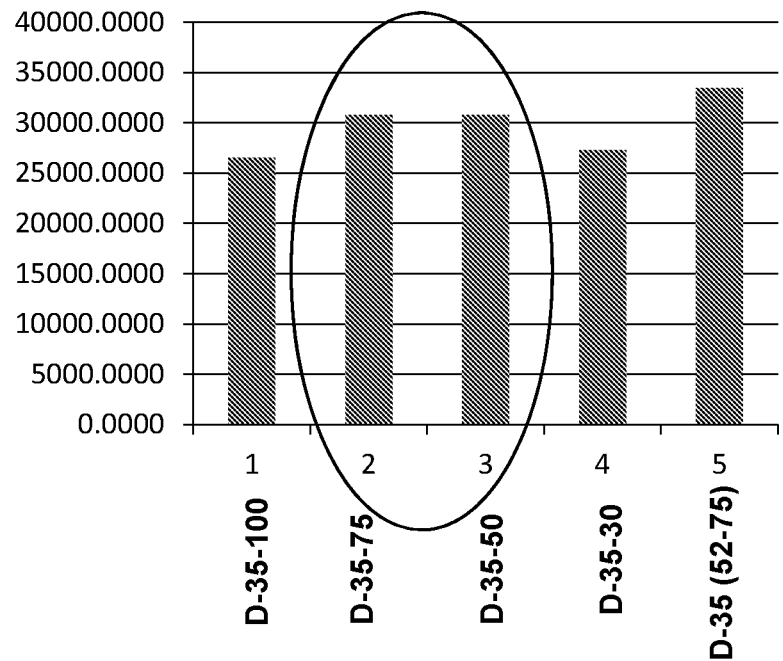
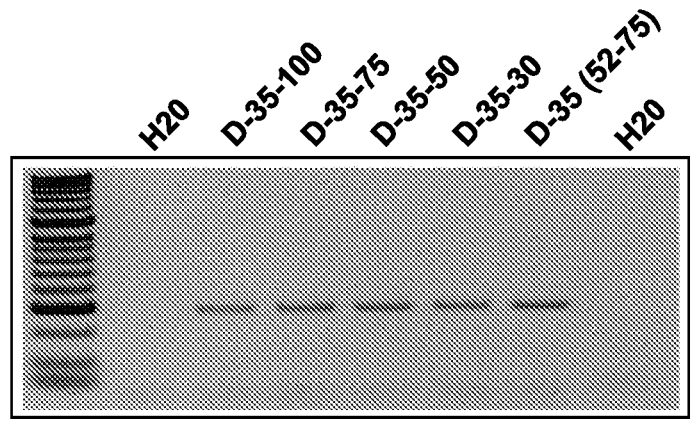
FIG. 32

Man-made designer chimeric RNA

- Perfect match
- Formed of two different sequences

Endogenous initiator chimeric RNA

Endogenous initiator chimeric RNA

- Can have loop or secondary structure in middle

Endogenous initiator chimeric RNA

- Can have loop or secondary structure at one side

Endogenous initiator chimeric RNA

- Can be perfect match
- Formed by trans-splicing of two different parental endogenous RNAs

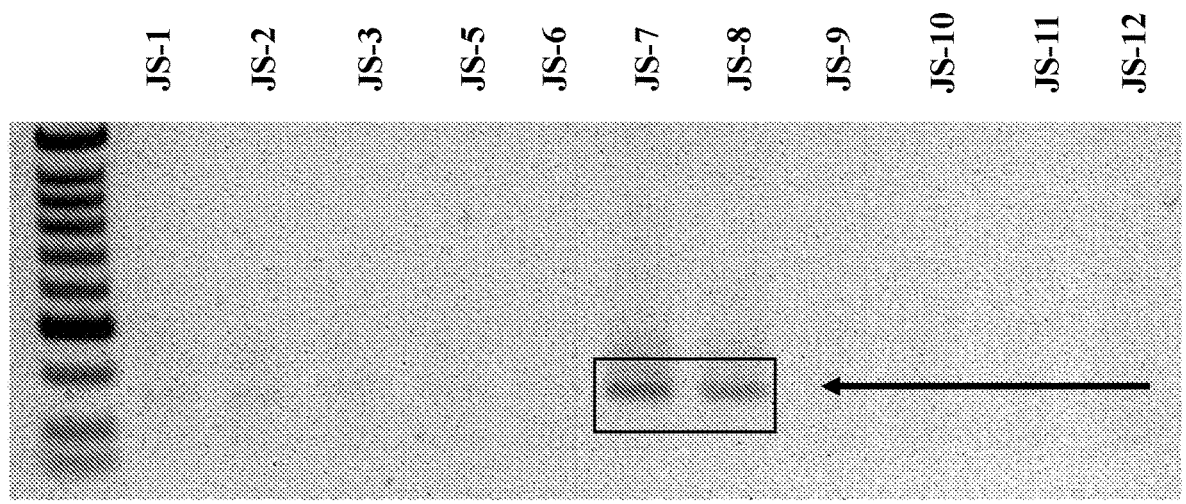
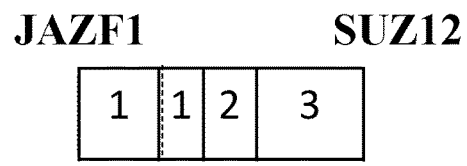
FIG. 39C

CHIMERIC RNA-DRIVEN GENOMIC REARRANGEMENT IN MAMMALIAN CELLS

This application is a national phase application under 35 U.S.C. § 371 that claims priority to International Application No. PCT/US2019/027672 filed Apr. 16, 2019, which claims priority to U.S. Provisional Patent Application Ser. No. 62/658,358, filed Apr. 16, 2018, both of which are incorporated by reference herein in their entirety.

STATEMENT REGARDING FEDERALLY SPONSORED RESEARCH OR DEVELOPMENT

This invention was made with government support under R01EB013584 awarded by National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jun. 7, 2019, is named BAYM_P0245WO-1001068754_SL.txt and is 64,058 bytes in size.

TECHNICAL FIELD

Embodiments of the disclosure include at least the fields of cell biology, molecular biology, recombinant nucleic acid technology, gene editing, and medicine.

BACKGROUND

Fusion genes are among the most cancer-specific molecular signatures known. They are important for understanding cancer mechanisms and developing useful clinical biomarkers and anti-cancer therapies (Mitelman et al., 2007). Fusion gene formation as a result of chromosomal translocations is presumed to occur prior to fusion RNA expression. However, several studies have reported the presence of fusion transcripts in individuals without detectable fusion genes at the genomic DNA level. For instance, the AML1-ETO fusion transcript, associated with a subtype of acute myeloid leukemia, was present in some patients who were negative for chromosomal translocations (Langabeer et al., 1997). Other fusion RNAs, such as BCR-ABL, MLL-AF4, TEL-AML1, PML-RARα, and NPM-ALK, were reported in healthy individuals (Janz et al., 2003). Although the discrepancy between the presence of fusion transcripts and the absence of fusion genes could result from detection limitations of the methodologies employed, fusion transcripts in normal cells could also arise from RNA trans-splicing in the absence of chromosomal translocations (Zaphiropoulos, 2011). Indeed, JAZF1-JJAZ1 fusion transcripts are expressed in normal human endometrial tissue and an endometrial cell line in the absence of chromosomal translocation (Li et al., 2008). Furthermore, trans-splicing between JAZF1 and JJAZ1 was demonstrated to occur in vitro using cellular extracts, resulting in a fusion RNA similar to that transcribed from the JAZF1-JJAZ1 fusion gene in endometrial stromal sarcomas (Li et al., 2008). These observations raise the possibility that cellular fusion RNAs created by trans-splicing act as guide RNAs to mediate genomic rearrangements. A precedent for RNA-mediated genomic arrangements is found in lower organisms such as ciliates (Fang and Landweber, 2012; Nowacki et al., 2008). Rowley and Blumenthal (Rowley and Blumenthal, 2008) coined this as "the cart before the horse" hypothesis, in that "RNA before DNA" defies the normal order of the central dogma of biology: DNA→RNA→protein (Crick, 1970). Despite important implications in biology and human cancer, RNA-mediated genomic rearrangement in mammalian cells has not been directly demonstrated. In this report, we provide the first evidence that expression of a specific chimeric RNA can lead to specified gene fusion in mammalian cells.

BRIEF SUMMARY

The present invention is directed to methods and compositions that regard RNA-mediated gene fusion in mammalian cells. Methods of the disclosure utilize one or more composition(s) of exogenously provided chimeric RNA that guides genomic rearrangements that ultimately result in gene fusions. In methods encompassed herein, expression of a chimeric RNA drives formation of a specified gene fusion via genomic rearrangement in mammalian cells. In particular embodiments, the methods lack the involvement of immunogenic exogenous proteins. Included herein are chimeric RNA compositions for use in methods of the disclosure, and in specific embodiments the chimeric RNA is antisense. In particular embodiments, endogenous chimeric RNAs directed to gene fusion are both a clinical marker and therapeutic target for one or more medical conditions.

Embodiments of the disclosure include methods of producing genomic DNA rearrangements between two different regions of genomic DNA, comprising the step of: exposing to the genomic DNA an effective amount of an exogenously provided chimeric RNA, said chimeric RNA comprising fusion of (1) a first part that is reverse complement with respect to a first genomic region and (2) a second part that is reverse complement with respect to a second genomic region, wherein upon exposing of the chimeric RNA to the genomic DNA, the first and second genomic regions become fused through DNA recombination. In some cases, wherein upon exposing the chimeric RNA to the genomic DNA, the chimeric RNA hybridizes with the respective strands of the first and second genomic regions of the genomic DNA through the first and second parts of the chimeric RNA, thereby forming a DNA/RNA hybrid in a sequence-specific manner. In some cases, wherein upon hybridization of the chimeric RNA with the respective strands of the first and second genomic regions of the genomic DNA, a double stranded DNA/DNA stem structure is produced between the first and second genomic regions adjacent to the site of hybridization with the chimeric RNA. In certain cases, wherein upon hybridizing of the chimeric RNA with the genomic DNA at the first and second genomic regions, a DNA spacer is produced in each of the respective strands of the first and second genomic regions between the DNA/DNA stem structure and the DNA/RNA hybrid structure. The two different regions of genomic DNA may be on the same chromosome or may be on different chromosomes. In some cases, at least one of the two different regions has active transcription. The chimeric RNA may be antisense with respect to the at least one region having active transcription. In certain embodiments, the two different regions lack active transcription. Whether or not a gene is being actively transcribed, for example in a cell, may be determined by northern to see if the RNA is being transcribed or it may be known based on the literature (for example, for certain genes and cell lines).

Regarding certain parameters for the chimeric RNA, in some cases the length of the first part of the chimeric RNA is in a range of 30-150, 30-125, 30-100, 30-75, 30-50, 50-150, 50-125, 50-100, 50-75, 75-150, 75-125, 75-100, 100-150, 100-125, 125-175, or 125-150 nucleotides in length. The length of the first part of the chimeric RNA may be in the range of 50-75 nucleotides. The length of the second part of the chimeric RNA may be in a range of 30-150, 30-125, 30-100, 30-75, 30-50, 50-150, 50-125, 50-100, 50-75, 75-150, 75-125, 75-100, 100-150, 100-125, 125-175, or 125-150 nucleotides in length. In some cases, the length of the second part of the chimeric RNA is in the range of 50-75 nucleotides. In particular embodiments, the length of the first part of the chimeric RNA and/or second part of the chimeric RNA is 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75 nucleotides. The length of the chimeric RNA may be in the range of 60-300, 60-250, 60-200, 60-150, 60-100, 75-300, 75-250, 75-200, 75-150, 75-100, 100-300, 100-250, 100-200, 100-150, 150-300, 150-250, 150-200, 150-175, 175-300, 175-250, 175-200, 200-300, 200-275, or 200-250 nucleotides.

Regarding certain parameters for the DNA spacer that may or may not have a particular form, such as a bulge or loop, the DNA spacer may be single stranded or double stranded. In specific cases, the DNA spacer of the first genomic region is a length in a range of 15-50, 15-45, 15-30, 15-25, 15-20, 20-50, 20-45, 20-40, 20-35, 20-30, 20-25, 25-50, 25-45, 25-40, 25-35, 25-30, 30-50, 30-45, 30-40, 30-35, 40-50, 40-45, or 45-50 nucleotides. The DNA spacer of the first genomic region may be a length in a range of 25-45 nucleotides. The DNA spacer of the first genomic region may be 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides, for example. In specific cases, the DNA spacer of the first genomic region is a length of 35 nucleotides. The DNA spacer of the second genomic region may be a length in a range of 15-50, 15-45, 15-30, 15-25, 15-20, 20-50, 20-45, 20-40, 20-35, 20-30, 20-25, 25-50, 25-45, 25-40, 25-35, 25-30, 30-50, 30-45, 30-40, 30-35, 40-50, 40-45, or 45-50 nucleotides. In some cases, the DNA spacer of the second genomic region may be a length in a range of 25-45 nucleotides. In specific embodiments, the single stranded DNA region of the second genomic region is 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides. The DNA spacer of the second genomic region may be a length of 35 nucleotides.

In particular embodiments, the genomic DNA is in a cell, such as an eukaryotic cell. The cell may be a mammalian cell, such as a human cell. The cell may be in a tissue or organ or body fluid. The cell may be in vivo. In some cases, the method occurs in vivo. The genomic DNA may be from a diseased cell or diseased cells. The genomic DNA may be from an individual in need of treatment. In specific embodiments, the method occurs at physiological hormone levels. In some cases, the chimeric RNA is produced in a cell. The cell may comprise the genomic DNA. In specific embodiments, the chimeric RNA is expressed from a vector, including a viral vector, such as a lentiviral vector, a retroviral vector, an adenoviral vector, or an adeno-associated viral vector, or or a non-viral vector, such as a plasmid.

In one embodiment, there is a method of inducing gene fusion between first and second target genes, comprising the steps of: designing or obtaining a chimeric RNA comprising (1) a first part that is antisense or sense with respect to the first target gene and (2) a second part that is antisense or sense with respect to a second target gene; and exposing an effective amount of the chimeric RNAs to nucleic acid comprising the first and second target genes, wherein upon exposing of the chimeric RNA to the nucleic acid, the first and second target genes become fused through DNA recombination.

In a particular embodiment, there is a method of identifying a cell, group of cells, or tissue at risk for becoming cancerous for an individual, comprising the step of identifying the presence of an endogenous chimeric RNA in the cell or one or more cells of the group of cells or tissue in a sample from the individual. The chimeric RNA may comprise sequence derived from the parental genes of an oncogenic fusion gene or comprises sequence that is partially complimentary to that of the parental genes. In specifici embodiments, the chimeric RNA is identified with reverse transcriptase-polymerase chain reaction, Northern gel analysis, and/or microarray chips desiged for detecting endogenous chimeric RNAs.

An individual being treated may be provided an effective amount of a preventative (such as a vaccine) or therapeutic for the cancer. In specific embodiments, the agent that inhibits the chimeric RNA directly by binding, or inhibits the chimeric RNA indirectly by reducing its expression in cells. The agent that directly inhibits the chimeric RNA may be siRNA or antisense oligo DNA. In specific embodiments, the agent that indirectly inhibits the chimeric RNA is a compound that methylates the promotor that drives the endogeneous chimeric RNA expression.

In some embodiments, there is a method of treating an individual for cancer, comprising the step of delivering an effective amount of an agent that inhibits a chimeric RNA in cancer cells of the individual. The agent may be a siRNA, for example one delivered to the individual in a vector, including a viral vector (lentiviral vector, a retroviral vector, an adenoviral vector, or an adeno-associated viral vector) or anti-viral vector.

The foregoing has outlined rather broadly the features and technical advantages of the present disclosure in order that the detailed description that follows may be better understood. Additional features and advantages will be described hereinafter which form the subject of the claims herein. It should be appreciated by those skilled in the art that the conception and specific embodiments disclosed may be readily utilized as a basis for modifying or designing other structures for carrying out the same purposes of the present designs. It should also be realized by those skilled in the art that such equivalent constructions do not depart from the spirit and scope as set forth in the appended claims. The novel features which are believed to be characteristic of the designs disclosed herein, both as to the organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

For a more complete understanding of the present disclosure, reference is now made to the following descriptions taken in conjunction with the accompanying drawing, in which:

FIGS. 1A-1E. Exogenously expressed input chimeric RNAs induce the expression of endogenous fusion transcripts. FIG. 1A. Upper: Schematics of the designed input RNAs containing complete TMPRSS2 exon-1 (78 nt, uc002yzj.3) and ERG exon-4 (218 nt, uc021 wjd.1), expressed in the sense or antisense orientation from the CMV or U6 promoters. pA: poly-A signal. ts: transcriptional stop "TTTTTT" for U6 promoter. Lower: RT-PCR detection of induced fusion transcript (top gel) and input RNA (bottom gel). Parental plasmid vector containing mCherry sequence, DHT treatment without plasmid transfection, and PCR reaction without cDNA served as the controls (land 5, 6, 8). FIG. 1B. Length and positional effect of antisense input RNAs. Upper: Antisense input RNAs with 75 nt targeting ERG exon-4 and varying lengths (82, 67, 52, and 33 nt, green) targeting TMPRSS2. Dashed line links ERG and TMPRSS2 sequence within the input RNA and contains no sequence. A 20-nt mutation (black line) was introduced to the input RN As to discern expressed input RN As from the induced fusion transcript (see FIG. 8B). Lower: RT-PCR detection of induced fusion transcript (top gel), input RNA (middle gel), or detection of induced fusion transcript using a different primer pair (bottom gel). FIG. 1C. Corresponding sense input RNAs all failed to induce the fusion transcript. FIG. 1D. Induction by antisense-5 occurred at physiologically relevant DHT concentrations as low as 20 nM. Three-rounds of nested PCR were performed to reveal the lowest amount of DHT required. FIG. 1E. Antisense-5 led to clear induction while antisense-3 and 7 did not, indicating that it is not the length of input RN As but targeted regions that is critical.

FIG. 2A. Left: Schematics of three-way junction that could be formed between genomic DNA (black) and antisense-5 input RNA (green/blue). The sense genomic strands of both TMPRSS2 and ERG genes are on the minus strand of chromosome 21, separated by 3 Mb. Short lines in shaded regions represent base-pairings. Imperfect stem A includes a high energy G·T and A·C wobble pair known to have Watson-Crick-like geometry in a DNA double helix (Kimsey and Al-Hashimi, 2014; Watson and Crick, 1953). A spacer region of 36 nt and 47 nt separate stem A from the regions targeted by antisense-5 input RNA. Right: Expressing antisense-5 as two separate halves that severed the link between TMPRSS2 (52 nt) and ERG (75 nt) sequence within the input RNA. FIG. 2A discloses SEQ ID NOS 181-182 and 181-182, respectively, in order of appearance. FIG. 2B. RT-PCR assays of fusion transcripts showed that the severed input RNAs resulted in the loss of induction. FIG. 2C. Locations of putative stems A to F identified by BLAST analyses. FIG. 2D. The putative three-way junction formed between the indicated genomic DNA stem B to G (Black) and designed antisense input RNA (green/blue). FIG. 2D discloses SEQ ID NOS 183-190, respectively, in order of appearance. FIG. 2E. Targeting genomic DNA stem B, C, and D that exhibit higher DNA stem stability (Tm=40° C., 40° C., and 44° C., respectively) by the corresponding antisense input RNAs induced fusion transcripts (lanes 2 to 4). In contrast, targeting less stable stem E, F, and G (Tm=30° C., 24° C., and 16° C., respectively) failed to induce fusion transcripts (lanes 5 to 7). FIG. 2F. Antisense input RNAs designed to invade each of the respective genomic DNA stem B, C, and D resulted in the loss of induction. FIG. 2G. Corresponding sense input RNAs targeting stem B, C, and D failed to induce fusion transcripts (lanes 2 to 4).

FIG. 3B. RT-PCR shows the transient nature of input RNA (lower panel) and the persistent nature of the induced fusion transcript (upper panel) in the enriched LNCaP population up to 52 days post initial treatment (see FIG. 18 for enrichment procedure). FIG. 3C. Schematics of identified genomic breakpoints and the primers used to amplify the breakpoints. The approximate location of genomic breakpoints were first determined using a primer set targeting TMPRSS2 intron-1 multiplexed with a primer set targeting ERG intron-3 (see FIG. 19A). The region near the breakpoint was then further examined using primers A, B, C, and D. FIG. 3D. The un-rearranged wildtype TMPRSS2 and ERG alleles were revealed by primer pair A/B (~1404 bp) and C/D (~1260 bp) respectively (lane 1, 2, 4, 5). The genomic fusion band of 862 bp amplified by fusion-specific primer pair A/D was present only in the enriched LNCaP population (lane 6) and absent in untransfected LNCaP cells (lane 3). FIG. 3E. Sanger sequencing of the fusion band showed a 500 bp segment of TMPRSS2 intron-1 fused to 362 bp of ERG intron-3. The genomic breakpoint contains a 'CTG' microhomology (boxed). FIG. 3E discloses SEQ ID NOS 191-193, respectively, in order of appearance. FIG. 3F. Prolonged expression of antisense-5 for 12 days induced the TMPRSS2-ERG fusion transcript in PNT1A cells as detected by three-round nested PCR. The results indicate that the induction of TMPRSS2-ERG fusion by antisense input RNA can occur in normal prostate epithelial cells prior to malignant transformation;

FIG. 4A. RT-PCR shows that only the antisense RNA designed to target stem TMPRSS2-ETV1-A, which has the highest stem stability (Tm=72° C.), led to induced fusion transcript (lane 1). Antisense RNAs targeting locations with lower genomic DNA stem stabilities (lanes 2 to 8), resulted in no detectable induction. FIG. 4B. The corresponding sense input RNA targeting the same TMPRSS2-ETV1-A stem failed to induce fusion transcript (lane 1 vs. 2). FIG. 4C. Gene fusion is specified by the sequence of input RNA used. The input RNA targeting TMPRSS2 and ETV1 induced TMPRSS2-ETV1 fusion but not TMPRSS2-ERG fusion (lane 2). Conversely, antisense-5 targeting TMPRSS2 and ERG induced TMPRSS2-ERG fusion but not TMPRSS2-ETV1 fusion (lane 1). FIG. 4D. RT-PCR shows the transient nature of input RNA which was present at day 3 but not day 47 post initial treatment (lower panel, lane 1 vs. 2), and the persistent nature of the induced fusion transcript (upper panel) up to 47 days post initial treatment in the enriched LNCaP population. FIG. 4E. Schematics of three identified genomic breakpoints marked as x, y, and z. The approximate location of genomic breakpoints were first determined using a primer set targeting TMPRSS2 intron-1 multiplexed with a primer set targeting ETV1 intron-2. The un-rearranged wildtype TMPRSS2 allele was then revealed by primer pair E/F (990 bp; lane 1 and 4) and G/H (956 bp; lane 7 and 10), and the un-rearranged wildtype ETV1 allele by primer pair M/N (1024 bp; lane 2, 5, 8, 11). The genomic fusion band x (1150 bp) and y (1044 bp) amplified by fusion-specific primer pair E/N, and z (1043 bp) amplified by primer pair G/N, were present only in the induced and enriched LNCaP population but absent in untransfected LNCaP cells (lane 6 vs. 3, and lane 6 vs. 12). FIG. 4F. Sanger sequencing of the x, y, and z fusion band identified the exact genomic breakpoints. Region of microhomology at the breakpoints are boxed by solid lines, and indels by dash lines. FIG. 4F discloses SEQ ID NOS 194-202, respectively, in order of appearance. FIG. 4G. FISH combined with 3D image reconstruction confirmed the gene fusion between TMPRSS2 with ETV1 in the enriched population. FISH probes against TMPRSS2 gene (red) located on chromosome 21 and against ETV1 gene (green) located on chromosome 7 were used to reveal gene fusion based on the co-localized FISH signals in reconstructed 3D images. Examples of FISH signal in an untransfected cell (i) and a cell carrying induced TMPRSS2-ETV1 gene fusion (ii) are shown. Arrow points to the co-localized FISH signals indicative of TMPRSS2-ETV1 fusion, which is shown at a higher magnification in the inlet. The table on the right shows the population analysis based on the 3D construction of FISH images. Approximately 0.9% of the enriched population (30 out of 3301 cells) was positive for TMPRSS2-ETV1 fusion gene based on the co-localized FISH signals. In contrast, none of the cells from the untransfected population (0 out 620 cells) showed co-localized FISH signals.

FIG. 5A. RNA mediated gene fusion mechanism requires DNA:RNA hybrid formation. Induction of TMPRSS2-ERG fusion gene by antisense chimeric RNA was significantly reduced in the presence of wildtype RNaseH vs. the mutant RNaseH (FIG. 5A, lane 2 vs. 1). Similarly, induction of TMPRSS2-ETV1 fusion gene was also significantly reduced in the presence of wildtype vs. the mutant RNaseH (FIG. 5A, lane 6 vs. 5). These results indicate that the induction of gene fusions requires the formation of an RNA/DNA hybrid. Consistent with previous observations, sense input RNAs failed to induce fusion regardless of the expression of RNaseH (FIG. 5A, lane 3, 4, 7, 8). FIG. 5B. The input RNAs were expressed by U6 (a pol-III promoter) for one day, followed by α-amanitin-mediated inhibition of pol-II transcription for various time periods (0, 2, 6, 12 and 24 hrs) to shut down parental gene transcription. α-amanitin was then removed to resume cellular transcription and the induction by sense vs. antisense input RNA were compared. The corresponding sense input RNAs that previously failed to induce fusion, began to induce TMPRSS2-ERG (lane 9, 10) after 12 hours of α-amanitin treatment, and TMPRSS2-ETV1 fusion (lane 20) after 24 hours of α-amanitin treatment, respectively. The results indicate that blocking the parental gene transcription by α-amanitin for a longer period (12-24 hrs for TMPRSS2-ERG and 24 hrs for TMPRSS2-ETV1) allows sense input RNA to induce gene fusion. Input RNAs used for the experiment: Antisense-5 vs. sense-5 for inducing TMPRSS2-ERG (upper panel, left two columns); antisense vs. sense TMPRSS2-ETV1-A for inducing TMPRSS2-ETV1 (upper panel, right two columns). As controls, transfecting cells with a parental plasmid containing no input RNA sequences (lower panel, left column), cells without transfection (lower panel, center column), and DHT and α-amanitin controls (lower panel, right column), also failed to induce fusion. In addition, GAPDH is used as internal control for the amount of RNA in each lane.

FIG. 6A. Expression of full-length AZI1 mRNA for 3 days induced TMPRSS-ERG fusion. The induction occurred at physiologically relevant concentrations of DHT as low as 40 nM (lane 4). Three-rounds of nested PCR were performed to reveal the lowest amount of DHT that permits AZI1-mediated fusion induction. FIG. 6B. Expression of AZI1 exon 16-17 (lane 2), but not its antiparallel sequence (lane 3), led to TMPRSS2-ERG fusion. Inductions by full-length AZI1 (lane 1) and by antisense-5 (lane 4) were used as positive controls. FIG. 6C. Endogenous AZI1 RNA is expressed in LNCaP cells at low level and the expression is upregulated by DHT treatment.

FIG. 7A. Our data support a model where the initiator RNA with chimeric sequence invades chromosomal DNA to stabilize a transient RNA/DNA duplex using DNA sequences located in two distant genes. Resolution of such an RNA/DNA duplex by DNA break/repair mechanisms might yield the final gene fusion through recombination in regions prone to DNA breaks. Such events however are infrequent (1 in $10^3$ or $10^4$ cells in the experimental cell population), and are dependent of the presence of hormone DHT in the case of LNCaP cells. FIG. 7B and FIG. 7C. The data also indicate that it is the antisense rather than sense chimeric RNAs that effectively drive gene fusion, and that this disparity can be explained by transcriptional conflict produced by the transcriptional activity of parental genes. The sense chimeric RNAs forming DNA/RNA hybrids with antisense strands of genomic DNA (the template strand used for transcription) are likely be frequently "bumped" off by RNA polymerase and unable to stabilize the structures required for initiating genomic rearrangements. The proposed RNA-driven model may provide a mechanism that can 'specify' gene fusion partners in early disease stages, and could have fundamental implications in the biology of mammalian genome stability, as well as gene editing technology via mechanisms native to mammalian cells.

FIGS. 8A-8B. Primer design used to distinguish induced endogenous fusion RNAs from exogenous input RNAs. FIG. 8A. The endogenous full-length TMPRSS2-ERG fusion RNA most commonly found in prostate cancer consisting of TMPRSS2 exon 1 (78 nt, uc002yzj.3) spliced to ERG exons 4-12 (1289 nt, uc021wjd.1). In FIG. 1A, the exogenous input RNAs expressed from plasmids consists of TMPRSS2 exon-1 (78 nt) fused to ERG exon-4 (218 nt). The RT-PCR results shown in FIGS. 1A and 1B (middle panel) were performed using a forward primer on TMPRSS2 exon-1 paired with a reverse primer on ERG exon-7, thereby specifically amplifying the endogenous fusion RNA transcribed from the TMPRSS2-ERG fusion gene, but not from transfected plasmids or input RNAs because both lack ERG exon-7. FIG. 8B. Because RNA-induced fusion is a low frequency event, a more efficient PCR method was developed to detect induced endogenous fusion RNA using a primer pair targeting TMPRSS2 exon-1 and ERG exon-4. To distinguish induced endogenous fusion RNAs from exogenous input RNAs, mutations were introduced at nucleotide positions 16-35 of the input RNAs (gray box in TMPRSS2 exon-1), allowing specific amplifications of induced endogenous fusion RNAs or exogenous input RNA using specific forward primers. The lower panel shows the wild type TMPRSS2 exon-1 sequence in green. The mutated area in input RNA is shown in black and underlined. The primer used to specifically recognize induced fusion RNA is shown as the green arrow and was used in most of the figures. The primer for input RNA is denoted by the black arrow and was used in FIGS. 1B, 1C, 1D, 1E, FIG. 2B, and FIG. 3B. FIG. 8B discloses SEQ ID NOS 203-204, respectively, in order of appearance.

FIG. 9A. Schematics of the designed input RNAs consisting of TMPRSS2 (uc002yzj.3) and ERG (uc021wjd.1) exons. Upper panels: antisense-2 and sense-2 input RNA consisting of TMPRSS2 exon-1 (78 nt) and ERG exon-4 (216 nt). Lower panel: sense-2-long RNA consisting of TMPRSS2 exon-1 (78 nt) with ERG exons-4, -5, -6 and partial -7 (618 nt). ts: transcriptional stop "TTTTTT" for the U6 promoter. FIG. 9B. RT-PCR detection of induced fusion transcript (top gel) and input RNA (bottom gel). For induced fusion transcript, RT-PCR was performed using a forward primer on TMPRSS2 exon-1 paired with a reverse primer on the 3' end of ERG exon-7 (see FIG. 8A), thereby specifically amplifying the endogenous fusion RNA transcribed from the TMPRSS2-ERG fusion gene, but not from transfected plasmids or input RNAs because both lack the 3' end of ERG exon-7. Control vector lacking input RNA sequence (lane 4), DHT treatment only (lane 5), and PCR reactions lacking cDNA (lane 7) were used as negative controls. Antisense RNA is capable of inducing the fusion transcript (lane 3), whereas sense RNAs failed to induce fusion transcripts regardless of their lengths (lanes 1 and 2).

FIG. 11A. Schematic of the expression plasmid containing a U6 promoter and antisense-5 sequence. Unique restriction sites are shown in red. The arrow indicates the transcriptional start. The plasmid was digested by SacII/KpnI, leaving U6 with antisense-5, or with SacII/PstI, separating U6 from antisense-5. FIG. 11B. Confirmation of complete digestion was visualized by agarose gel. Uncut plasmid vector was used as control. FIG. 11C. Induction of TMPRSS2-ERG fusion after transfection of digested plasmid fragments. The TMPRSS2-ERG fusion transcript was induced only when the U6 promoter was attached to antisense-5 sequence, indicating that it is the input RNA expressed by the U6 promoter, not the transfected DNA plasmid per se, that leads to fusion induction.

FIG. 12. DHT dosage effect in facilitating RNA-mediated gene fusion as assayed by one round RT-PCR. To determine the DHT concentrations that facilitate RNA-mediated gene fusion detectable by one round RT-PCR, we generated a dose-response curve using LNCaP cells transfected with antisense-5 and treated with different DHT concentrations for 3 days. Relative RT-PCR intensities of induced fusion transcript bands as generated by one round RT-PCR were plotted against DHT concentrations. In the presence of antisense-5, fusion induction is detectable at ~0.6 µM DHT, reaches its maximum at 1.5 µM DHT, with the effective concentration that yields 50% of maximal induction ($EC_{50}$) at ~0.9 µM. In the absence of antisense-5, no induction was observed in the entire DHT range tested up to 2.0 µM (upper panel), indicating that DHT alone is ineffective in inducing TMPRSS2-ERG fusion. To streamline the experimental procedures, 0.9 µM DHT (the $EC_{50}$ concentration) were used for 3 days followed by one round of RT-PCR. However, it is important to note that all key experiments were also performed under physiologically relevant DHT concentrations (<100 nM), and in those cases three-rounds of nested PCR were used to reveal the lowest amount of DHT required. As shown in FIG. 1D and FIG. 6A, gene fusion events induced by antisense-5 occurred at physiologically relevant DHT concentrations as low as 20 nM, and gene fusion events induced by endogenous AZI1 mRNA occurred at as low as 40 nM DHT.

FIG. 14. Complementary base pairing of the genomic DNA sequences comprising the stems and their flanking sequences. The sense strand of genomic sequences from TMPRSS2 and ERG that form the putative stems (in red boxes) with various degrees of stability as identified by BLAST analyses. Regions showing perfect complementary base pairing (A-T and G-C) are shaded in gray. FIG. 14 discloses SEQ ID NOS 205-218, respectively, in order of appearance.

FIG. 15 discloses SEQ ID NOS 183-184; 183 and 184; 183 and 184; 185-186; 185 and 186; 185 and 186; 187 188; 187 and 188; and, 187 and 188, respectively, in order of appearance.

FIG. 16A. Disruption of the putative genomic stem using tailor-made input RNAs that directly hybridize to one side of the stem A. FIG. 16A discloses SEQ ID NOS 219, 182, and 181-182, respectively, in order of appearance. FIG. 16B. RT-PCR assays of fusion transcripts induced by the input RNAs illustrated in A. Interfering with three-way junction formation eliminated (lane 2) or significantly reduced the induction (lane 3). Controls include: vector lacking input RNA sequence (lane 4), DHT treatment only (lane 5), and PCR reaction lacking cDNA (lane 7).

FIG. 17A. Nested primer pairs used to detect low levels of endogenous ERG mRNA from LNCaP cells. Forward primers for ERG exon-3 are shown in green whereas reverse primers for ERG exon-7 are shown in blue (primer sequences are listed in the Materials and Methods). FIG. 17B. Endogenous ERG mRNA was not detected in LNCaP cells in the presence or absence of DHT or antisense-5 (lane 1 to 11) by three-rounds of nested RT-PCR. cDNA prepared from VCaP cells which express ERG mRNA was used as positive control (lane 13). FIGS. 17C and 17D. Similarly, using forward primers on ERG exon-1 and reverse primers on ERG exon-4 also failed to detect endogenous ERG mRNA by three-rounds of nested RT-PCR (lane 1 to 11, primer sequences are listed in Example 3). These primer sets were chosen because they specifically amply endogenous ERG mRNA but not TMPRSS2-ERG fusion transcript that contains ERG exon-3 to exon-12.

FIGS. 19A-19B. Locations targeted by primers for mapping the genomic breakpoint and locations of identified TMPRSS2-ERG genomic breakpoints. FIG. 19A. The locations of 44 forward primers (green) spacing across TMPRSS2 intron-1 (~10 kb) and 112 reverse primers (blue) spacing across ERG intron-3 (~130 kb). ERG intron-3 is significantly larger than that of TMPRSS2 intron-1. Each vertical line represents a target location by a primer or a set of nested primers. The primers targeting ERG intron-3 are designed to concentrate in the region near exon-4 and in the hot spot regions previously identified from prostate cancer patients. The specific primers that amplify the genomic breakpoint shown in FIG. 3D are labeled as red. FIG. 19B. Locations of identified TMPRSS2-ERG genomic breakpoints. Locations of previously identified TMPRSS2-ERG genomic breakpoints from prostate cancer patients (Weier et al.) are shown in green in TMPRSS2 intron-1 and blue in ERG intron-3. The number on top of each location is the ID number of a patient. The genomic breakpoint identified in our study is shown in red. Short arrows indicate sites targeted by antisense-5.

FIG. 20 discloses SEQ ID NOS 220-235, respectively, in order of appearance.

FIG. 22. Locations targeted by primers for mapping the TMPRSS2-ETV1 genomic breakpoints. The locations of 23 forward primers (green) spacing across TMPRSS2 intron-1 (~10 kb) and 7 reverse primers (purple) spacing across ETV1 intron-2 (~0.8 kb). Each vertical line represents a target location by a primer or a set of nested primers. The specific primers that amplify the genomic breakpoint shown in FIG. 4E are labeled as red.

FIG. 23 discloses SEQ ID NOS 181-188, respectively, in order of appearance.

FIG. 25 shows testing of different size of DNA spacers (bulge) for the Stem B 3-way junction stem formation for TMPRSS2-ERG gene fusion. In each test, the DNA bulge was set to the same size on both the left and the right side. For example, B-31 has bulge size of 31 nt on the TMPRSS2 side as well as the ERG side. RT-PCR was performed to detect the level of induced TMPRSS2-ERG fusion RNA. The optimum size of the bulge for fusion induction was examined in FIGS. 25, 26, and 27 for the corresponding Stem B, C, and D of FIG. 23. As is shown, for fusion gene induction the optimum size of the bulge is around 35 nucleotides on each side, although other lengths also work.

FIG. 28 discloses SEQ ID NOS 187 and 188, respectively, in order of appearance.

FIGS. 29-32 provide results of testing the various sizes of the chimeric RNA when using Stem A, Stem B, Stem C, or Stem D, respectively. For fusion gene induction, an optimum size for the chimeric RNAs is around 50-75 nucleotides on each side.

FIG. 30 shows testing of the different sizes for the different chimeric RNA parts corresponding to TMPRSS2 and ERG using the Stem B 3-way junction.

FIG. 31 shows testing of the different sizes for the different chimeric RNA parts corresponding to TMPRSS2 and ERG using the Stem C 3-way junction.

FIG. 32 shows testing of the different sizes for the different chimeric RNA parts corresponding to TMPRSS2 and ERG using the Stem D 3-way junction.

FIGS. 39A-39D. RNA-mediated inter-chromosomal JAZF1-SUZ12 fusion in 293T cells. FIG. 39A. The design of chimeric RNA is based on the three-way junction that could be formed between genomic DNA (in the stem) and chimeric RNA (perpendicular and below the stem). The three-way junction comprises an RNA/DNA hybrid and a genomic DNA stem between the parental genes (JAZF1 and SUZ12). The sense genomic strand of JAZF1 gene is on the negative strand of chromosome 7 while that of SUZ12 is on the positive strand of chromosome 17. Short vertical lines in gray regions between the chromosome and the chimeric RNA represent base pairings. FIG. 39B. An example of chimeric RNA sequences used to induce JAZF1-SUZ12 fusion. This chimeric RNA target intron regions and has GC content of 27%. The fusion RNA transcribed from the induced fusion gene contains an annotated splice junction. In this particular case, two different fusion RNAs were confirmed based on the results derived from the Sanger sequencing data. FIG. 39B discloses the JAZF1 targeting sequence as SEQ ID NO: 236, the SUZ12 targeting sequence as SEQ ID NO: 237, and the chimeric sequence as SEQ ID NO: 238. FIG. 39C. Example of inter-chromosomal JAZF1-SUZ12 fusion transcript (arrow) induced by sequence-specific chimeric RNAs in 293T cells without additional hormone or other stimuli. 293T cells were transfected with chimeric RNA expression plasmid. Total RNA was then harvested at day 3. Nested RT-PCR using specific primer pairs were used to detect the induced fusion transcript. Bands were then excised and cloned in pGEM-T vector for Sanger sequencing which confirmed the identity of the chimeric RNA as JAZF1 exon 1 spliced to a cryptic splice site of SUZ12 exon 1. FIG. 39D. Another example of inter-chromosomal JAZF1-SUZ12 fusion transcript (arrow) induced by sequence-specific chimeric RNAs in 293T cells without additional hormone or other stimuli. 293T cells were transfected with chimeric RNA expression plasmid. Total RNA was then harvested at day 3. Nested RT-PCR using specific primer pairs were used to detect the induced fusion transcript. Band marked by asterisk was then excised and cloned in pGEM-T vector for Sanger sequencing. The fusion transcript was from splicing JAZF1 exon 2 to SUZ12 exon 2.

FIG. 40A. The design of chimeric RNA is based on the three-way junction that could be formed between genomic DNA (in the stem) and chimeric RNA (perpendicular and below the stem). The three-way junction consists of an RNA/DNA hybrid and a genomic DNA stem between the parental genes (BCR and RANGAP1). The sense genomic strand of BCR gene is on the positive strand of chromosome 22 while that of RANGAP1 is on the negative strand of chromosome 22, separated by 18 Mb. Short lines in gray regions represent base pairings. FIG. 40B. An example of chimeric RNA sequence used to induce BCR-RANGAP1 fusion. This chimeric RNA target intron regions and has GC content of 48.4%. The fusion RNA transcribed from the induced fusion gene contains an annotated splice junction. FIG. 40B discloses the BCR targeting sequence as SEQ ID NO: 239, the RANGAP1 targeting sequence as SEQ ID NO: 240, and the chimeric sequence as SEQ ID NO: 241. FIG. 40C. Intra-chromosomal BCR-RANGAP1 fusion transcript (arrow) induced by sequence-specific chimeric RNA in 293T cells without additional hormone or other stimuli. 293T cells were transfected with chimeric RNA expression plasmid. Total RNA was then harvested at day 3. Nested RT-PCR using specific primer pairs were used to detect the induced fusion transcript. The production of BCR-RANGAP1 fusion transcript was confirmed by Sanger sequencing to comprise BCR exon14 spliced to RANGAP1 exon3

(RANGAP1 isoform 1, NM_001278651.1). The RNA fusion junction is an annotated splice junction for both genes.

Figure 41A:
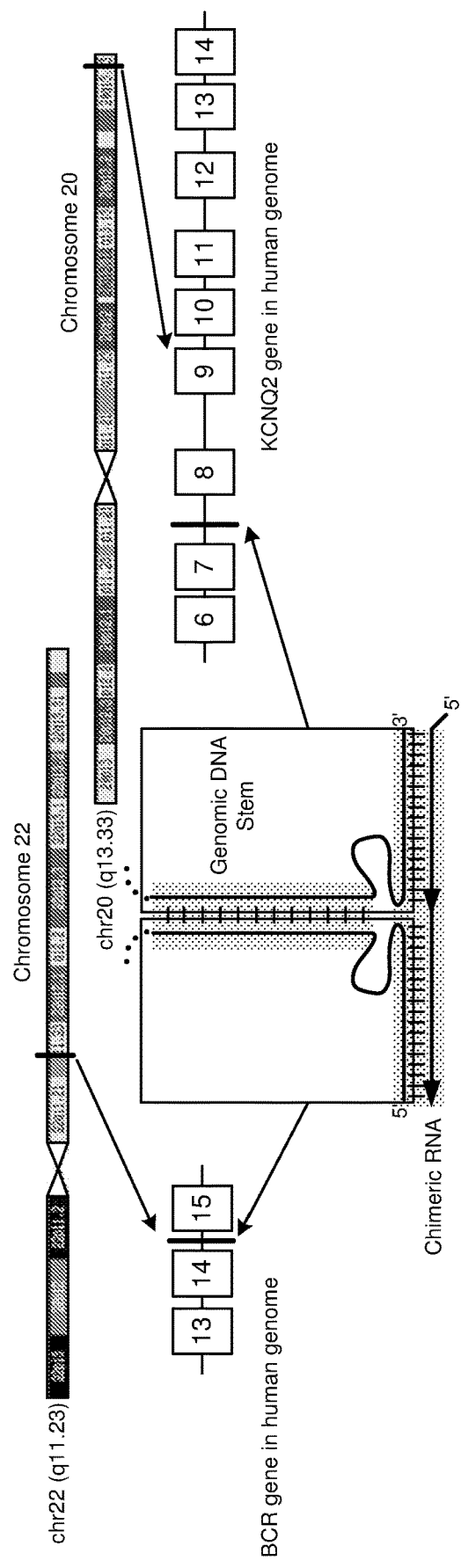
Figure 41B:
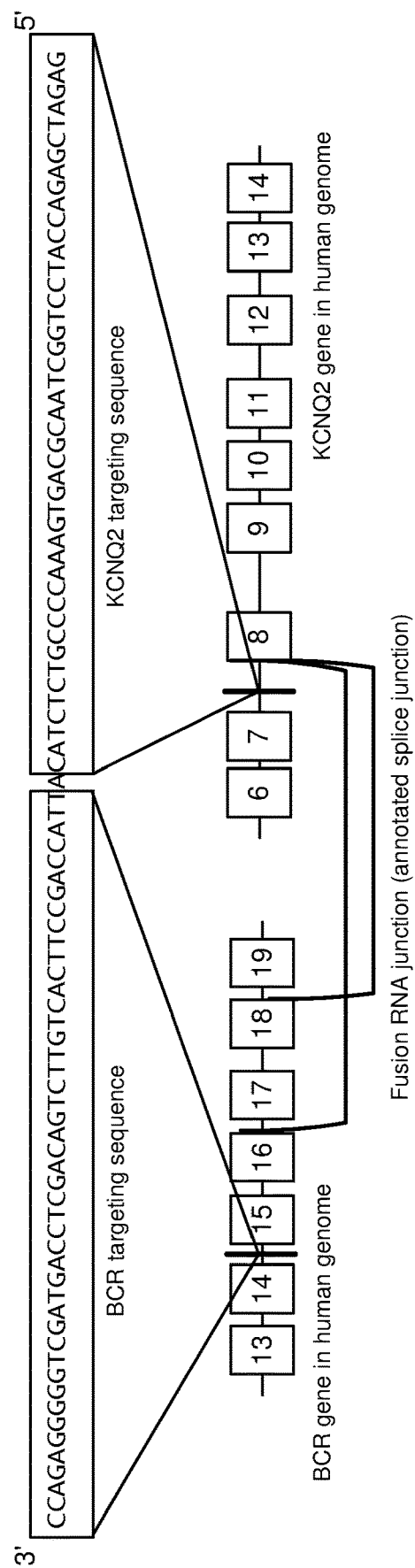
Figures 41C, 41D:
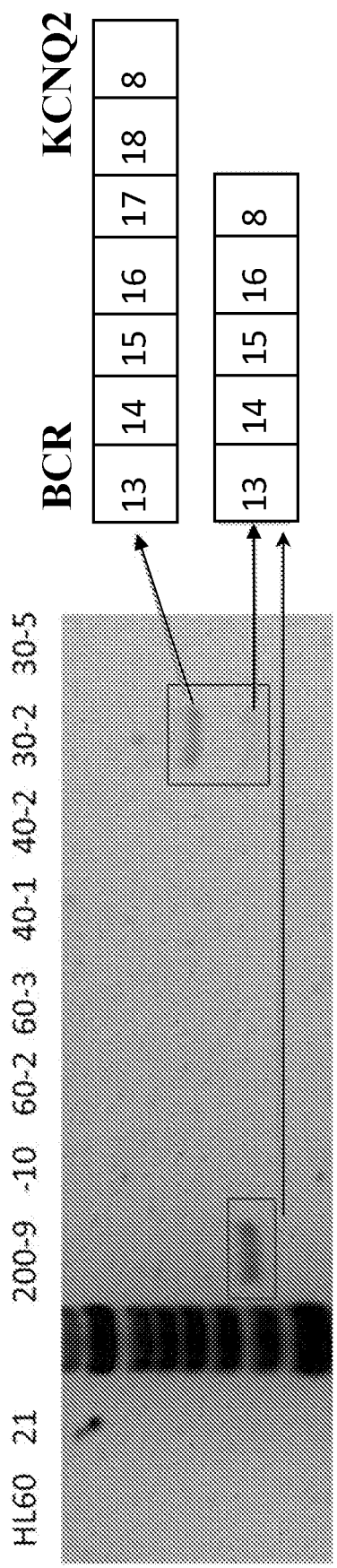

FIGS. 41A-41D. RNA-mediated inter-chromosomal BCR-KCNQ2 fusion in HL-60 cells by designed chimeric RNA. FIG. 41A. The design of chimeric RNA is based on the three-way junction that could be formed between genomic DNA (in the stem) and chimeric RNA (perpendicular and below the stem). The three-way junction consists of an RNA/DNA hybrid and a genomic DNA stem (black) between the parental genes (BCR and KCNQ2). The sense genomic strand of BCR gene is on the positive strand of chromosome 22 while that of KCNQ2 is on the negative strand of chromosome 20. Short lines in gray regions represent base pairings. FIG. 41B. An example of chimeric RNA sequence used to induce BCR-KCNQ2 fusion. This chimeric RNA target intron regions and has GC content of 55.4%. The fusion RNA transcribed from the induced fusion gene contains an annotated splice junction. In this case, two different fusion RNAs were confirmed based on the results derived from the Sanger sequencing data. FIG. 41B discloses the BCR targeting sequence as SEQ ID NO: 242, the KCNQ2 targeting sequence as SEQ ID NO: 243, and the chimeric sequence as SEQ ID NO: 244. FIG. 41C. Two BCR-KCNQ2 fusion transcript variants were induced in HL-60 cells by chimeric RNA targeting BCR and KCNQ2 genes in the genome without hormone or other stimuli. FIG. 41D. Schematic of induced BCR-KCNQ2 fusion transcripts derived from the Sanger sequencing data. HL-60 cells were transfected with chimeric RNA expression plasmid by nucleofection (Lonza) at day 1. Total RNA was then harvested at day 7. Nested RT-PCR using specific primer pairs were used to detect the induced fusion transcript.

Figure 42A:
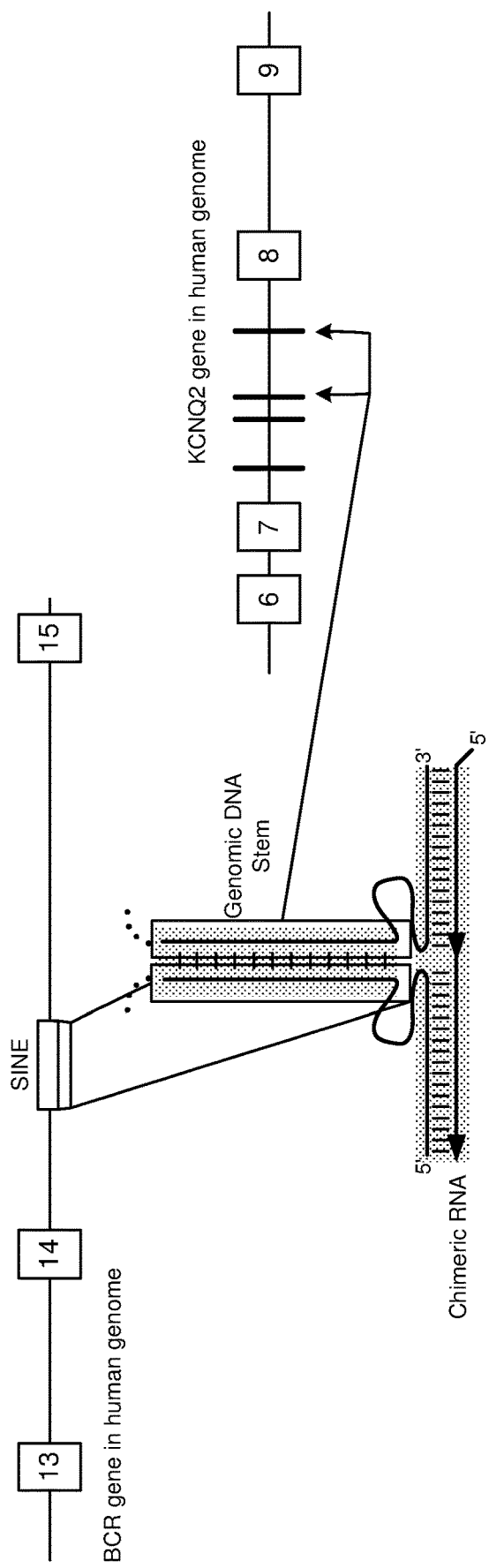
Figure 42B:
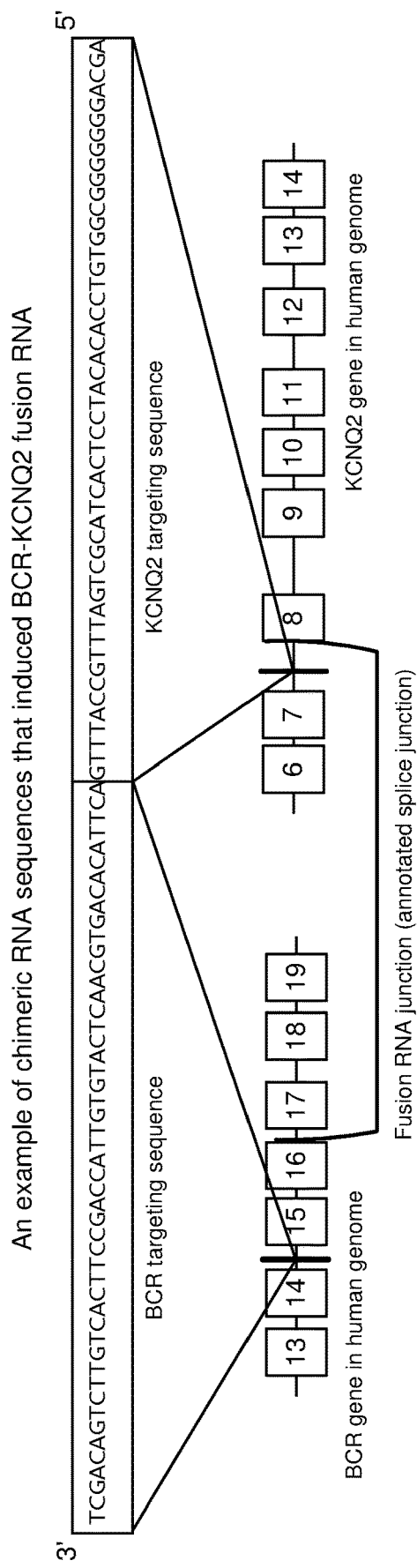
Figure 42C:
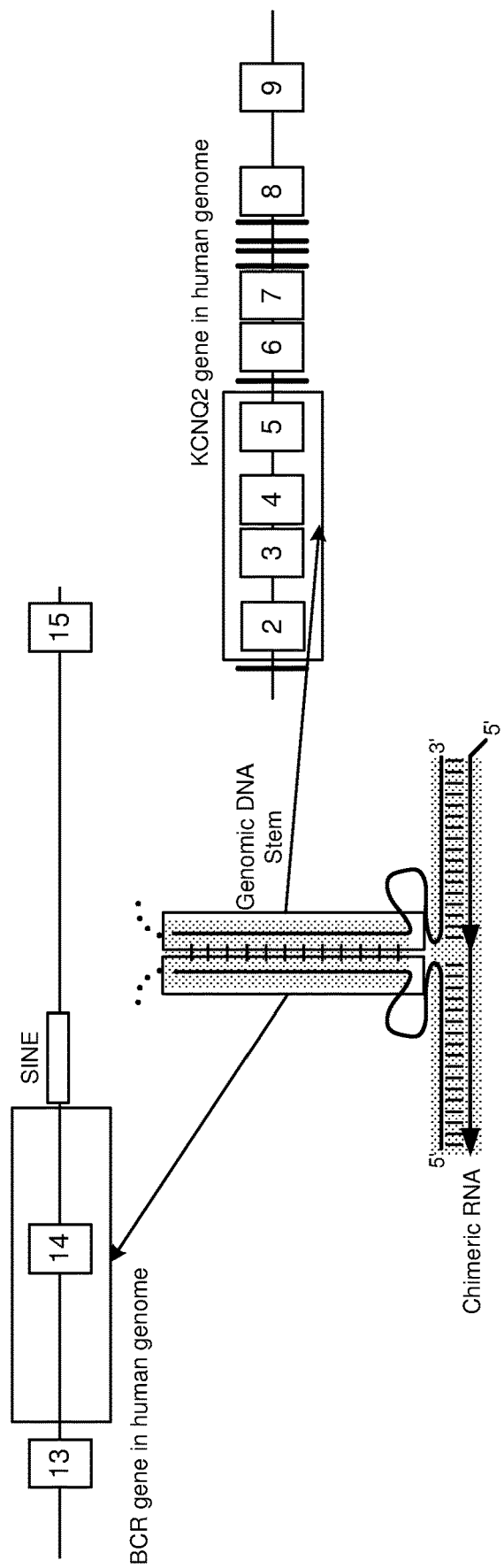
Figure 42D:
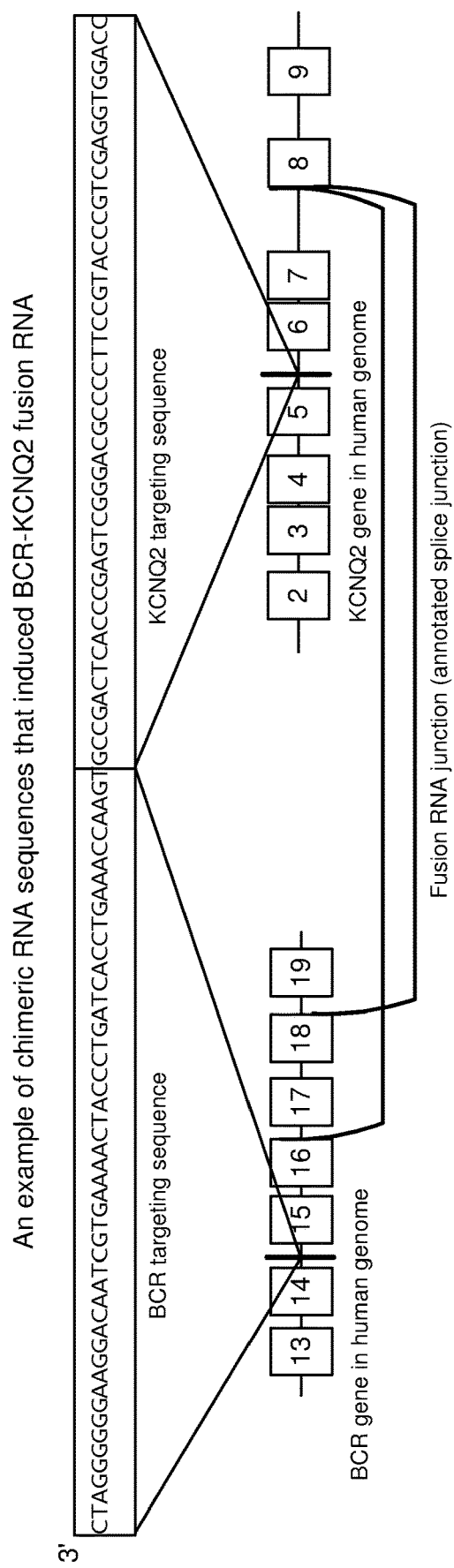
Figure 42E:
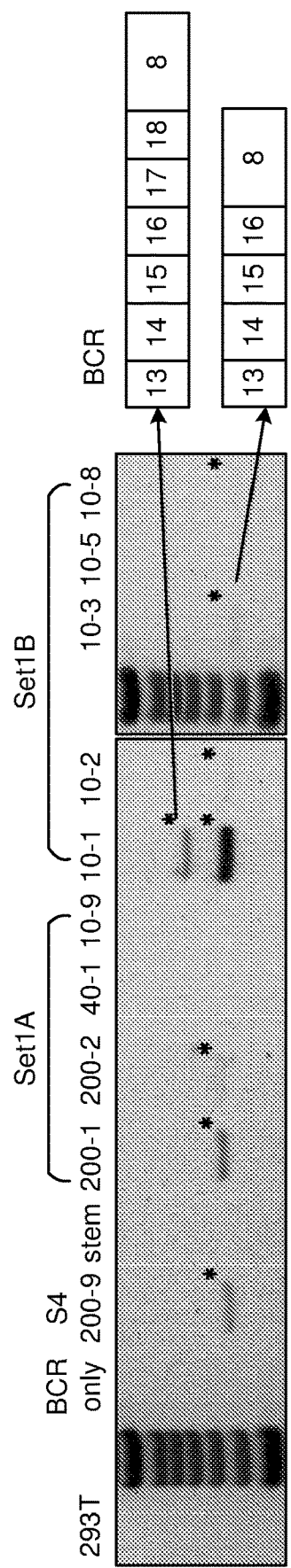

FIGS. 42A-42E. BCR-KCNQ2 fusion induced in 293T cells by chimeric RNAs utilizing/excluding the SINE element for three-way junction formation. FIG. 42A. Examples of chimeric RNA design using Short Interspersed Nuclear Element (SINE) commonly present in the human genome. The designed chimeric RNA forge a three-way junction that could be formed between two SINEs in genomic DNA (in the stem) and chimeric RNA (perpendicular and below the stem). Genomic DNA stems formed by DNA repeats such as SINE/SINE repeats may constitute stems over 300 nts in length. Short lines in gray regions represent base pairings. SINEs are in crimson. FIG. 42B. An example of chimeric RNA sequence utilizing the SINE element for three-way junction formation to induce BCR-KCNQ2 fusion. This chimeric RNA has GC content of 52%. FIG. 42B discloses the BCR targeting sequence as SEQ ID NO: 245, the KCNQ2 targeting sequence as SEQ ID NO: 246, and the chimeric sequence as SEQ ID NO: 247. FIG. 42C. Examples of chimeric RNA design targeting DNA sequences of BCR and KCNQ2 genes in the genome which form genomic stems using regions outside of known DNA repeats such as Short Interspersed Nuclear Element (SINE). SINEs are commonly present in the human genome are shown in solid boxes. The DNA stem could range from 10 bp to >100 bp with some mismatches. FIG. 42D. An example of chimeric RNA sequence used to induce BCR-KCNQ2 fusion in 293T cells. This chimeric RNA target intron regions and has GC content of 60.4%. FIG. 42D discloses the BCR targeting sequence as SEQ ID NO: 248, the KCNQ2 targeting sequence as SEQ ID NO: 249, and the chimeric sequence as SEQ ID NO: 250. FIG. 42E. BCR-KCNQ2 fusion can be induced by chimeric RNAs that form 3-way junction with genomic stems using SINE repeats (Set1A) or outside of SINE repeats (Set1B). 293T cells were transfected with chimeric RNA expression plasmid for 3 days and then harvested for nested RT-PCR.

DETAILED DESCRIPTION

As used herein the specification, "a" or "an" may mean one or more. As used herein in the claim(s), when used in conjunction with the word "comprising", the words "a" or "an" may mean one or more than one. As used herein "another" may mean at least a second or more. In specific embodiments, aspects of the invention may "consist essentially of" or "consist of" one or more sequences of the invention, for example. Some embodiments of the invention may consist of or consist essentially of one or more elements, method steps, and/or methods of the invention. It is contemplated that any method or composition described herein can be implemented with respect to any other method or composition described herein. The scope of the present application is not intended to be limited to the particular embodiments of the process, machine, manufacture, composition of matter, means, methods and steps described in the specification.

I. RNA-Driven Genomic Rearrangement Methods

The present disclosure provides an example of a process that (1) utilizes three-way junction formation between genomic DNAs base-pairing with chimeric RNA, (2) is generally permissible regardless of intra-chromosomal or inter-chromosomal fusion, (3) in some cases may be facilitated by physiological hormone levels (androgen in the disclosed examples, although other hormone(s) or no hormones may be utilized, and (4) can occur in normal cells prior to malignant transformation. With respect to gene fusion of actively transcribed genes, it may be the antisense rather than sense chimeric RNAs that drives gene fusion, in specific embodiments, although the gene to be fused may dictate whether or not the chimeric RNA comprises sense sequence for both regions of the chimeric RNA, antisense sequence for both regions of the chimeric RNA or one of the regions of the chimeric RNA is sense while the other region of the chimeric RNA is antisense. While in some embodiments a three-way junction facilitates gene fusion induction, in specific cases RNA/DNA hybrid alone without a three-way junction induces gene fusion, for example under certain conditions.

Methods of the disclosure may or may not be practiced with exogenously provided hormone. In cases wherein hormone may be enhancing to the method or is known to be enhancing to the method, an effective amount of the hormone may be utilized. Whether or not hormone is utilized may depend on the gene(s) to be fused. For example, in cases wherein the cells in which the chimeric RNA is utilized are responsive to hormone, or the expression of one or both of the genes is sensitive to hormone, then an effective amount of hormone may be utilized in the method. As one example, if the cells in which the chimeric RNA is delivered are prostate cancer cells and at least one of the genes being fused is responsive to androgen or testosterone, then androgen, testosterone, or one of their derivatives may be employed in the method. In a situation where the cells are breast cancer cells, for example, and at least one of the genes being fused is responsive to estrogen, then estrogen may by employed in the method.

The formation of fusion genes (cancer fusion genes, merely as examples) demonstrated herein also represents a new and safer way of achieving gene editing in human cells, for example without involving immunogenic exogenous proteins such as Zinc finger or CRISPR/Cas9. Thus the RNA-driven genomic rearrangements encompassed by the disclosure are a useful technology for gene editing in mammalian cells in general, and overcomes certain difficulties in gene/cell therapy in particular.

Thus, provided herein are methods for rearranging regions of a genome. The method can produce genomic DNA rearrangements regardless of whether those genomic DNA segments are actively transcribed genes or untranscribed regions (or one of both). In the case of actively transcribed DNA segments (active genes), the chimeric RNA may comprise sequence that is antisense with respect to the gene sequences. In the case of untranscribed DNA segments (silent genes or intergenic space, for example), the chimeric RNA may comprise sequence that is either sense or antisense with respect to the genomic DNA segments. Thus, the method can target any segment of a genome.

The present disclosure concerns methods of generating fusion of two different regions of nucleic acid, including in particular two different regions of genomic DNA. Demonstrated herein is expression of an example of a synthetic chimeric RNA that drives formation of a specified gene fusion via genomic translocation in mammalian cells. In particular embodiments, a first region of a first gene in a genome is fused with a second region of a second gene in the genome, and the fusion is dictated by the sequence of one or more chimeric RNAs, and in some cases by the sequence of one or more antisense chimeric RNAs.

In particular embodiments, provided herein are methods of producing genomic DNA rearrangements between two different regions of genomic DNA by exposing to the genomic DNA an effective amount of an exogenously provided chimeric RNA. The particular chimeric RNA is not endogenous, in specific cases, and it may be synthetic and made by the hand of man. It may be derived from other chemically modified nucleic acids, from proteins, etc. In other cases the chimeric RNA is similar or identical to an endogenous chimeric RNA but is exogenously provided to the genomic DNA. In specific embodiments, the chimeric RNA comprises fusion of (1) a first part that is reverse complement with respect to a first genomic region and (2) a second part that is reverse complement with respect to a second genomic region. Upon exposing of the chimeric RNA to the genomic DNA, the first and second genomic regions become fused through DNA recombination.

In particular embodiments when the chimeric RNA is exposed to the genomic DNA, the chimeric RNA then hybridizes with the respective strands of first and second genomic regions of the genomic DNA through the corresponding first and second parts of the chimeric RNA. Such hybridization thereby forms a DNA/RNA hybrid in a sequence-specific manner, in particular embodiments. In certain embodiments following or simultaneously with this hybridization of the chimeric RNA with the respective strands of the first and second genomic regions of the genomic DNA, a double stranded DNA/DNA stem structure is produced. The DNA/DNA stem structure is wholly genomic DNA and may be particularly produced between the first and second genomic regions. In specific embodiments the DNA/DNA stem structure is adjacent to the site of hybridization with the chimeric RNA. As used herein in this embodiment, adjacent to the site refers to within 15 and 50 nucleotides of the site of hybridization with the chimeric RNA. That is, in particular embodiments upon hybridization of the chimeric RNA with the genomic DNA at the first and second genomic regions, a DNA spacer is produced in each of the respective strands of the first and second genomic regions between the DNA/DNA stem structure and the DNA/RNA hybrid structure, and this DNA spacer separates the DNA/DNA stem structure from the DNA/RNA hybrid structure. The DNA spacer may or may not be considered as a bulge or loop, in specific aspects, and the DNA spacer may be double stranded or single stranded, or have regions of both.

Figure 24:
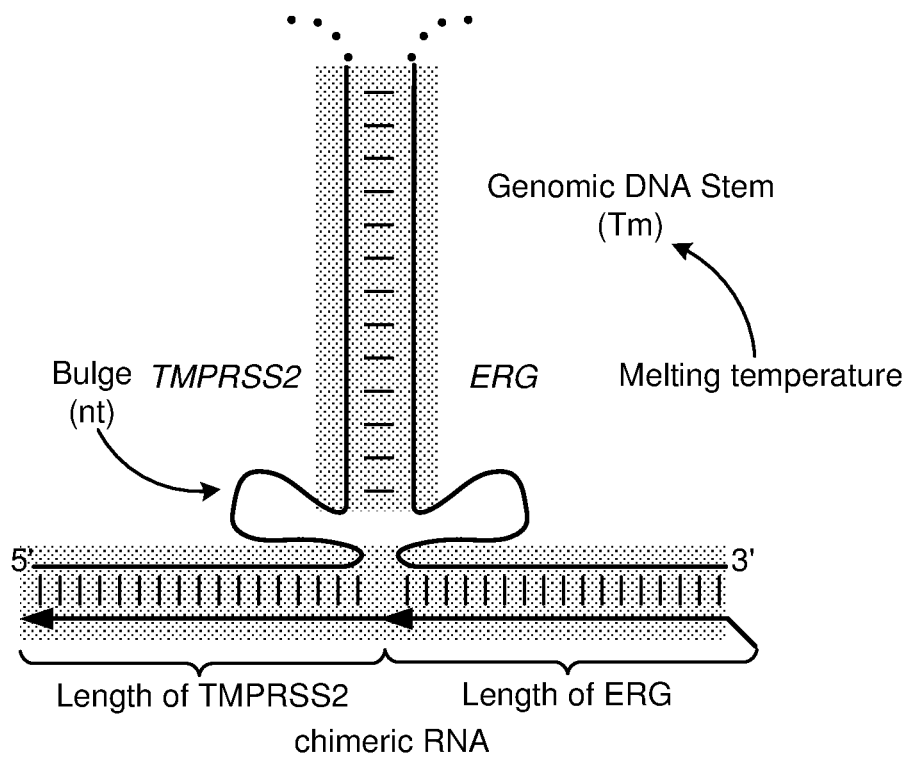
FIG. 24. Illustration of a generic 3-way junction stem formation for TMPRSS2-ERG gene fusion. The illustration shows the different regions of the 3-way junction stem formation that may be variable, including length of the bulge and lengths of the respective regions of the chimeric RNA, and the genomic DNA/DNA stem. The important variables important for gene fusion induction are highlighted in red.

Turning to FIG. 24, illustrated therein is one example of targeting of a specifically designed chimeric RNA for the purpose of fusing the TMPRSS2 and ERG genes, merely as examples. The particular structure produced upon this targeting generally approaches a 3-way stem formation. The chimeric RNA having particular sequence from the TMPRRS2 and ERG genes may be designed specifically for the purpose of fusing the TMPRRS2 and ERG genes. In this example, given that the genes are transcribed (as opposed to intergenic sequences, for example) the chimeric RNA is antisense with respect to the respective sense sequences of both TMPRRS2 and ERG genes. Upon hybridization of the TMPRSS2 and ERG genes with the chimeric RNA, a double-stranded DNA/DNA hybrid (which may be referred to as a stem) is generated as well as a spacer region (that may be referred to as a bulge) in the genomic DNA between the stem and the point of joint hybridization of the chimeric RNA with its corresponding sense sequences of TMPRSS2 and ERG genes. Thus, in a 3-way junction one "piece" comprises a DNA/RNA hybrid and another "piece" comprises a DNA spacer and DNA/DNA hybrid that in some cases may or may not be generally perpendicular with respect to the DNA/RNA hybrid. The DNA spacer may be single-stranded, double-stranded, or have regions of both single-strandedness and double-strandedness. Following this formation, endogenous machinery and/or reagents in the cell may then generate double-stranded breaks in the genomic regions and fusion. The double-stranded DNA breaks may occur outside or within the 3-way stem formation.

Also included herein are methods of inducing gene fusion between first and second target genes by designing or obtaining a chimeric RNA comprising (1) a first part that is antisense with respect to the first target gene and (2) a second part that is antisense with respect to a second target gene; and exposing an effective amount of the chimeric RNAs to nucleic acid comprising the first and second target genes, wherein upon exposing of the chimeric RNA to the nucleic acid, the first and second target genes become fused through DNA recombination.

In some cases, the fusion of two genomic DNA regions occurs in regions that are prone to DNA breaks, such as "hot spots" or at other DNA motifs, such as those with ALU elements and the repeated sequences.

In specific embodiments the genomic DNA is from or in a mammalian subject, although the genomic DNA may not be mammalian in some cases. The first and second parts of the chimeric RNA are non-identical and may be on the same chromosome or they may be on different chromosomes. The genomic DNA of the cell may be from any type of normal cell or any type of diseased cell. The methods may or may not be performed in vivo, such as ex vivo or in vitro. The cell or cells from which the genomic DNA is derived may be a human cell. The cell may be in a tissue or organ or body fluid. The genomic DNA may be from a diseased cell or diseased cells. In some cases, the genomic DNA is from an individual in need of treatment or suspected to be in need of treatment or prevention of a medical condition associated with one or more chimeric RNAs. In specific embodiments, the method occurs at physiological hormone levels.

In particular cases, recombination is induced by chimeric RNA that are designed such that the genomic DNA stem produced upon formation of a three-way junction with the chimeric RNA comprises sequence that is common in the genome, such as sequences that are repeats in the genome, including retrotransposons, such as short interspersed nuclear elements (SINE) and long interspersed nuclear elements (LINE). In such cases, the SINEs or LINEs provide stability to the genomic stem of the three-way junction.

II. Chimeric RNA Compositions

Chimeric RNA compositions of the disclosure are utilized to induce genomic rearrangements, in particular cases. The chimeric RNAs in particular embodiments are synthetic and not from nature, although in specific embodiments they are isolated from nature. The synthetic chimeric RNAs may be used for a non-natural method of producing fusion of two different genomic DNA regions. The synthetic chimeric RNAs may be designed specifically for the purpose of generating fusion of two genomic DNA regions. The chimeric RNAs are the product of the hand of man and not natural. In such cases, two known genomic DNA regions are considered for targeting and the sequence of the chimeric RNA is determined based on the sequence of the two known genomic DNA regions. In cases wherein the two known genomic DNA regions are genes being transcribed (or in some cases, capable of being transcribed), the chimeric RNA is antisense with respect to one or both of the genomic DNA regions. In cases wherein the two known genomic DNA regions are genomic DNA regions that are not transcribed (for example, intergenic regions), the chimeric RNA may be designed to hybridize to either strand of the target genomic DNA non-transcribed region(s). In some cases, one of the targeted genomic DNA regions is not being transcribed and the corresponding region of the chimeric RNA may be either sense or antisense while the other targeted genomic region is transcribed and the corresponding region of the chimeric RNA is antisense.

In some cases, the synthetic chimeric RNA may have reverese complementary regions only at the ends, and in some cases reverse complementary for genomic region A at 5' end and reverse complementary for genomic region B at 3' separated by a loop-out stretch of unknown sequence of varying length.

In particular embodiments, the synthetic chimeric RNA comprises sequence and/or structure that is capable of producing a 3-way junction stem formation in the genomic DNA between the two regions (see, for example, FIG. 24). In producing the 3-way junction stem formation in the genomic DNA between the two regions, there is a DNA spacer (that may or may not structurally bulge from the junction) on both sides of the base of the 3-way junction. In at least some cases, there is an optimum size of the DNA spacer for fusion induction. In specific embodiments the size of the DNA spacer of either genomic DNA strand is around 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides on each side. In particular embodiments the size of the DNA spacer of either genomic DNA strand is around 35 nucleotides in size. In some cases, the length of the DNA spacer in a first genomic DNA strand is the same or different compared to the length of the DNA spacer in a second genomic DNA strand. For example, the DNA spacer of first and second genomic DNA strand may be in a length in a range of 15-50, 15-45, 15-30, 15-25, 15-20, 20-50, 20-45, 20-40, 20-35, 20-30, 20-25, 25-50, 25-45, 25-40, 25-35, 25-30, 30-50, 30-45, 30-40, 30-35, 40-50, 40-45, or 45-50 nucleotides at either side. In some cases, the length of the DNA spacer in a first genomic DNA strand is the same or different compared to the length of the DNA spacer in a second genomic DNA strand.

In particular cases, there is an optimum synthetic chimeric RNA size for fusion induction. In specific embodiments, the chimeric RNA is a fusion of RNA corresponding to two different genes and each region of the chimeric RNA may be of a particular length. In specific embodiments, the two different regions of the chimeric RNA are substantially the same in length, although in other embodiments the two different regions of the chimeric RNA are not the same or are not substantially the same in length. In specific embodiments, the length of each side of the chimeric RNA is about 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, and so on. In some embodiments, the length of two different regions of the chimeric RNA may be in a range of 30-150, 30-125, 30-100, 30-75, 30-50, 50-150, 50-125, 50-100, 50-75, 75-150, 75-125, 75-100, 100-150, 100-125, 125-175, or 125-150. In a particular embodiment, the length of each side of the chimeric RNA is in a range of 50-75 nucleotides. In specific embodiments, the length of 50-75 nucleotides on each side of the chimeric RNA may be utilized when the DNA spacer bulge is 35 nt. In some embodiments, any length of each side of the chimeric RNA may be utilized when the DNA spacer bulge is in a range of 15-50 nt.

The length of the synthetic chimeric RNA may be of any suitable length but in specific embodiments it is in the range of 60-300, 60-250, 60-200, 60-150, 60-100, 75-300, 75-250, 75-200, 75-150, 75-100, 100-300, 100-250, 100-200, 100-150, 150-300, 150-250, 150-200, 150-175, 175-300, 175-250, 175-200, 200-300, 200-275, or 200-250 nucleotides, for example. The length of the chimeric RNA may be 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, or 155 nucleotides, or shorter or longer.

In specific embodiments for fusion gene induction, an optimum size of chimeric RNA is around 50nt on each side to 75nt on each side.

In some embodiments, chimeric RNAs are designed to have a particular percentage of GC content. In specific embodiments, the GC content is from about 27-65, 27-60, 27-55, 27-50, 27-45, 27-40, 27-35, 27-30, 35-65, 35-60, 35-55, 35-55, 35-50, 35-45, 35-40, 40-65, 40-60, 40-55, 40-50, 40-45, 50-65, 50-60, 50-55, 55-65, 55-60, or 60-65% GC. The GC content may be about or may be 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, or 65% GC.

Figure 33:
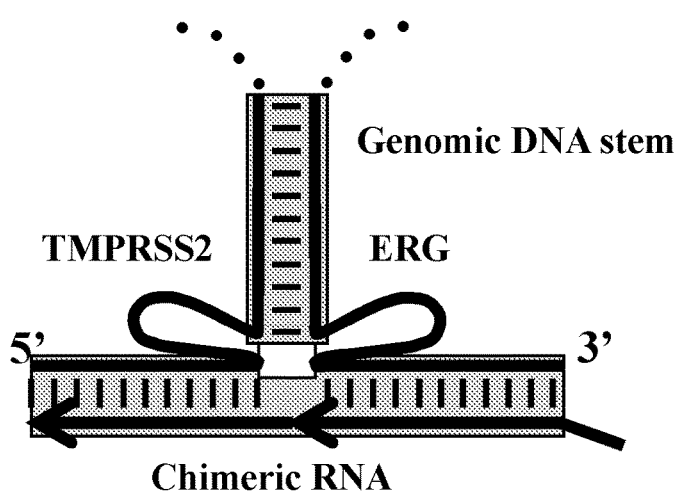
FIG. 33 illustrates a man-made designer chimeric RNA having a perfect match to the genes to be fused.
Figure 34:
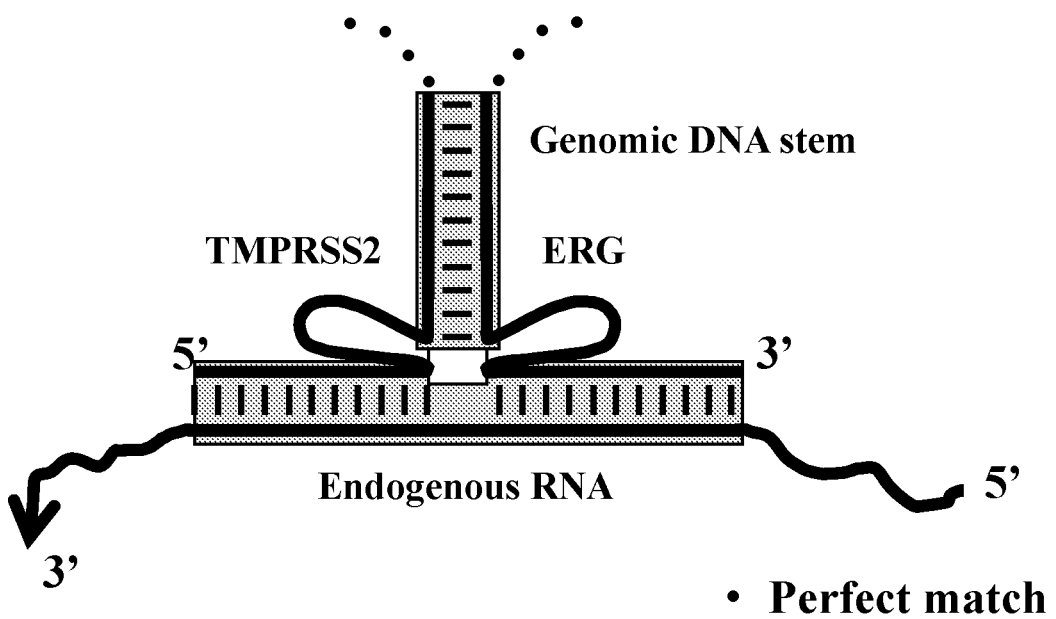
FIG. 34 illustrates an endogenous initiator chimeric RNA having a perfect match to the genes to be fused.
Figure 35:
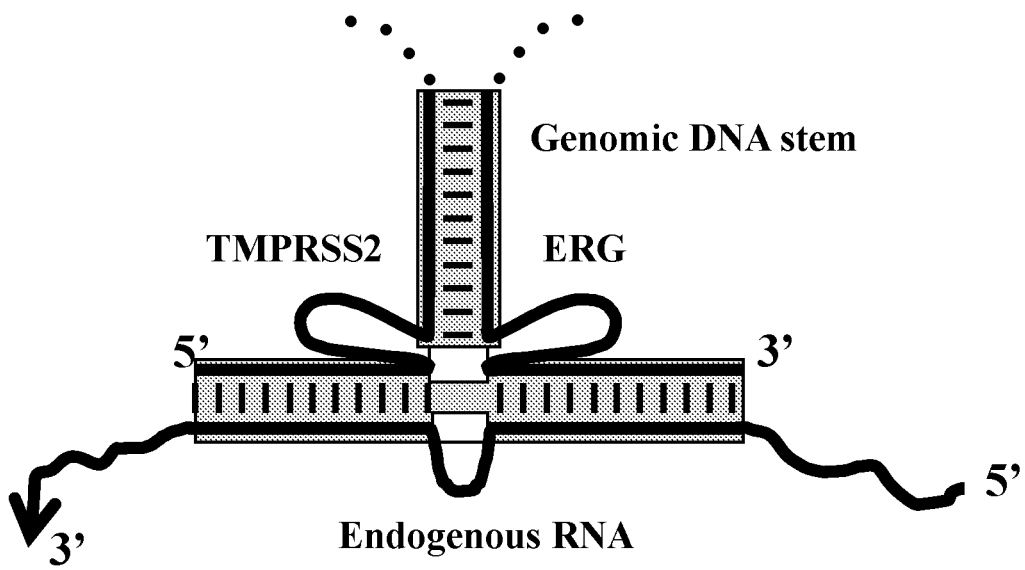
FIG. 35 shows an endogenous initiator chimeric RNA having a match to the genes to be fused that is no exact and may have a loop or secondary structure in the middle, such as at the point of fusion.
Figure 36:
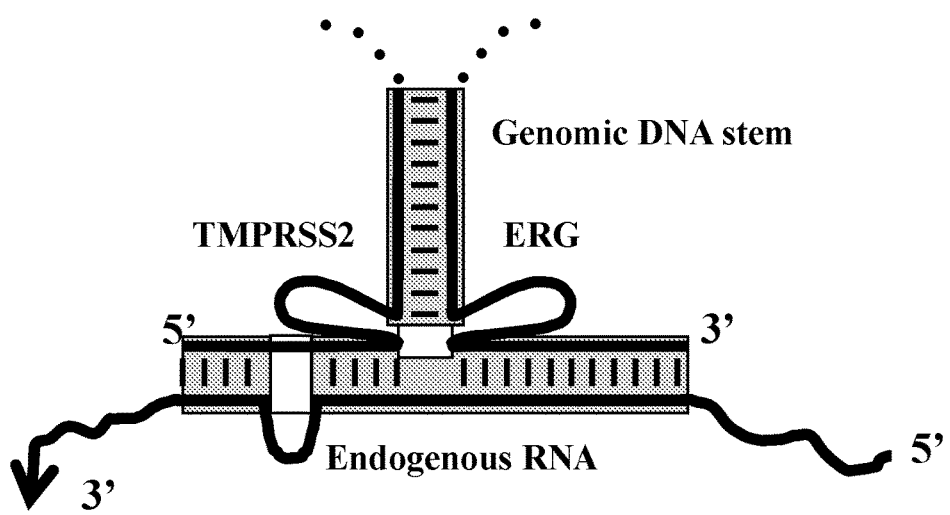
FIG. 36 demonstrates an endogenous initiator chimeric RNA wherein the endogenous RNA can have a non-perfect match adfacent to the point of fusion.
Figure 37:
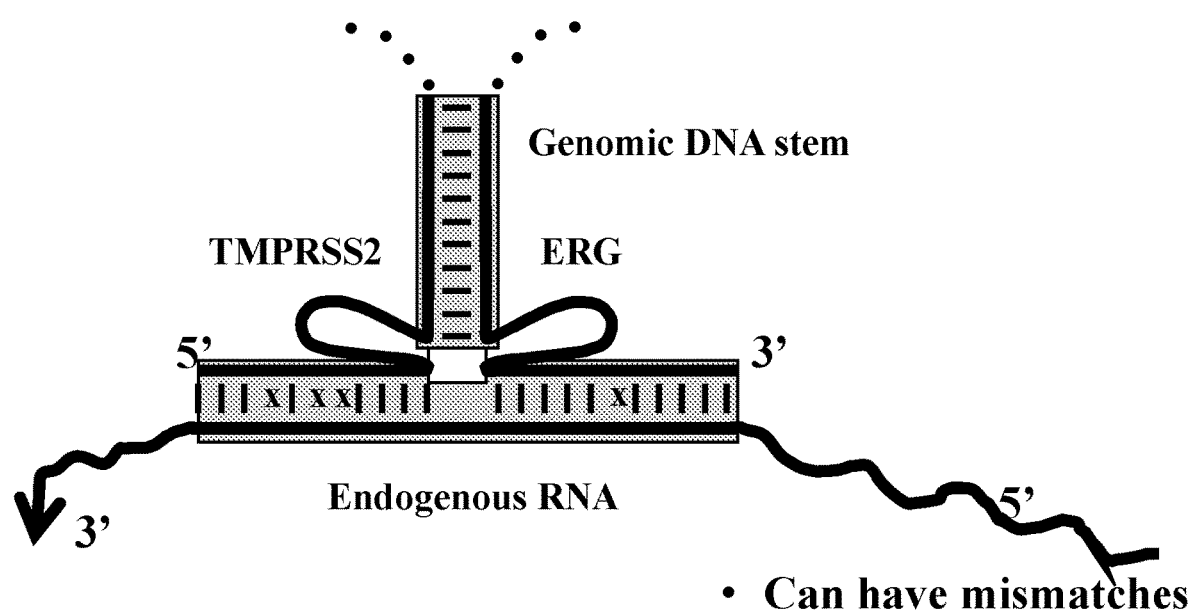
FIG. 37 shows an endogenous initiator chimeric RNA having mismatches with the genes to be fused.
Figure 38:
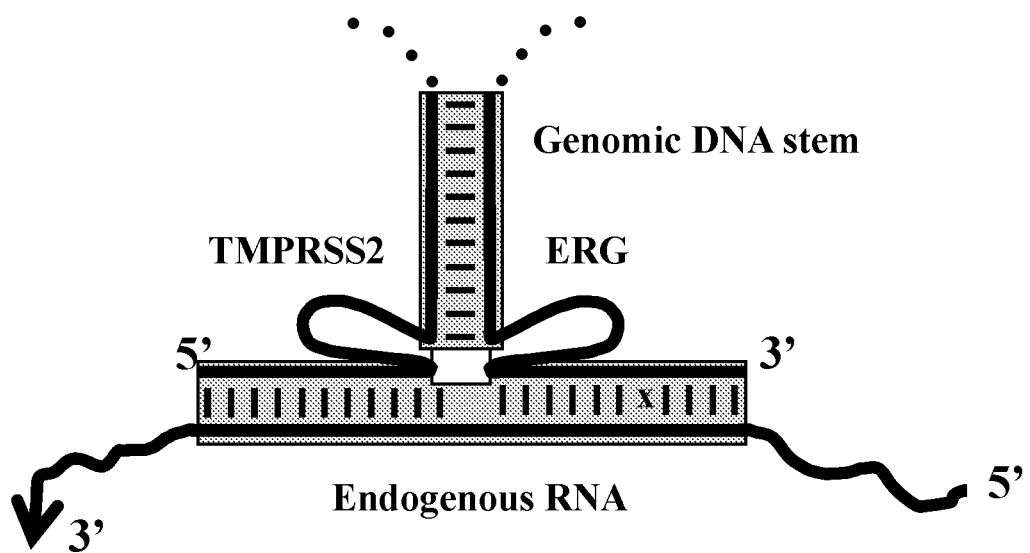
FIG. 38 demonstrates an endogenous initiator chimeric RNA that is formed by trans-splicing of two different parental endogenous RNAs.

The sequence of endogenous or exogenously provided chimeric RNA need not be identical or 100% match to that of the parental genes for induction of fusion. For example, where FIG. 33 and FIG. 34 illustrate examples where a man-made chimeric RNA and an endogenous initiator chimeric RNA, respectively have a perfect match to the genes to be fused, there are examples where the match may or may not be perfect (FIGS. 35-38).

In specific embodiments, the chimeric RNA is designed such that upon generation of a three-way junction with a genomic DNA as the stem, the genomic DNA may comprise SINE or LINE sequence, or the chimeric RNA may be designed to exclude SINE or LINE sequence. In particular cases, the design of the chimeric RNA is such that the genomic DNA stem comprises SINE or LINE and the length of such elements (for example, 200-300 bp) provides stability to the stem of the junction.

Delivery of the chimeric RNA to cells of interest (whether cell lines or other cells) may be by any suitable method, including in a vector or without a vector. In cases wherein the chimeric RNA is delivered without a vector, the delivery may comprise electroporation. In cases wherein the RNA is delivered with or in a vector, the delivery may be via viral vectors or non-viral vectors. Examples of viral vectors include adenoviral-associated, lentiviral, adenoviral, or retroviral, and examples of non-viral vectors include plasmids, nanoparticles, liposomes, and so forth.

III. Methods of Detecting and Targeting Endogenous Chimeric RNAs

Endogenous chimeric RNAs, as opposed to synthetically produced, man-made chimeric RNAs for other embodiments of the disclosure, may be a component of methods for detecting and targeting. The detecting and targeting methods may be related to clinical aspects of the disclosure, including diagnosis, treatment, and monitoring of therapy, for example.

A. Detecting Endogenous Chimeric RNAs

Embodiments of the disclosure include diagnostic, prognostic, preventive, and therapeutic strategies relating to endogenous chimeric RNAs present in vivo. In particular embodiments, prior to the occurrence of a disease-causing fusion gene, the presence of an endogenous chimeric RNA that is directed to two different genomic regions in a cell is a clinical marker that the cell is cancerous or is at elevated risk for becoming cancerous. The cancer may be of any kind, including any solid tumor or blood cancers.

Identification of an endogenous chimeric RNA, prior to the occurance of a disease-causing fusion gene, in one or more cells from a tissue from an individual may indicate that the cell(s) (and by extrapolation, the tissue) is cancerous or at risk for becoming cancerous. Therefore, the present disclosure encompasses methods of identifying endogenous chimeric RNAs from samples from individuals for the purpose of diagnosing cancer or determining a risk for cancer for the individual. In particular embodiments, the chimeric RNA corresponds to a certain cancer fusion gene, and many cancer fusion genes are known in the art (see, for example, the TCGA Fusion Gene Database and ChimerDB 3.0 database on the world wide web). Therefore, in particular embodiments, from samples from an individual suspected of having cancer or at risk for cancer, the presence of one or more particular chimeric RNAs are searched for based on known sequences of known cancer fusion genes.

For example, the sequence of the chimeric RNA may be predicted based on the known sequences of cancer fusion genes, and the methods of identifying whether or not there are chimeric RNAs in a sample utilize such sequences. For example, a method of identifying the presence of chimeric RNAs in a sample may be based on identifying the nucleic acid sequence of an endogenous chimeric RNA based on known cancer fusion genes that are associated with the cells and tissue of interest. For example, an endogenous chimeric RNA may have antisense sequences that are corresponding to the intronic or exonic genomic regions of actively transcribing genes. For example, an endogenous chimeric RNA may have sense or antisense sequences that are corresponding to the intronic or exonic genomic regions of the untranscribed genes. For example, the sequence of an endogenous chimeric RNA may be fully complementary or partially complementarity to the sequence of genes of interest. or comprises sequence that is partially complimentary to that of the parental genes.

An example of such a method includes reverse transcriptase-polymerase chain reaction (RT-PCR), Northern RNA gel analysis, and microarray chips designed for detecting endogenous chimeric RNAs. In such cases for RT-PCR as an example, primers for the PCR may be designed to determine the presence of the chimeric RNA based on the sequence of the cancer gene fusion. For example, the sequence of the chimeric RNA may be determined based on sequence from the cancer gene fusion and in specific cases may include the fusion point between the two genes of the cancer gene fusion.

The endogenous chimeric RNAs may be considered to be initiatory RNAs to induce gene fusion. In some cases, their presence in cells from a sample indicates that gene fusion to produce cancer fusion gene(s) may or may not have already occurred or will occur.

A particular type of cancer may have multiple cancer gene fusions, and one or more chimeric RNAs directed to one or more of the multiple cancer gene fusions may be assayed for in a sample.

In some embodiments, the presence of one or more endogenous chimeric RNAs may be assayed for as a means to monitor therapy for a medical condition, such as cancer or another medical condition. The monitoring of therapy may include analysis of samples for one or more endogenous chimeric RNAs before and after at least one round of therapy for the individual. In some cases, analysis of a sample for endogenous chimeric RNAs occurs after a therapy but not before. When a treatment is effective, there is a detectable reduction in the amount of chimeric RNAs following the treatment.

In alternative embodiments, the presence of one or more endogenous chimeric RNAs is an indicator of presence or risk for a medical condition other than cancer, such as heart disease, neurodegenerative disease, or diabetes.

Following identification of endogenous chimeric RNAs, an individual may be given one or more treatments because of the chimeric RNA presence. The treatment may or may not be directed against the chimeric RNA itself. In cases wherein a cancer treatment does not directly target the endogenous chimeric RNA, the treatment may include chemotherapy, immunotherapy, radiation, hormone therapy, surgery, or a combination thereof, as examples.

Samples from which the presence or absence of endogenous chimeric RNA is analyzed generally comprise one or more cells. The samples may be of any kind, including blood, urine, biopsy, hair, sputum, semen, saliva, cheek scrapings, cerebrospinal fluid, nipple aspirate, gastric fluid, Pap smears, or a combination thereof.

B. Targeting Endogenous Chimeric RNAs

In particular embodiments of the disclosure, there are methods of targeting endogenous chimeric RNAs to treat a medical condition associated with the presence of the chimeric RNAs. In specific embodiments, the targeting methods neutralize the disease-causing endogenous chimeric RNA. Thus, the chimeric RNA may be a therapeutic target for treatment methods and may be targeted with a structural and/or functional inhibitor of the chimeric RNA. In specific embodiments, an agent that directly binds the chimeric RNA is utilized, such as a siRNA or other RNA interference molecule or antisense oligo DNA. In specific embodiments, an agent that indirectly inhibits the chimeric RNA is utilized, such as a compound that methylates the promotor that drives the expression of endogeneous chimeric RNA.

Knowing the sequence of an endogenous chimeric RNA, one can develop siRNA to target the chimeric RNA as a therapy. In particular embodiments, the siRNA is delivered via a vector that expresses the siRNA, such as a viral vector or non-viral vector (such as a plasmid). Viral vectors include lentiviral, retroviral, adenoviral, or adeno-associated viral vectors. Promoters suitable for effective expression of the siRNA are known in the art. The siRNA may be provided to the individual locally or systemically.

In some cases, an individual is given an effective amount of an inhibitor of endogenous chimeric RNAs associated with cancer or other deleterious gene fusions when the individual has not been proven to have the presence of the cancer. That is, a medical practitioner finding cancer in an individual can presume that chimeric RNAs are present and provide an effective amount of one or more agents that inhibit the chimeric RNA.

A particular type of cancer may have multiple cancer gene fusions, and one or more agents directed to one or more endogenous chimeric RNAs may be utilized for a particular therapy.

EXAMPLES

The following examples are presented in order to more fully illustrate the preferred embodiments of the invention. They should in no way, however, be construed as limiting the broad scope of the invention.

Example 1

RNA-Mediated Gene Fusion in Mammalian Cells

One of the hallmarks of cancer is the formation of oncogenic fusion genes as a result of chromosomal translocations. Fusion genes are presumed to occur prior to fusion RNA expression. However, studies have reported the presence of fusion RNAs in individuals who were negative for chromosomal translocations. These observations give rise to "the cart before the horse" hypothesis, in which fusion RNA precedes the fusion gene and guides the genomic rearrangements that ultimately result in gene fusions. Yet RNA-mediated genomic rearrangement in mammalian cells has never been demonstrated. Here the inventors provide evidence that expression of a chimeric RNA drives formation of a specified gene fusion via genomic rearrangement in mammalian cells. The process is (1) specified by the sequence of chimeric RNA involved, (2) facilitated by physiological hormone levels, (3) permissible regardless of intra-chromosomal (TMPRSS2-ERG) or inter-chromosomal (TMPRSS2-ETV1) fusion, and (4) can occur in normal cells prior to malignant transformation. It is demonstrated that in at least some cases, contrary to "the cart before the horse" model, it is the antisense rather than sense chimeric RNAs that effectively drive gene fusion, and that this disparity can be explained by transcriptional conflict. Furthermore, an endogenous RNA AZI1 is identified that acts as the 'initiator' RNA to induce TMPRSS2-ERG fusion. RNA-driven gene fusion demonstrated in this disclosure provides important insight in early disease mechanism, and allows for applications in the biology of mammalian genome stability, as well as gene editing technology via mechanisms native to mammalian cells.

Example 2

RNA-Mediated Gene Fusion in Mammalian Cells

To test whether the expression of a fusion RNA in mammalian cells can lead to a specific gene fusion, the TMPRSS2-ERG fusion (Perner et al., 2006; Tomlins et al., 2005), found in ~50% of prostate cancers, was selected as a model. Both the TMPRSS2 and ERG genes are located on chromosome 21, an intra-chromosomal configuration prone to rearrangements. To recapitulate TMPRSS2-ERG fusion gene formation, the LNCaP prostate cancer cell line that lacks the TMPRSS2-ERG fusion (Horoszewicz et al., 1980; Tomlins et al., 2005) was used. Furthermore, treating LNCaP cells with androgen increases the chromosomal proximity between the TMPRSS2 and ERG genes (Bastus et al., 2010; Lin et al., 2009; Mani et al., 2009), which was thought to increase the possibility of gene fusion. To test "the cart before the horse" hypothesis (Rowley and Blumenthal, 2008; Zaphiropoulos, 2011), a short fusion RNA was transiently expressed consisting of two exons, TMPRSS2 exon-1 joined to ERG exon-4, which is a short fragment of a full-length TMPRSS2-ERG fusion RNA that is most common in prostate cancer (FIG. 1A, upper panel). This short fusion RNA mirrors the presumptive trans-spliced fusion RNA product that is generated only in the sense orientation because the correct splice sites are absent in the antisense orientation. However, because the 'antisense' sequence should, in theory, contain the same template information for guiding genomic rearrangements, both the sense and antisense short fusion RNA were tested. Each was individually expressed using either a CMV or a U6 promoter (FIG. 1A, upper panel) and designated as 'input RNA' to distinguish them from the 'endogenous' full-length fusion RNA transcribed from the genome.

Figure 9A:
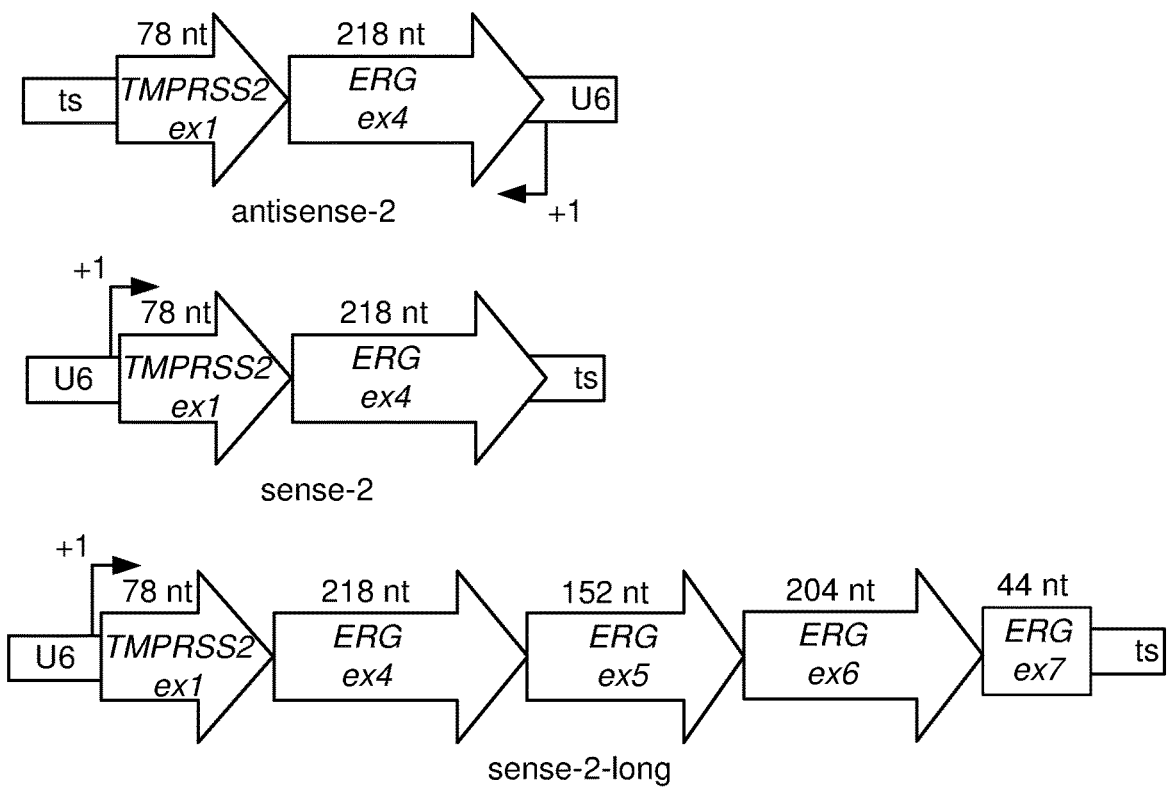
FIGS. 9A-9B. Sense input RNAs that mimic trans-spliced products failed to induce fusion transcripts.
Figure 9B:
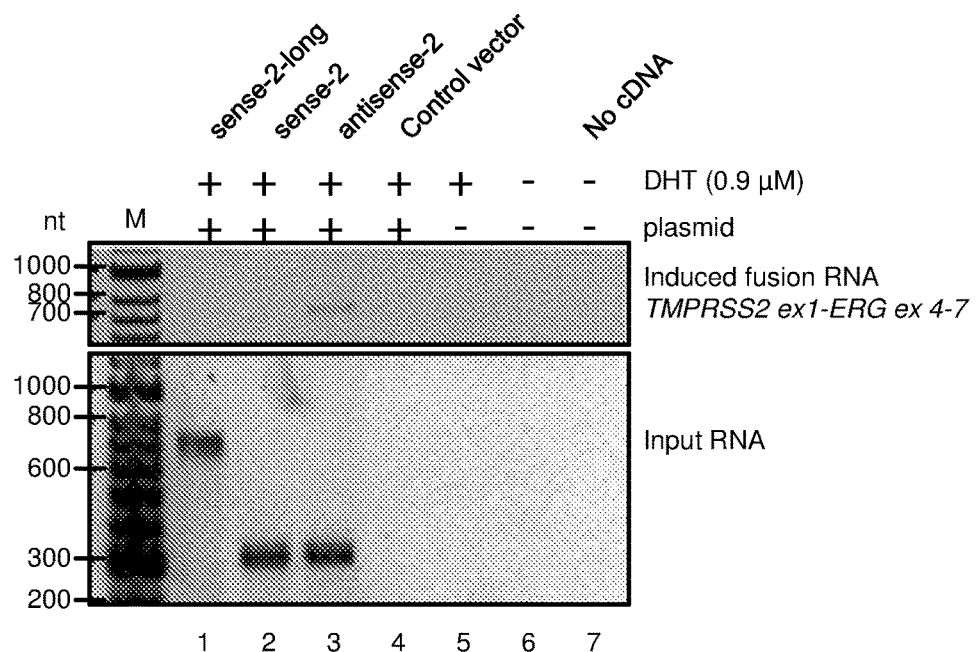

LNCaP cells were transiently transfected with either plasmid and treated the cells with dihydrotestosterone (DHT, a metabolite of testosterone) for 3 days. If the expression of an input RNA leads to a TMPRSS2-ERG gene fusion, it is expected that the endogenous full-length fusion RNAs would be transcribed from the newly induced fusion gene. Specific RT-PCR assays were designed to distinguish between endogenous full-length fusion RNAs and the input RNAs exogenously expressed from the plasmids (see FIG. 8A for primer designs). As shown in FIG. 1A, expression of the sense short fusion RNA resembling the trans-spliced product, either by the CMV or U6 promoter (FIG. 1A lower panel, lane 1 and 2 respectively), led to no detection of an induced endogenous fusion transcript. Expression of a longer version of sense fusion RNA consisting of four exons (TMPRSS2 exon-1 joined to ERG exon-4/5/6) also failed to induce the endogenous fusion transcript (FIGS. 9A-9B). In contrast, expression of antisense short fusion RNAs induced a clear band of 721 bp (FIG. 1A lower panel, lane 3 and 4). Sanger sequencing revealed that the induced band contains TMPRSS2 exon-1 fused to ERG exons-4/5/6/7, and that the exons are joined by annotated splice sites, which would be expected of mature endogenous fusion mRNA derived from the TMPRSS2-ERG fusion gene. This induced fusion transcripts cannot possibly arise from the sequence of input RNAs as the expression plasmids used contain only TMPRSS2 exon-1 and ERG exon-4 without the ERG exon-5/6/7 sequence. Notably, the induction was more pronounced when the antisense input RNA was driven by the U6 promoter (FIG. 1A lower panel, antisense-2, lane 4) compared to the CMV promoter (antisense-1, lane 3). These differences (antisense vs. sense, U6 vs. CMV) are not caused by differing amounts of input RNA because all input RNAs were expressed at relatively equal levels (FIG. 1A, lower panel). Transfection with a parental plasmid containing mCherry sequence (FIG. 1A, lane 5), DHT treatment without plasmid transfection (FIG. 1A, lane 6), and PCR reaction without cDNA served as RT-PCR controls (FIG. 1A, lane 8), all resulted in no endogenous fusion transcript. In addition, all experiments were performed independently at least four times and results were identical. Together, the data suggest that expression of an input RNA with chimeric sequence can lead to the induction of a specified endogenous fusion transcript in human cells. Surprisingly, the antisense, rather than the sense version of input RNA, exhibits the capacity of induction.

Figure 10:
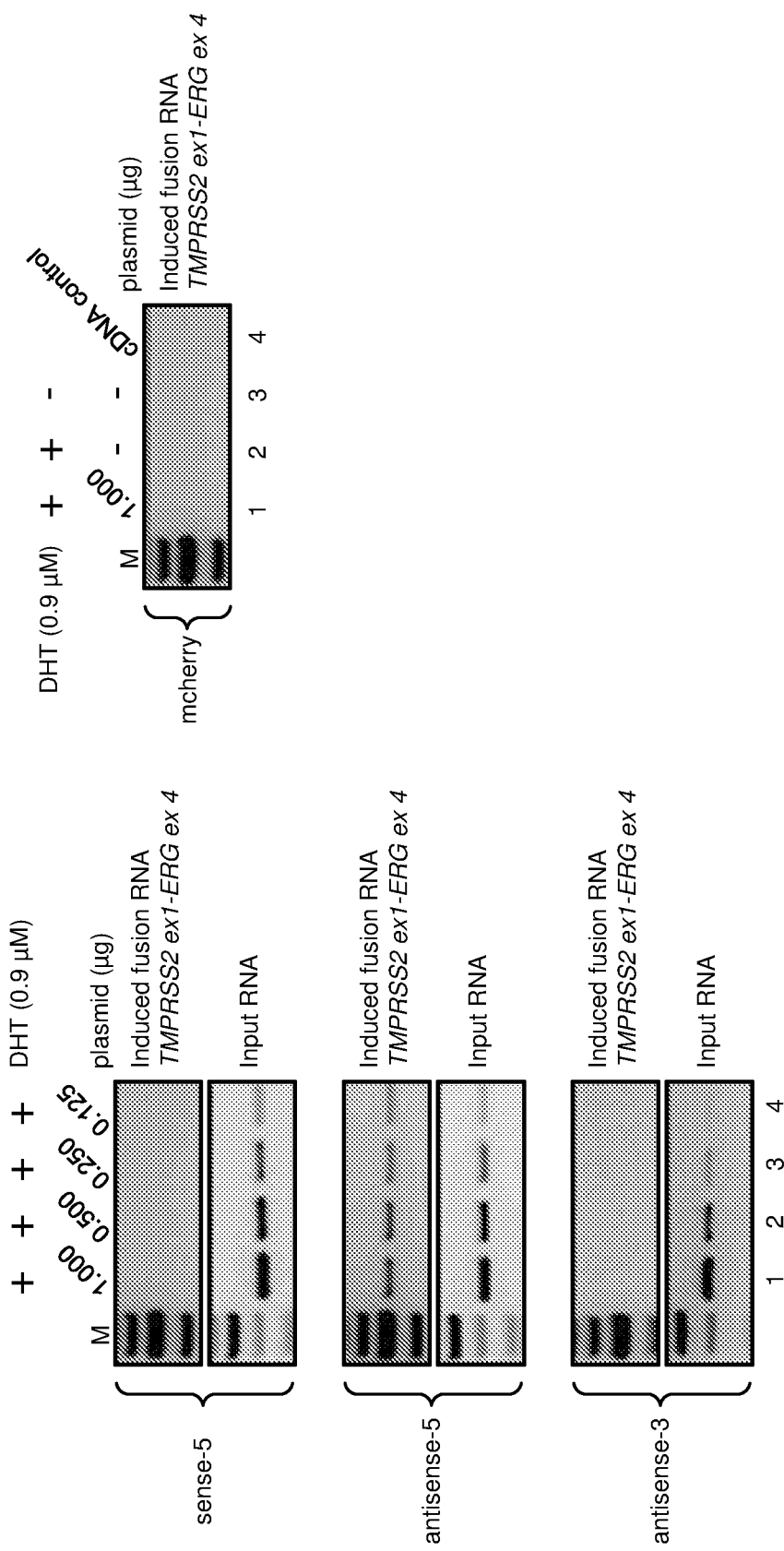
FIG. 10. Antisense-5 but not its corresponding sense-5 induces TMPRSS2-ERG gene-fusion. Different amount of plasmids (1.000 µg, 0.500 µg, 0.250 µg and 0.125 µg) expressing either sense-5 or antisense-5 were transfected to produce different amount of corresponding input RNAs in LNCaP cells. To maintain transfection efficiency, mCherry control plasmid was added to each transfection to make the final amount of plasmid to 1.0 µg. Induction was done for three days in the presence of 0.9 µM DHT. RT-PCR was performed to detect the levels of both induced TMPRSS2-ERG transcript and input RNA. RT-PCR results shows that even very low amount of antisense-5 input RNA is sufficient to induce TMPRSS2-ERG gene fusion (middle panel, lane 4) whereas very high level of sense-5 input RNA fails to induce TMPRSS2-ERG gene fusion (upper panel, lane 1). Thus, it is not the amount of the input RNA but the orientation of the input RNA (antisense vs. sense) that is important for fusion induction. Antisense-3, which is unable to induce fusion, was used as a negative control. mCherry alone was also transfected as a negative control. Additional controls (right panel): a vector expressing mCherry lacking input RNA sequence (lane 1), DHT treatment only (lane 2), and PCR reaction lacking cDNA (lane 4).
Figure 11A:
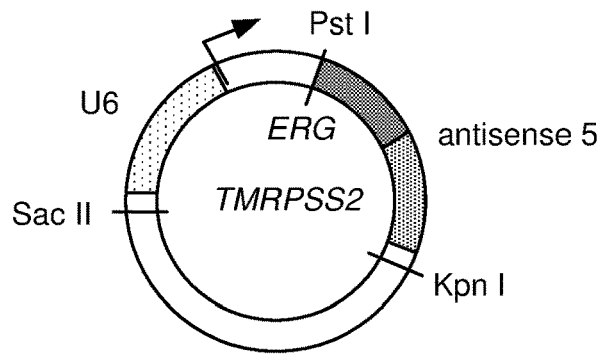
FIGS. 11A-11C. Expressed input RNA, but not the DNA plasmid, induces fusion transcript.
Figure 11B:
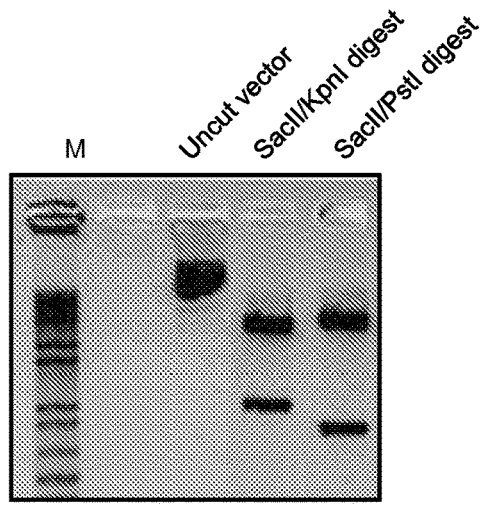
Figure 11C:
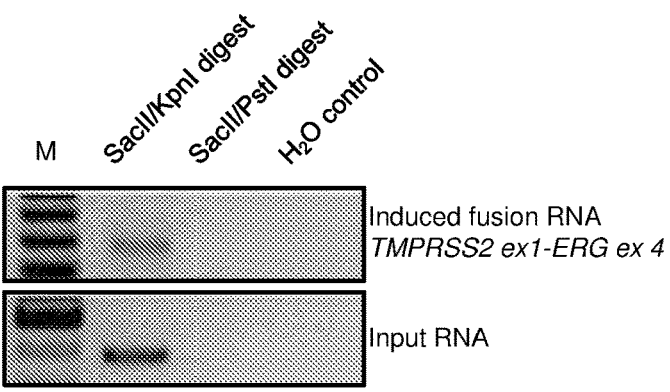

Antisense input RNAs described above contain 218 nt against the entire ERG exon-4 and 78 nt against the entire TMPRSS2 exon-1 (FIG. 1A), suggesting that 78 nt is sufficient to specify a parental gene for gene fusion. Furthermore, because the effective input RNAs are of the 'antisense' orientation, the data imply that the input RNAs may not require an RNA junction resembling that of the TMPRSS2-ERG fusion transcript generated by splicing in the sense orientation. To further analyze the sequence requirement, the U6 promoter was used to express a series of antisense input RNAs with 75 nt complementary to ERG exon-4 joined to various segments (33, 52, 67, 82 nt) that are complementary to TMPRSS2 near the exon-1/intron-1 boundary (FIG. 1B). A parallel set of sense input RNAs were also tested as controls (FIG. 1C). As shown in FIG. 1B (lower panel), all antisense RNAs, with the exception of antisense-3, induced fusion transcripts even though their target regions span the exon/intron boundary. The level of induction peaked for antisense-5, which contains 52 nt designed to anneal with TMPRSS2, suggesting that this number of nucleotides might be optimal to specify a parental gene for induction. The results were confirmed using a different, but more efficient, primer pair (FIG. 1B, lower panel; primer design in FIG. 8B) followed by Sanger sequencing of the induced band. In contrast to the antisense input RNA, all corresponding sense input RNAs failed to induce endogenous fusion transcripts (FIG. 1C, lower panel). This was true even when the sense input RNA was intentionally expressed at a much higher level than the antisense RNA (FIG. 10). Additional experiments using plasmids with a severed U6 promoter (FIGS. 11A-11C), to eliminate input RNA expression, also confirmed that it is the antisense input RNAs expressed from plasmids, not the DNA sequence of plasmids, that induce the observed TMPRSS2-ERG fusion transcripts.

Figure 1D:
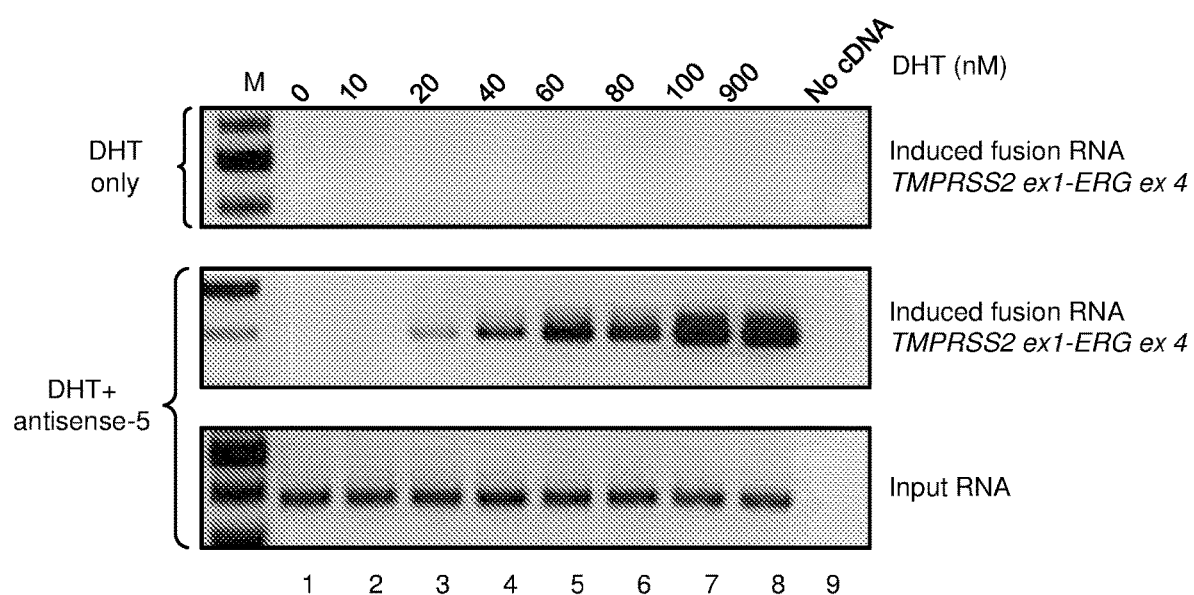
Figure 13:
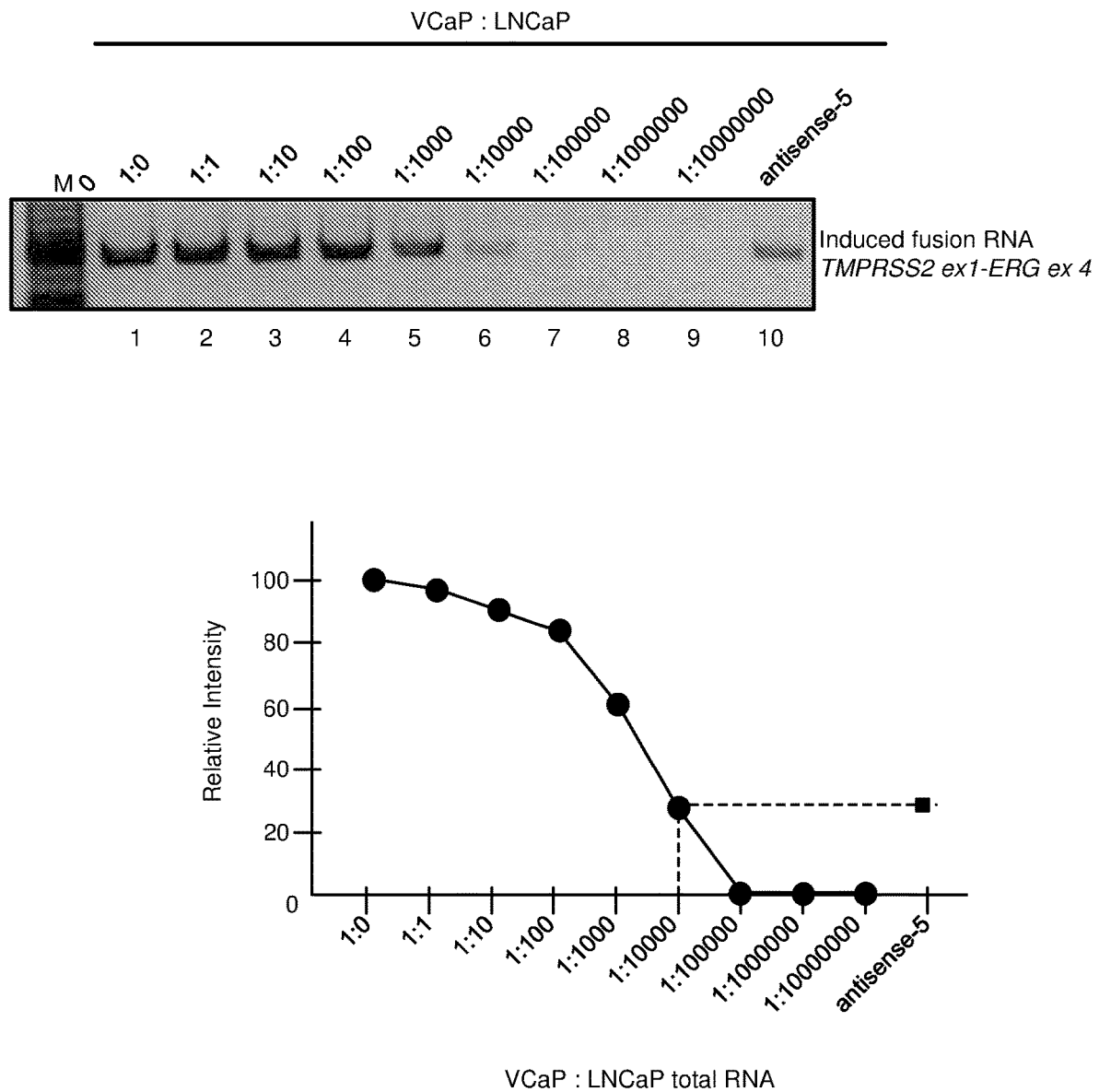
FIG. 13. Estimation of the percentage of LNCaP cells transfected with antisense-5 that carry the induced TMPRSS2-ERG fusion. To estimate the percentage of LNCaP cells that underwent TMPRSS2-ERG gene fusion mediated by antisense-5 at 0.9 µM DHT (the $EC_{50}$), we mixed various amounts of total RNA from VCaP cells that express TMPRSS2-ERG (Mertz et al., 2007; Teles Alves et al., 2013) with the total RNA from untransfected LNCaP cells in ratios of 1:1 up to 1:10⁷. A standard dilution curve was determined using the relative RT-PCR intensity of the TMPRSS2-ERG fusion transcript. The relative intensity of induction by antisense-5 in LNCaP cells, as assayed under the same RT-PCR conditions, is shown as a red dot that corresponds to an equivalent dilution of $1:10^3$ to $1:10^4$, suggesting that approximately 1 in $10^3$ or $10^4$ LNCaP cells is positive of TMPRSS2-ERG fusion.

As shown in FIG. 1D, the amount of endogenous fusion transcript induced by antisense-5 (the most effective antisense input RNA) appears to correlate with the concentration of DHT used, presumably because the hormone increases the chromosomal proximity between the TMPRSS2 and ERG genes (Bastus et al., 2010; Lin et al., 2009; Mani et al., 2009). Antisense-5 was effective at DHT concentrations as low as 20 nM as revealed by sensitive nested PCR (FIG. 1D lane 3), indicating that fusion events induced by input RNA can occur under physiologically relevant androgen conditions (Boyce et al., 2004). As a control, DHT treatment alone up to 2 µM failed to induce fusion (FIG. 12). Titration of DHT showed that the induction by antisense-5 reaches the 50% of maximal level ($EC_{50}$) at 0.9 µM DHT (FIG. 12). Under this standard $EC_{50}$ condition, we estimated that the percentage of LNCaP cells induced by antisense-5 to express the TMPRSS2-ERG fusion transcript is approximately 1 in $10^3$ or $10^4$ cells (see assay in FIG. 13). Together, these results demonstrated that the induction by input RNA can occur at physiologically relevant hormone levels, but does not represent a high frequency event.

Figure 1E:
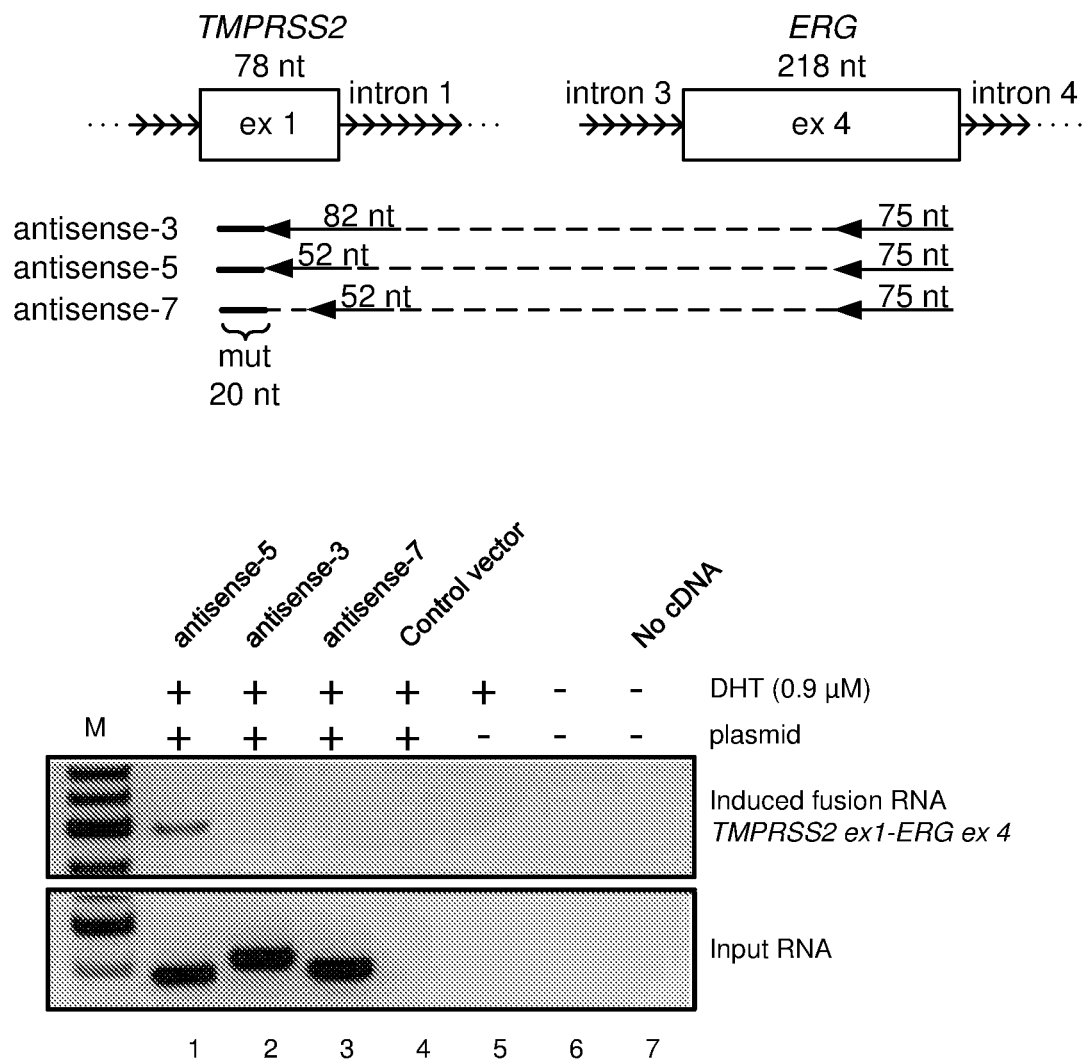
Figure 2A:
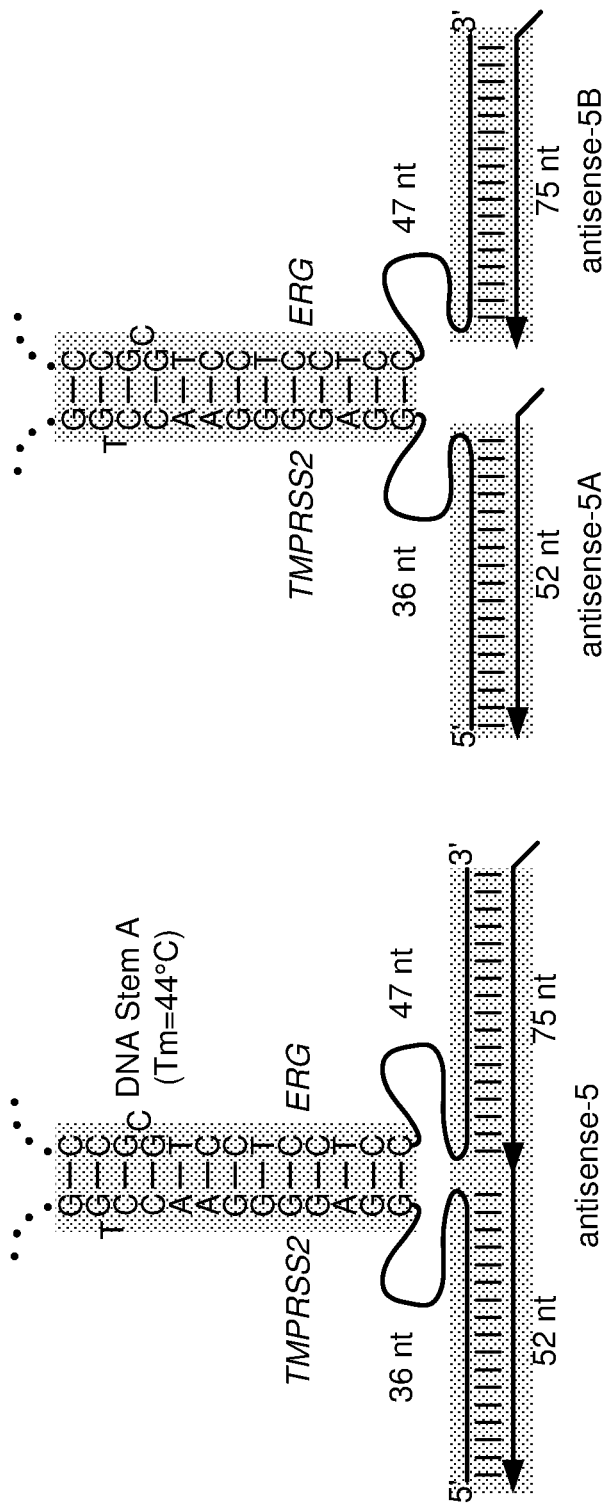
FIGS. 2A-2G. Formation of a three-way junction may facilitate fusion induction.
Figure 2B:
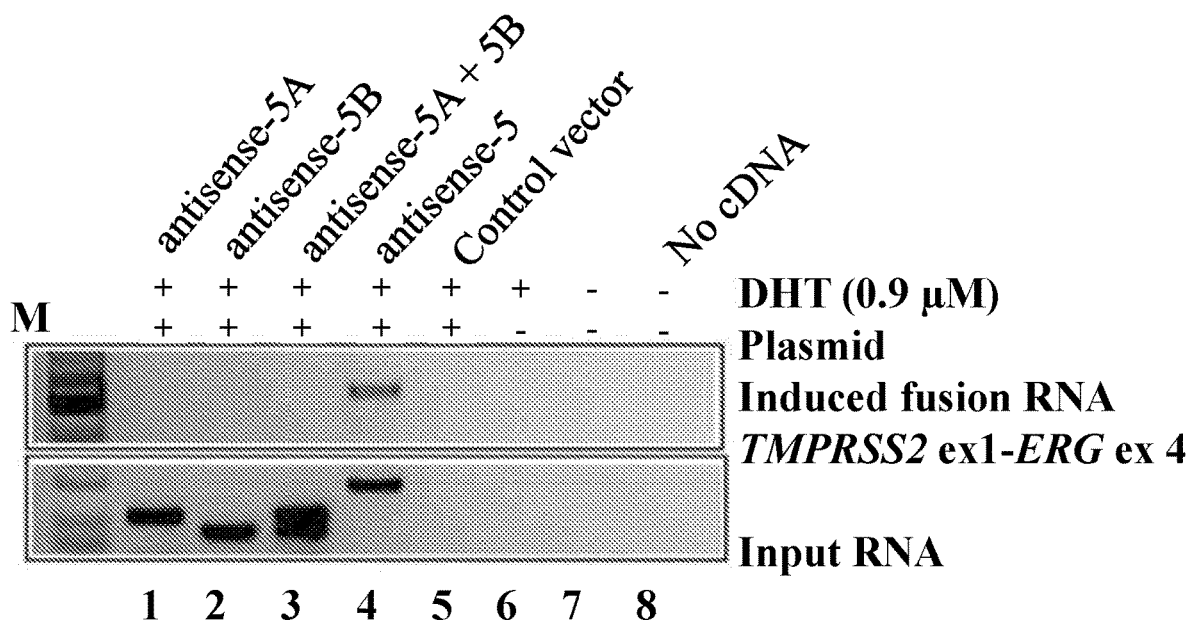

Although induced fusion is infrequent, all antisense RNAs described in FIG. 1B successfully induced endogenous fusion RNA except antisense-3, which is only 30 nt longer than antisense-5 in the arm targeting TMPRSS2 intron-1 (FIG. 1B, upper panel). To test whether its inability to induce was due to input RNA length or the specific target sequence in TMPRSS2 intron-1, we constructed a hybrid antisense (antisense-7) that shifted the 52 nt recognition window of antisense-5 to target the TMPRSS2 intron-1 region covered by antisense-3 (FIG. 1E). This alteration resulted in the loss of induction (FIG. 1E, lane 1 vs. 3), implying that the inability of antisense-3 to induce is not reflective of input RNA length. Rather its targeting arm may interfere with a motif important for the fusion process. BLAST alignment of the genomic DNA sequence revealed an imperfect stem (named stem A) potentially formed by the sense genomic TMPRSS2 sequence complementary to the sense genomic ERG sequence (FIG. 2A, left). It was considered that this genomic DNA stem (Tm=~44° C.) could potentially stabilize a three-way junction that involves an RNA/DNA duplex formed by the antisense-5 RNA and its targeted genomic DNA in a sequence-specific manner (FIG. 2A, left). If correct, then the formation of this putative three-way junction would be disrupted by antisense-3 because its recognition sequence invades the genomic DNA stem (FIG. 2A, left). Consistent with the idea that induction requires bringing TMPRSS2 and ERG gene in close proximity, expression of antisense-5 as two separate halves (FIG. 2A right panel, antisense-5A and -5B) severed the link between TMPRSS2 (52 nt) and ERG (75 nt) sequence within the input RNA, resulting in the loss of induction (FIG. 2B, lane 1 to 3).

Figure 2C:
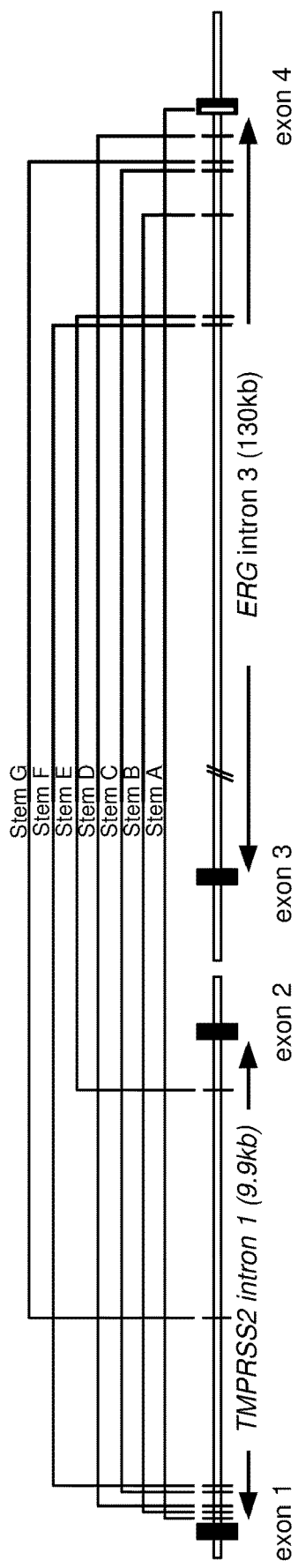
Figure 2D:
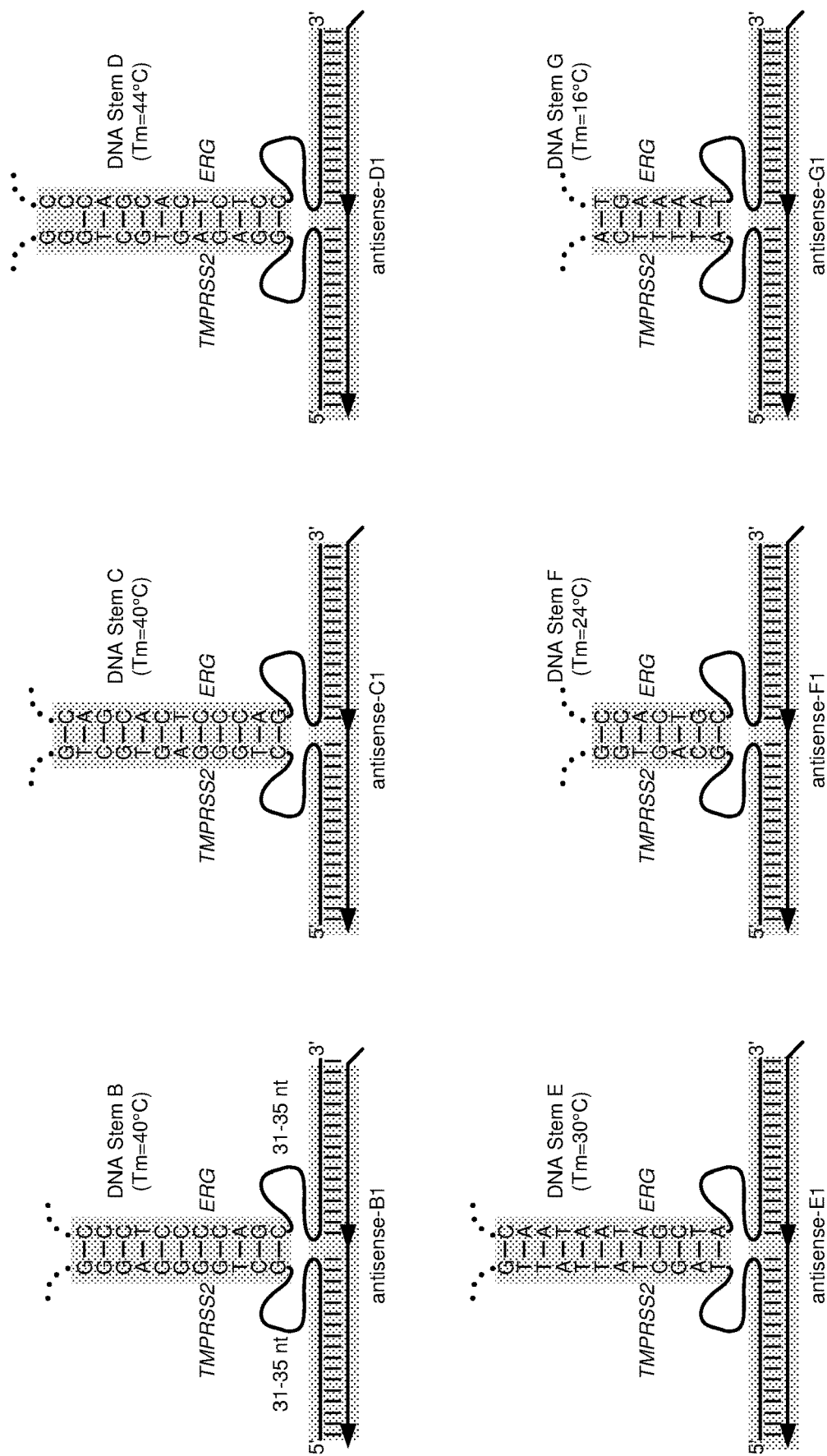
Figure 2E:
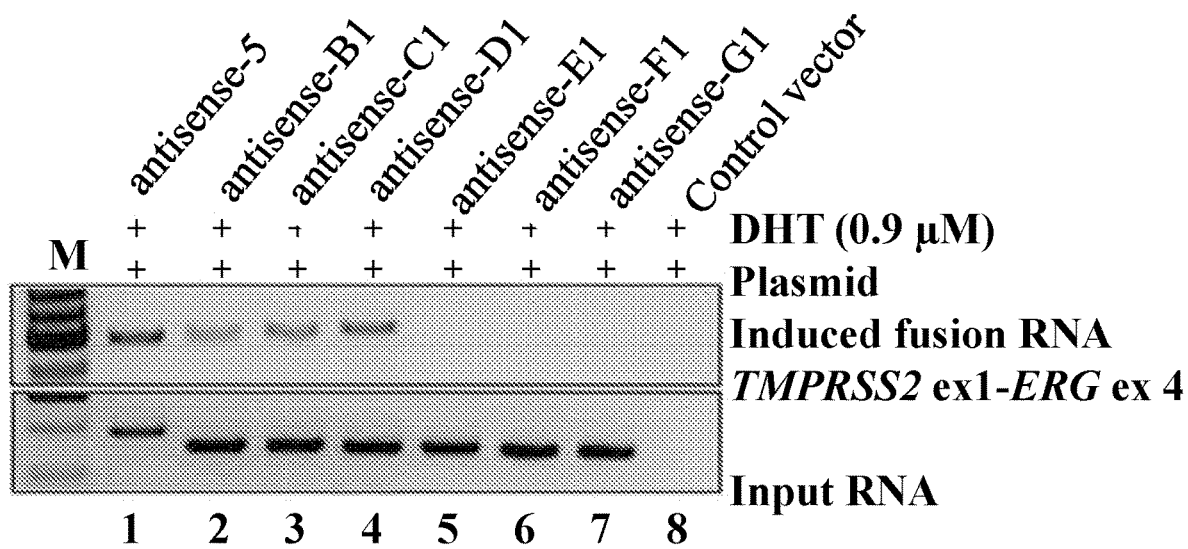
Figure 2F:
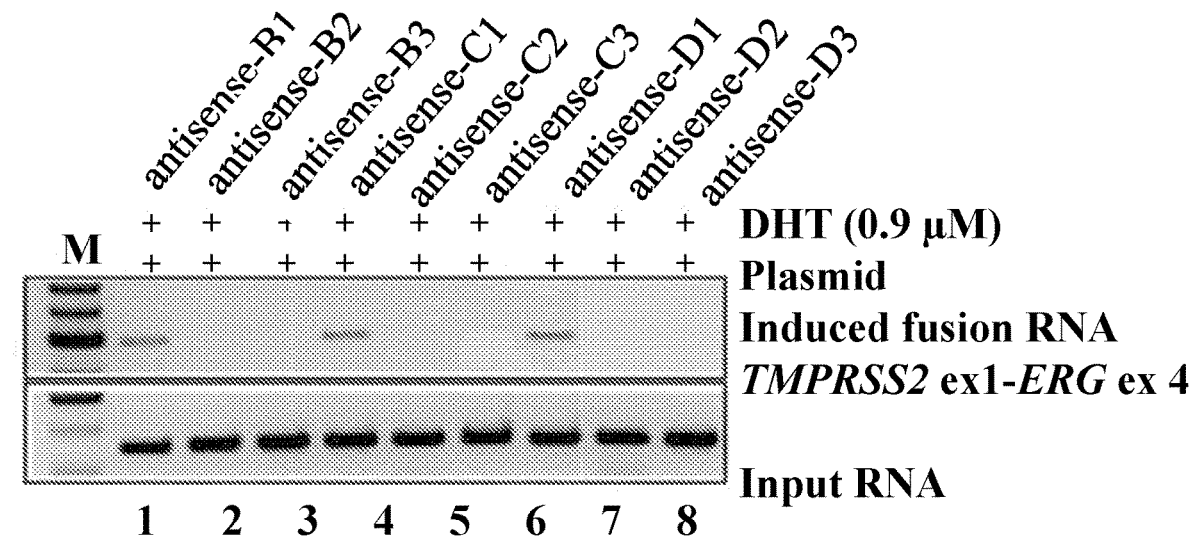
Figure 2G:
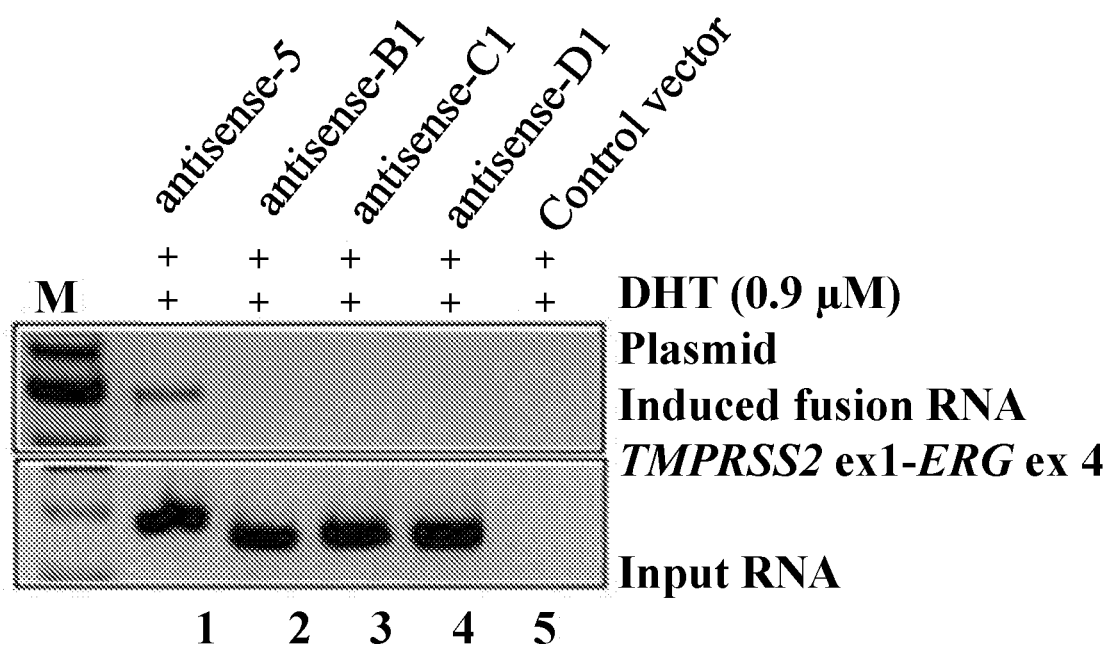
Figure 15:
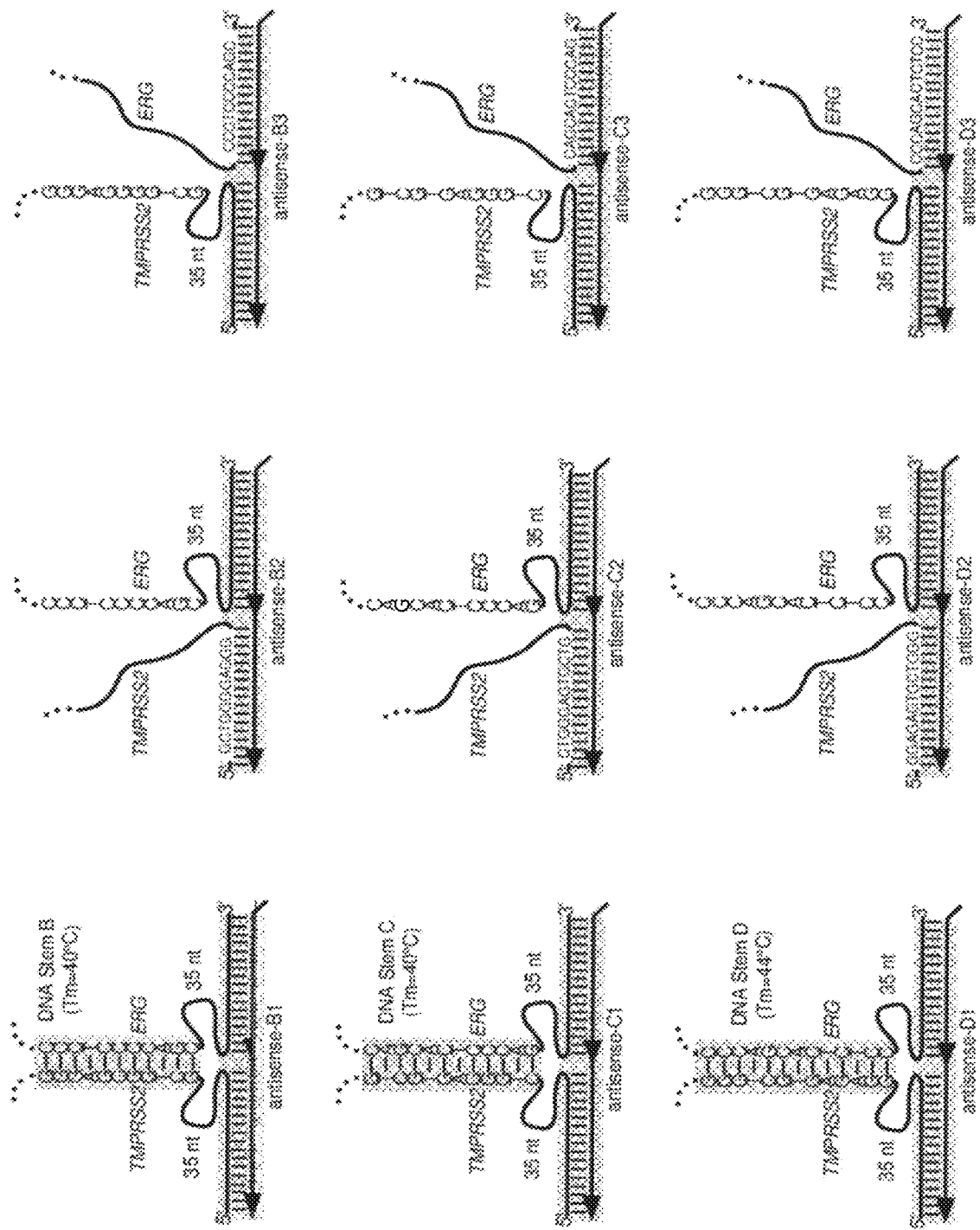
FIG. 15. Antisense input RNAs designed to disrupt the genomic stems B, C, and D. Stem B (upper row). Stem C (middle row). Stem D (lower row). Left column: Illustrations show the three-way junction formed by genomic DNA and corresponding antisense input RNA (antisense-B1, C1, and D1). Middle column: Disruption of stems via the TMPRSS2 side using tailor-made input RNAs (antisense-B2, C2, and D2) that directly hybridize to the TMPRSS2 stem sequence. Right column: Disruption of stems via the ERG side using tailor-made input RNAs (antisense-B3, C3, and D3) that directly hybridize to the ERG stem sequence. Shaded regions indicate base pairing. The TMPRSS2 portion of the input RNA and the ERG portion are labeled.
Figure 16A:
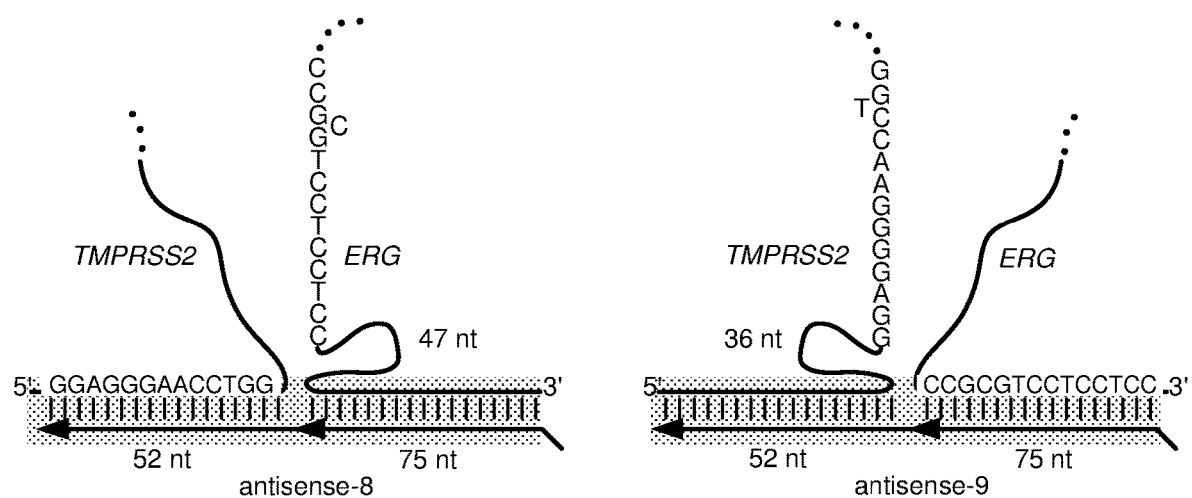
FIGS. 16A-16B. Antisense input RNAs designed to disrupt the genomic stems A.
Figure 16B:
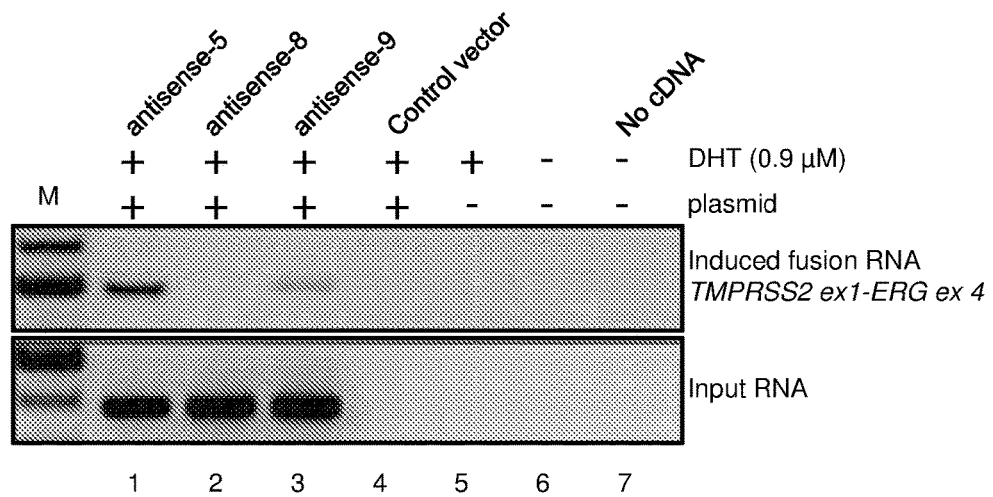
Figure 17A:
FIGS. 17A-17D. Endogenous ERG mRNA is not detected in LNCaP cells by three-rounds of nested RT-PCR.
Figure 17B:
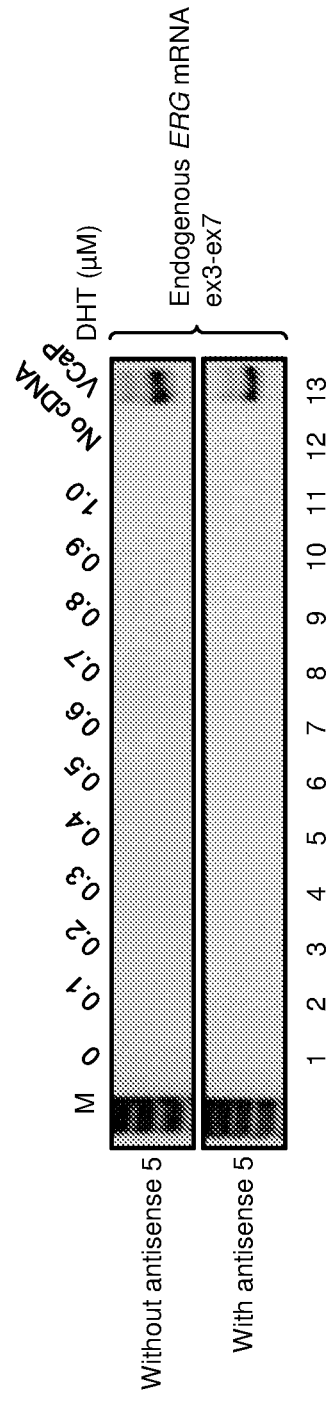
Figure 17C:
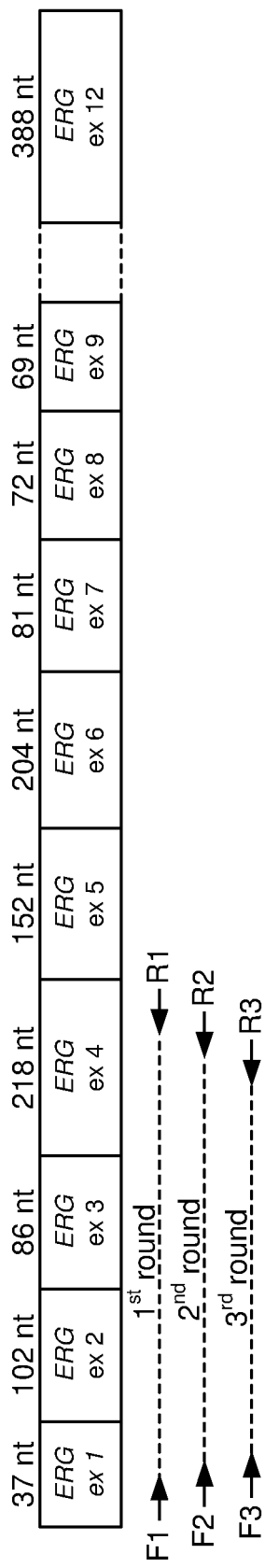
Figure 17D:
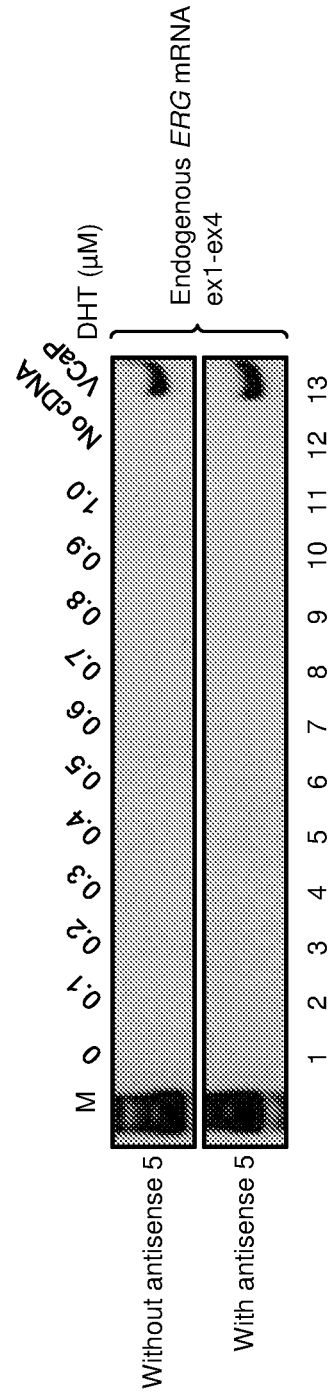

To test whether the proposed three-way junction formation could facilitate induction, BLAST alignment was used to identify several intron locations where genomic DNA stems could be formed by the sense genomic TMPRSS2 sequence paired with the sense genomic ERG sequence (stems B to G in FIGS. 2C and 2D; sequences flanking the stems in FIG. 14). Matching antisense input RNAs (termed antisense-B1 to G1) were then designed to facilitate the formation of a three-way junction with the possible intron stems (FIG. 2D) that would mirror the three-way junction formed by antisense-5 on stem A as postulated in FIG. 2A. Because these input RNAs target the introns (FIG. 2C) and contain no exon sequence, any observed induction of endogenous fusion transcripts composed of exons cannot arise from the sequence of input RNAs or plasmids used to express them. As shown in FIG. 2E, targeting genomic DNA stem B, C, and D that exhibit higher DNA stem stability (Tm=40° C., 40° C., and 44° C., respectively) by the corresponding antisense input RNAs clearly induced fusion transcripts (FIG. 2E, lanes 2 to 4). In contrast, targeting less a stable stem E, F, and G (Tm=30° C., 24° C., and 16° C., respectively) failed to induce fusion transcripts (FIG. 2E, lanes 5 to 7). To disrupt the three-way junction involving stem B, C, and D, six additional antisense RNAs (antisense-B2, B3, C2, C3, D2, and D3) were designed with one side of their recognition sequence altered to invade each of the respective genomic DNA stems on the TMPRSS2 side or the ERG side (FIG. 15). These modifications were chosen to mirror the interference on stem A by antisense-3. Similar antisense RNAs were also designed to invade stem A (FIGS. 16A-16B). In all cases, invasion of the genomic DNA stems by the modified input RNAs resulted in the complete loss of induction (FIG. 2F). While these results by no means necessitate that a three-way junction is required for fusion transcript induction, they nevertheless suggest that such transiently stabilized structures may 'facilitate' the process and could have important implications in developing gene editing technologies via mechanisms native to mammalian cells. Consistent with earlier observations, the corresponding sense version of the effective antisense input RNAs (sense-B1, C1, D1) all failed to induce fusion transcripts (FIG. 2G, lanes 2 to 4).

Figure 3A:
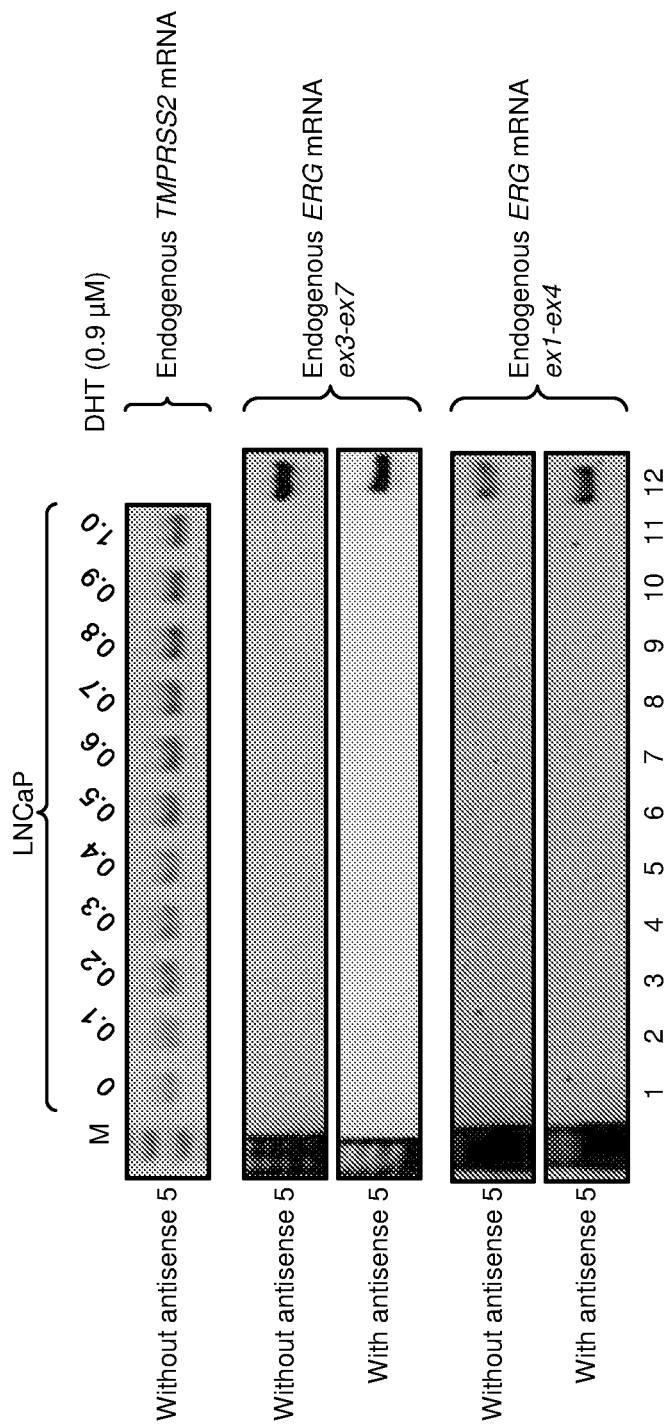
FIGS. 3A-3F. Induced TMPRSS2-ERG fusion is the result of genomic rearrangements FIG. 3A. Upper: RT-PCR shows that LNCaP cells express TMPRSS2 mRNA, and that the expression is upregulated by DHT. Primers used are specific to TMPRSS2 exon-2 and exon-4. Middle and lower: ERG mRNA however was not detected in LNCaP cells under a wide range of DHT in the presence or absence of antisense-5 (lanes 1 to 11). Assays were performed using two independent primer pairs, one specific to exon-3 and -7 (middle panel), the other to exon-1 and -4 (lower panel), both capable of detecting ERG mRNA in VCaP cells (lane 12). These primer pairs were chosen because they selectively amplified endogenous ERG mRNA but not the induced TMPRSS2-ERG fusion transcript which has ERG exon-3 to exon-12.

The fact that antisense input RNAs, but not their sense counterparts, induce fusion transcripts, raises the possibility that the former act as a docking station to mediate trans-splicing between endogenous sense TMPRSS2 and ERG pre-mRNAs. Because that the antisense, but not the sense input RNAs, are complimentary to both sense TMPRSS2 and ERG pre-mRNAs, they can base-pare with both parental pre-mRNAs, thus resulting in spliced fusion transcripts without the requirement of genomic rearrangement. This mechanism, however, is unlikely as the major contributor to the observed induction for the following reasons. First, although TMPRSS2 is expressed in LNCaP cells (FIG. 3A, upper panel), endogenous ERG mRNA is not detected in LNCaP cells (Tomlins et al., 2005) in the presence or absence of DHT or before and after transfection of antisense-5 (FIG. 3A, middle and lower panel with different primer pairs). In fact, parental ERG mRNA was not detected even using three rounds of nested RT-PCR using various primer sets (FIGS. 17A-17D). Therefore prior to and during induction, no or an insufficient number of parental ERG mRNAs are available in LNCaP cells as raw material for trans-splicing to account for the level of induced fusion transcript. Second, after initial transient transfection and DHT treatment for 3 days, we continued to propagate and enrich the induced LNCaP population for 52 days in the absence of DHT (experimental procedures described in FIG. 18). As shown in the lower panel of FIG. 3B, antisense-5 RNA transiently expressed by plasmids was degraded and completely absent beyond day 17. In contrast, the induced fusion transcript was continuously expressed and enriched up to day 52 in the absence of antisense input RNA and DHT (FIG. 3B upper panel), indicating the persistent nature of the induced fusion product. Taken together, these results strongly suggest that the induced expression of the TMPRSS2-ERG fusion transcript is the consequence of gene fusion at the DNA level, which has a permanent nature. This is in contrast to the result of induced trans-splicing at the RNA level mediated by antisense input RNA, which is transient and requires the continuous presence of input RNAs.

Figure 3B:
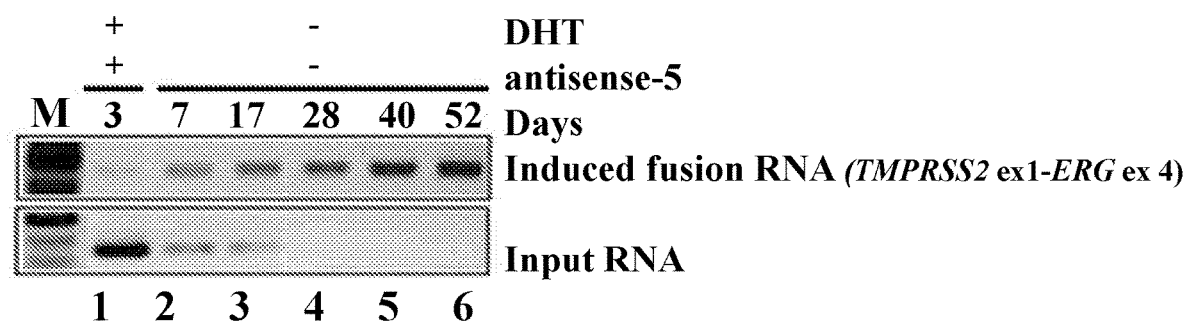
Figure 3C:
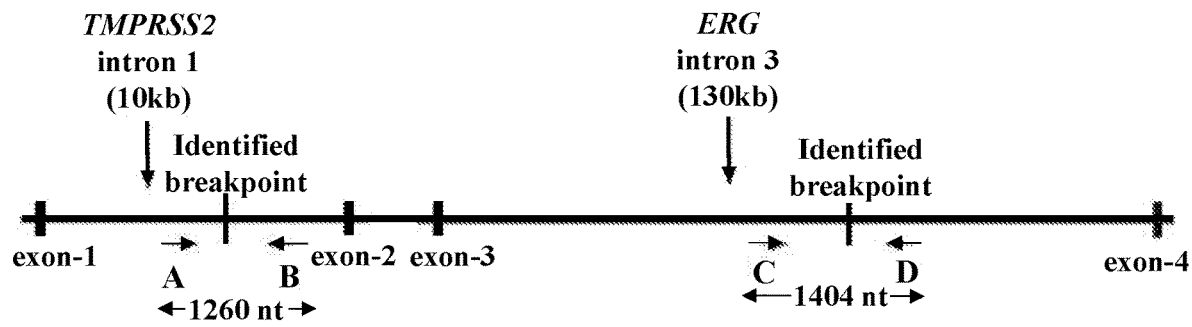
Figure 3D:
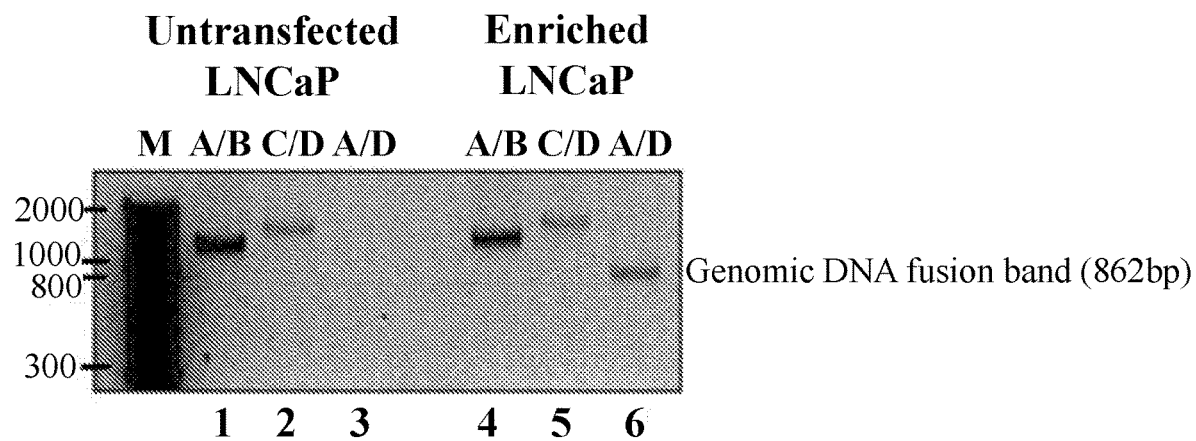
Figure 3E:
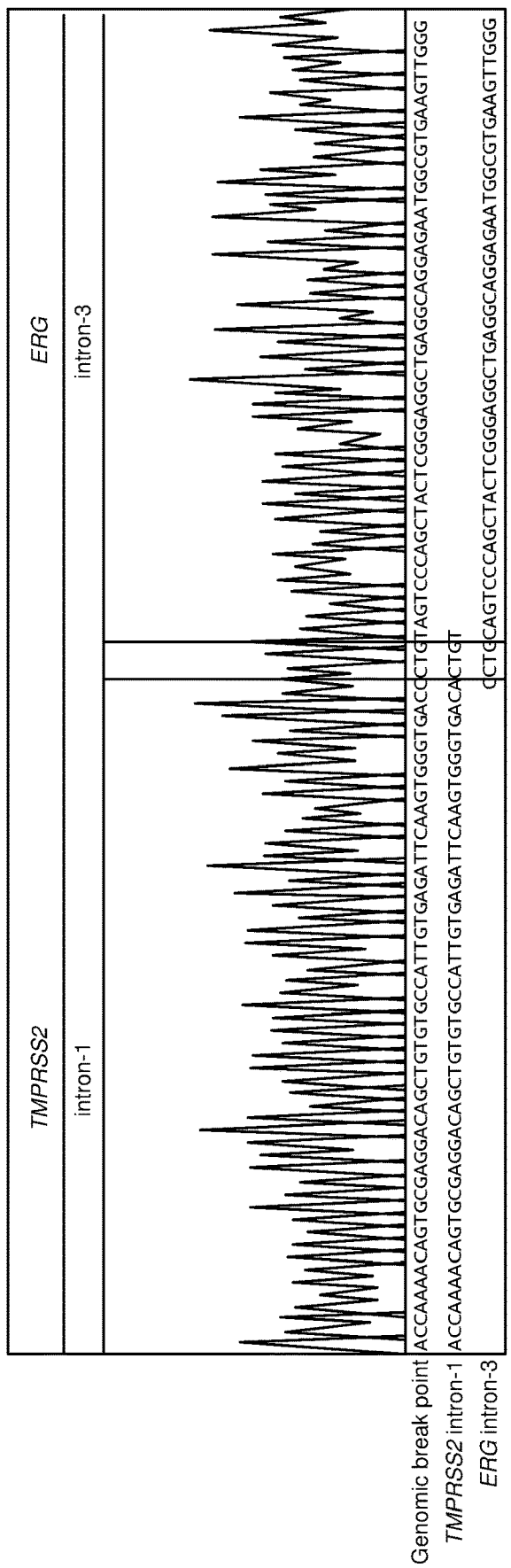

To provide definite evidence of gene fusion via genomic rearrangement, genomic PCR was used to identify the genomic breakpoint induced by antisense-5 in the enriched LNCaP population (primer designs in FIG. 19A and FIG. 3C). As shown in FIG. 3D, the un-rearranged wildtype TMPRSS2 and ERG alleles were amplified by gene-specific primer pair A/B and C/D both in untransfected cells (FIG. 3D, lane 1 and 2) and enriched LNCaP cells (FIG. 3D, lane 4 and 5). In contrast, a genomic fusion band of ~862 bp amplified by fusion-specific primer pair A/D was present only in the enriched LNCaP population (FIG. 3D, lane 6) and absent in untransfected LNCaP cells (lane 3). Sanger sequencing of the excised fusion band (FIG. 3D, lane 6) revealed the exact genomic breakpoint located within TMPRSS2 intron-1 (chr21:41502038, GRCh38/hg38) and ERG intron-3 (chr21:38501207, GRCh38/hg38) (FIG. 3E). Intriguingly, within TMPRSS2 intron-1 the induced breakpoint lies within an Alu, a transposable element known to contribute to genomic rearrangements (Rudiger et al., 1995). In ERG intron-3, the breakpoint resides in a hot spot clustered with genomic breakpoints previously identified in prostate cancer patients (FIG. 19B) (Weier et al., 2013). There is no obvious sequence homology between TMPRSS2 and ERG at the genomic breakpoint except for a three nucleotide 'CTG' microhomology (FIG. 3E), suggesting that this gene fusion may be mediated by non-homologous break repair mechanisms (Lieber, 2010; Zhang et al., 2009).

Figure 3F:
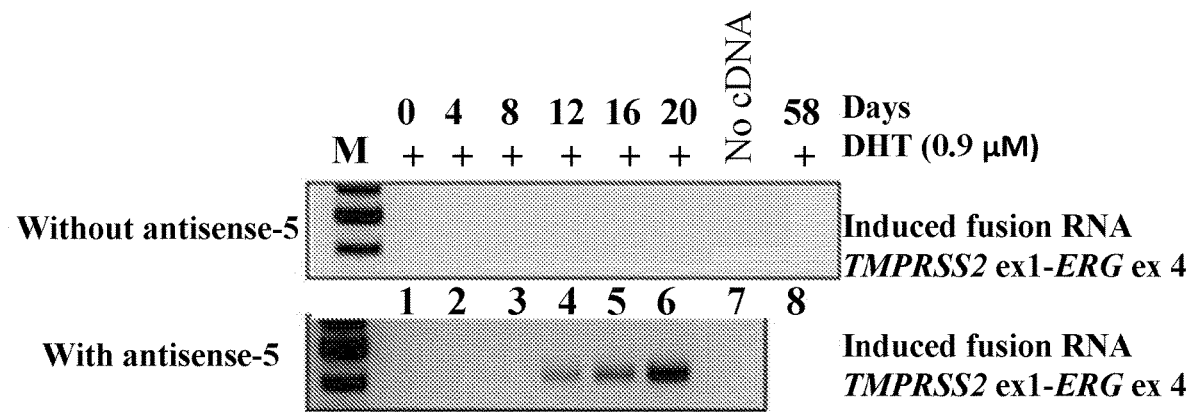

To test whether antisense input RNA can cause TMPRSS2-ERG fusion in non-malignant cells prior to cancerous transformation, experiments were performed using immortalized normal prostate epithelium cells (PNT1A), that express very low levels of androgen receptors (Coll-Bastus et al., 2015). As shown in the lower panel of FIG. 3F, prolonged expression of antisense-5 for 12 days induced fusion transcripts. This induction was not due to prolonged exposure to DHT because continuous treatment of 0.9 μM DHT alone for up to 2 months resulted in no detectable fusion transcripts in PNT1A cells (FIG. 3F, lane 8). Thus, the results indicate that the induction of TMPRSS2-ERG fusion by antisense input RNA can occur in normal prostate epithelial cells prior to malignant transformation and is not restricted to the pathological cellular context of malignant cells.

Figure 4A:
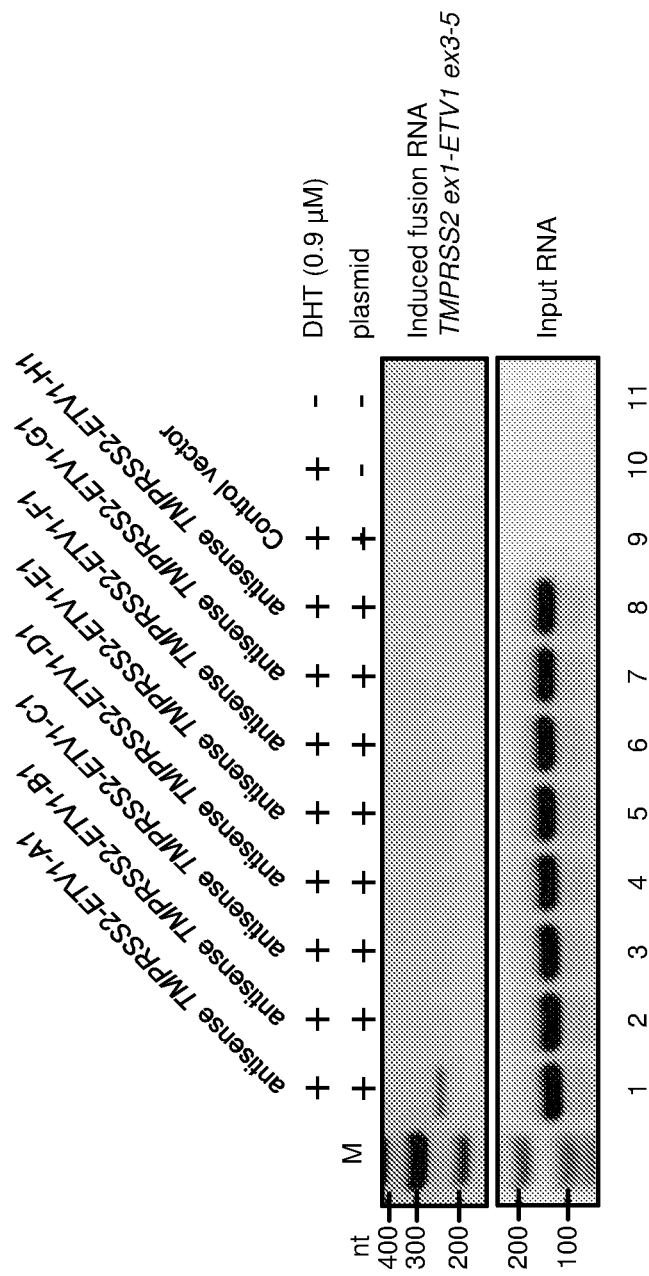
FIGS. 4A-4G. RNA-mediated inter-chromosomal gene fusion between TMPRSS2 and ETV1.
Figure 4B:
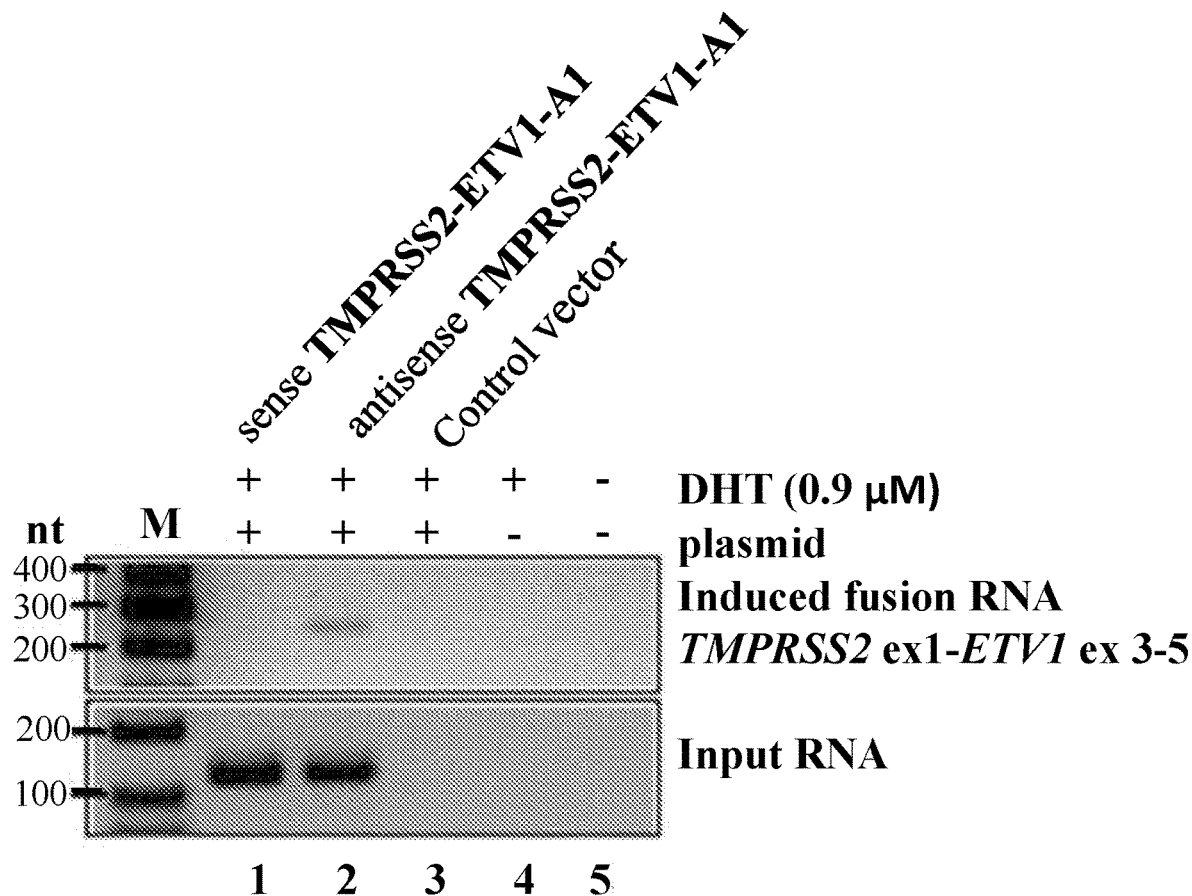
Figure 4C:
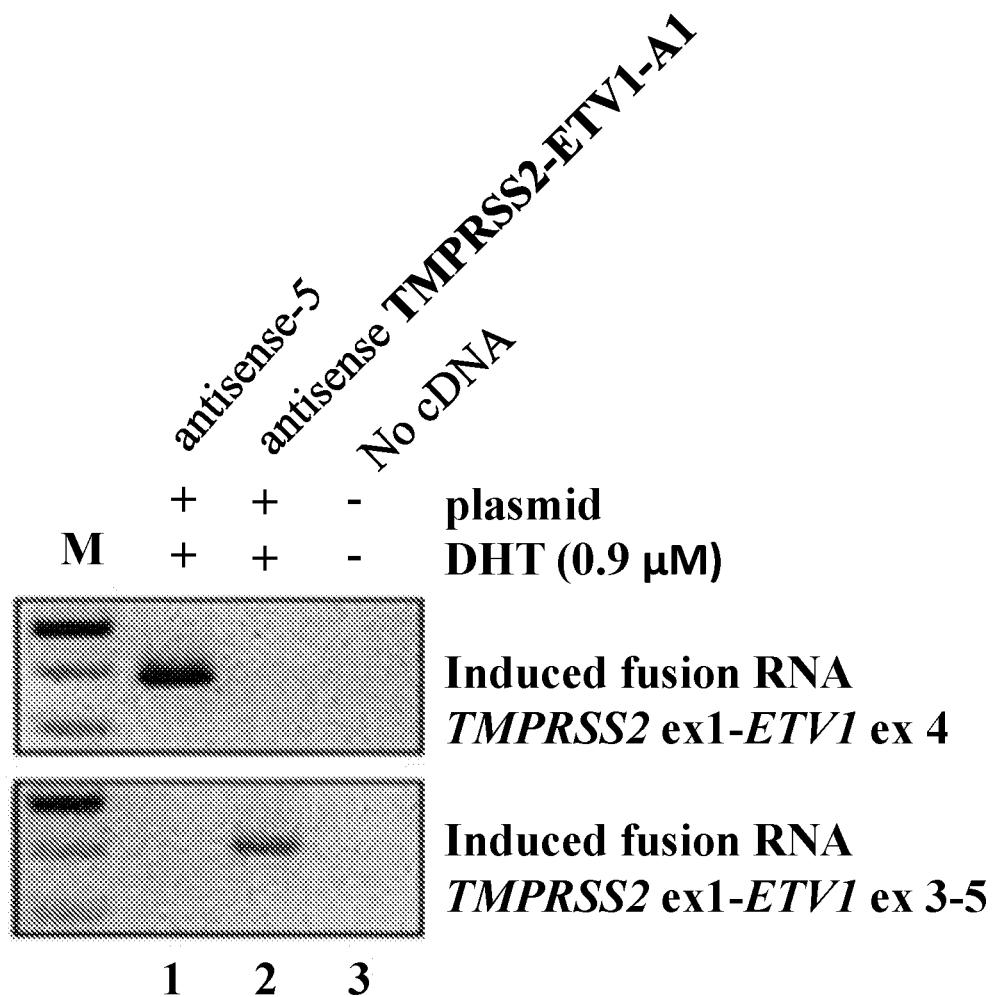
Figure 20:
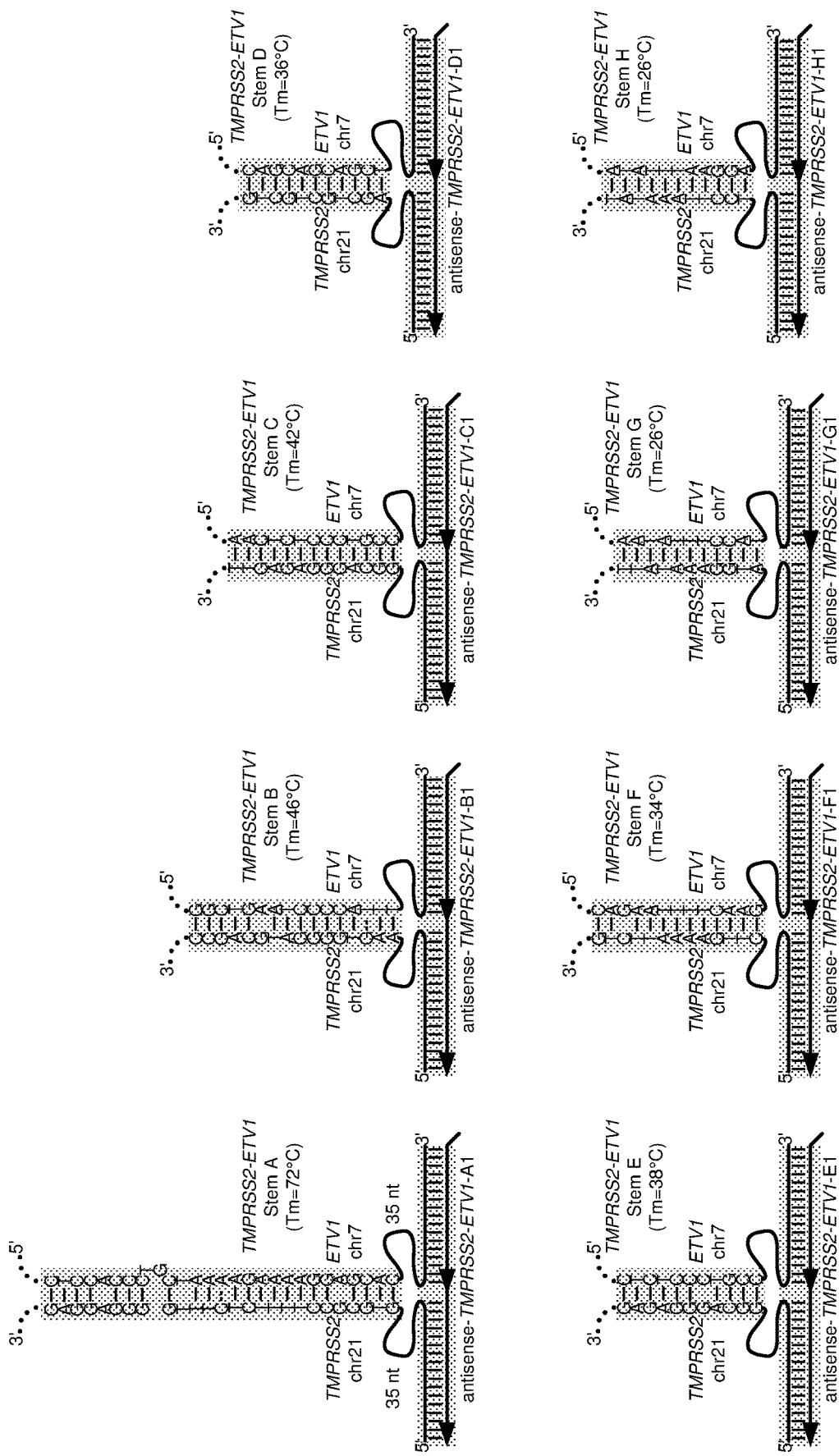
FIG. 20. Schematics of the putative three-way junctions formed between TMPRSS2 and ETV1 genomic DNA and the corresponding antisense input RNA. BLAST alignment was used to identify eight stems that could be formed with varying degrees of stability by the sense genomic TMPRSS2 sequence paired with the sense genomic ETV1 sequence. Matching antisense RNAs were then designed to forge the three-way junction with these putative intron stems. Shaded regions indicate base pairing between antisense input RNA (in green and purple) and genomic DNA (in black). TMPRSS2 is on chromosome 21 whereas ETV1 is on chromosome 7. For both, the genomic minus strand is the sense strand.
Figure 21:
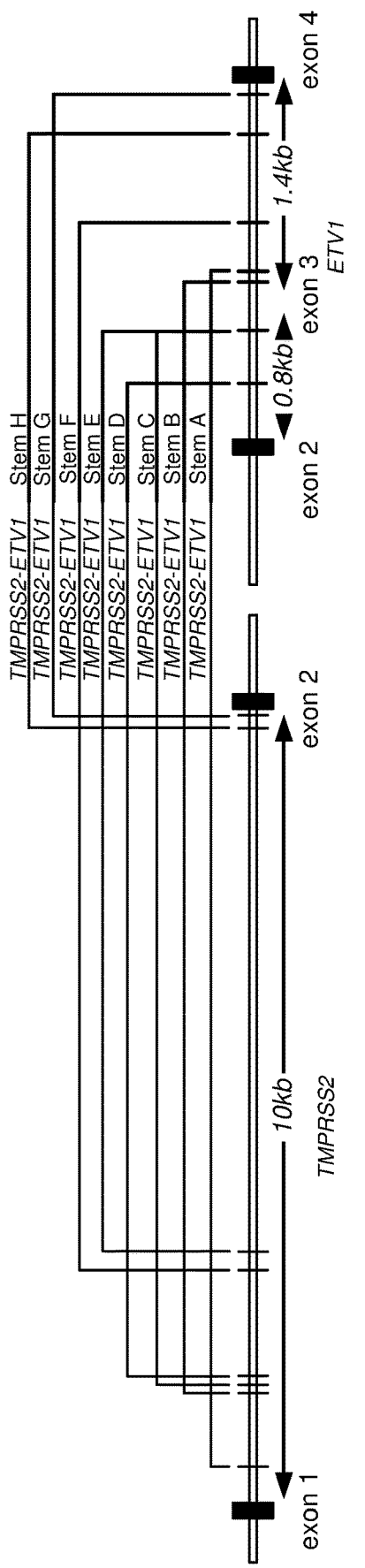
FIG. 21. Genome coordinates and Tm for the putative TMPRSS2-ETV1 genomic stems described in FIG. 20. Upper panel: Locations of putative TMPRSS2-ETV1 stems A, B, C, D, E, F, G, and H identified by BLAST alignment. All stem sequences are located in TMPRSS2 intron-1 (chromosome 21) paired with sequences in ETV1 intron-2 or -3 (chromosome 7). Genome coordinates are based on GRCh38/hg38 version. Coordinates of the exons (TMPRSS2 exons-1 and -2; ETV1 exons-2, -3, and -4) are also shown.

To test whether an input RNA can specify a pair of genes to undergo fusion other than TMPRSS2-ERG in a sequence-specific manner, a series of input RNAs were designed to induce TMPRSS2-ETV1, an inter-chromosomal fusion gene found in approximately 1% of prostate cancers (Rubin et al., 2011; Tomlins et al., 2005). Eight antisense RNAs (FIG. 20) were designed to target different chosen regions in the introns where three-way junctions potentially can be forged between the genomic DNA and input RNAs (FIGS. 20 and 21). Again, because these input RNAs target introns and contain no exon sequence, it rules out the possibility that induced endogenous fusion transcripts composed of exons arise from the sequence of input RNAs or the plasmids. As shown in FIG. 4A, targeting stem TMPRSS2-ETV1-A, which has the highest genomic DNA stem stability (Tm=72° C.) among this group, led to clear induction of the TMPRSS2-ETV1 fusion transcript (FIG. 4A, lane 1). Sanger sequencing validated that the induced transcript contains TMPRSS2 exon-1 joined with ETV1 exon-3 (uc003ssw.4) by annotated splice sites. Similar to earlier observations, targeting with sense versions of input RNAs (FIG. 4B, lane 1 vs. 2), or using antisense input RNAs designed to form three-way junctions with lower genomic DNA stem stabilities (FIG. 4A, lanes 2 to 8; FIG. 20), resulted in no detectable induction. Furthermore, the input RNA designed to target TMPRSS2 and ETV1 induced TMPRSS2-ETV1 fusion but not TMPRSS2-ERG fusion (FIG. 4C, lane 2). Conversely, antisense-5 targeting TMPRSS2 and ERG induced TMPRSS2-ERG fusion but not TMPRSS2-ETV1 fusion (FIG. 4C, lane 1), indicating that fusion formation is specified by the sequence of input RNA and not secondary effects such as global genomic stability.

Figure 4D:
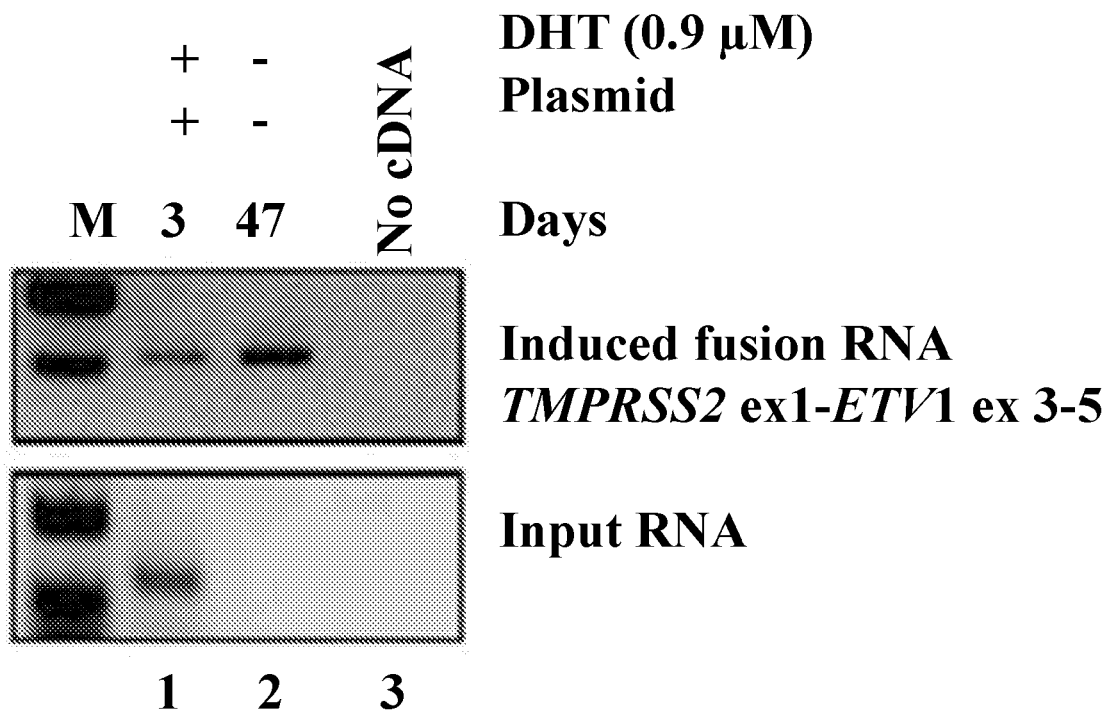
Figure 4E:
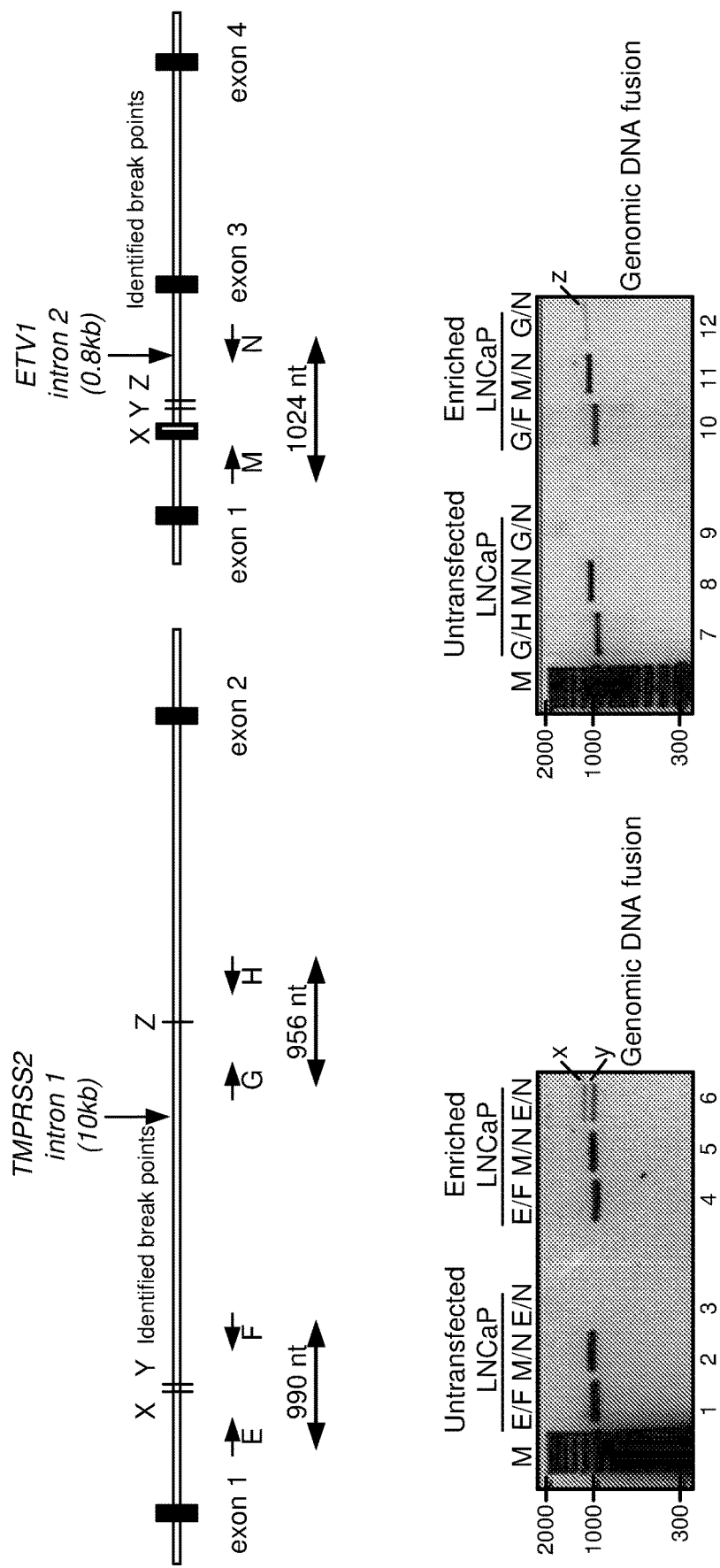
Figure 4F:
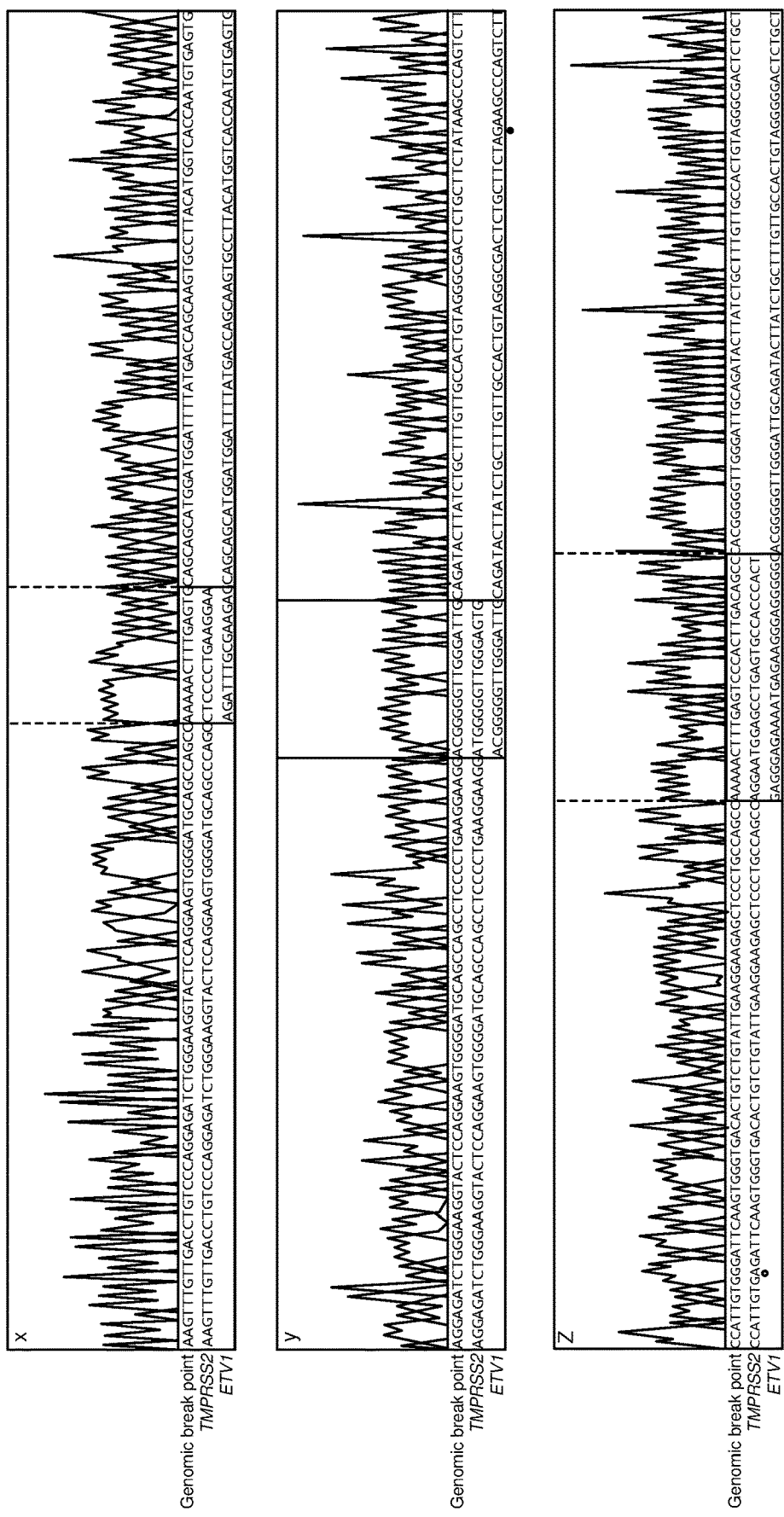
Figure 18:
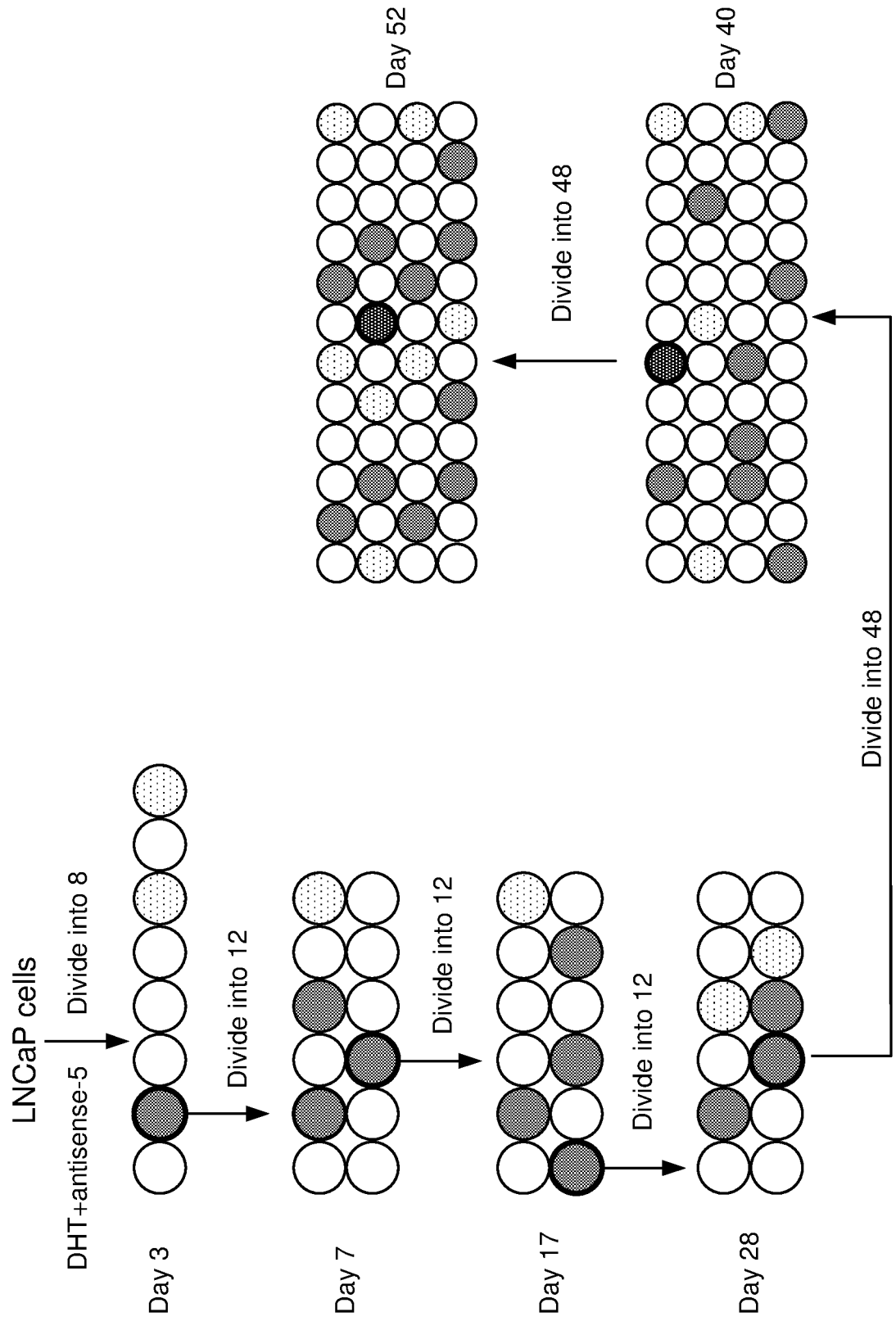
FIG. 18. Procedure used to propagate and enrich the induced LNCaP population for 52 days in the absence of DHT. LNCaP cells were transfected on day 1 with antisense-5 and incubated for 3 days with DHT. Cells were then divided into sub-populations. Half of the cells from each sub-population were harvested for RT-PCR assays to detect the induced fusion transcript whereas the other half was used to propagate the population. The sub-population containing the highest intensity of induced fusion transcripts (circled in red) was selected for continuous propagation for the next round of division and RT-PCR assays. The process was continued for 52 days. RT-PCR was performed to detect both induced fusion transcripts and antisense input RNA during each division as shown in FIG. 3B.

To verify that TMPRSS2-ETV1 as a second example of induced fusion that is indeed the consequence of genomic translocation, the inventors propagated and enriched the induced LNCaP population for 47 days after the initial transfection of input RNA and DHT treatment (experimental procedures same as described for TMPRSS2-ERG enrichment in FIG. 18). The transiently expressed antisense input RNA had been degraded and was absent by day 47 (FIG. 4D, lane 1 vs. 2). The induced TMPRSS2-ETV1 fusion transcript, however, was continuously expressed beyond day 47 (FIG. 4D, lane 2). Once again this observation indicated that the sustained expression of an induced fusion does not require the continuous presence of input RNA. Moreover, genomic PCR assays identified three distinct genomic breakpoints between TMPRSS2 and ETV1 gene (labeled as x, y, z in FIG. 4E) that were present only in the enriched LNCaP population but absent in untransfected LNCaP cells (FIG. 4E, lane 3 vs. 6, lane 9 vs. 12). Similar to earlier observations, no obvious sequence homology between TMPRSS2 and ETV1 was observed at the genomic breakpoints except for a few nt of microhomology (FIG. 4F), indicating that the gene fusion is mediated by non-homologous break repair mechanisms (Lieber, 2010; Zhang et al., 2009).

Figure 4G:
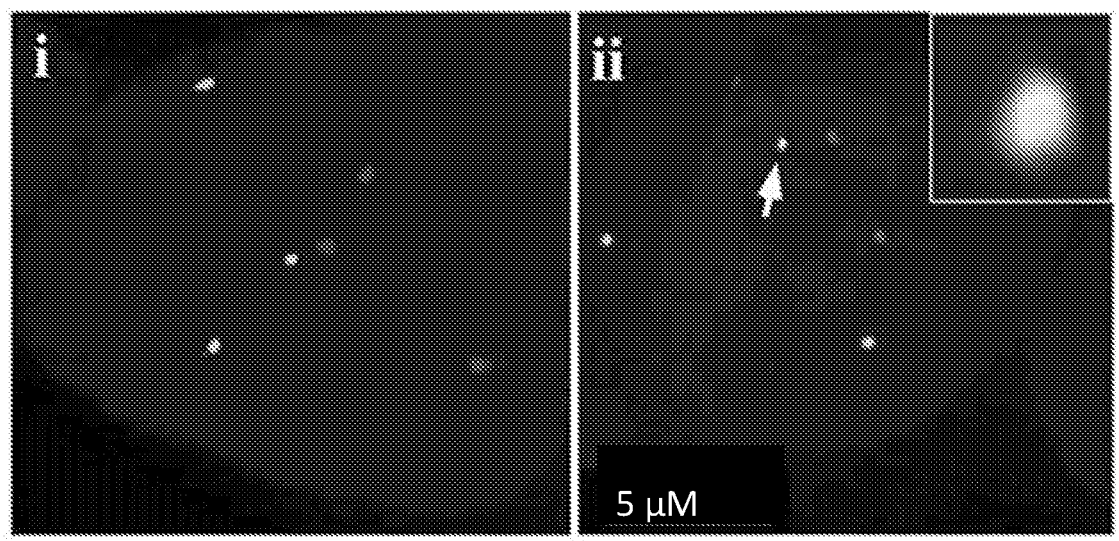

Unlike TMPRSS2 and ERG that are located near each other on the same chromosome, TMPRSS2 and ETV1 are located on different chromosomes. Thus, gene fusion as a result of chromosomal translocation could be confirmed unequivocally by evidence of chromosomal co-localization of the latter pair. Using probes specific to TMPRSS2 and ETV1, fluorescence in situ hybridization (FISH) was performed, followed by deconvolution microscopic imaging, of 3301 cells from the enriched LNCaP cell population and 620 cells from the control untransfected LNCaP population. Analyses of constructed 3D images showed that approximately 0.9% of the enriched population (30 out of 3301 cells) were positive for co-localization of TMPRSS2 and ETV1 gene in the cellular nucleus (FIG. 4G). In contrast, none of the cells from the untransfected population showed co-localized FISH signals as determined by the same 3D image criteria. These results, together with the genomic breakpoints identified by genomic PCR at single base resolution (FIGS. 4E and 4F), provide strong evidence that the induced expression of the TMPRSS2-ETV1 fusion transcript represents the consequence of gene fusion caused by chromosomal translocation.

Figure 5A:
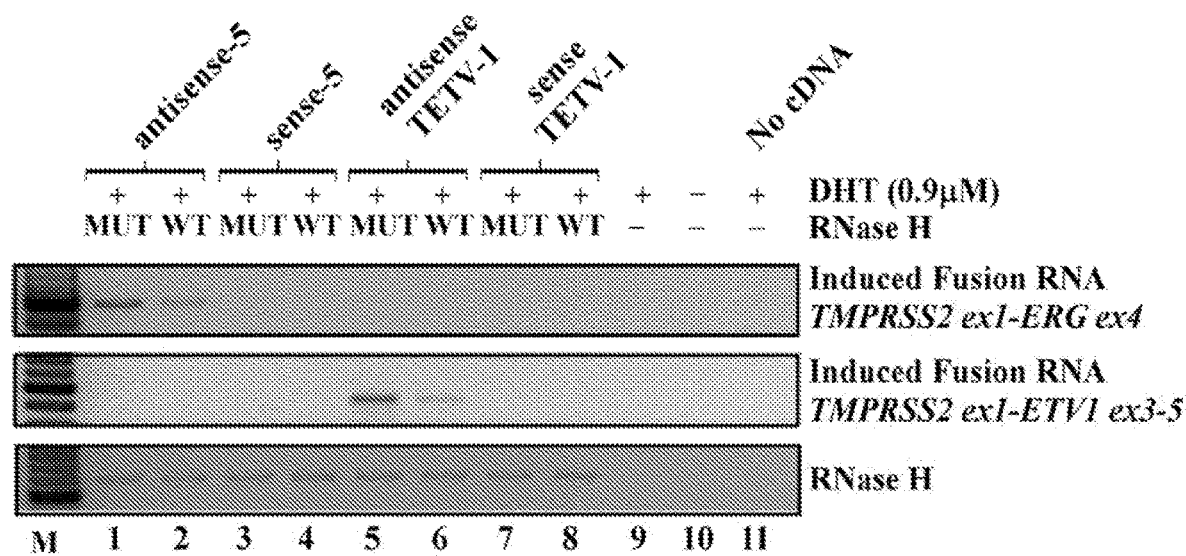
FIGS. 5A-5B. The disparity between antisense versus sense input RNA is due to transcriptional conflict.

RNA mediated gene fusion mechanism requires DNA:RNA hybrid formation. The mechanism central to at least certain embodiments of the disclosure is that the input chimeric RNA acts as a guide RNA to mediate genome rearrangement by annealing to TMPRSS2 or ERG genes. Resolving such an RNA/DNA duplex by DNA break/repair mechanisms yield the final gene fusion through recombination in regions prone to DNA breaks. Accordingly, overexpression of RNaseH in cells, which degrades the RNA in an RNA/DNA duplex, should reduce the probability of fusion gene formation. To test whether RNA/DNA duplex is indeed required for RNA-mediated fusion gene, the inventors co-transfected input chimeric RNA expression plasmid together with a second plasmid that expresses wildtype RNaseH (Britton, Dernoncourt et al. 2014) which degrades the RNA in the RNA/DNA duplex. As a control, an inactive mutant RNaseH (D10R E48R mutant) (Britton, Dernoncourt et al. 2014) that lacks the ability to degrade RNA was used for head-to-head comparisons. As shown in FIG. 5A, induction of TMPRSS2-ERG fusion gene by antisense chimeric RNA was significantly reduced in the presence of wildtype RNaseH vs. the mutant RNaseH (FIG. 5A, lane 2 vs.1). Similarly, induction of TMPRSS2-ETV1 fusion gene was also significantly reduced in the presence of wildtype vs. the mutant RNaseH (FIG. 5A, lane 6 vs. 5). These results indicate that the induction of gene fusions requires the formation of an RNA/DNA hybrid. Consistent with previous observations, sense input RNAs failed to induce fusion regardless of the expression of RNaseH (FIG. 5A, lane 3, 4, 7, 8).

Figure 5B:
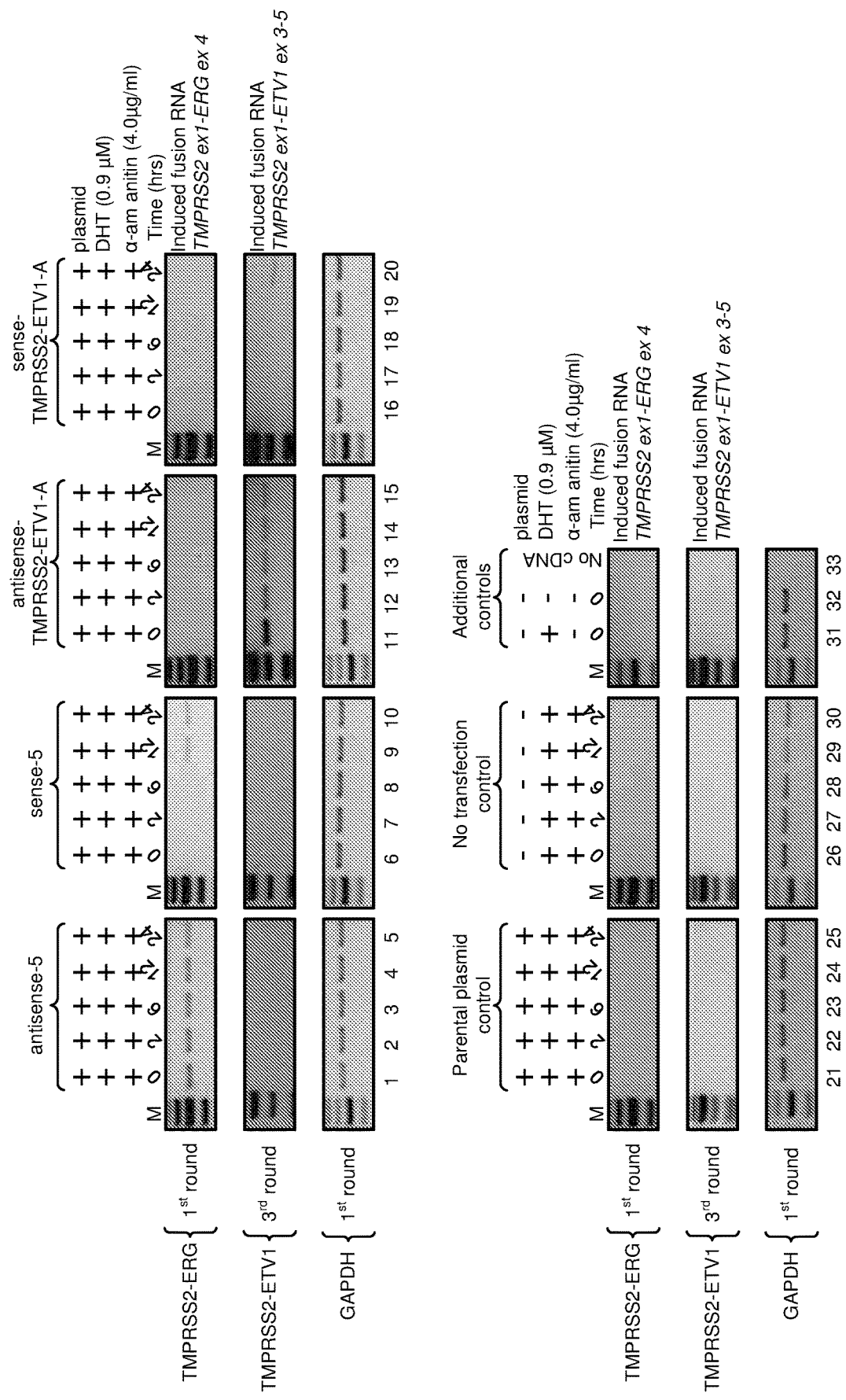

One important observation emerging from our study is that all sense input RNAs failed to induce gene fusion. In particular, of the ten antisense input RNAs that were demonstrated to induce fusion (FIGS. 1A, 1B, 2E, 4A), all of their corresponding sense counterparts failed to induce fusion (FIGS. 1A, 1C, 2G, 4B). This specificity was observed despite the fact that sense input RNAs in theory can anneal to the same genomic sites targeted by their antisense counterparts and form similarly stable DNA/RNA hybrids. To test whether the disparity between antisense and sense is due to transcriptional activity of parental genes, the input RNAs were expressed by U6 (a pol-III promoter) for one day, followed by α-amanitin-mediated inhibition of pol-II transcription for various time periods to shut down parental gene transcription. α-amanitin was then removed to resume cellular transcription and the induction by sense vs. antisense input RNA were compared. As shown in FIG. 5B upper panel, the corresponding sense input RNAs that previously failed to induce fusion began to induce TMPRSS2-ERG after 12 hours of α-amanitin treatment (lane 9 and 10), and TMPRSS2-ETV1 fusion (lane 20) after 24 hours of α-amanitin treatment. This latent induction is not a property of general cellular toxicity of α-amanitin because the toxicity caused by the same treatment actually reduced the induction by antisense input RNAs (lane 1 vs. 5 for TMPRSS2-ERG, lane 11 vs. 15 for TMPRSS2-ETV1). Furthermore, the input RNAs designed to target TMPRSS2 and ERG, regardless of their sense or antisense nature, induced TMPRSS2-ERG fusion but not that of TMPRSS2-ETV1 (lane 1 to 10). Conversely, input RNAs targeting TMPRSS2 and ETV1, regardless of their directional orientation, induced TMPRSS2-ETV1 fusion but not TMPRSS2-ERG fusion (lane 11 to 20). Additional control experiments using a parental plasmid vector lacking the input RNA sequences, DHT treatment without plasmid transfection, and PCR reactions without cDNA, all induced no endogenous fusion transcript under the same α-amanitin treatment (FIG. 5B, lower panel). The specificity exhibited by these experiments argues against general toxicity effects. The results suggest that the antisense versus sense disparity is largely due to transcriptional conflict.

Figure 6A:
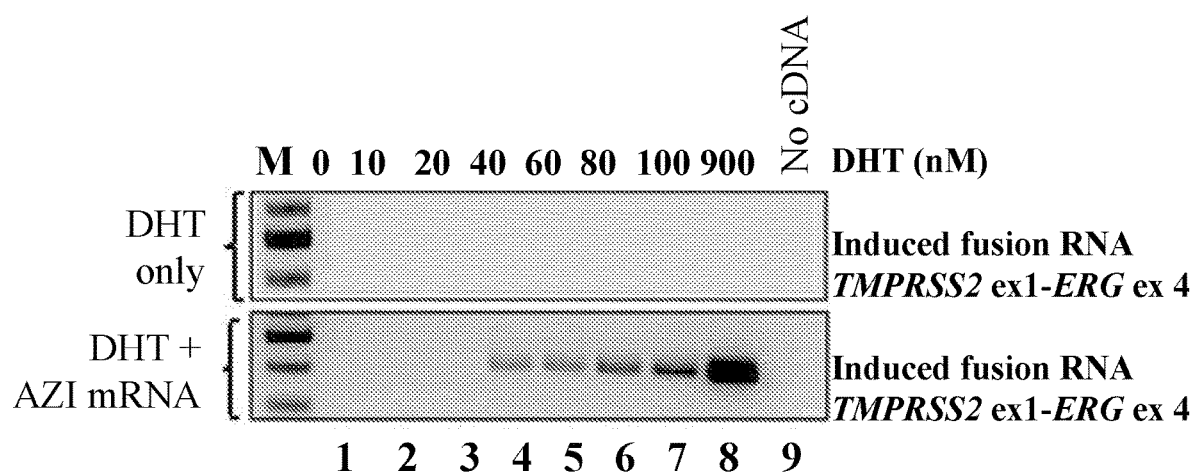
FIGS. 6A-6C. Specific endogenous RNA acts as the 'initiator' RNA to mediate gene fusion.
Figure 6B:
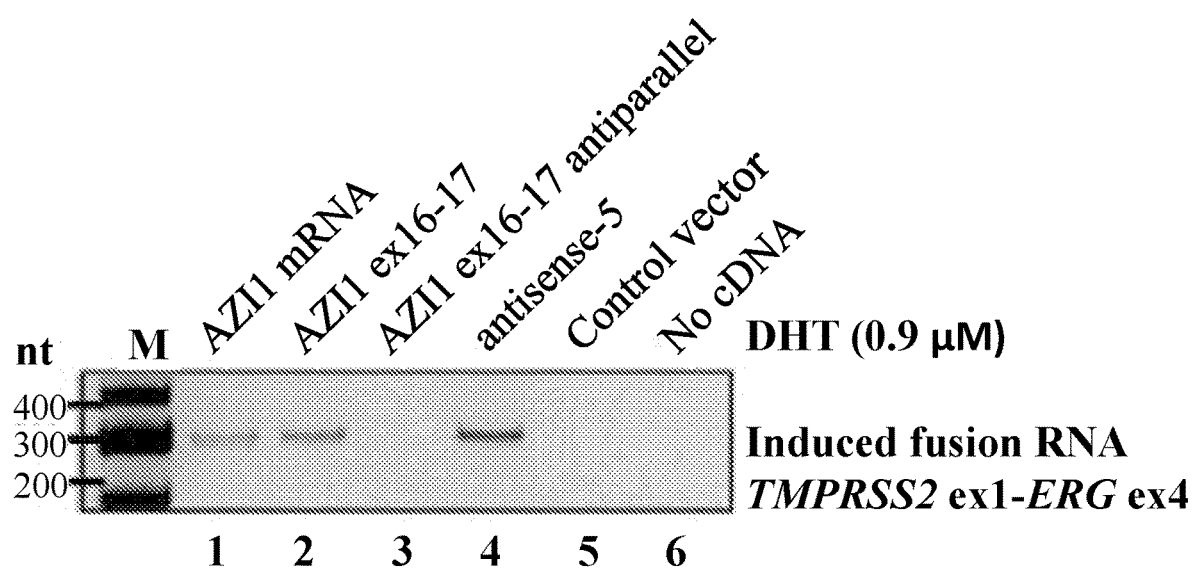
Figure 6C:
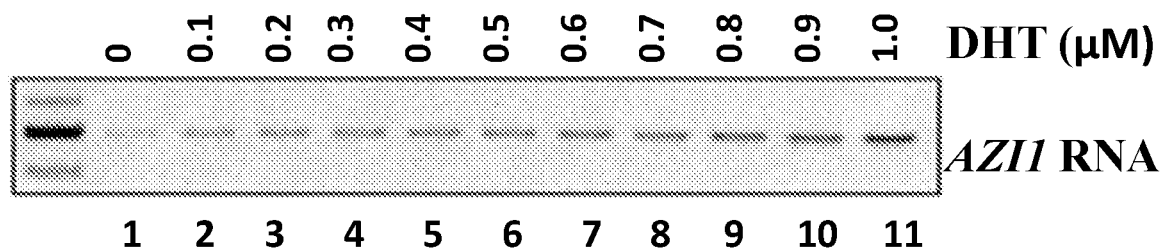

With the plausibility of RNA-mediated gene fusion established, it was considered that specific endogenous cellular RNAs can act as the 'initiator' to induce TMPRSS2-ERG fusion, which is found in ~50% of prostate cancers. To identify candidate cellular initiator RNAs, an available mRNA-seq database was analyzed consisting of prostate tumors and matched benign tissues (Kannan et al., 2011). However, there was no evidence of perfect endogenous antisense chimeric RNAs in which the TMPRSS2 sequence was joined to any ERG sequence by discernable 5' and 3' splice sites in the antisense orientation. This suggests that if endogenous initiator RNAs do exist, they might arise from unrelated genomic sources that coincidentally resemble an imperfect chimeric RNA antisense to both TMPRSS2 and ERG. Thermodynamic calculations of RNA/DNA hybrids are performed to identify cellular RNAs with partial sequence complementarity to the TMPRSS2 and ERG genes. AZI1 mRNA (also known as CEP131) (Aoto et al., 1997; Aoto et al., 1995) could form high affinity RNA/DNA hybrids with TMPRSS2 and ERG genomic sequences. As shown in FIG. 6A, overexpressing full-length AZI1 mRNA (3619 nt, uc002jzn.1) induced the TMPRSS2-ERG fusion transcript in LNCaP cells. The induction was observed at a physiologically relevant concentration (40 nM) of DHT (FIG. 6A, lane 4). Furthermore, expression of exon16-17 of AZI1, a short 220 nt segment containing an imperfect sequence antisense to TMPRSS2 and ERG, was sufficient to induce TMPRSS2-ERG fusion (FIG. 6B, lane 2). This result indicates that the induction of gene fusion is mediated by an RNA sequence that resides in exon16-17 and requires no AZI1 protein. Consistent with previous observations that sense input RNAs are ineffective for the fusion process, the expression of exon16-17 in the antiparallel orientation also failed to induce TMPRSS2-ERG fusion (FIG. 6B, lane 3).

Significance of Certain Embodiments

Figure 7A:
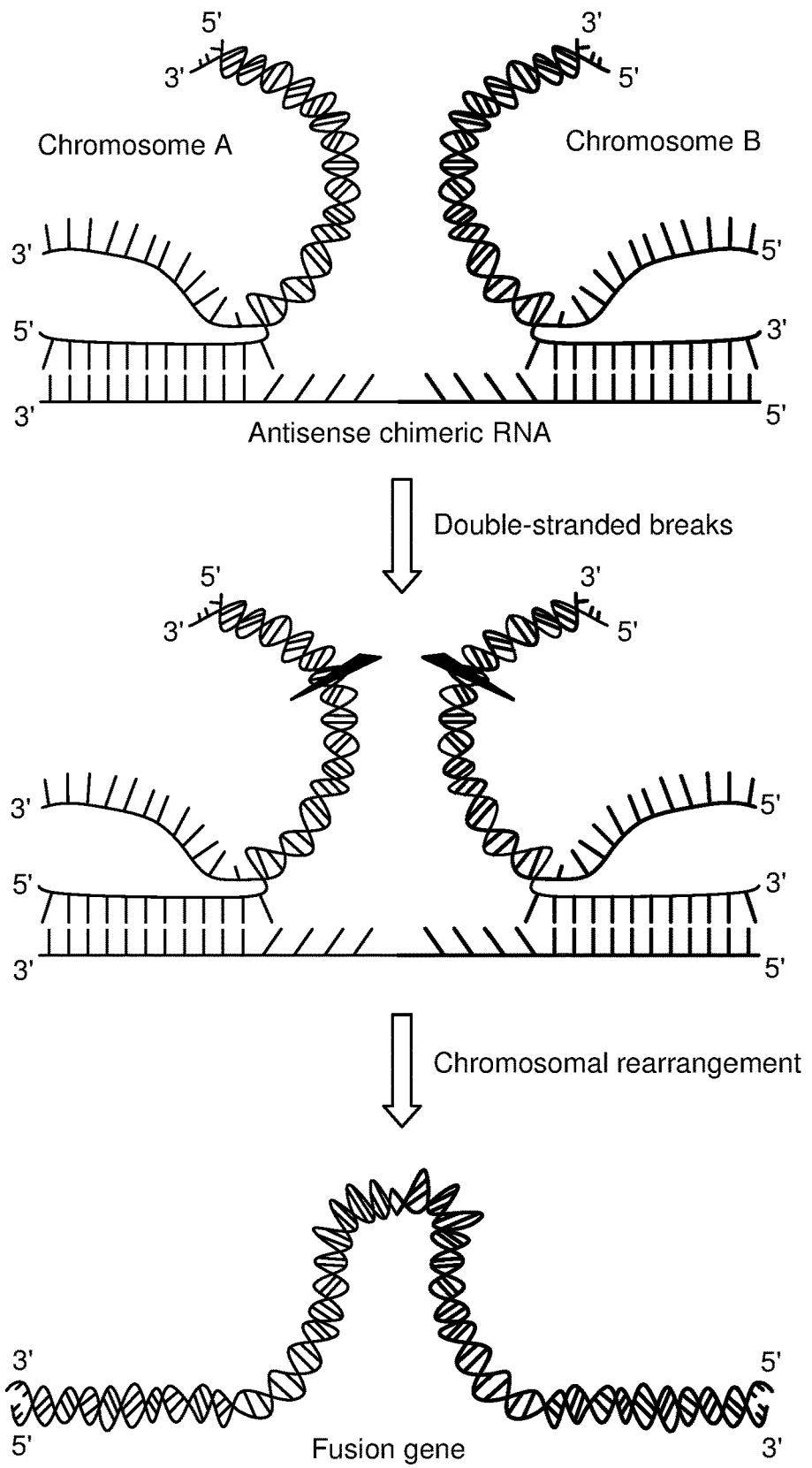
FIGS. 7A-7C. A model of RNA-mediated gene fusion in mammalian cells.

In summary, this disclosure provides the first evidence that expression of a chimeric RNA can drive the formation of gene fusions in mammalian cells. The data support an embodiment (shown in FIG. 7) where the initiator RNA with chimeric sequence invades chromosomal DNA to stabilize a transient RNA/DNA duplex using DNA sequences located in two distant genes. Resolution of such an RNA/DNA duplex by DNA repair mechanisms would yield the final gene fusion through recombination in regions prone to DNA breaks (FIG. 7A). Such events were rare in the initial population of transfected cells (1 in $10^3$ or $10^4$ cells occurred within 3 days). However, the necessary machinery is clearly present in normal prostate epithelial cells prior to malignant transformation. If the resulting gene fusion (such as TMPRSS2-ERG) provides a growth advantage, a single affected cell among billions of cells in a normal prostate tissue may proliferate abnormally and eventually contribute to cancer formation. Identifying such initiator RNAs might provide novel insights into early disease mechanisms, as well as the discovery of new preventive and therapeutic strategies to combat diseases such as cancer.

Figure 7B:
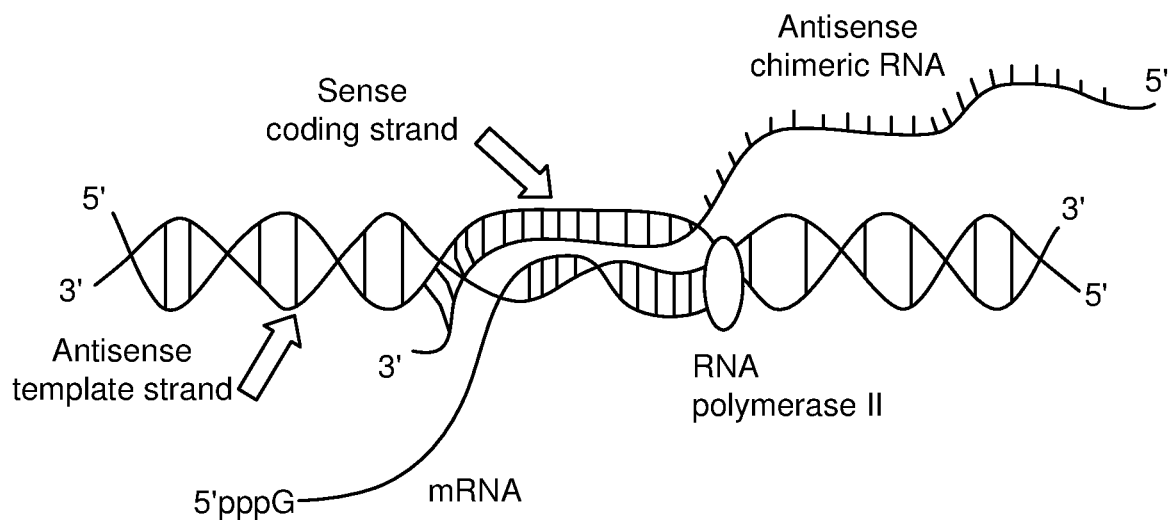
Figure 7C:
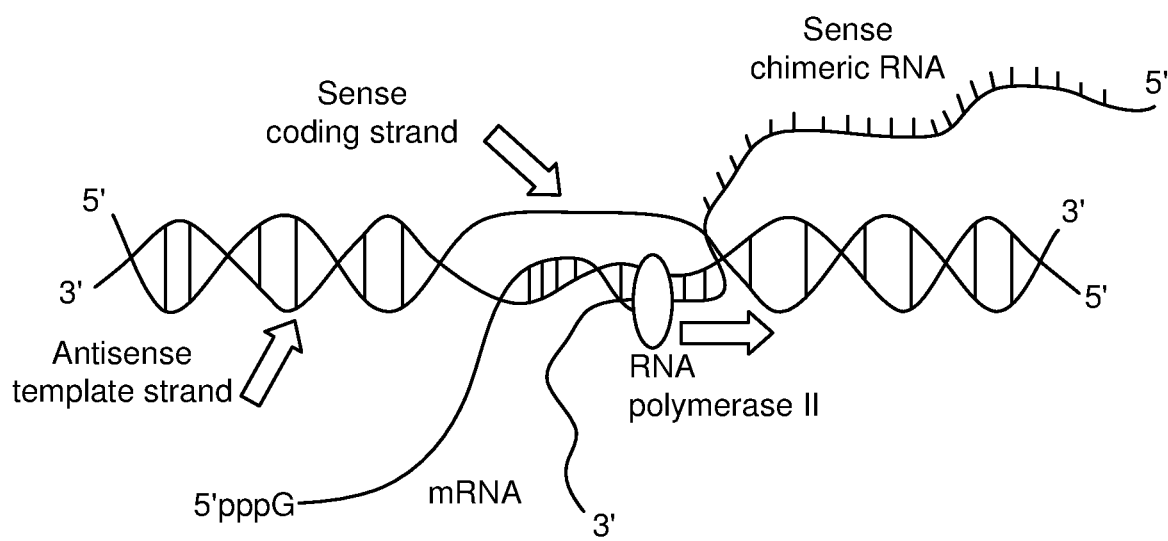

Contrary to the previous "cart before the horse" model (Rowley and Blumenthal, 2008; Zaphiropoulos, 2011), the results do not support the postulation that a sense fusion mRNA derived from trans-splicing between two pre-mRNAs effectively directs gene fusion. Expressing sense input RNAs mirroring the trans-spliced mRNA failed to induce fusion in LNCaP cells (FIGS. 1A and 9). Of ten antisense RNAs that were demonstrated to be capable of inducing fusion (FIGS. 1A, 1B, 2E, 4A, 6B), all of their corresponding sense RNAs failed to induce fusion (FIGS. 1A, 1C, 2G, 4B, 6B). This occurred even though the sense RNAs could, in theory, anneal to the same genomic sites targeted by their antisense counterparts and form similar DNA/RNA hybrids when paired with the antisense strand of genomic DNA. As demonstrated in FIG. 5, this antisense versus sense disparity can be explained by transcriptional conflict (FIGS. 7B and 7C). Because the TMPRSS2 promoter is highly active in LNCaP cells, sense chimeric RNAs forming DNA/RNA hybrids with antisense strands of genomic DNA (the template strand used for transcription) would be frequently "bumped" off and unable to stabilize the structures required for initiating genomic rearrangements. The mechanistic basis for the antisense versus sense RNA, and whether these phenomena can be generalized, may be characterized.

The results also do not support the hypotheses that antisense input RNAs, acting as a docking station, mediate trans-splicing by base-pairing with both endogenous sense parental pre-mRNAs, or by bringing the parental genes in close proximity thus facilitating trans-splicing of parental pre-mRNAs transcribed from two genomic loci. Both mechanisms would require the continuous presence of antisense input RNAs to sustain the expression of induced fusion transcripts. Yet it was shown that the induced fusion expression has a permanent nature and requires no continuous presence of input RNAs (FIG. 3B and FIG. 4D). Furthermore, in the case of TMPRSS2-ERG there is no detectable ERG parental RNA as raw material (FIG. 3A) to account for the trans-splicing models. Moreover, sense input RNAs, which are not complimentary to the sense parental pre-mRNAs thus cannot act as their docking station, are able to induce the fusion transcripts after a brief period of transcriptional inhibition, again arguing against the docking model. On the contrary, the genomic breakpoints identified by genomic PCR and chromosomal co-localization provided by FISH, strongly support that the induced expression of fusion transcript is largely the consequence of gene fusion resulting from chromosomal translocation. While prior works have shown that infrequent TMPRSS2-ERG fusions can by induced through genotoxic stress such as gamma radiation in the presence of DHT that increases double-stranded DNA breaks (Lin et al., 2009; Mani et al., 2009), such mechanisms of general genotoxicity fail to account for the specificity of gene fusion partners found in cancer. This report is the first to demonstrate RNA-mediated gene fusion in mammalian cells, and provides an RNA-driven mechanism that can account for the 'specificity' of gene fusion partners that were selected to undergo gene fusion in early disease stages. In specific embodiments the results represent a pathological example in a broad spectrum of potential RNA-mediated genome rearrangements and could have fundamental implications in the biology of mammalian genome stability, as well as gene editing technology via mechanisms native to mammalian cells.

Example 3

Examples of Materials and Methods

LNCaP Cell Culture

LNCaP cells were routinely cultured in RPMI 1640 medium (RPM1 1640, 1×, with L-glutamine, #10-040-CV, CORNING cellgro) containing 10% fetal bovine serum (premium grade FBS, #1500-500, Seradigm) and 1% penicillin/streptomycin (#15140-122, Gibco) in a 5% $CO_2$ humidified incubator. For experiments involving the induction of fusion gene by input RNA, regular fetal bovine serum in the culture medium was replaced by Charcoal:Dextran stripped fetal bovine serum (catalog #100-119, Gemini Bioproducts) to remove hormones present in serum. LNCaP cells were cultured in this special medium for 24 hrs prior to plasmid transfection.

PNT1A Cell Culture

PNT1A cells were routinely cultured in RPMI 1640 medium containing 10% fetal bovine serum (premium grade FBS, #1500-500, Seradigm) and 1% penicillin/streptomycin (#15140-122, Gibco) in a 5% $CO_2$ humidified incubator.

Transient Transfection of Plasmids for Expressing the Chimeric RNAs

Twenty hours prior to transfection, LNCaP cells were seeded in 12-wells plate (BioLite 12 Well Multidish, #130185, Thermo Fisher Scientific) with a density of $5\times10^5$ cells/well and 1 ml/well of culture medium containing Charcoal:Dextran stripped fetal bovine as described above. Transfection was performed using Turbofect transfection reagent (Thermo Scientific, #R0531) according to manufacturer's protocol. Briefly, 1 µg of a particular plasmid was first diluted in 100 µl of the serum-free DMEM followed by immediate mixing by pipetting. 4 µl of the transfection reagent was then added to the diluted DNA followed by mixing and incubation for 20 min. The DNA/transfection reagent mixture was then added drop wise to a well containing LNCaP cells in 1 ml medium.

For transfection in PNT1A cells, $5\times10^5$ cells/well were plated in 12-wells plate in 1 ml/well of cultured medium 24 hrs prior to transfection. Transfection was performed using the same formula described for LNCaP cells. For repetitive transfections, initially transfected PNT1A cell population were split every three days, half was processed for RT-PCR assay and half was seeded again in a new well for the next transfection.

DHT Preparation and Treatment

DHT (Dihydrotestosterone) was purchased from Sigma Adlrich (5α-Androstan-17β-ol-3-one, #A8380). Concentrated stock of 1500 μM was prepared by dissolving 4.3566 mg of DHT powder in 10 ml of 100% ethanol (200 proof ethanol, Koptec, #V1016) and then aliquoted in 1 ml tubes and stored at −80° C.

For treating cultured cells, concentrated DHT stock was diluted as 10× working solutions (for example, for 0.9 μM final concentration, 10× is prepared as 9.0 μM) with the appropriate complete culture medium and used immediately. Complete media for LNCaP cells: RPMI 1640+10% Charcoal:Dextran stripped fetal bovine serum+1% penicillin/streptomycin. Complete media for PNT1A: RPMI 1640+ 10% fetal bovine serum+1% penicillin/streptomycin. Six hrs post transfection, 111 μl of fresh 10× DHT working solutions was added to each well of 12-wells plate containing 1 ml medium and transfected cells.

For long-term treatment, medium was changed with fresh DHT every three days.

RNA Isolation

Total RNA from cultured cells was extracted using High Pure RNA isolation Kit according to manufacturer's instructions (#11828665001, Roche). Briefly, cells were suspended in 200 μl of PBS buffer and were then lysed with 400 μl of lysis buffer. The sample was then passed through the filter assembly resulting in the binding of the nucleic acids to the filter. The filter containing nucleic acids was then incubated with DNase I dissolved in DNase incubation buffer to degrade genomic and plasmid DNAs. The column was then rinsed with wash buffer and total RNA then eluted in a new tube for further analysis.

For detection of residual genomic and plasmid DNA, eluted RNA was subject to PCR reaction with primers specific to intron regions of house-keeping gene GAPDH, and with primers specific to plasmid transfected. Total RNA was converted to cDNA only if it is validated as free of DNA contamination.

Reverse Transcription Reaction

1 μg of total RNA was used for each reverse transcription reaction according to manufacturer instruction (superscript III RT, #18080-051, Invitrogen). RNA was converted to cDNA either with Oligo dT primer (for induced fusion transcripts) or with random hexamers (for input RNAs expressed by U6 promoter). After the addition of dNTPs, the mixture was denatured at 65° C. for 5 minutes. This was followed by the addition of a master-mix containing 1× superscript buffer, 10 mM DTT, 5 mM Magnesium chloride, RNaseOUT and Superscript III reverse transcriptase. Reactions were carried out at 50° C. for 50 minutes and then terminated by incubation at 85° C. for 5 minutes. cDNA was then treated with RNase-H for 20 minutes at 37° C. to degrade RNA in DNA/RNA hybrid. 1 μl of cDNA was used as template for each subsequent PCR reaction.

RT-PCR for Detecting Induced Fusion Transcripts

The majority of induced fusion RNAs in this manuscript were detected using one-round RT-PCR. The following cases were assayed using three-round nested PCR: (1) the results of DHT treatment at physiological concentrations as shown in FIGS. 1D and 6A, (2) the induction of TMPRSS2-ERG fusion transcript in non-malignant PNT1A cells as shown in FIG. 3F, (3) the specificity of input RNAs assayed in FIG. 4C, and (4) endogenous ERG level detection in LNCaP cells in FIGS. 17A-17D. The following cases were assayed using two-round nested PCR: the induction of TMPRSS2-ETV1 fusion RNA as shown in FIGS. 4A and 4B, and the detection of TMPRSS2-ETV1 fusion in the enriched population in FIG. 4D.

PCR was done with a standard three-step protocol using REDTaq DNA polymerase (#D5684-1KU, Sigma) according to manufacturer instruction.

Reaction was set as follows:

PCR reaction:
Forward primer: 1.0 μl (from 10 μM stock, Sigma)
Reverse primer: 1.0 μl (from 10 μM stock, Sigma)
10× reaction buffer: 5.0 μl (comes with REDTaq, Sigma)
dNTPs: 1.0 μl (from 10 mM stock, #11969064001, Roche)
DMSO: 1.5 μl (#154938, Sigma-Aldrich)
cDNA: 1.0 μl (from 20 μl stock prepared from 1 μg RNA)
Autoclaved Milli-Q water: 38.5 μl
REDTaq DNA polymerase: 1.0 μl (#D5684-1KU, Sigma)
Total volume: 50 μl Standard One-Round PCR Conditions for TMPRSS2-ERG:
Pre-denaturation 94° C., 4 min
Denaturation 94° C., 30 sec
Annealing 58° C., 45 sec
Extension 72° C., 60 sec
Final Extension 72° C., 5 min The Denaturation, Annealing and Extension steps were performed 32 cycles for induced fusion RNA and 27 cycles for input RNA.

PCR Conditions for Three-Round Nested PCR for TMPRSS2-ERG:
  $1^{st}$ round: PCR with TMPRSS2 ex-1 F1 and ERG ex-4 R1 on 1 μl of cDNA
  Pre-denaturation 94° C., 4 min
  Denaturation 94° C., 30 sec
  Annealing 58° C., 45 sec
  Extension 72° C., 60 sec
  Final Extension 72° C., 5 min The Denaturation, Annealing and Extension steps were performed 32 cycles for induced fusion RNA.
  $2^{nd}$ round: PCR with TMPRSS2 ex-1 F2 and ERG ex-4 R2 on 1 μl of 1 round product, PCR conditions same as $1^{st}$ round.
  $3^{rd}$ round: PCR with TMPRSS2 ex-1 F3 and ERG ex-4 R3 on 1 μl of $2^{nd}$ round product, PCR conditions same as $1^{st}$ round.

PCR Conditions for Two-Round Nested PCR for TMPRSS2-ETV1:
  $1^{st}$ Round: Top down PCR with TMPRSS2 ex-1 F1 and ETV1 ex-6 R1
  Denaturation 94° C., 30 sec
  Annealing *, 45 sec
  Extension 72° C., 60 sec The Denaturation, Annealing and Extension steps were performed 2 cycles.
  2 cycles at each temperature: 62° C., 61° C., 60° C. . . . 49° C. followed by
  Denaturation 94° C., 30 sec
  Annealing 48° C., 45 sec Extension 72° C., 60 sec The Denaturation, Annealing and Extension steps were performed 20 cycles 2$^{nd}$ Round: PCR with TMPRSS2 ex-1 F2 and ETV1 ex-5 R1 on 1 µl of 1st round.

Pre-denaturation 94° C., 4 min

Denaturation 94° C., 30 sec

Annealing 57° C., 45 sec

Extension 72° C., 60 sec

Final Extension 72° C., 5 min

The Denaturation, Annealing and Extension steps were performed 32 cycles for Induced fusion RNA.

3$^{rd}$ round (for FIG. 4D): PCR with TMPRSS2 ex-1 F3 and ETV1 ex-5 R2 on 1 µl of 2$^{nd}$ round, PCR conditions same as 2$^{nd}$ round.

Long Range PCR for Detecting Genomic DNA Fusion Junction

Nested long-range PCRs according to the manufacturer's protocols using LA PCR kit (Takara, #RR002M). 200 ng of genomic DNA was used in each reaction and PCR was performed with annealing and extension at 68° C. for 20 minutes. 1 µl from the above reaction (1st round PCR) was used as template for the 2nd round PCR.

For the genomic breakpoint identified in this manuscript, 1st round long range PCR was done using primers TMPRSS2 genomic bk-F1 and ERG genomic bk-R1 shown in primer list below. 1 µl from the above reaction (1st round PCR) was used as template for the 2nd round PCR using inner primers TMPRSS2 genomic bk-F2 and ERG genomic bk-R2.

Cloning and Sanger Sequencing of Induced Fusion Transcripts

PCR amplified cDNA bands were excised from the gel and eluted using QIAquick Gel Extraction Kit (#28706, Qiagen). The eluted bands were then cloned to pGEM-T vector (pGEM-T vector system I, #A3600) following manufacturer instruction. Sanger sequencing was performed using the service of Beckman Coulter Genomics.

Tm Calculations

Melting temperature (Tm) of putative genomic DNA stems were calculated using the following formula (Rychlik and Rhoads, 1989):

$$Tm(° C.)=4\times(\text{number of } G's \text{ and } C's)+2\times(\text{number of } A's \text{ and } T's)$$

A high energy G·T and A·C wobble pair known to have Watson-Crick like geometry in DNA double helix (Kimsey and Al-Hashimi, 2014; Watson and Crick, 1953) are considered as having the same stability as an A·T pair.

Fluorescent In Situ Hybridization (FISH)

Enriched population carrying TMPRRS2-ETV1 fusion events were first grown on 18 mm round #1 coverglass in a 12-well cell culture plate at the initial density of 200-400 k/well. Cells were then fixed with 4% (vol./vol.) formaldehyde followed by denaturation of DNA with 0.1 N HCl for 5 min and with 70% formamide at 85° C. for 7 min. Hybridization of target DNA with probes were done at 37° C. for 16 hr in a humidified chamber. Cells were then washed, stained with DAPI and imaged with microscope. FISH probes for TMPRSS2 (RP11-35C4, red) and ETV1 (RP11-769K2, green) were purchased from Empire Genomics.

α-Amanitin Assay

Twenty hours prior to transfection, LNCaP cells were seeded in 12-wells plate (BioLite 12 Well Multidish, #130185, Thermo Fisher Scientific) with a density of 5×10$^5$ cells/well and transfection was performed using Turbofect transfection reagent (Thermo Scientific, #R0531) as described earlier. DHT was added at the final concentration of 0.9 µM six hours post transfection. Following overnight incubation, cells were then treated with 4 µg/ml α-amanitin for various time periods (0, 2, 6, 12 and 24 hours). Cells were then revived in fresh medium containing 0.9 µM DHT without α-amanitin and RT-PCR was performed for either TMPRSS2-ERG or TMPRSS2-ETV1 fusion.

Examples of Input RNA Sequences

Sense-1

(SEQ ID NO: 1)

+1tcagatcgcctggagacgccatccacgctgttttgacctccatagaa gacaccgggaccgatccagcctccctcgaagctgatcctgagaacttc aggctcctgggcaacgtgctggtctgtgtgctggcccatcactttggca aagaattcGAGTAGGCGCGAGCTAAGCAGGAGGCGGAGGCGGAGGCGGA

GGGCGAGGGCGGGGAGCGCCGCCTGGAGCGCGGCAGGAAGCCTTATCA

GTTGTGAGTGAGGACCAGTCGTTGTTTGAGTGTGCCTACGGAACGCCAC

ACCTGGCTAAGACAGAGATGACCGCGTCCTCCTCCAGCGACTATGGACA

GACTTCCAAGATGAGCCCACGCGTCCCTCAGCAGGATTGGCTGTCTCAA

CCCCCAGCCAGGGTCACCATCAAAATGGAATGTAACCCTAGCCAGGTGA

ATGGCTCAAGaagcttatcgataccgtcgacctcgagggcccagatcta attcacccaccagtgcaggctgcctatcagaaagtggtggctggtgtg gctaatgccctggcccacaagtatcactaagctcgctttcttgctgtcc aatttctattaaaggttcctttgttccctaagtccaactactaaactgg gggatattatgaagggccttccggagcatctggattctgcctaataaaa aacatttattttcattgcaaaaaa..........a In BOLD CAPS: TMPRSS2 double underline CAPS: ERG +1: Transcription start aataaa: poly(A) signal aaaaaa..........a: poly(A) tail gaattc: EcoRI aagctt: HindIII Sense-2

(SEQ ID NO: 2)

+1tgtgctcgcttcggcagcacatatactaacattggaacgatcctgca gGAGTAGGCGCGAGCTAAGCAGGAGGCGGAGGCGGAGGCGGAGGGCGAG

GGGCGGGGAGCGCCGCCTGGAGCGCGGCAGGAAGCCTTATCAGTTGTGA

GTGAGGACCAGTCGTTGTTTGAGTGTGCCTACGGAACGCCACACCTGGC

TAAGACAGAGATGACCGCGTCCTCCTCCAGCGACTATGGACAGACTTCC

AAGATGAGCCCACGCGTCCCTCAGCAGGATTGGCTGTCTCAACCCCCAG

CCAGGGTCACCATCAAAATGGAATGTAACCCTAGCCAGGTGAATGGCTC

AAG

In BOLD CAPS: TMPRSS2 double underline CAPS: ERG +1: Transcription start ctgcag: PstI
Sense-2 Long (SEQ ID NO: 3)
+1tgtgctcgcttcggcagcacatatactaacattggaacgatcctgca gGAGTAGGCGCGAGCTAAGCAGGAGGCGGAGGCGGAGGCGGAGGGCGAG

GGGGGGGAGCGCCGCCTGGAGCGCGGCAGGAAGCCTTATCAGTTGTGAG

TGAGGACCAGTCGTTGTTTGAGTGTGCCTACGGAACGCCACACCTGGCT

AAGACAGAGATGACCGCGTCCTCCTCCAGCGACTATGGACAGACTTCCA

AGATGAGCCCACGCGTCCCTCAGCAGGATTGGCTGTCTCAACCCCCAGC

CAGGGTCACCATCAAAATGGAATGTAACCCTAGCCAGGTGAATGGCTCA

AGGAACTCTCCTGATGAATGCAGTGTGGCCAAAGGCGGGAAGATGGTGG

GCAGCCCAGACACCGTTGGGATGAACTACGGCAGCTACATGGAGGAGAA

GCACATGCCACCCCAAACATGACCACGAACGAGCGCAGAGTTATCGTG

CCAGCAGATCCTACGCTATGGAGTACAGACCATGTGCGGCAGTGGCTGG

AGTGGGCGGTGAAAGAATATGGCCTTCCAGACGTCAACATCTTGTTATT

CCAGAACATCGATGGGAAGGAACTGTGCAAGATGACCAAGGACGACTTC

CAGAGGCTCACCCCCAGCTACAACGCCGACATCCTTCTCTCACATCTCC

ACTACCTCAGAGAGACTCCTCTTCCACATTTGACTTCAGATGATGTTGA

TAAAGCCTTA

BOLD CAPS: TMPRSS2 double underline CAPS: ERG +1: Transcription start ctgcag: PstI
Antisense-1

(SEQ ID NO: 4)
+1tcagatcgcctggagacgccatccacgctgttttgacctccatagaa gacacegggaccgatccagcctccctcgaagctgatcctgagaacttc aggctcctgggcaacgtgctggtctgtgtgctggccatcactttggca aagaattcCTTGAGCCATTCACCTGGCTAGGGTTACATTCCATTTTGAT

GGTGACCCTGGCTGGGGGTTGAGACAGCCAATCCTGCTGAGGGACGCGT

GGGCTCATCTTGGAAGTCTGTCCATAGTCGCTGGAGGAGGACGCGGTCA

TCTCTGTCTTAGCCAGGTGTGGCGTTCCGTAGGCACACTCAAACAACGA

CTGGTCCTCACTCACAACTGATAAGGCTTCCTGCCGCGCTCCAGGCGGC

GCTCCCCGCCCCTCGCCCTCCGCCTCCGCCTCCGCCTCCTGCTTAGCTC

GCGCCTACTCaagcttatcgataccgtcgacctcgagggcccagatcta attcacccaccagtgcaggctgcctatcagaaagtggtggctggtgtg gctaatgccctggcccacaagtatcactaagctcgctttcttgctgtcc aatttctattaaaggttcctttgttccctaagtccaactactaaactgg gggatattatgaagggccttccggagcatctggattctgctaataaaa aacatttattttcattgaaaaaa..........a:

BOLD CAPS: TMPRSS2 double underline CAPS: ERG +1: Transcription start aataaa: poly(A) signal aaaaaa.........a: poly(A) tail gaattc: EcoRI aagctt: HindIII
Antisense-2

(SEQ ID NO: 5)
+1tgtgctcgcttcggcagcacatatactaacattggaacgatcctgca gCTTGAGCCATTCACCTGGCTAGGGTTACATTCCATATTGATGGTGACC

CTGGCTGGGGGTTGAGACAGCCAATCCTGCTGAGGGACGCGTGGGCTCA

TCTTGGAAGTCTGTCCATAGTCGCTGGAGGAGGACGCGGTCATCTCTGT

CTTAGCCAGGTGTGGCGTTCCGTAGGCACACTCAAACAACGACTGGTCC

TCACTCACAACTGATAAGGCTTCCTGCCGCGCTCCAGGCGGCGCTCCCC

GCCCCTCGCCCTCCGCCTCCGCCTCCGCCTCCTGCTTAGCTCGCGCCTA

CTC

BOLD CAPS: TMPRSS2 double underline CAPS: ERG +1: Transcription start
BOLD CAP and double underline A: T to A change to inactivate the cryptic transcription termination by U6 promoter ctgcag: PstI
Antisense-3

(SEQ ID NO: 6)
+1tgtgctcgcttcggcagcacatatactaacattggaacgatcctgca gCTTGAGCCATTCACCTGGCTAGGGTTACATTCCATATTGATGGTGACC

CTGGCTGGGGGTTGAGACAGCCAATCCCGGACCCCGAGCCGGGACCCTG

GTACCGGCGCCGCTCACCTGCCGCGCTCCAGGCGGCGCTCCCCGCCCCT

CGCCCTCCGCCagacaggagtgagagatggaagctcgcgcctactc

BOLD CAPS: TMPRSS2 double underline CAPS: ERG G: Mutated region of TMPRSS2 +1: Transcription start A: T to A change to inactivate the cryptic transcription termination by U6 promoter ctgcag: PstI
Antisense-4

(SEQ ID NO: 7)
+1tgtgctcgcttcggcagcacatatactaacattggaacgatcctgca gCTTGAGCCATTCACCTGGCTAGGGTTACATTCCATATTGATGGTGACC

CTGGCTGGGGGTTGAGACAGCCAATCCGACCCTGGTACCGGCGCCGCTC

ACCTGCCGCGCTCCAGGCGGCGCTCCCCGCCCCTCGCCCTCCGCCagac aggagtgagagatggaagctcgcgcctactc BOLD CAPS: TMPRSS2 double underline CAPS: ERG G: Mutated region of TMPRSS2 +1: Transcription start
BOLD CAP and double underline A: T to A change to inactivate the cryptic transcription termination by U6 promoter ctgcag: PstI
Antisense-5

(SEQ ID NO: 8)
+1tgtgctcgcttcggcagcacatatactaacattggaacgatcctgca gCTTGAGCCATTCACCTGGCTAGGGTTACATTCCATATTGATGGTGACC

CTGGCTGGGGGTTGAGACAGCCAATCCGCCGCTCACCTGCCGCGCTCCA

```
GGCGGCGCTCCCCGCCCCTCGCCCTCCGCCagacaggagtgagagatgg aagctcgcgcctactc
```

BOLD CAPS: TMPRSS2 double underline CAPS: ERG lower case bold: Mutated region of TMPRSS2 +1: Transcription start BOLD CAP and double underline A: T to A change to inactivate the cryptic transcription termination by U6 promoter
ctgcag: PstI
Antisense-6

(SEQ ID NO: 9)
```
+1tgtgctcgcttcggcagcacatatactaacattggaacgatcctgca gCTTGAGCCATTCACCTGGCTAGGGTTACATTCCATATTGATGGTGACC

CTGGCTGGGGGTTGAGACAGCCAATCCCCAGGCGGCGCTCCCCGCCCCT

CGCCCTCCGCCagacaggagtgagagatggaagctcgcgcctactc
```

BOLD CAPS: TMPRSS2 double underline CAPS: ERG lower case bold: Mutated region of TMPRSS2 +1: Transcription start BOLD CAP and double underline A: T to A change to inactivate the cryptic transcription termination by U6 promoter ctgcag: PstI
Antisense-7

(SEQ ID NO: 10)
```
+1tgtgctcgcttcggcagcacatatactaacattggaacgatcctgca gCTTGAGCCATTCACCTGGCTAGGGTTACATTCCATATTGATGGTGACC

CTGGCTGGGGGTTGAGACAGCCAATCCCGGACCCCGAGCCGGGACCCTG

GTACCGGCGCCGCTCACCTGCCGCGCTCCAagacaggagtgagagatgg aagctcgcgcctactc
```

BOLD CAPS: TMPRSS2 double underline CAPS: ERG lower case bold: Mutated region of TMPRSS2 +1: Transcription start BOLD CAP and double underline A: T to A change to inactivate the cryptic transcription termination by U6 promoter ctgcag: PstI
Antisense-8

(SEQ ID NO: 11)
```
+1tgtgctcgcttcggcagcacatatactaacattggaacgatcctgca gCTTGAGCCATTCACCTGGCTAGGGTTACATTCCATATTGATGGTGACC

CTGGCTGGGGGTTGAGACAGCCAATCCCCAGGTTCCCCTCCCCAGCCCG

GACCCCGAGCCGGGACCCTGGTACCGGCGCagacaggagtgagagatgg aagctcgcgcctactc
```

BOLD CAPS: TMPRSS2 double underline CAPS: ERG lower case bold: Mutated region of TMPRSS2 +1: Transcription start BOLD CAP and double underline A: T to A change to inactivate the cryptic transcription termination by U6 promoter ctgcag: PstI
Antisense-9

(SEQ ID NO: 12)
```
+1tgtgctcgcttcggcagcacatatactaacattggaacgatcctgca gGAGACAGCCAATCCTGCTGAGGGACGCGTGGGCTCATCTTGGAAGTCT

GTCCATAGTCGCTGGAGGAGGACGCGGGCCGCTCACCTGCCGCGCTCCA

GGCGGCGCTCCCCGCCCCTCGCCCTCCGCCagacaggagtgagagatgg aagctcgcgcctactc
```

BOLD CAPS: TMPRSS2 double underline CAPS: ERG lower case bold: Mutated region of TMPRSS2 +1: Transcription start ctgcag: PstI
Antisense-5A (SEQ ID NO: 13)
```
+1tgtgctcgcttcggcagcacatatactaacattggaacgatcctgca gGCCGCTCACCTGCCGCGCTCCAGGCGGCGCTCCCCGCCCCTCGCCCTC CGCCagacaggagtgagagatggaagctcgcgcctactc
```

BOLD CAPS: TMPRSS2 G: Mutated region of TMPRSS2 +1: Transcription start ctgcag: PstI
Antisense-5B (SEQ ID NO: 14)
```
+1tgtgctcgcttcggcagcacatatactaacattggaacgatcctgca gCTTGAGCCATTCACCTGGCTAGGGTTACATTCCATATTGATGGTGACC

CTGGCTGGGGGTTGAGACAGCCAATCC
``` double underline CAPS: ERG +1: Transcription start ctgcag: PstI BOLD CAP and double underline A: T to A change to inactivate the cryptic transcription termination by U6 promoter
Antisense-B1

(SEQ ID NO: 15)
```
+1tgtgctcgcttcggcagcacatatactaacattggaacgatcctgca gTGGCCTGAGCCTTGAAGAATGGGGTGTACTGGGTAAATCAAAATGGTG

GGGAGCATTTCCAGATGGAGAAACTGCCTCACCTGCCGCGCTCCAGGCG

GCGCTCCCCGCCCCTCGCCCTCCGCCTCCG
```

BOLD CAPS: TMPRSS2 double underline CAPS: ERG +1: Transcription start ctgcag: PstI
Antisense-B2

(SEQ ID NO: 16)
```
+1tgtgctcgcttcggcagcacatatactaacattggaacgatcctgca gTGGCCTGAGCCTTGAAGAATGGGGTGTACTGGGTAAATCAAAATGGTG

GGGAGCATTTCCAGATGGAGAAACTGCCCCTCCCCAGCCCGGACCCCGA

GCCGGGACCCTGGTACCGGCGCCGCTCACC
```

BOLD CAPS: TMPRSS2 double underline CAPS: ERG +1: Transcription start ctgcag: PstI
Antisense-B3

(SEQ ID NO: 17)
```
+1tgtgctcgcttcggcagcacatatactaacattggaacgatcctgca gTGGGGAGCATTTCCAGATGGAGAAACTGCAAGGAAAAGCATAGAAGTG

GGGCCACCCCTCGTGAGCTGGGGAGGGCTCACCTGCCGCGCTCCAGGCG

GCGCTCCCCGCCCCTCGCCCTCCGCCTCCG
```

BOLD CAPS: TMPRSS2 double underline CAPS: ERG
+1: Transcription start ctgcag: PstI
Antisense-C1

(SEQ ID NO: 18)
+1tgtgctcgcttcggcagcacatatactaacattggaacgatctgca gTGAGCTCATGCTATTCCTATGACATAGATGAGCACTGGGTAGACCCCG

TCCTGGTAACACTATTCATGCACTAACCCCAGGCGGGGGCCGTGGAGGG

CAGGCGGACTAGGAGCCAGCTTTGGGGACC

BOLD CAPS: TMPRSS2 double underline CAPS: ERG
+1: Transcription start BOLD CAP and double underline A:
T to A change to inactivate the cryptic transcription termination by U6 promoter ctgcag: PstI
Antisense-C2

(SEQ ID NO: 19)
+1tgtgctcgcttcggcagcacatatactaacattggaacgatctgca gTGAGCTCATGCTATTCCTATGACATAGATGAGCACTGGGTAGACCCCG

TCCTGGTAACACTATTCATGCACTAACCAGCACTCCCAGTCCTCCTCCC

CAAAGAGAAAAGGCGCACCGGTGCTCCCAG

BOLD CAPS: TMPRSS2 double underline CAPS: ERG
+1: Transcription start BOLD CAP and double underline A:
T to A change to inactivate the cryptic transcription termination by U6 promoter ctgcag: PstI
Antisense-C3

(SEQ ID NO: 20)
+1tgtgctcgcttcggcagcacatatactaacattggaacgatctgca gGTCCTGGTAACACTATTCATGCACTAACAAGTTGGTTGCCAGTGAGAC

TTGATTATTATGACTCTGGGAGTGCTGCCCAGGCGGGGGCCGTGGAGGG

CAGGCGGACTAGGAGCCAGCTTTGGGGACC

BOLD CAPS: TMPRSS2 double underline CAPS: ERG
+1: Transcription start BOLD CAP and double underline A:
T to A change to inactivate the cryptic transcription termination by U6 promoter ctgcag: PstI
Antisense-D1

(SEQ ID NO: 21)
+1tgtgctcgcttcggcagcacatatactaacattggaacgatctgca gGAGAGACAGAGAGAGAGAGGCTGGTAGAGGGAAGAGACAGAAGAAAGA

TGAAGGGATAAGTGTCCAGAATCCCTGAGCGCTCGACCCTCGGGCGCAC

TCACCTGCCGCGCCGCGCTCCTCACACCCG

BOLD CAPS: TMPRSS2 double underline CAPS: ERG
+1: Transcription start ctgcag: PstI
Antisense-D2

(SEQ ID NO: 22)
+1tgtgctcgcttcggcagcacatatactaacattggaacgatctgca gGAGAGACAGAGAGAGAGAGGCTGGTAGAGGGAAGAGACAGAAGAAAGA

TGAAGGGATAAGTGTCCAGAATCCCTGCCCAGCACTCTCCCAGCACCCC

GGGAGGCGCCCTGCCCGGCTGGCCCCAGCG

BOLD CAPS: TMPRSS2 double underline CAPS: ERG
+1: Transcription start ctgcag: PstI
Antisense-D3

(SEQ ID NO: 23)
+1tgtgctcgcttcggcagcacatatactaacattggaacgatctgca gTGAAGGGATAAGTGTCCAGAATCCCTGGATCTGGGATGGAATAAAGGA

TCTGGATGGTAAACGGAGAGTGCTGGGAGCGCTCGACCCTCGGGCGCAC

TCACCTGCCGCGCCGCGCTCCTCACACCCG

BOLD CAPS: TMPRSS2 double underline CAPS: ERG
+1: Transcription start ctgcag: PstI
Antisense-E1

(SEQ ID NO: 24)
+1tgtgctcgcttcggcagcacatatactaacattggaacgatctgca gAGGGTATTCAGTATTACTATTTGGCTTAGATAAGCTGGTAGTTACTTG

CTAAAATTAATCTTTATTATAAAGCAGAAAGCCGCATTCTGACATCACT

CTCCATGGACAAAGATTCTTCGCTTGATCA

BOLD CAPS: TMPRSS2 double underline CAPS: ERG
+1: Transcription start BOLD CAP and double underline A:
T to A change to inactivate the cryptic transcription termination by U6 promoter ctgcag: PstI
Antisense-F1

(SEQ ID NO: 25)
+1tgtgctcgcttcggcagcacatatactaacattggaacgatctgca gAATGGATGAATACATAAAATAAATTGTGGTGGATATATACAACGGAAT

ATCATTTAGCCTTTATTATTATTGAGAACTGTGCCGAGCCGGGCAGGAC

AGGATGAGGTGGACCGAAGCGCCCAGGTGC

BOLD CAPS: TMPRSS2 double underline CAPS: ERG
+1: Transcription start BOLD CAP and double underline A:
T to A change to inactivate the cryptic transcription termination by U6 promoter ctgcag: PstI
Antisense-G1

(SEQ ID NO: 26)
+1tgtgctcgcttcggcagcacatatactaacattggaacgatctgca gTTTATTCATGAGAAAATTCTGGCACAATGGAAAACCCTGGCAAGCAAA

AGATAGGGGCAGCAGATGTCCTGGCCTACAAAGAACTCCAAGCCCATCG

TCCCTAGAAAGCATGGTCTCCCATGACCCC

BOLD CAPS: TMPRSS2 double underline CAPS: ERG
+1: Transcription start ctgcag: PstI
Sense-3

(SEQ ID NO: 27)
+1tgtgctcgcttcggcagcacatatactaacattggaacgatctgca ggagtaggcgcgagcttccatctctcactcctgtctGGCGGAGGGCGAG

GGGCGGGGAGCGCCGCCTGGAGCGCGGCAGGTGAGCGGCGCCGGTACCA

GGGTCCCGGCTCGGGGTCCGGGATTGGCTGTCTCAACCCCCAGCCAGGG

TCACCATCAAAATGGAATGTAACCCTAGCCAGGTGAATGGCTCAAG

BOLD CAPS: TMPRSS2 double underline CAPS: ERG
Bold lower case: Mutated region of TMPRSS2 +1: Transcription start ctgcag: PstI
Sense-4

(SEQ ID NO: 28)
<u>+1</u>tgtgctcgcttcggcagcacatatactaacattggaacgat<u>ctgca</u> ggagtaggcgcgagcttccatctctcactcctgtctGGCGGAGGGCGAG

GGGCGGGGAGCGCCGCCTGGAGCGCGGCAGGTGAGCGGCGCCGGTACCA

GGGTC<u>GGATTGGCTGTCTCAACCCCCAGCCAGGGTCACCATCAATATGG</u>

<u>AATGTAACCCTAGCCAGGTGAATGGCTCAAG</u>

BOLD CAPS: TMPRSS2 double underline CAPS: ERG
Bold lower case: Mutated region of TMPRSS2 +1: Transcription start ctgcag: PstI
Sense-5

(SEQ ID NO: 29)
<u>+1</u>tgtgctcgcttcggcagcacatatactaacattggaacgat<u>ctgca</u> ggagtaggcgcgagcttccatctctcactcctgtctGGCGGAGGGCGAG

GGGCGGGGAGCGCCGCCTGGAGCGCGGCAGGTGAGCGGC<u>GGATTGGCTG</u>

<u>TCTCAACCCCCAGCCAGGGTCACCATCAAAATGGAATGTAACCCTAGCC</u>

<u>AGGTGAATGGCTCAAG</u>

BOLD CAPS: TMPRSS2 double underline CAPS: ERG
Bold lower case: Mutated region of TMPRSS2 +1: Transcription start ctgcag: PstI
Sense-6

(SEQ ID NO: 30)
<u>+1</u>tgtgctcgcttcggcagcacatatactaacattggaacgat<u>ctgca</u> ggagtaggcgcgagcttccatctctcactcctgtctGGCGGAGGGCGAG

GGGCGGGGAGCGCCGCCTGG<u>GGATTGGCTGTCTCAACCCCCAGCCAGGG</u>

<u>TCACCATCAAAATGGAATGTAACCCTAGCCAGGTGAATGGCTCAAG</u>

BOLD CAPS: TMPRSS2 double underline CAPS: ERG
bold lower case: Mutated region of TMPRSS2 +1: Transcription start ctgcag: PstI
Sense-B1

(SEQ ID NO: 31)
<u>+1</u>tgtgctcgcttcggcagcacatatactaacattggaacgat<u>ctgca</u> g<u>CGGAGGCGGAGGGCGAGGGCGGGAGCGCCGCCTGGAGCGCGGCAGG</u>

<u>TGAG</u>GCAGTTTCTCCATCTGGAAATGCTCCCCACCATATTGATTTACCC

<u>AGTACACCCCATTCTTCAAGGCTCAGGCCA</u>

BOLD CAPS: TMPRSS2 double underline CAPS: ERG
+1: Transcription start BOLD CAP and double underline A:
T to A change to inactivate the cryptic transcription termination by U6 promoter ctgcag: PstI
Sense-C1

(SEQ ID NO: 32)
<u>+1</u>tgtgctcgcttcggcagcacatatactaacattggaacgat<u>ctgca</u> g<u>GGTCCCCAAAGCTGGCTCCTAGTCCGCCTGCCCTCCACGGCCCCCGCC</u>

TGGG<u>GTTAGTGCATGAAGAGTGTTACCAGGACGGGGTCTACCCAGTGCT</u>

<u>CATCTATGTCATAGGAAGAGCATGAGCTCA</u>

BOLD CAPS: TMPRSS2 double underline CAPS: ERG
+1: Transcription start ctgcag: PstI
Sense-D1

(SEQ ID NO: 33)
<u>+1</u>tgtgctcgcttcggcagcacatatactaacattggaacgat<u>ctgca</u> g<u>C</u>GGGTGTGAGGAGCGCGGCGCGGCAGGTGAGTGCGCCCGAGGGTCGAG

<u>CGCT</u>CAGGGATTCTGGACACTTATCCCTTCATCTTTCTTCTGTCTCTTC

CCTCTACCAGCCTCTCTCTCTCTGTCTCTC

BOLD CAPS: TMPRSS2 double underline CAPS: ERG
+1: Transcription start promoter ctgcag: PstI
Antisense-TMPRSS2-ETV1-A1

(SEQ ID NO: 34)
<u>+1</u>tgtgctcgcttcggcagcacatatactaacattggaacgat<u>ctgca</u> g<u>TGCCGCATTATGTAAATCGTTCCAAGTTAAAGTCTTAGTTAGATTCAG</u>

<u>TA</u>GACTAGGAGCCAGCTTTGGGGACCCCGGGGGACTCTCTTCCACCAAC

TGG

BOLD CAPS: TMPRSS2 double underline CAPS: ETV1
+1: Transcription start ctgcag: PstI
Antisense-TMPRSS2-ETV1-B1

(SEQ ID NO: 35)
<u>+1</u>tgtgctcgcttcggcagcacatatactaacattggaacgat<u>ctgca</u> g<u>GATTCAGTAATTTCAAAGTTTATTATATTTAAGATAAGACTGAAGTGC</u>

<u>TC</u>AACAAACTTAGTCTCACTTTAGGTATTCCAAATGCCTTGTAACTGGG

CTG

BOLD CAPS: TMPRSS2 double underline CAPS: ETV1
+1: Transcription start BOLD CAP and double underline A:
T to A change to inactivate the cryptic transcription termination by U6 promoter ctgcag: PstI
Antisense-TMPRSS2-ETV1-C1

(SEQ ID NO: 36)
<u>+1</u>tgtgctcgcttcggcagcacatatactaacattggaacgat<u>ctgca</u> g<u>CTCTGAATAGAAAAATAGAAGTCCATAGTATCAACTCTAATATTCATA</u>

<u>TTT</u>GGCTGCATCCCCACTTCCTGGAGTACCTTCCCAGATCTCCTGGGAC

AGG

BOLD CAPS: TMPRSS2 double underline CAPS: ETV1
+1: Transcription start BOLD CAP and double underline A:
T to A change to inactivate the cryptic transcription termination by U6 promoter ctgcag: PstI
Antisense-TMPRSS2-ETV1-D1

(SEQ ID NO: 37)
<u>+1</u>tgtgctcgcttcggcagcacatatactaacattggaacgat<u>ctgca</u> g<u>ATATAAACAAAAAGTGTCAGCATTTGTCTCAACTTCATTCTATTCAAT</u>

-continued

<u>GT</u>AAGGCCCTTTGCGCTGGTAAACTCTCCCTGCCACACTCCCAACCCCC

ATC

BOLD CAPS: TMPRSS2 double underline CAPS: ETV1
+1: Transcription start ctgcag: PstI
Antisense-TMPRSS2-ETV1-E1

(SEQ ID NO: 38)

+1tgtgctcgcttcggcagcacatatactaacattggaacgatcctgca g<u>CTCTGAATAGAAAAATAGAAGTCCATAGTATCAACTCTAATATTCATA</u>

<u>TTCTTCAGCAACCAAAACTGAACAAGCACTCCATTGACCATTCACCTTT</u>

CCT

BOLD CAPS: TMPRSS2 double underline CAPS: ETV1
+1: Transcription start BOLD CAP and double underline A:
T to A change to inactivate the cryptic transcription termination by U6 promoter ctgcag: PstI
Antisense-TMPRSS2-ETV1-F1

(SEQ ID NO: 39)

+1tgtgctcgcttcggcagcacatatactaacattggaacgatcctgca g<u>AGGAGGCCTTAAGTATGATTCAGTGAACACATTATGGTCGATAAACAA</u>

<u>GGTGGGCCCCATTCTCAGAGTCTGATGTAATAATTGGGACCAAGGCAAT</u>

GA

BOLD CAPS: TMPRSS2 double underline CAPS: ETV1
+1: Transcription start ctgcag: PstI
Antisense-TMPRSS2-ETV1-G1

(SEQ ID NO: 40)

+1tgtgctcgcttcggcagcacatatactaacattggaacgatcctgca gTGTAATTGACTTAGATCTTGAAAGAGTTCTAAAAAACAAGTCAAAGAC

ATCTAGAAGAATCTCTAGATGAAGGTTACCTACAACAAAGACCAGTGTT

GCC

BOLD CAPS: TMPRSS2 double underline CAPS: ETV1
+1: Transcription start ctgcag: PstI
Antisense-TMPRSS2-ETV1-Hi (SEQ ID NO: 41)

+1tgtgctcgcttcggcagcacatatactaacattggaacgatcctgca g<u>TTAACAAACAGCTTAATAAATAAGCTCAGGGATACCAGAATTCACAAA</u>

<u>AA</u>GAAGCACTCTCCTCTGGGATCAGAGTGGGTAGGAGGATGGGGTGCAA

TTG

BOLD CAPS: TMPRSS2 double underline CAPS: ETV1
+1: Transcription start ctgcag: PstI
Sense-TMPRSS2-ETV1-A1

(SEQ ID NO: 42)

+1tgtgctcgcttcggcagcacatatactaacattggaacgatcctgca gCCAGTTGGTGGAAGAGAGTCCCCCGGGGTCCCCAAAGCTGGCTCCTAG

TC<u>TACTGAATCTAACTAAGACTTTAACTTGGAACGATTTACATAATGCG</u>

<u>GCA</u>

BOLD CAPS: TMPRSS2 double underline CAPS: ETV1
+1: Transcription start ctgcag: PstI
List of Primers Used
RT-PCR primers for amplifying induced fusion RNAs:

| Induced fusion RNA (TMPRSS2 ex1-ERG ex7 |
|---|
| TMPRSS2 ex-1 F1   5'-TAGGCGCGAGCTAAGCAGGAG-3' (SEQ ID NO: 43) |
| ERG ex-7 R1      5'-TAGCATGCATTAACCGTGGAGA-3' (SEQ ID NO: 44) |
| Induced fusion RNA (TMPRSS2 ex1-ERG ex4) |
| TMPRSS2 ex-1 F1   5'-TAGGCGCGAGCTAAGCAGGAG-3' (SEQ ID NO: 45) |
| ERG ex-4 R1      5'-CTTGAGCCATTCACCTGGCTAG-3' (SEQ ID NO: 46) |
| Induced fusion RNA (TMPRSS2 ex1-ETV ex5) |
| TMPRSS2 ex-1 F1   5'-TAGGCGCGAGCTAAGCAGGAG-3' (SEQ ID NO: 47) |
| ETV1 ex-6 R1     5'-TTCTTGACTGCAGGCAGAGCT-3' (SEQ ID NO: 48) |
| TMPRSS2 ex-1 F2   5'-CAGGAGGCGGAGGCGGA-3' (SEQ ID NO: 49) |
| ETV1 ex-5 R1     5'-CTTTCAGCCTGATAGTCTGGT-3' (SEQ ID NO: 50) |
| TMPRSS2 ex-1 F3   5'-CGGAGGGCGAGGGGGGGGA-3' (SEQ ID NO: 51) |
| ETV1 ex-5 R2     5'-AACTGCTCATCATTGTCAGGT-3' (SEQ ID NO: 52) |

Primers used in three-round PCR for amplifying induced fusion RNAs:

| 1st round PCR | |
| --- | --- |
| TMPRSS2 ex-1 F1 | 5'-TAGGCGCGAGCTAAGCAGGAG-3' (SEQ ID NO: 53) |
| ERG ex-4 R1 | 5'-CTTGAGCCATTCACCTGGCTAG-3' (SEQ ID NO: 54) |
| 2nd round PCR | |
| TMPRSS2 ex-1 F2 | 5'-CAGGAGGCGGAGGCGGA-3' (SEQ ID NO: 55) |
| ERG ex-4 R2 | 5'-TGACCCTGGCTGGGGGTTGAGA-3' (SEQ ID NO: 56) |
| 3rd round PCR | |
| TMPRSS2 ex-1 F3 | 5'-CGGAGGGCGAGGGGGGGGGA-3' (SEQ ID NO: 57) |
| ERG ex-4 R3 | 5'-TCCTGCTGAGGGACGCGTGG-3' (SEQ ID NO: 58) |

RT-PCR primers for amplifying endogenous parental mRNAs:

| TMPRSS2 parental mRNA (TMPRSS2 ex2-TMPRSS2 ex4) | |
| --- | --- |
| TMPRSS2 ex-2 F1 | 5'-GTCATATTGAACATTCCAGA-3' (SEQ ID NO: 59) |
| TMPRSS2 ex-4 R1 | 5'-GCGCAGCTCCCACGAGGAAGGT-3' (SEQ ID NO: 60) |
| ERG parental mRNA (ERG ex3-ERG ex7): one-round PCR | |
| ERG ex-3 F1 | 5'-CAGGTTCTGAACAGCTGGTA-3' (SEQ ID NO: 61) |
| ERG ex-7 R1 | 5'-TAGCATGCATTAACCGTGGAGA-3' (SEQ ID NO: 62) |
| ERG ex-1 F1 | 5'-CCCCCGAGGGACATGAGAGAA-3' (SEQ ID NO: 63) |
| ERG ex-4 R1 | 5'-TGGGGGTTGAGACAGCCAAT-3' (SEQ ID NO: 64 |
| ERG parental mRNA (ERG ex3-ERG ex7): three-round PCR | |
| ERG ex-3 F1 | 5'-CAGGTTCTGAACAGCTGGTA-3' (SEQ ID NO: 65) |
| ERG ex-7 R1 | 5'-TAGCATGCATTAACCGTGGAGA-3' (SEQ ID NO: 66) |
| ERG ex-3 F2 | 5'-TGGGCTGGCTTACTGAAGGA-3' (SEQ ID NO: 67) |
| ERG ex-7 R2 | 5'-TTGTAAGGCTTTATCAACAT-3' (SEQ ID NO: 68) |
| ERG ex-3 F3 | 5'-ATGATTCAGACTGTCCCGGA-3' (SEQ ID NO: 69) |
| ERG ex-7 R3 | 5'-CATCTGAAGTCAAATGTGGA-3' (SEQ ID NO: 70) |
| ERG parental mRNA (ERG ex1-ERG ex4): three-round PCR | |
| ERG ex-1 F1 | 5'-CCCCCGAGGGACATGAGAGAA-3' (SEQ ID NO: 71) |
| ERG ex-4 R1 | 5'-TGGGGGTTGAGACAGCCAAT-3' (SEQ ID NO: 72) |
| ERG ex-1 F2 | 5'-AGGGACATGAGAGAAGAGGA-3' (SEQ ID NO: 73) |
| ERG ex-4 R2 | 5'-TGAGGGACGCGTGGGCTCAT-3' (SEQ ID NO: 74) |
| ERG ex-1 F3 | 5'-GAGAGAAGAGGAGCGGCGCT-3' (SEQ ID NO: 75) |
| ERG ex-4 R3 | 5'-CTTGGAAGTCTGTCCATAGT-3' (SEQ ID NO: 76) |

RT-PCR primers for amplifying BCAM-AKT2 chimeric RNA:

1st round PCR

| | |
|---|---|
| BCAM-AKT2 F1 | 5'-GTGAGCAGCTCTCTGACCCTGA-3' (SEQ ID NO: 77) |
| BCAM-AKT2 R1 | 5'-CGCACCAGGATGACTTTGCCA-3' (SEQ ID NO: 78) |

2nd round PCR

| | |
|---|---|
| BCAM-AKT2 F2 | 5'-TGTCTTCTACTGCGTGAGACGCA-3' (SEQ ID NO: 79) |
| BCAM-AKT2 R2 | 5'-TCTCCTCAGTCGTGGAGGAGT-3' (SEQ ID NO: 80) |

RT-PCR primers for amplifying input RNAs:

Sense-1

| | |
|---|---|
| Sense 1 F1 | 5'-ACGGAATTCGAGTAGGCGCGAGCTAAGCA-3' (SEQ ID NO: 81) |
| Sense 1 R1 | 5'-TAGAAGCTTCTTGAGCCATTCACCTGGCT-3' (SEQ ID NO: 82) |

Sense-2

| | |
|---|---|
| Sense 2 F1 | 5'-ACGCTGCAGGAGTAGGCGCGAGCTAAGCA-3' (SEQ ID NO: 83) |
| Sense 2 R1 | 5'-TAGAAGCTTAAAAAACTTGAGCCATTCACCTGGCT-3' (SEQ ID NO: 84) |

Sense-2 long

| | |
|---|---|
| Sense 2 long F1 | 5'-ACGCTGCAGGAGTAGGCGCGAGCTAAGCA-3' (SEQ ID NO: 85) |
| Sense 2 long R1 | 5'-TAGAAGCTTAAAAAATAAGGCTTTATCAACATCAT-3' (SEQ ID NO: 86) |

Antisense-1

| | |
|---|---|
| Antisense 1 F1 | 5'-ACGGAATTCCTTGAGCCATTCACCTGGCT-3' (SEQ ID NO: 87) |
| Antisense 1 R1 | 5'-TAGAAGCTTGAGTAGGCGCGAGCTAAGCA-3' (SEQ ID NO: 88) |

Antisense-2

| | |
|---|---|
| Antisense 2 F1 | 5'-ACGCTGCAGCTTGAGCCATTCACCTGGCTAGGGTT-3' (SEQ ID NO: 89) |
| Antisense 2 R1 | 5'-TAGAAGCTTAAAAAAGAGTAGGCGCGAGCTAAGCA-3' (SEQ ID NO: 90) |

Antisense-3

| | |
|---|---|
| Antisense 3 F1 | 5'-ACGCTGCAGCTTGAGCCATTCACCTGGCTAGGGTT-3' (SEQ ID NO: 91) |
| Antisense 3 R1 | 5'-TAGAAGCTTAAAAAAGAGTAGGCGCGAGCTTCCAT-3' (SEQ ID NO: 92) |

Antisense-4

| | |
|---|---|
| Antisense 4 F1 | 5'-ACGCTGCAGCTTGAGCCATTCACCTGGCTAGGGTT-3' (SEQ ID NO: 93) |
| Antisense 4 R1 | 5'-TAGAAGCTTAAAAAAGAGTAGGCGCGAGCTTCCAT-3' (SEQ ID NO: 94) |

Antisense-5

| | |
|---|---|
| Antisense 5 F1 | 5'-ACGCTGCAGCTTGAGCCATTCACCTGGCTAGGGTT-3' (SEQ ID NO: 95) |
| Antisense 5 R1 | 5'-TAGAAGCTTAAAAAAGAGTAGGCGCGAGCTTCCAT-3' (SEQ ID NO: 96) |

Antisense-6

| | |
|---|---|
| Antisense 6 F1 | 5'-ACGCTGCAGCTTGAGCCATTCACCTGGCTAGGGTT-3' (SEQ ID NO: 97) |
| Antisense 6 R1 | 5'-TAGAAGCTTAAAAAAGAGTAGGCGCGAGCTTCCAT-3' (SEQ ID NO: 98) |

Antisense-7

| | |
|---|---|
| Antisense 7 F1 | 5'-ACGCTGCAGCTTGAGCCATTCACCTGGCTAGGGTT-3' (SEQ ID NO: 99) |
| Antisense 7 R1 | 5'-TAGAAGCTTAAAAAAGAGTAGGCGCGAGCTTCCAT-3' (SEQ ID NO: 100) |

Antisense-8

| | |
|---|---|
| Antisense 8 F1 | 5'-ACGCTGCAGCTTGAGCCATTCACCTGGCTAGGGTT-3' (SEQ ID NO: 101) |
| Antisense 8 R1 | 5'-TAGAAGCTTAAAAAAGAGTAGGCGCGAGCTTCCAT-3' (SEQ ID NO: 102) |

-continued

| Antisense-9 | |
|---|---|
| Antisense 9 F1 | 5'-ACGCTGCAGGAGACAGCCAATCCTGCTGAGGGACGCGTGGGC-3' (SEQ ID NO: 103) |
| Antisense 9 R1 | 5'-TAGAAGCTTAAAAAAGAGTAGGCGCGAGCTTCCAT-3' (SEQ ID NO: 104) |
| Antisense-5A | |
| Antisense 5A F1 | 5'-TAGAAGCTTAAAAAAGAGTAGGCGCGAGCTTCCAT-3' (SEQ ID NO: 105) |
| Antisense 5A R1 | 5'-TAGCTGCAGGCCGCTCACCTGCCGCGCTCC-3' (SEQ ID NO: 106) |
| Antisense-5B | |
| Antisense 5B F1 | 5'-ACGAAGCTTAAAAAAGGATTGGCTGTCTCAACCCCCA-3' (SEQ ID NO: 107) |
| Antisense 5B R1 | 5'-ACGCTGCAGCTTGAGCCATTCACCTGGCTAGGGTT-3' (SEQ ID NO: 108) |
| Antisense-B1 | |
| Antisense B1 F1 | 5'-TAGCTGCAGTGGCCTGAGCCTTGAAGAAT-3' (SEQ ID NO: 109) |
| Antisense B1 R1 | 5'-ACGAAGCTTAAAAAACGGAGGCGGAGGGCGAGGGG-3' (SEQ ID NO: 110) |
| Antisense-B2 | |
| Antisense B2 F1 | 5'-TAGCTGCAGTGGCCTGAGCCTTGAAGAAT-3' (SEQ ID NO: 111) |
| Antisense B2 R1 | 5'-ACGAAGCTTAAAAAAGGTGAGCGGCGCCGGTAC-3' (SEQ ID NO: 112) |
| Antisense-B3 | |
| Antisense B3 F1 | 5'-TAGCTGCAGTGGGGAGCATTTCCAGATGGAGAAACTGCAAGG-3' (SEQ ID NO: 113) |
| Antisense B3 R1 | 5'-ACGAAGCTTAAAAAACGGAGGCGGAGGGCGAGGG-3' (SEQ ID NO: 114) |
| Antisense-C1 | |
| Antisense C1 F1 | 5'-TAGCTGCAGTGAGCTCATGCTATTCCTATGA-3' (SEQ ID NO: 115) |
| Antisense C1 R1 | 5'-ACGAAGCTTAAAAAAGGTCCCCAAAGCTGGCTCCT-3' (SEQ ID NO: 116) |
| Antisense-C2 | |
| Antisense C2 F1 | 5'-TAGCTGCAGTGAGCTCATGCTATTCCTATGA-3' (SEQ ID NO: 117) |
| Antisense C2 R1 | 5'-ACGAAGCTTAAAAAACTGGGAGCACCGGTGCGC-3' (SEQ ID NO: 118) |
| Antisense-C3 | |
| Antisense C3 F1 | 5'-TAGCTGCAGGTCCTGGTAACACTATTCATGCACTAACAAGTT-3' (SEQ ID NO: 119) |
| Antisense C3 R1 | 5'-ACGAAGCTTAAAAAAGGTCCCCAAAGCTGGCTCCT-3' (SEQ ID NO: 120) |
| Antisense-D1 | |
| Antisense D1 F1 | 5'-TAGCTGCAGGAGAGACAGAGAGAGAGAGG-3' (SEQ ID NO: 121) |
| Antisense D1 R1 | 5'-ACGAAGCTTAAAAAACGGGTGTGAGGAGCGCGGCG-3' (SEQ ID NO: 122) |
| Antisense-D2 | |
| Antisense D2 F1 | 5'-TAGCTGCAGGAGAGACAGAGAGAGAGAGG-3' (SEQ ID NO: 123) |
| Antisense D2 R1 | 5'-ACGAAGCTTAAAAAACGCTGGGGCCAGCCGGGC-3' (SEQ ID NO: 124) |
| Antisense-D3 | |
| Antisense D3 F1 | 5'-TAGCTGCAGTGAAGGGATAAGTGTCCAGAATCCCTGGATCTG-3' (SEQ ID NO: 125) |
| Antisense D3 R1 | 5'-ACGAAGCTTAAAAAACGGGTGTGAGGAGCGCGGCG-3' (SEQ ID NO: 126) |
| Antisense-E1 | |
| Antisense E1 F1 | 5'-TAGCTGCAGAGGGTATTCAGTATTACTATTT-3' (SEQ ID NO: 127) |
| Antisense E1 R1 | 5'-ACGAAGCTTAAAAAATGATCAAGCGAAGAATCTTTGTCCATG-3' (SEQ ID NO: 128) |

| Antisense-F1 | |
|---|---|
| Antisense F1 F1 | 5'-TAGCTGCAGAATGGATGAATACATAAAATAA-3' (SEQ ID NO: 129) |
| Antisense F1 R1 | 5'-ACGAAGCTTAAAAAAGCACCTGGGCGCTTCGGTCCACCTCAT-3' (SEQ ID NO: 130) |
| Antisense-G1 | |
| Antisense G1 F1 | 5'-TAGCTGCAGTTTATTCATGAGAAAATTCTGG-3' (SEQ ID NO: 131) |
| Antisense G1 R1 | 5'-ACGAAGCTTAAAAAAGGGGTCATGGGAGACCATGCTTTCTAG-3' (SEQ ID NO: 132) |
| Sense-3 | |
| Sense 3 F1 | 5'-ACGCTGCAGGAGTAGGCGCGAGCTTCCAT-3' (SEQ ID NO: 133) |
| Sense 3 R1 | 5'-TAGAAGCTTAAAAAACTTGAGCCATTCACCTGGCT-3' (SEQ ID NO: 134) |
| Sense-4 | |
| Sense 4 F1 | 5'-ACGCTGCAGGAGTAGGCGCGAGCTTCCAT-3' (SEQ ID NO: 135) |
| Sense 4 R1 | 5'-TAGAAGCTTAAAAAACTTGAGCCATTCACCTGGCT-3' (SEQ ID NO: 136) |
| Sense-5 | |
| Sense 5 F1 | 5'-ACGCTGCAGGAGTAGGCGCGAGCTTCCAT-3' (SEQ ID NO: 137) |
| Sense 5 R1 | 5'-TAGAAGCTTAAAAAACTTGAGCCATTCACCTGGCT-3' (SEQ ID NO: 138) |
| Sense-6 | |
| Sense 6 F1 | 5'-ACGCTGCAGGAGTAGGCGCGAGCTTCCAT-3' (SEQ ID NO: 139) |
| Sense 6 R1 | 5'-TAGAAGCTTAAAAAACTTGAGCCATTCACCTGGCT-3' (SEQ ID NO: 140) |
| Sense-B1 | |
| Sense B1 F1 | 5'-TAGCTGCAGCGGAGGCGGAGGGCGAGGGG-3' (SEQ ID NO: 141) |
| Sense B1 R1 | 5'-ACGAAGCTTAAAAAATGGCCTGAGCCTTGAAGAAT-3' (SEQ ID NO: 142 |
| Sense-C1 | |
| Sense C1 F1 | 5'-TAGCTGCAGGGTCCCCAAAGCTGGCTCCT-3' (SEQ ID NO: 143) |
| Sense C1 R1 | 5'-ACGAAGCTTAAAAAATGAGCTCATGCTCTTCCTAT-3' (SEQ ID NO: 144) |
| Sense-D1 | |
| Sense D1 F1 | 5'-TAGCTGCAGCGGGTGTGAGGAGCGCGGCG-3' (SEQ ID NO: 145) |
| Sense D1 R1 | 5'-ACGAAGCTTAAAAAAGAGAGACAGAGAGAGAGAGG-3' (SEQ ID NO: 146) |
| Antisense TMPRSS2-ETV1-A1 | |
| Antisense TMPRSS2-ETV1-A1 F1 | 5'-TAGCTGCAGTGCCGCATTATGTAAATCGTTCCAAGTTAAAGTC-3' (SEQ ID NO: 147) |
| Antisense TMPRSS2-ETV1-A1 R1 | 5'-ACGAAGCTTAAAAAACCAGTTGGTGGAAGAGAGTCCCCCGGG-3' (SEQ ID NO: 148) |
| Antisense TMPRSS2-ETV1-B1 | |
| Antisense TMPRSS2-ETV1-B1 F1 | 5'-TAGCTGCAGGATTCAGTAATTTCAAAGTTTATTATATTTAAGA-3' (SEQ ID NO: 149) |
| Antisense TMPRSS2-ETV1-B1 R1 | 5'-ACGAAGCTTAAAAAACAGCCCAGTTACAAGGCATTTGGAATA-3' (SEQ ID NO: 150) |

-continued

Antisense TMPRSS2-ETV1-C1

| Antisense TMPRSS2-ETV1-C1 F1 | 5'-TAGCTGCAGCTCTGAATAGAAAAATAGAAGTCCATAGTATCAA-3' (SEQ ID NO: 151) |
|---|---|
| Antisense TMPRSS2-ETV1-C1 R1 | 5'-ACGAAGCTTAAAAAACCTGTCCCAGGAGATCTGGGAAGGTAC-3' (SEQ ID NO: 152) |

Antisense TMPRSS2-ETV1-D1

| Antisense TMPRSS2-ETV1-D1 F1 | 5'-TAGCTGCAGATATAAACAAAAAGTGTCAGCATTTGTCTCAACT-3' (SEQ ID NO: 153) |
|---|---|
| Antisense TMPRSS2-ETV1-D1 R1 | 5'-ACGAAGCTTAAAAAAGATGGGGGTTGGGAGTGTGGCAGGGAG-3' (SEQ ID NO: 154) |

Antisense TMPRSS2-ETV1-E1

| Antisense TMPRSS2-ETV1-E1 F1 | 5'-TAGCTGCAGCTCTGAATAGAAAAATAGAAGTCCATAGTATCAA-3' (SEQ ID NO: 155) |
|---|---|
| Antisense TMPRSS2-ETV1-E1 R1 | 5'-ACGAAGCTTAAAAAAAGGAAAGGTGAATGGTCAATGGAGTGC-3' (SEQ ID NO: 156) |

Antisense TMPRSS2-ETV1-F1

| Antisense TMPRSS2-ETV1-F1 F1 | 5'-TAGCTGCAGAGGAGGCCTTAAGTATGATTCAGTGAACACATTA-3' (SEQ ID NO: 157) |
|---|---|
| Antisense TMPRSS2-ETV1-F1 R1 | 5'-ACGAAGCTTAAAAAAATCATTGCCTTGGTCCCAATTATTACA-3' (SEQ ID NO: 158) |

Antisense TMPRSS2-ETV1-G1

| Antisense TMPRSS2-ETV1-G1 F1 | 5'-TAGCTGCAGTGTAATTGACTTAGATCTTGAAAGAGTTCTAAAA-3' (SEQ ID NO: 159) |
|---|---|
| Antisense TMPRSS2-ETV1-G1 R1 | 5'-ACGAAGCTTAAAAAAGGCAACACTGGTCTTTGTTGTAGGTAA-3' (SEQ ID NO: 160) |

Antisense TMPRSS2-ETV1-H1

| Antisense TMPRSS2-ETV1-H1 F1 | 5'-TAGCTGCAGTTAACAAACAGCTTAATAAATAAGCTCAGGGATA-3' (SEQ ID NO: 161) |
|---|---|
| Antisense TMPRSS2-ETV1-H1 R1 | 5'-ACGAAGCTTAAAAAACAATTGCACCCCATCCTCCTACCCACT-3' (SEQ ID NO: 162) |

Sense TMPRSS2-ETV1-A1

| Sense TMPRSS2-ETV1-A1 F1 | 5'-TAGCTGCAGCCAGTTGGTGGAAGAGAGT-3' (SEQ ID NO: 163) |
|---|---|
| Sense TMPRSS2-ETV1-A1 R1 | 5'-ACGAAGCTTAAAAAATGCCGCATTATGTAAATC-3' (SEQ ID NO: 164) |

PCR primers used for amplifying the identified TMPRSS2-ERG genomic DNA breakpoint:

| TMPRSS2 intron 1 | | |
|---|---|---|
| TMPRSS2 genomic bk F1 | 5'-ATGTGATATTAGTGCGGTTA-3' | (SEQ ID NO: 165) |
| TMPRSS2 genomic bk F2 | 5'-GGCTGGGATGTGTCCGTGGA-3' | (SEQ ID NO: 166) |
| ERG intron 3 | | |
| ERG genomic bk R1 | 5'-CCATAAGTTTTACTGCGTCT-3' | (SEQ ID NO: 167) |
| ERG genomic bk R2 | 5'-GATACTGAGTGGTAAATTCT-3' | (SEQ ID NO: 168) |

The rest of PCR primers used for genomic breakpoint analyses are not listed, but their locations are shown in FIG. 18A.

PCR primers used for amplifying the identified TMPRSS2-ETV1 genomic DNA breakpoint:

| TMPRSS2 | | |
|---|---|---|
| TMPRSS2 genomic bk pt A1 | 5'-TCTGCTCGAGCACGGGTCCA-3' | (SEQ ID NO: 169) |
| TMPRSS2 genomic bk pt A2 | 5'-AAAACTGCCCCATGTCCAG-3' | (SEQ ID NO: 170) |
| TMPRSS2 genomic bk pt B1 | 5'-CAACCTGGGAGGCCCTGCCT-3' | (SEQ ID NO: 171) |
| TMPRSS2 genomic bk pt B2 | 5'-CAGCAACAGCACAAGCTTGT-3' | (SEQ ID NO: 172) |
| TMPRSS2 genomic bk pt C1 | 5'-GGCTGGGATGTGTCCGTGGA-3' | (SEQ ID NO: 173) |
| TMPRSS2 genomic bk pt C2 | 5'-TGGTGGTGGTGCTGTCTGGA-3' | (SEQ ID NO: 174) |
| TMPRSS2 genomic bk pt D1 | 5'-CAGGAGAATCACTTGAACCT-3' | (SEQ ID NO: 175) |
| TMPRSS2 genomic bk pt D2 | 5'-AGGCCACTGCACTCCAGCCT-3' | (SEQ ID NO: 176) |
| ERG intron 3 | | |
| ETV1 genomic bk pt M1 | 5'-GCAAGTCTCGTTGATCGCCA-3' | (SEQ ID NO: 177) |
| ETV1 genomic bk pt M2 | 5'-TTGCACACGTTTGCGAATCA-3' | (SEQ ID NO: 178) |
| ETV1 genomic bk pt N1 | 5'-AGGGAGAGTTGCTTCCCAGT-3' | (SEQ ID NO: 179) |
| ETV1 genomic bk pt N2 | 5'-GCCGATCTTAGCACATTACT-3' | (SEQ ID NO: 180) |

Example 4

Characterization of Chimeric RNAs

Figure 23:
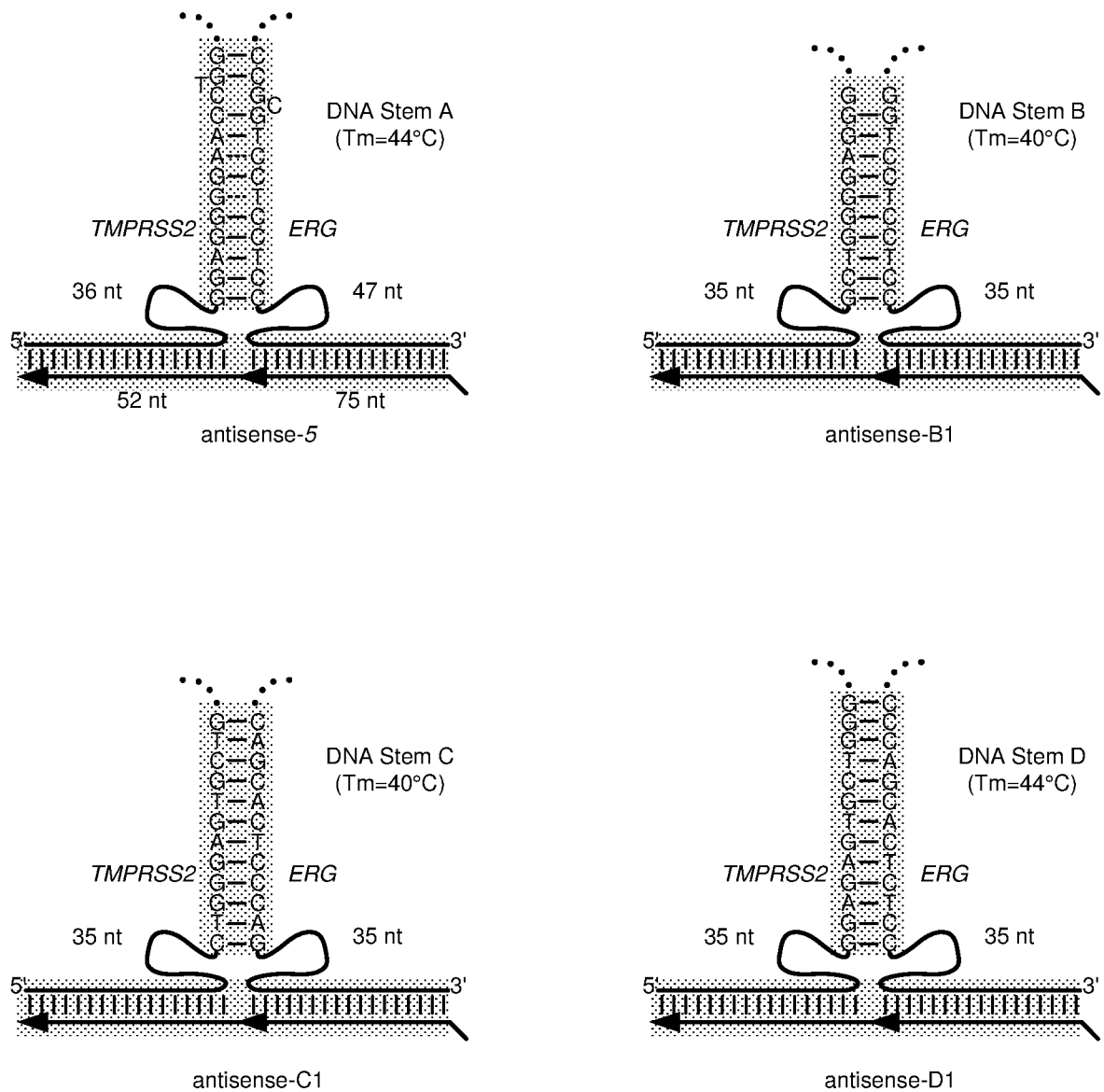
FIG. 23. Illustration of 3-way junction stem formation for TMPRSS2-ERG gene fusion having multiple different DNA/DNA genomic stems (Stem A-Stem D). Certain parameters for design of chimeric RNAs are characterized. Each illustration in this figure demonstrates 3-way junction stem formation between the chimeric RNA and two separate genomic regions of TMPRSS2 and ERG concomitantly. In each example, the 3-way junction produces regions of genomic DNA loop or spacer that in at least some cases may be described as a bulge at or near the base of the junction. Upper panel, Left: Schematics of three-way junction that could be formed between genomic DNA (black) and antisense-5 chimeric RNA (green/blue). The sense genomic strands of both TMPRSS2 and ERG genes are on the minus strand of chromosome 21, separated by 3 Mb. Short lines in shaded regions represent base-pairings. Imperfect stem A includes a high energy G. T and A. C wobble pair known to have Watson-Crick-like geometry in a DNA double helix (Kimsey and Al-Hashimi, 2014; Watson and Crick, 1953). A DNA spacer region of 36 nt and 47 nt separate stem A from the regions targeted by antisense-5 chimeric RNA. Upper panel, Right: The putative three-way junction formed between the indicated genomic DNA stem B (black) and designed antisense chimeric RNA B1 (green/blue). Lower panel, Left: The putative three-way junction formed between the indicated genomic DNA stem C (black) and designed antisense chimeric RNA C1 (green/blue). Lower panel, Right: The putative three-way junction formed between the indicated genomic DNA stem D (black) and designed antisense chimeric RNA D1 (green/blue).

Certain parameters for design of chimeric RNAs are characterized. FIG. 23 shows examples of engineered chimeric RNAs for TMPRSS2-ERG. Each illustration in FIG. 23 demonstrates 3-way junction stem formation between the chimeric RNA and two separate genomic regions of TMPRSS2 and ERG concomitantly. In each example, the 3-way junction produces regions of single-stranded genomic DNA loop or spacer that in at least some cases may be described as a bulge at or near the base of the junction. To examine the parameters, FIG. 24 illustrates different regions of the 3-way junction stem formation that may be variable, including length of the bulge and lengths of the respective regions of the chimeric RNA.

Figure 26:
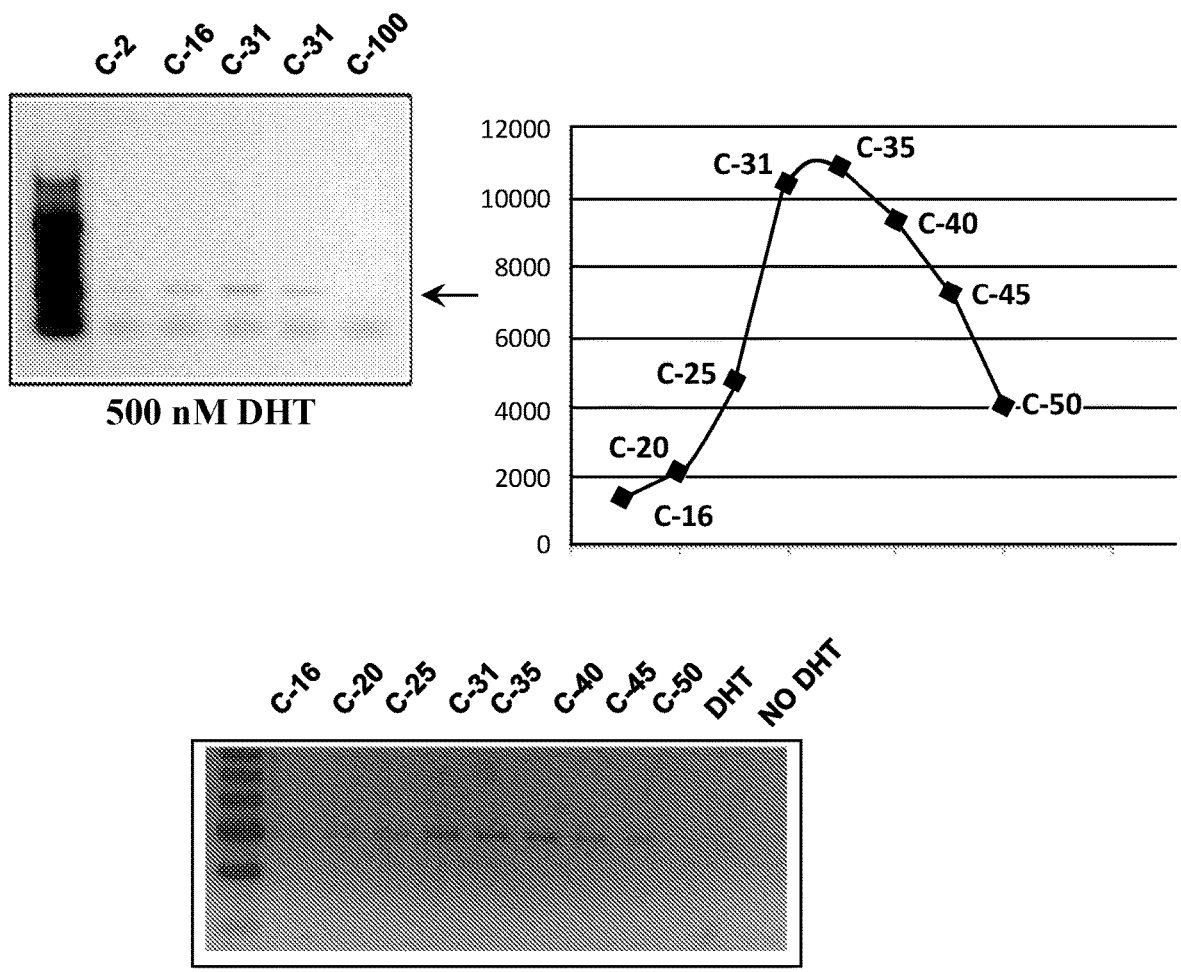
FIG. 26 shows testing of different size of DNA spacers (bulge) for the Stem C 3-way junction stem formation for TMPRSS2-ERG gene fusion.
Figure 27:
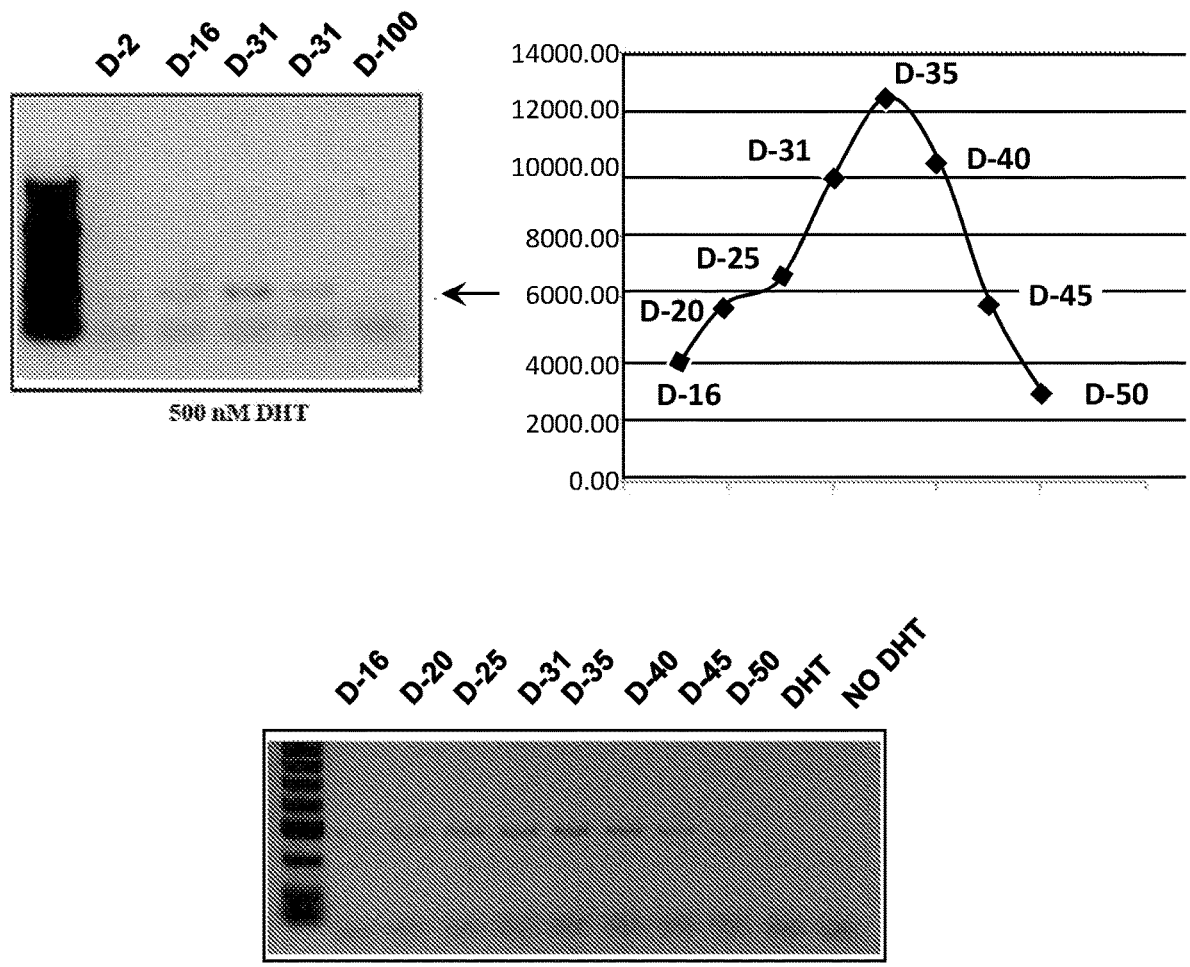
FIG. 27 shows testing of different size of DNA spacers (bulge) for the Stem D 3-way junction stem formation for TMPRSS2-ERG gene fusion.

The optimum size of the bulge for fusion induction was examined in FIGS. 25, 26, and 27 for the corresponding Stem B, C, and D of FIG. 23. As is shown, for fusion gene induction the optimum size of the bulge is around 35 nucleotides on each side, although other lengths also work.

Figure 28:
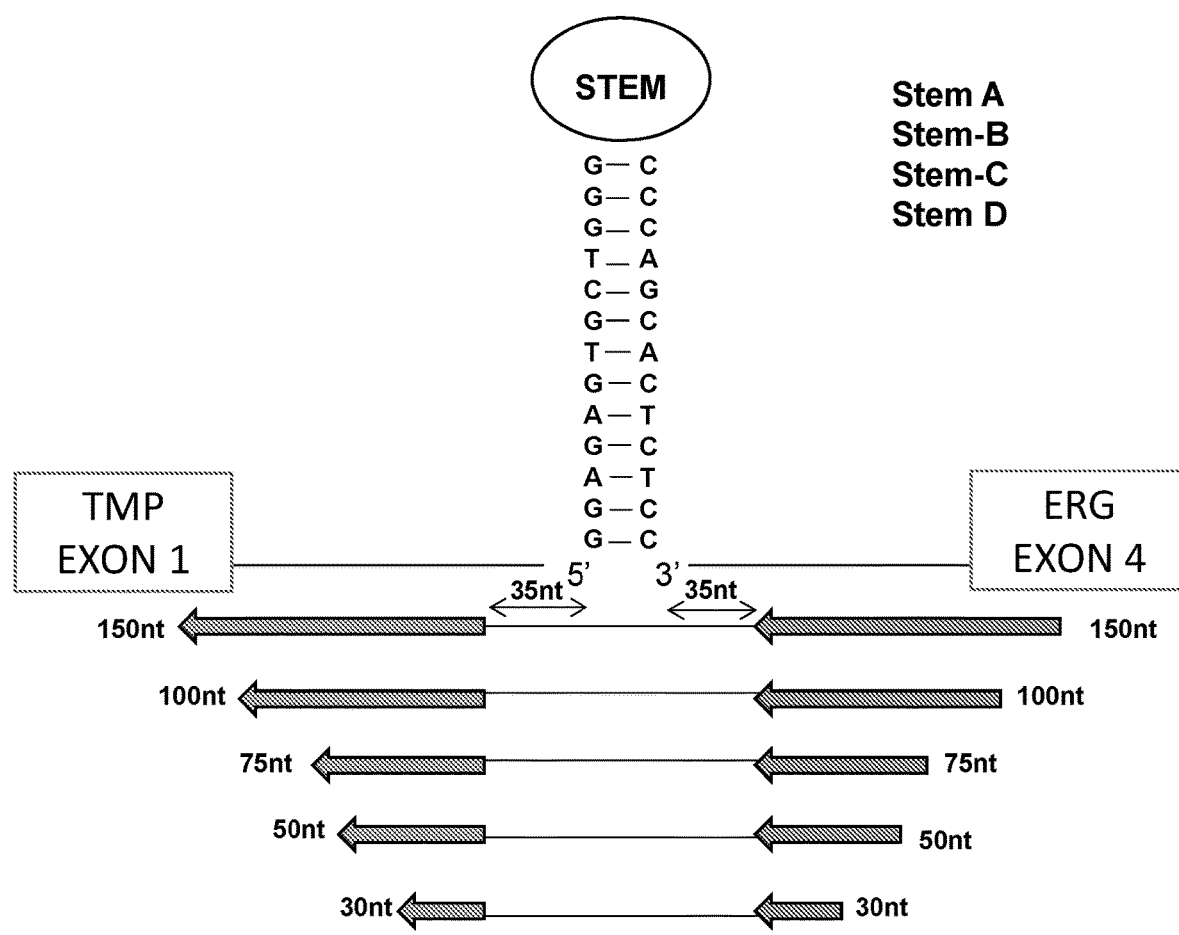
FIG. 28 illustrates a schematic for testing particular lengths sizes for the different chimeric RNA designed to hybridize to TMPRSS2 and ERG. The length of chimeric RNA on each side was varied while the bulge is fixed at 35 nucleotides. The length variations were then tested for their ability to induce fusion gene. Length variations: 30nt-30nt, 50nt-50nt, 75nt-75nt, 100nt-100nt, 150nt -150nt). The part of chimeric RNA targeting TMPRSS2 genomic locations are in blue whereas targeting ERG genomic locations are in red.
Figure 29:
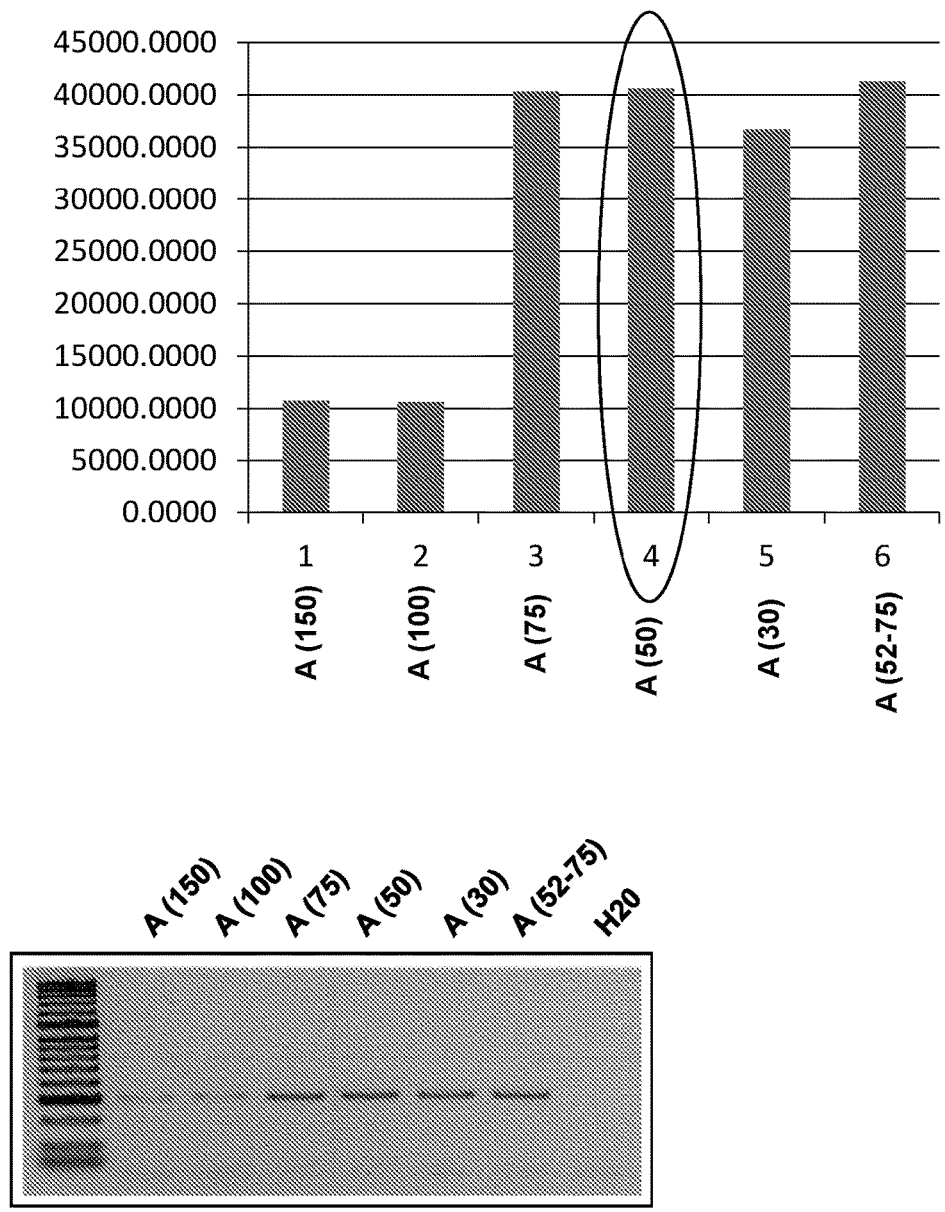
FIG. 29 shows testing of the different sizes for the different chimeric RNA parts corresponding to TMPRSS2 and ERG using the Stem A 3-way junction. For example, A(50) has 50 nt on each side of the chimeric RNA. RT-PCR was performed to detect the level of induced TMPRSS2-ERG fusion RNA.

It was next examined if there was an optimum chimeric RNA size for fusion induction when the bulge is fixed at 35 nucleotides. FIG. 28 illustrates a schematic for testing of chimeric RNAs at varying sizes when the bulge is 35 nucleotides. FIGS. 29-32 provide results of testing the various sizes of the chimeric RNA when using Stem A, Stem B, Stem C, or Stem D, respectively. For fusion gene induction, an optimum size for the chimeric RNAs is around 50-75 nucleotides on each side.

Example 5

Chimeric RNA-Driven Genomic Rearrangement in Mammalian Cells

The present example and others demonstrate the chimeric RNA technology with respect to five experimentally induced gene fusions, merely as examples. These induced gene fusions involve different gene partners and different cell types, further supporting the embodiment of the disclosure that RNA-induced genomic rearrangement is permissible in mammalian cells using the chimeric RNA technology of the present disclosure.

Examples in the present disclosure include the following:
TMPRSS2-ERG, a prostate cancer fusion gene, in LNCaP cells and PNT1A cells TMPRSS2-ETV1, a prostate cancer fusion gene, in LNCaP cells JAZF1-SUZ12, an endometrial cancer fusion gene, in 293T cells BCR-RANGAP1, not known to be disease-relevant but an experimentally induced fusion gene, in 293T cells BCR-KCNQ2, not known to be disease-relevant but an experimentally induced fusion gene, in 293T and HL-60 cells In the data provided in this example, it is shown that gene fusion can be induced by chimeric RNAs that are designed to target genomic DNA in a sequence-dependent manner. As indicated elsewhere herein, formation of a three-way junction between genomic DNA and chimeric RNA facilitates fusion induction. The three-way junction comprises an RNA/DNA hybrid and a genomic DNA stem between the two parental genes. The genomic DNA sequences that form the stem can be sense pairing to a sense strand of the gene partners, or sense pairing to an antisense strand of the gene partners.

This example demonstrates that genomic DNA stems could be formed by DNA repeats, such as the SINE and the LINE repeats, that may constitute stems over 300 nts in length. Genomic DNA stems could also be formed without using the SINE and the LINE repeats that may constitute stems ranging from 10 nts to <100 nts in length.

The present example indicates that RNA-driven gene fusion can be induced without hormone or other stimuli or can be facilitated by hormone stimulation in at least some cases. RNA-driven gene fusion can occur in adherent and suspension mammalian cell lines such as, but not limited to, 293T and HL-60 cells as examples. Furthermore, the designed chimeric RNAs could have a wide range of GC content, such as, but not limited to from about 27% to 65%.

Figure 39A:
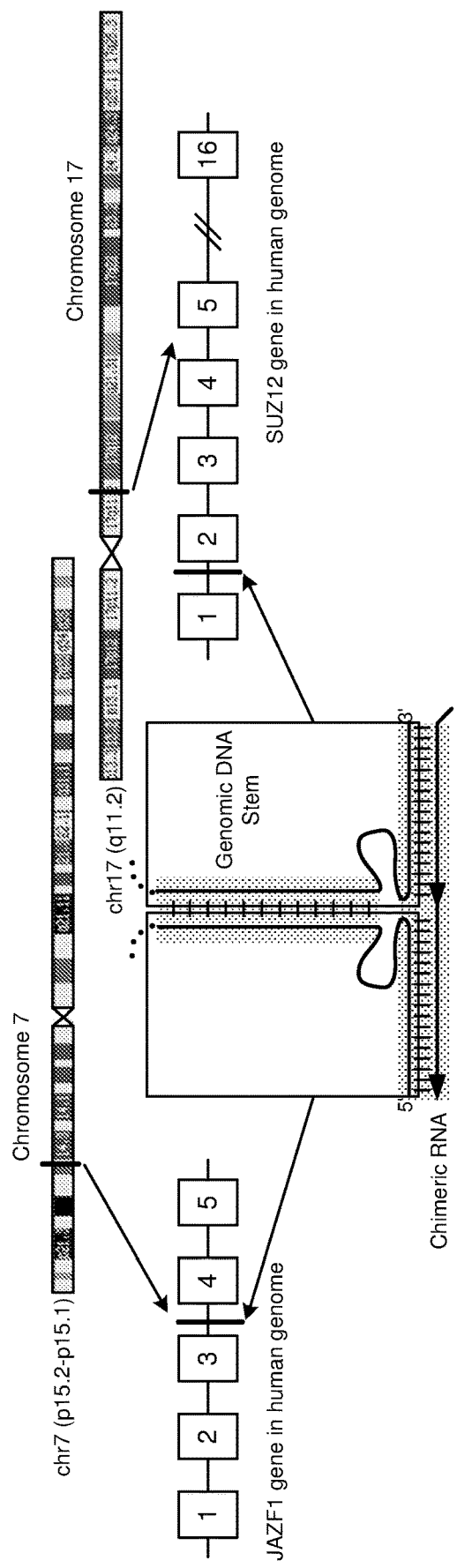
Figure 39B:
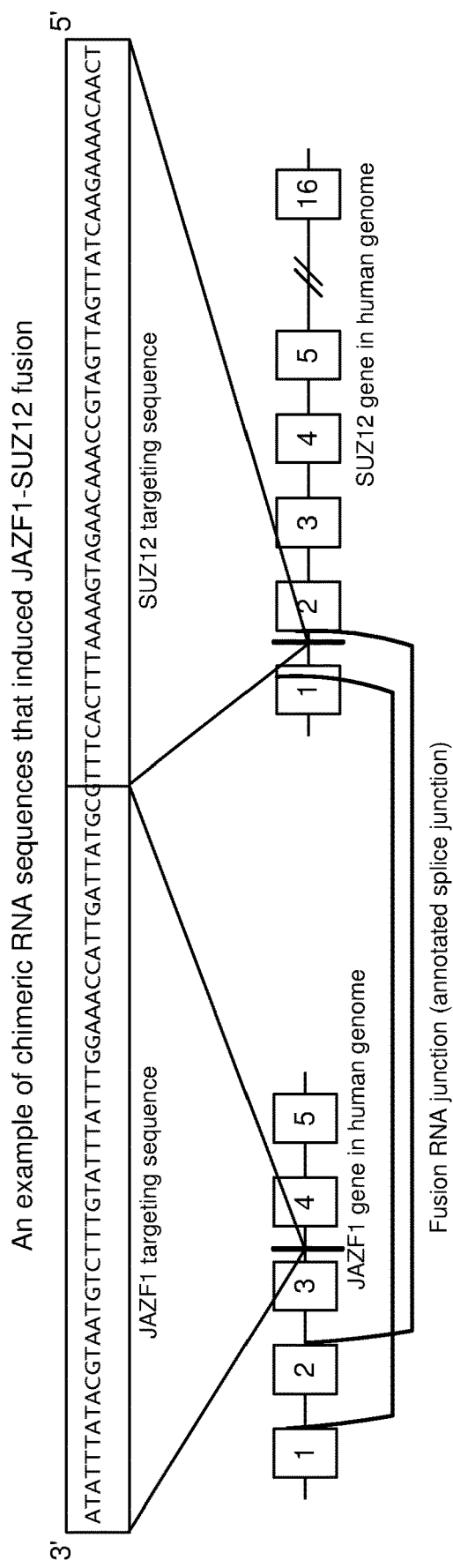
Figure 39D:
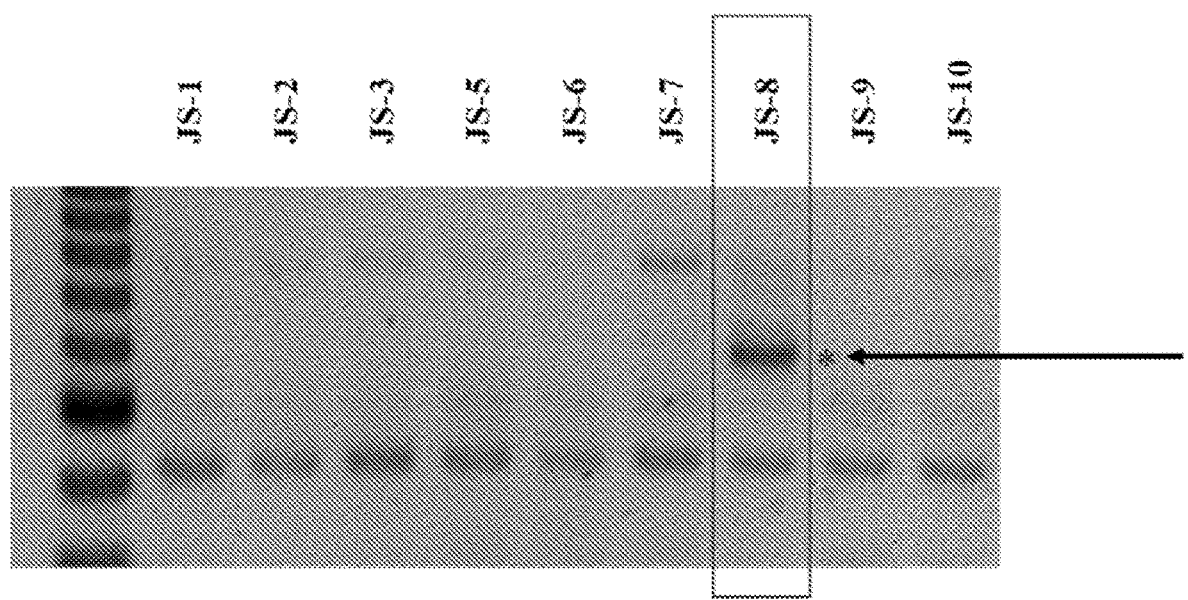

FIGS. 39A-39D concern RNA-mediated inter-chromosomal JAZF1-SUZ12 fusion in 293T cells, as one example of RNA-driven gene fusion. FIG. 39A illustrates an inter-chromosomal fusion between JAZF1 and SUZ12 in which the design of the produced chimeric RNA forms part of a three-way junction between genomic DNA and the chimeric RNA. That is, the three-way junction comprises an RNA/DNA hybrid and a genomic DNA stem between the parental genes. In this specific case, the sense genomic strand of JAZF1 is on the negative strand (of chromosome 7) but SUZ12 is on the positive strand of chromosome 17. For a particular fusion between JAZF1 and SUZ12, FIG. 39B provides an example of the chimeric RNA sequences that induced the JAZF1-SUZ12 fusion. FIG. 39C demonstrates successful generation of produced JAZF1-SUZ12 fusion transcripts; these were confirmed by Sanger sequencing to be a fusion of JAZF1 exon 1 spliced to a cryptic splice site of SUZ12 exon 1. FIG. 39D demonstrates production of a different chimeric RNA of JAZF1-SUZ12 fusion transcript than what is shown in FIG. 39C. In this case, there was production of a different JAZF1-SUZ12 fusion transcript, as confirmed by Sanger sequencing; the fusion transcript was from splicing JAZF1 exon 2 to SUZ12 exon 2.

Figure 40A:
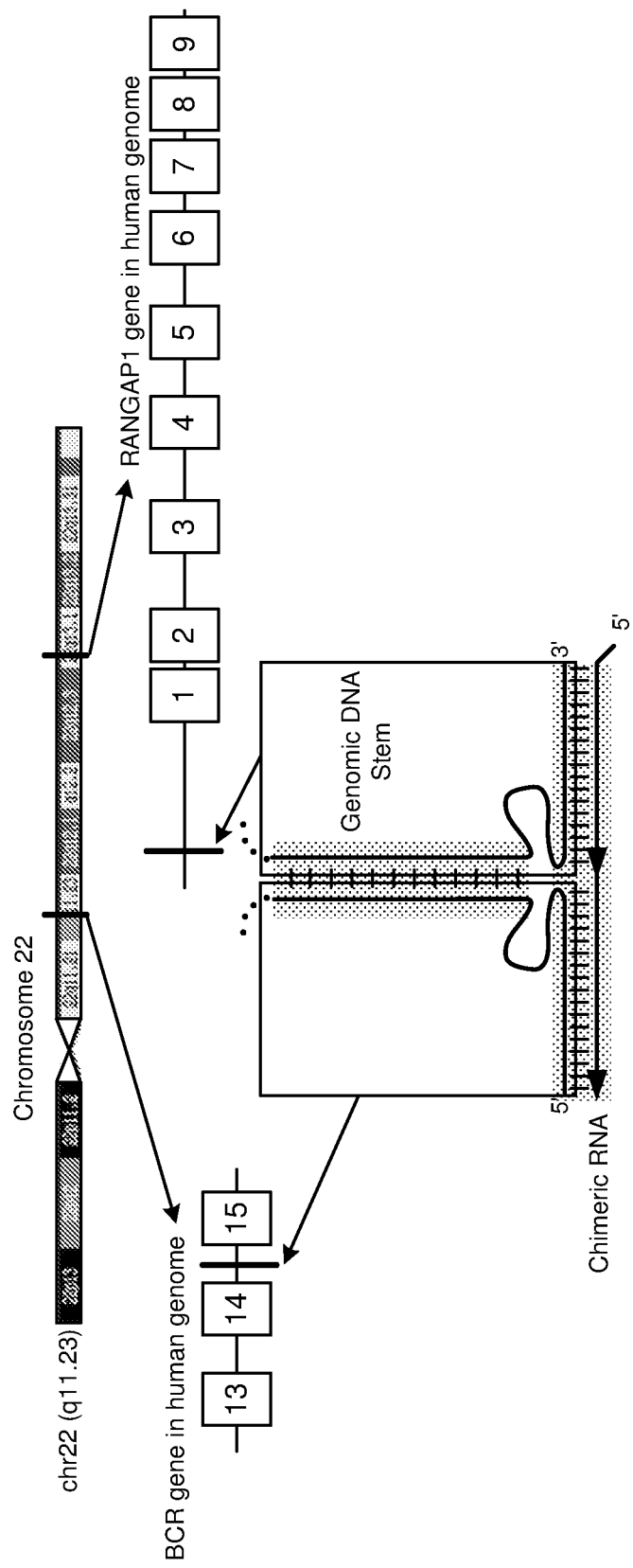
FIGS. 40A-40C. RNA-mediated intra-chromosomal BCR-RANGAP1 fusion in 293T cells by designed chimeric RNA.
Figure 40B:
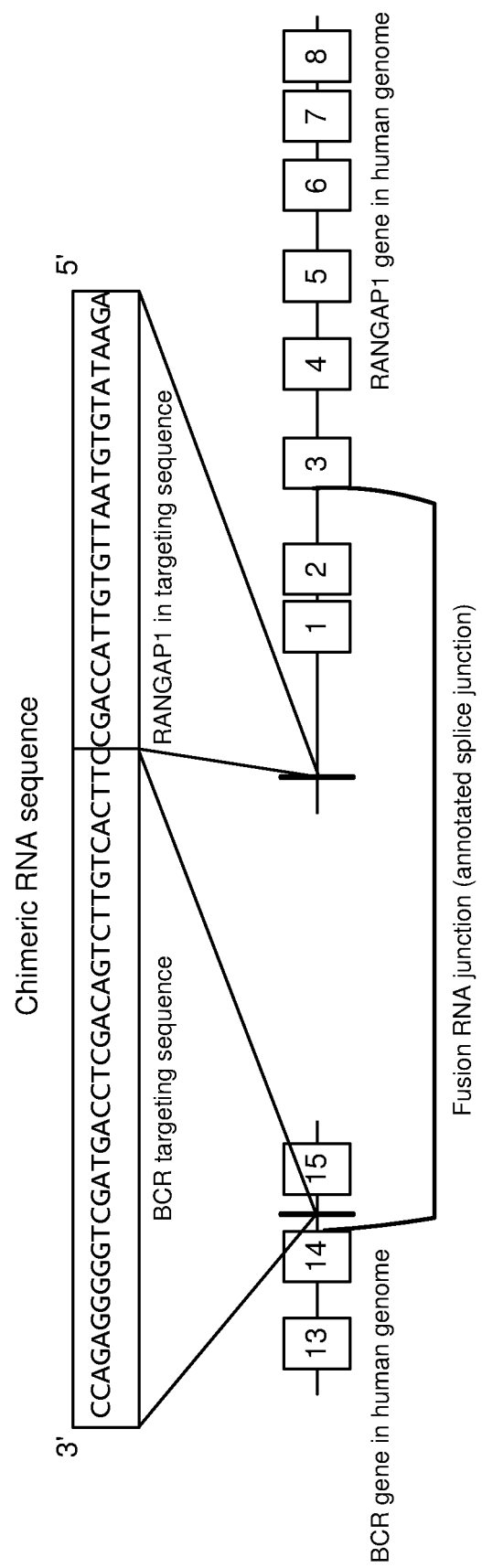
Figure 40C:
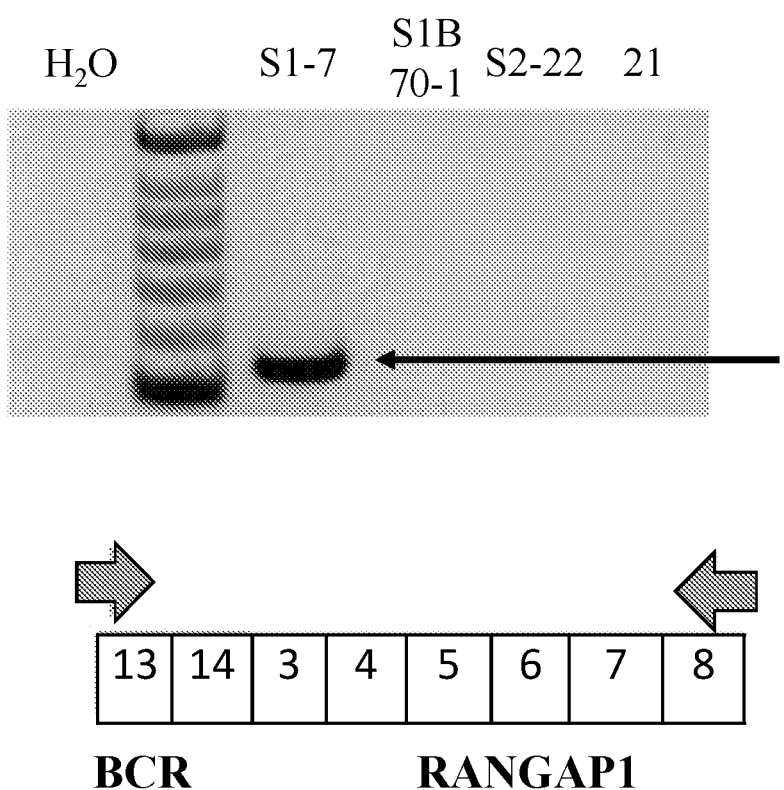

FIGS. 40A-40C concern RNA-mediated intra-chromosomal BCR-RANGAP1 fusion by a designed chimeric RNA. FIG. 40A provides an illustration of design using a three-way junction that could be formed between the parental genes BCR and RANGAP1. In this case, the sense genomic strand of BCR is on the positive strand of chromosome 22 and RANGAP1 is on the negative strand of chromosome 22. FIG. 40B provides one example of the chimeric RNA sequence used to induce fusion of BCR and RANGAP1, and FIG. 40C shows production of the fusion transcript induced by sequence-specific chimeric RNA. The BCR-RANGAP1 fusion transcript sequence was confirmed by Sanger sequencing to comprise BCR exon14 spliced to RANGAP1 exon3 (RANGAP1 isoform 1, NM_001278651.1). The RNA fusion junction is an annotated splice junction for both genes.

FIGS. 41A-41D regard RNA-mediated inter-chromosomal BCR-KCNQ2 fusions by designed chimeric RNA. FIG. 41A shows a design of chimeric RNA utilizing a three-way junction between the genomic DNA and the parental genes of BCR and KCNQ2. In this case, the sense genomic strand of BCR is on the positive strand of chromosome 22 while KCNQ2 is on the negative strand of chromosome 20. FIG. 41B shows one example of a particular chimeric RNA sequence used to induce BCR-KCNQ2 fusion. Two specific BCR-KCNQ2 fusion transcripts were produced (FIG. 41C), and a schematic of their induced transcripts with particular exon fusion configurations is depicted (FIG. 41D). Sanger sequencing confirmed that BCR-KCNQ2 fusion transcript contains BCR exon16 spliced to KCNQ2 exon8 (KCNQ2 isoform 5, NM_172109.2). RNA fusion junction is an annotated splice junction for both genes. Sanger sequencing confirmed the presence of another BCR-KCNQ2 fusion transcript contains BCR exon18 spliced to KCNQ2 exon8 (KCNQ2 isoform 5, NM_172109.2). RNA fusion junction is an annotated splice junction for both genes.

FIGS. 42A-42E concern BCR-KCNQ2 fusions induced by chimeric RNAs utilizing or excluding the short interspersed nuclear element (SINE) for three-way junction formation. FIG. 42A shows an illustration of chimeric RNA design utilizing a three-way junction between two SINEs in genomic DNA and the chimeric RNA. In this case, the stem of the junction is formed from DNA repeats, such as SINE/SINE repeats. In FIG. 42B, there is provided one example of a designed chimeric RNA sequence that induced BCR-KCNQ2 fusion RNA. FIG. 42C shows an example of chimeric RNA design targeting sequences of the respective genes in which the genomic stems are formed from regions outside of known DNA repeats, such as SINEs. FIG. 42D provides a specific example of chimeric RNA sequence that was able to induce BCR-KCNQ2 fusion RNA. FIG. 42E shows that fusion of two parental genes can be induced by chimeric RNAs having genomic stems comprising SINE repears or outside of SINE repeats. Sanger sequencing confirmed that BCR-KCNQ2 fusion transcript contains BCR exon16 spliced to KCNQ2 exon8 (KCNQ2 isoform 5, NM_172109.2). RNA fusion junction is an annotated splice junction for both genes. Sanger sequencing also confirmed the presence of another BCR-KCNQ2 fusion transcript contains BCR exon18 spliced to KCNQ2 exon8 (KCNQ2 isoform 5, NM_172109.2). RNA fusion junction is an annotated splice junction for both genes.

A summary of properties of examples of chimeric RNAs is below:

| Chimeric RNA ID | Fusion gene partners | Sizes of targeting region on each gene (nt) | G-C content (%) | Cell line(s) identified |
| --- | --- | --- | --- | --- |
| JS-7 | JAZF1-SUZ12 | 50-50 | 46% | 293T |
| JS-8 | JAZF1-SUZ12 | 50-50 | 27% | 293T |
| JS-11 | JAZF1-SUZ12 | 50-50 | 47% | 293T |
| S1-7 | BCR-RANGAP1 | 38-26 | 48.4% | 293T |
| S4 30-2 | BCR-KCNQ2 | 46-45 | 55.4% | HL-60 |

-continued

| Chimeric RNA ID | Fusion gene partners | Sizes of targeting region on each gene (nt) | G-C content (%) | Cell line(s) identified |
|---|---|---|---|---|
| S4 200-9 | BCR-KCNQ2 | 46-22 | 50% | HL-60 |
| S1A 200-1 | BCR-KCNQ2 | 50-50 | 52% | 293T |
| S1A 200-2 | BCR-KCNQ2 | 50-50 | 52% | 293T |
| S1A 10-9 | BCR-KCNQ2 | 50-50 | 58% | 293T |
| S1B 10-1 | BCR-KCNQ2 | 48-50 | 59.2% | 293T |
| S1B 10-2 | BCR-KCNQ2 | 48-50 | 63.3% | 293T |
| S1B 10-3 | BCR-KCNQ2 | 48-50 | 55.1% | 293T |
| S1B 10-8 | BCR-KCNQ2 | 51-50 | 60.4% | 293T |

An additional summary of properties of examples of chimeric RNAs is below:

| Chimeric RNA ID | Fusion gene partners | Sizes of targeting region on each gene (nt) | G-C content (%) | Cell line(s) identified |
|---|---|---|---|---|
| Antisense-1 | TMPRSS2-ERG | 78-218 | 61% | LNCaP |
| Antisense-2 | TMPRSS2-ERG | 78-218 | 61% | LNCaP |
| Antisense-5 | TMPRSS2-ERG | 52-75 | 65% | LNCaP, PNT1A |
| Antisense-B1 | TMPRSS2-ERG | 52-75 | 62% | LNCaP |
| Antisense-C1 | TMPRSS2-ERG | 52-75 | 57% | LNCaP |
| Antisense-D1 | TMPRSS2-ERG | 52-75 | 60% | LNCaP |
| Sense AZI1 ex16-17 | TMPRSS2-ERG | 117-103 | 54% | LNCaP |
| Antisense-TETV-1 | TMPRSS2-ETV1 | 50-50 | 49% | LNCaP |

REFERENCES

All patents and publications mentioned in this specification are indicative of the level of those skilled in the art to which the invention pertains. All patents and publications herein are incorporated by reference to the same extent as if each individual publication was specifically and individually indicated to be incorporated by reference in their entirety.

Aoto, H., Miyake, Y., Nakamura, M., and Tajima, S. (1997). Genomic organization of the mouse AZ1 gene that encodes the protein localized to preacrosomes of spermatids. Genomics 40, 138-141.

Aoto, H., Tsuchida, J., Nishina, Y., Nishimune, Y., Asano, A., and Tajima, S. (1995). Isolation of a novel cDNA that encodes a protein localized to the pre-acrosome region of spermatids. Eur J Biochem 234, 8-15.

Bastus, N. C., Boyd, L. K., Mao, X., Stankiewicz, E., Kudahetti, S. C., Oliver, R. T., Berney, D. M., and Lu, Y. J. (2010). Androgen-induced TMPRSS2:ERG fusion in nonmalignant prostate epithelial cells. Cancer Res 70, 9544-9548.

Boyce, M. J., Baisley, K. J., Clark, E. V., and Warrington, S. J. (2004). Are published normal ranges of serum testosterone too high? Results of a cross-sectional survey of serum testosterone and luteinizing hormone in healthy men. in BJU Int, pp. 881-885.

Coll-Bastus, N., Mao, X., Young, B. D., Sheer, D., and Lu, Y. J. (2015). DNA replication-dependent induction of gene proximity by androgen. Hum Mol Genet 24, 963-971.

Crick, F. (1970). Central dogma of molecular biology. Nature 227, 561-563.

Fang, W., and Landweber, L. F. (2012). RNA-mediated genome rearrangement: hypotheses and evidence. Bioessays 35, 84-87.

Horoszewicz, J. S., Leong, S. S., Chu, T. M., Wajsman, Z. L., Friedman, M., Papsidero, L., Kim, U., Chai, L. S., Kakati, S., Arya, S. K., et al. (1980). The LNCaP cell line—a new model for studies on human prostatic carcinoma. Prog Clin Biol Res 37, 115-132.

Janz, S., Potter, M., and Rabkin, C. S. (2003). Lymphoma- and leukemia-associated chromosomal translocations in healthy individuals. Genes Chromosomes Cancer 36, 211-223.

Kannan, K., Wang, L., Wang, J., Ittmann, M. M., Li, W., and Yen, L. (2011). Recurrent chimeric RNAs enriched in human prostate cancer identified by deep sequencing. Proc Natl Acad Sci USA 108, 9172-9177.

Kimsey, I., and Al-Hashimi, H. M. (2014). Increasing occurrences and functional roles for high energy purine-pyrimidine base-pairs in nucleic acids. Curr Opin Struct Biol 24, 72-80.

Langabeer, S. E., Walker, H., Rogers, J. R., Burnett, A. K., Wheatley, K., Swirsky, D., Goldstone, A. H., and Linch, D. C. (1997). Incidence of AML1/ETO fusion transcripts in patients entered into the MRC AML trials. MRC Adult Leukaemia Working Party. Br J Haematol 99, 925-928.

Li, H., Wang, J., Mor, G., and Sklar, J. (2008). A neoplastic gene fusion mimics trans-splicing of RNAs in normal human cells. Science 321, 1357-1361.

Lieber, M. R. (2010). The mechanism of double-strand DNA break repair by the nonhomologous DNA end-joining pathway. Annu Rev Biochem 79, 181-211.

Lin, C., Yang, L., Tanasa, B., Hutt, K., Ju, B. G., Ohgi, K., Zhang, J., Rose, D. W., Fu, X. D., Glass, C. K., et al. (2009). Nuclear receptor-induced chromosomal proximity and DNA breaks underlie specific translocations in cancer. Cell 139, 1069-1083.

Mani, R. S., Tomlins, S. A., Callahan, K., Ghosh, A., Nyati, M. K., Varambally, S., Palanisamy, N., and Chinnaiyan, A. M. (2009). Induced chromosomal proximity and gene fusions in prostate cancer. Science 326, 1230.

Mertz, K. D., Setlur, S. R., Dhanasekaran, S. M., Demichelis, F., Perner, S., Tomlins, S., Tchinda, J., Laxman, B., Vessella, R. L., Beroukhim, R., et al. (2007). Molecular characterization of TMPRSS2-ERG gene fusion in the NCI-H660 prostate cancer cell line: a new perspective for an old model. Neoplasia 9, 200-206.

Mitelman, F., Johansson, B., and Mertens, F. (2007). The impact of translocations and gene fusions on cancer causation. Nat Rev Cancer 7, 233-245.

Nowacki, M., Vijayan, V., Zhou, Y., Schotanus, K., Doak, T. G., and Landweber, L. F. (2008). RNA-mediated epigenetic programming of a genome-rearrangement pathway. Nature 451, 153-158.

Perner, S., Demichelis, F., Beroukhim, R., Schmidt, F. H., Mosquera, J. M., Setlur, S., Tchinda, J., Tomlins, S. A., Hofer, M. D., Pienta, K. G., et al. (2006). TMPRSS2:ERG fusion-associated deletions provide insight into the heterogeneity of prostate cancer. Cancer Res 66, 8337-8341.

Rowley, J. D., and Blumenthal, T. (2008). Medicine. The cart before the horse. Science 321, 1302-1304.

Rubin, M. A., Maher, C. A., and Chinnaiyan, A. M. (2011). Common gene rearrangements in prostate cancer. J Clin Oncol 29, 3659-3668.

Rudiger, N. S., Gregersen, N., and Kielland-Brandt, M. C. (1995). One short well conserved region of Alu-sequences is involved in human gene rearrangements and has homology with prokaryotic chi. Nucleic Acids Res 23, 256-260.

Rychlik, W., and Rhoads, R. E. (1989). A computer program for choosing optimal oligonucleotides for filter hybridization, sequencing and in vitro amplification of DNA. Nucleic Acids Res 17, 8543-8551.

Teles Alves, I., Hiltemann, S., Hartjes, T., van der Spek, P., Stubbs, A., Trapman, J., and Jenster, G. (2013). Gene fusions by chromothripsis of chromosome 5q in the VCaP prostate cancer cell line. Hum Genet 132, 709-713.

Tomlins, S. A., Rhodes, D. R., Perner, S., Dhanasekaran, S. M., Mehra, R., Sun, X. W., Varambally, S., Cao, X., Tchinda, J., Kuefer, R., et al. (2005). Recurrent fusion of TMPRSS2 and ETS transcription factor genes in prostate cancer. Science 310, 644-648.

Watson, J. D., and Crick, F. H. (1953). Genetical implications of the structure of deoxyribonucleic acid. Nature 171, 964-967.

Weier, C., Haffner, M. C., Mosbruger, T., Esopi, D. M., Hicks, J., Zheng, Q., Fedor, H., Isaacs, W. B., De Marzo, A. M., Nelson, W. G., et al. (2013). Nucleotide resolution analysis of TMPRSS2 and ERG rearrangements in prostate cancer. J Pathol 230, 174-183.

Zaphiropoulos, P. G. (2011). Trans-splicing in Higher Eukaryotes: Implications for Cancer Development? Front Genet 2, 92.

Zhang, F., Carvalho, C. M., and Lupski, J. R. (2009). Complex human chromosomal and genomic rearrangements. Trends Genet 25, 298-307.

Although the present disclosure and its advantages have been described in detail, it should be understood that various changes, substitutions and alterations can be made herein without departing from the spirit and scope of the design as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A method of producing a genomic fusion product through endogenous genomic DNA rearrangements between a first and a second region of genomic DNA in a cell, in vitro, comprising the step of: exposing to the genomic DNA an effective amount of an exogenously provided synthetic chimeric RNA, said chimeric RNA comprising (1) a first RNA sequence that is reverse complement with respect to a portion of the first region of genomic DNA and (2) a second RNA sequence that is reverse complement with respect to a portion of the second region of genomic DNA, wherein the first RNA sequence is between 30-150 nucleotides long and the second RNA sequence is between 30-150 nucleotides long, wherein a portion of the first genomic region that is not reverse complement to the first RNA sequence is reverse complementary to a portion of the second genomic region that is not reverse complement to the second RNA sequence, and wherein upon exposing of the chimeric RNA to the genomic DNA, the first and second genomic regions become fused to each other thereby producing the genomic fusion product through endogenous DNA recombination.

2. The method of claim 1, wherein upon exposing the chimeric RNA to the genomic DNA, the chimeric RNA hybridizes with the complementary portions of the first and second regions of genomic DNA through the first and second RNA sequences of the chimeric RNA, thereby forming a DNA/RNA hybrid in a sequence-specific manner.

3. The method of claim 2, wherein upon hybridization of the chimeric RNA with the respective complementary sequences of the first and second genomic regions of the genomic DNA, a double stranded DNA/DNA stem structure is produced between the portions of genomic DNA that are complementary to each other.

4. The method of claim 1, wherein the first and second regions of genomic DNA are on the same chromosome.

5. The method of claim 1, wherein the first and second regions of genomic DNA are on different chromosomes.

6. The method of claim 1, wherein at least one of the first and second regions of genomic DNA has active transcription.

7. The method of claim 6, wherein the chimeric RNA is antisense with respect to the at least one region having active transcription.

8. The method of claim 1, wherein at least one of the first and second regions of genomic DNA lacks transcriptional activity.

9. The method of claim 8, wherein one or both of the first RNA sequence and second RNA sequence of the chimeric RNA is either antisense or sense with respect to the at least one of the two different regions lacking active transcription.

10. The method of claim 1, wherein the chimeric RNA has or is designed to have between 27% and 65% GC content.

11. The method of claim 1, wherein the cell is a diseased cell.

12. The method of claim 1, wherein the method occurs at physiological hormone levels.

13. The method of claim 1, wherein the synthetic chimeric RNA is produced in a cell.

14. The method of claim 3, wherein the DNA region between the DNA stem structure and the DNA/RNA hybrid in the first genomic region is between 15-50 nucleotides long and wherein the DNA region between the DNA stem structure and the DNA/RNA hybrid in the second genomic region is between 15-50 nucleotides long.

15. The method of claim 14, wherein the DNA region between the DNA stem structure and the DNA/RNA hybrid in the first genomic region is single stranded.

16. The method of claim 14, wherein the DNA region between the DNA stem structure and the DNA/RNA hybrid in the second genomic region is single stranded.

* * * * *

SEQUENCE LISTING

```
<160> NUMBER OF SEQ ID NOS: 250

<210> SEQ ID NO 1
<211> LENGTH: 709
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
tcagatcgcc tggagacgcc atccacgctg ttttgacctc catagaagac accgggaccg      60
atccagcctc ccctcgaagc tgatcctgag aacttcaggc tcctgggcaa cgtgctggtc     120
tgtgtgctgg cccatcactt tggcaaagaa ttcgagtagg cgcgagctaa gcaggaggcg     180
gaggcggagg cggagggcga ggggcgggga gcgccgcctg gagcgcggca ggaagcctta     240
tcagttgtga gtgaggacca gtcgttgttt gagtgtgcct acggaacgcc acacctggct     300
aagacagaga tgaccgcgtc ctcctccagc gactatggac agacttccaa gatgagccca     360
cgcgtccctc agcaggattg gctgtctcaa cccccagcca gggtcaccat caaaatggaa     420
tgtaacccta gccaggtgaa tggctcaaga agcttatcga taccgtcgac ctcgagggcc     480
cagatctaat tcaccccacc agtgcaggct gcctatcaga aagtggtggc tggtgtggct     540
aatgccctgg cccacaagta tcactaagct cgctttcttg ctgtccaatt tctattaaag     600
gttcctttgt tccctaagtc caactactaa actgggggat attatgaagg gccttccgga     660
gcatctggat tctgcctaat aaaaaacatt tattttcatt gcaaaaaaa                 709

<210> SEQ ID NO 2
<211> LENGTH: 344
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
tgtgctcgct tcggcagcac atatactaac attggaacga tcctgcagga gtaggcgcga      60
gctaagcagg aggcggaggc ggaggcggag ggcgaggggc ggggagcgcc gcctggagcg     120
```

```
cggcaggaag ccttatcagt tgtgagtgag gaccagtcgt tgtttgagtg tgcctacgga      180
acgccacacc tggctaagac agagatgacc gcgtcctcct ccagcgacta tggacagact      240
tccaagatga gcccacgcgt ccctcagcag gattggctgt ctcaacccc agccagggtc       300 accatcaaaa tggaatgtaa ccctagccag gtgaatggct caag                      344
```

<210> SEQ ID NO 3
<211> LENGTH: 744
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
tgtgctcgct tcggcagcac atatactaac attggaacga tcctgcagga gtaggcgcga      60
gctaagcagg aggcggaggc ggaggcggag ggcgaggggc ggggagcgcc gcctggagcg     120
cggcaggaag ccttatcagt tgtgagtgag gaccagtcgt tgtttgagtg tgcctacgga     180
acgccacacc tggctaagac agagatgacc gcgtcctcct ccagcgacta tggacagact     240
tccaagatga gcccacgcgt ccctcagcag gattggctgt ctcaacccc agccagggtc      300 accatcaaaa tggaatgtaa ccctagccag gtgaatggct caaggaactc tcctgatgaa     360
tgcagtgtgg ccaaaggcgg gaagatggtg ggcagcccag acaccgttgg gatgaactac     420
ggcagctaca tggaggagaa gcacatgcca cccccaaaca tgaccacgaa cgagcgcaga     480
gttatcgtgc cagcagatcc tacgctatgg agtacagacc atgtgcggca gtggctggag     540
tgggcggtga agaatatgg ccttccagac gtcaacatct tgttattcca gaacatcgat      600
gggaaggaac tgtgcaagat gaccaaggac gacttccaga ggctcacccc cagctacaac     660
gccgacatcc ttctctcaca tctccactac tcagagaga ctcctcttcc acatttgact      720
tcagatgatg ttgataaagc ctta                                            744
```

<210> SEQ ID NO 4
<211> LENGTH: 709
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

```
tcagatcgcc tggagacgcc atccacgctg ttttgacctc catagaagac accgggaccg      60
atccagcctc ccctcgaagc tgatcctgag aacttcaggc tcctgggcaa cgtgctggtc     120
tgtgtgctgg cccatcactt tggcaaagaa ttccttgagc cattcacctg gctagggtta     180
cattccattt tgatggtgac cctggctggg ggttgagaca gccaatcctg ctgagggacg     240
cgtgggctca tcttggaagt ctgtccatag tcgctggagg aggacgcggt catctctgtc     300
ttagccaggt gtggcgttcc gtaggcacac tcaaacaacg actggtcctc actcacaact     360
gataaggctt cctgccgcgc tccaggcggc gctccccgcc cctcgccctc cgcctccgcc     420
tccgcctcct gcttagctcg cgcctactca agcttatcga taccgtcgac ctcgagggcc     480
cagatctaat tcaccccacc agtgcaggct gcctatcaga aagtggtggc tggtgtggct     540
aatgccctgg cccacaagta tcactaagct cgctttcttg ctgtccaatt tctattaaag     600
gttcctttgt tccctaagtc caactactaa actggggat attatgaagg gccttccgga      660
```

```
gcatctggat tctgcctaat aaaaaacatt tattttcatt gcaaaaaaa          709
```

<210> SEQ ID NO 5
<211> LENGTH: 344
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

```
tgtgctcgct tcggcagcac atatactaac attggaacga tcctgcagct tgagccattc    60
acctggctag ggttacattc catattgatg gtgaccctgg ctgggggttg agacagccaa   120
tcctgctgag ggacgcgtgg gctcatcttg gaagtctgtc catagtcgct ggaggaggac   180
gcggtcatct ctgtcttagc caggtgtggc gttccgtagg cacactcaaa caacgactgg   240
tcctcactca caactgataa ggcttcctgc cgcgctccag gcggcgctcc ccgcccctcg   300
ccctccgcct ccgcctccgc ctcctgctta gctcgcgcct actc                    344
```

<210> SEQ ID NO 6
<211> LENGTH: 240
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
tgtgctcgct tcggcagcac atatactaac attggaacga tcctgcagct tgagccattc    60
acctggctag ggttacattc catattgatg gtgaccctgg ctgggggttg agacagccaa   120
tcccggaccc cgagccggga ccctggtacc ggcgccgctc acctgccgcg ctccaggcgg   180
cgctccccgc ccctcgccct ccgccagaca ggagtgagag atggaagctc gcgcctactc   240
```

<210> SEQ ID NO 7
<211> LENGTH: 225
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

```
tgtgctcgct tcggcagcac atatactaac attggaacga tcctgcagct tgagccattc    60
acctggctag ggttacattc catattgatg gtgaccctgg ctgggggttg agacagccaa   120
tccgaccctg gtaccggcgc cgctcacctg ccgcgctcca ggcggcgctc ccgcccctc    180 gccctccgcc agacaggagt gagagatgga agctcgcgcc tactc                   225
```

<210> SEQ ID NO 8
<211> LENGTH: 210
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

```
tgtgctcgct tcggcagcac atatactaac attggaacga tcctgcagct tgagccattc    60
acctggctag ggttacattc catattgatg gtgaccctgg ctgggggttg agacagccaa   120
tccgccgctc acctgccgcg ctccaggcgg cgctccccgc ccctcgccct ccgccagaca   180
```

```
ggagtgagag atggaagctc gcgcctactc                                     210
```

<210> SEQ ID NO 9
<211> LENGTH: 191
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

```
tgtgctcgct tcggcagcac atatactaac attggaacga tcctgcagct tgagccattc    60
acctggctag ggttacattc catattgatg gtgaccctgg ctgggggttg agacagccaa   120
tccccaggcg cgctccccg cccctcgccc tccgccagac aggagtgaga gatggaagct   180
cgcgcctact c                                                       191
```

<210> SEQ ID NO 10
<211> LENGTH: 210
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

```
tgtgctcgct tcggcagcac atatactaac attggaacga tcctgcagct tgagccattc    60
acctggctag ggttacattc catattgatg gtgaccctgg ctgggggttg agacagccaa   120
tcccggaccc cgagccggga ccctggtacc ggcgccgctc acctgccgcg ctccaagaca   180
ggagtgagag atggaagctc gcgcctactc                                   210
```

<210> SEQ ID NO 11
<211> LENGTH: 210
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

```
tgtgctcgct tcggcagcac atatactaac attggaacga tcctgcagct tgagccattc    60
acctggctag ggttacattc catattgatg gtgaccctgg ctgggggttg agacagccaa   120
tccccaggtt ccctccccca gcccggaccc cgagccggga ccctggtacc ggcgcagaca   180
ggagtgagag atggaagctc gcgcctactc                                   210
```

<210> SEQ ID NO 12
<211> LENGTH: 210
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

```
tgtgctcgct tcggcagcac atatactaac attggaacga tcctgcagga gacagccaat    60
cctgctgagg gacgcgtggg ctcatcttgg aagtctgtcc atagtcgctg gaggaggacg   120
cgggccgctc acctgccgcg ctccaggcgg cgctccccgc ccctcgccct ccgccagaca   180
ggagtgagag atggaagctc gcgcctactc                                   210
```

<210> SEQ ID NO 13
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
tgtgctcgct tcggcagcac atatactaac attggaacga tcctgcaggc cgctcacctg    60
ccgcgctcca ggcggcgctc cccgcccctc gccctccgcc agacaggagt gagagatgga   120
agctcgcgcc tactc                                                    135

<210> SEQ ID NO 14
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
tgtgctcgct tcggcagcac atatactaac attggaacga tcctgcagct tgagccattc    60
acctggctag ggttacattc catattgatg gtgaccctgg ctgggggttg agacagccaa   120
tcc                                                                 123

<210> SEQ ID NO 15
<211> LENGTH: 175
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
tgtgctcgct tcggcagcac atatactaac attggaacga tcctgcagtg gcctgagcct    60
tgaagaatgg ggtgtactgg gtaaatcaaa atggtgggga gcatttccag atggagaaac   120
tgcctcacct gccgcgctcc aggcggcgct ccccgcccct cgccctccgc ctccg        175

<210> SEQ ID NO 16
<211> LENGTH: 175
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
tgtgctcgct tcggcagcac atatactaac attggaacga tcctgcagtg gcctgagcct    60
tgaagaatgg ggtgtactgg gtaaatcaaa atggtgggga gcatttccag atggagaaac   120
tgcccctccc cagcccggac cccgagccgg gaccctggta ccggcgccgc tcacc        175

<210> SEQ ID NO 17
<211> LENGTH: 175
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
tgtgctcgct tcggcagcac atatactaac attggaacga tcctgcagtg gggagcattt    60
ccagatggag aaactgcaag gaaaagcata gaagtggggc caccctcgt gagctgggga    120 gggctcacct gccgcgctcc aggcggcgct ccccgcccct cgccctccgc ctccg        175

<210> SEQ ID NO 18
<211> LENGTH: 175
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
tgtgctcgct tcggcagcac atatactaac attggaacga tcctgcagtg agctcatgct    60
attcctatga catagatgag cactgggtag accccgtcct ggtaacacta ttcatgcact    120
aaccccaggc gggggccgtg gagggcaggc ggactaggag ccagctttgg ggacc        175

<210> SEQ ID NO 19
<211> LENGTH: 175
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
tgtgctcgct tcggcagcac atatactaac attggaacga tcctgcagtg agctcatgct    60
attcctatga catagatgag cactgggtag accccgtcct ggtaacacta ttcatgcact    120
aaccagcact cccagtcctc ctccccaaag agaaaaggcg caccggtgct cccag        175

<210> SEQ ID NO 20
<211> LENGTH: 175
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
tgtgctcgct tcggcagcac atatactaac attggaacga tcctgcaggt cctggtaaca    60
ctattcatgc actaacaagt tggttgccag tgagacttga ttattatgac tctgggagtg    120
ctgcccaggc gggggccgtg gagggcaggc ggactaggag ccagctttgg ggacc        175

<210> SEQ ID NO 21
<211> LENGTH: 175
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
tgtgctcgct tcggcagcac atatactaac attggaacga tcctgcagga gagacagaga    60
gagagaggct ggtagaggga agagacagaa gaaagatgaa gggataagtg tccagaatcc    120
ctgagcgctc gaccctcggg cgcactcacc tgccgcgccg cgctcctcac acccg        175

<210> SEQ ID NO 22
<211> LENGTH: 175
<212> TYPE: DNA
<213> ORGANISM: Artificial Sequence
```

```
<220> FEATURE:
<223> OTHER INFORMATION: Description of Artificial Sequence: Synthetic
      polynucleotide

<400> SEQUENCE: 22
tgtgctcgct tcggcagcac atatactaac attggaacga tcctgcagga gagacagaga      60
gagagaggct ggtagaggga agagacagaa gaaagatgaa gggataagtg tccagaatcc     120
ctgcccagca ctctcccagc accccgggag gcgccctgcc cggctggccc cagcg          175

<210> SEQ ID NO 23
<211> LENGTH: 175
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
tgtgctcgct tcggcagcac atatactaac attggaacga tcctgcagtg aagggataag      60
tgtccagaat ccctggatct gggatggaat aaaggatctg gatggtaaac ggagagtgct     120
gggagcgctc gaccctcggg cgcactcacc tgccgcgccg cgctcctcac acccg          175

<210> SEQ ID NO 24
<211> LENGTH: 175
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
tgtgctcgct tcggcagcac atatactaac attggaacga tcctgcagag ggtattcagt      60
attactattt ggcttagata agctggtagt tacttgctaa aattaatctt tattataaag     120
cagaaagccg cattctgaca tcactctcca tggacaaaga ttcttcgctt gatca          175

<210> SEQ ID NO 25
<211> LENGTH: 175
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
tgtgctcgct tcggcagcac atatactaac attggaacga tcctgcagaa tggatgaata      60
cataaaataa attgtggtgg atatatacaa cggaatatca tttagccttt attattattg     120
agaactgtgc cgagccgggc aggacaggat gaggtggacc gaagcgccca ggtgc          175

<210> SEQ ID NO 26
<211> LENGTH: 175
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
tgtgctcgct tcggcagcac atatactaac attggaacga tcctgcagtt tattcatgag      60
aaaattctgg cacaatggaa aaccctggca agcaaaagat aggggcagca gatgtcctgg     120
cctacaaaga actccaagcc catcgtccct agaaagcatg gtctcccatg acccc          175
```

```
<210> SEQ ID NO 27
<211> LENGTH: 240
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
tgtgctcgct tcggcagcac atatactaac attggaacga tcctgcagga gtaggcgcga     60
gcttccatct ctcactcctg tctggcggag ggcgaggggc ggggagcgcc gcctggagcg    120
cggcaggtga gcggcgccgg taccagggtc ccggctcggg gtccgggatt ggctgtctca    180 accccccagcc agggtcacca tcaaaatgga atgtaaccct agccaggtga atggctcaag   240

<210> SEQ ID NO 28
<211> LENGTH: 225
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
tgtgctcgct tcggcagcac atatactaac attggaacga tcctgcagga gtaggcgcga     60
gcttccatct ctcactcctg tctggcggag ggcgaggggc ggggagcgcc gcctggagcg    120
cggcaggtga gcggcgccgg taccagggtc ggattggctg tctcaacccc cagccagggt    180
caccatcaat atggaatgta accctagcca ggtgaatggc tcaag                    225

<210> SEQ ID NO 29
<211> LENGTH: 210
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
tgtgctcgct tcggcagcac atatactaac attggaacga tcctgcagga gtaggcgcga     60
gcttccatct ctcactcctg tctggcggag ggcgaggggc ggggagcgcc gcctggagcg    120
cggcaggtga gcggcggatt ggctgtctca accccccagcc agggtcacca tcaaaatgga   180
atgtaaccct agccaggtga atggctcaag                                     210

<210> SEQ ID NO 30
<211> LENGTH: 191
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
tgtgctcgct tcggcagcac atatactaac attggaacga tcctgcagga gtaggcgcga     60
gcttccatct ctcactcctg tctggcggag ggcgaggggc ggggagcgcc gcctgggat     120 tggctgtctc aaccccccagc cagggtcacc atcaaaatgg aatgtaaccc tagccaggtg   180
aatggctcaa g                                                         191

<210> SEQ ID NO 31
```

```
<211> LENGTH: 175
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
tgtgctcgct tcggcagcac atatactaac attggaacga tcctgcagcg gaggcggagg      60
gcgaggggcg gggagcgccg cctggagcgc ggcaggtgag gcagtttctc catctggaaa     120
tgctccccac catattgatt tacccagtac accccattct tcaaggctca ggcca          175

<210> SEQ ID NO 32
<211> LENGTH: 175
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
tgtgctcgct tcggcagcac atatactaac attggaacga tcctgcaggg tccccaaagc      60
tggctcctag tccgcctgcc ctccacggcc cccgcctggg gttagtgcat gaagagtgtt     120
accaggacgg ggtctaccca gtgctcatct atgtcatagg aagagcatga gctca          175

<210> SEQ ID NO 33
<211> LENGTH: 175
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
tgtgctcgct tcggcagcac atatactaac attggaacga tcctgcagcg ggtgtgagga      60
gcgcggcgcg gcaggtgagt gcgcccgagg gtcgagcgct cagggattct ggacacttat     120
cccttcatct ttcttctgtc tcttccctct accagcctct ctctctctgt ctctc          175

<210> SEQ ID NO 34
<211> LENGTH: 148
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
tgtgctcgct tcggcagcac atatactaac attggaacga tcctgcagtg ccgcattatg      60
taaatcgttc caagttaaag tcttagttag attcagtaga ctaggagcca gctttgggga     120
ccccggggga ctctcttcca ccaactgg                                        148

<210> SEQ ID NO 35
<211> LENGTH: 148
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
tgtgctcgct tcggcagcac atatactaac attggaacga tcctgcagga ttcagtaatt      60
```

-continued

```
tcaaagttta ttatatttaa gataagactg aagtgctcaa caaacttagt ctcactttag      120
gtattccaaa tgccttgtaa ctgggctg                                         148
```

<210> SEQ ID NO 36
<211> LENGTH: 148
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36

```
tgtgctcgct tcggcagcac atatactaac attggaacga tcctgcagct ctgaatagaa      60
aaatagaagt ccatagtatc aactctaata ttcatatttg gctgcatccc cacttcctgg     120
agtaccttcc cagatctcct gggacagg                                        148
```

<210> SEQ ID NO 37
<211> LENGTH: 148
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37

```
tgtgctcgct tcggcagcac atatactaac attggaacga tcctgcagat ataaacaaaa      60
agtgtcagca tttgtctcaa cttcattcta ttcaatgtaa ggccctttgc gctggtaaac     120
tctccctgcc acactcccaa cccccatc                                        148
```

<210> SEQ ID NO 38
<211> LENGTH: 148
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38

```
tgtgctcgct tcggcagcac atatactaac attggaacga tcctgcagct ctgaatagaa      60
aaatagaagt ccatagtatc aactctaata ttcatattct tcagcaacca aaactgaaca     120
agcactccat tgaccattca cctttcct                                        148
```

<210> SEQ ID NO 39
<211> LENGTH: 147
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39

```
tgtgctcgct tcggcagcac atatactaac attggaacga tcctgcagag gaggccttaa      60
gtatgattca gtgaacacat tatggtcgat aaacaaggtg ggccccattc tcagagtctg     120
atgtaataat tgggaccaag gcaatga                                         147
```

<210> SEQ ID NO 40
<211> LENGTH: 148
<212> TYPE: DNA
<213> ORGANISM: Artificial Sequence
<220> FEATURE:
<223> OTHER INFORMATION: Description of Artificial Sequence: Synthetic -continued polynucleotide

<400> SEQUENCE: 40
tgtgctcgct tcggcagcac atatactaac attggaacga tcctgcagtg taattgactt    60
agatcttgaa agagttctaa aaaacaagtc aaagacatct agaagaatct ctagatgaag   120
gttacctaca acaaagacca gtgttgcc                                      148

<210> SEQ ID NO 41
<211> LENGTH: 148
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
tgtgctcgct tcggcagcac atatactaac attggaacga tcctgcagtt aacaaacagc    60
ttaataaata agctcaggga taccagaatt cacaaaaaga agcactctcc tctgggatca   120
gagtgggtag gaggatgggg tgcaattg                                      148

<210> SEQ ID NO 42
<211> LENGTH: 148
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
tgtgctcgct tcggcagcac atatactaac attggaacga tcctgcagcc agttggtgga    60
agagagtccc ccggggtccc caaagctggc tcctagtcta ctgaatctaa ctaagacttt   120
aacttggaac gatttacata atgcggca                                      148

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
taggcgcgag ctaagcagga g                                              21

<210> SEQ ID NO 44
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tagcatgcat taaccgtgga ga                                             22

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 45
taggcgcgag ctaagcagga g                                              21

<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
cttgagccat tcacctggct ag                                             22

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
taggcgcgag ctaagcagga g                                              21

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ttcttgactg caggcagagc t                                              21

<210> SEQ ID NO 49
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
caggaggcgg aggcgga                                                   17

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ctttcagcct gatagtctgg t                                              21

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
```

```
cggagggcga ggggcgggga                                                  20
```

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52

```
aactgctcat cattgtcagg t                                                21
```

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53

```
taggcgcgag ctaagcagga g                                                21
```

<210> SEQ ID NO 54
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54

```
cttgagccat tcacctggct ag                                               22
```

<210> SEQ ID NO 55
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55

```
caggaggcgg aggcgga                                                     17
```

<210> SEQ ID NO 56
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56

```
tgaccctggc tggggttga ga                                                22
```

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
cggagggcga ggggcgggga                                          20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
tcctgctgag ggacgcgtgg                                          20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gtcatattga acattccaga                                          20

<210> SEQ ID NO 60
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gcgcagctcc cacgaggaag gt                                       22

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
caggttctga acagctggta                                          20

<210> SEQ ID NO 62
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
tagcatgcat taaccgtgga ga                                       22

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
cccccgaggg acatgagaga a                                        21

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
tgggggttga gacagccaat                                              20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
caggttctga acagctggta                                              20

<210> SEQ ID NO 66
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
tagcatgcat taaccgtgga ga                                           22

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
tgggctggct tactgaagga                                              20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ttgtaaggct ttatcaacat                                              20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
atgattcaga ctgtcccgga                                              20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 70
catctgaagt caaatgtgga                                          20

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 71
cccccgaggg acatgagaga a                                        21

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 72
tgggggttga gacagccaat                                          20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 73
agggacatga gagaagagga                                          20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 74
tgagggacgc gtgggctcat                                          20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 75
gagagaagag gagcggcgct                                          20

```
<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
cttggaagtc tgtccatagt                                              20

<210> SEQ ID NO 77
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
gtgagcagct ctctgaccct ga                                           22

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
cgcaccagga tgactttgcc a                                            21

<210> SEQ ID NO 79
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
tgtcttctac tgcgtgagac gca                                          23

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
tctcctcagt cgtggaggag t                                            21

<210> SEQ ID NO 81
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
acggaattcg agtaggcgcg agctaagca                                    29

<210> SEQ ID NO 82
```

```
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
tagaagcttc ttgagccatt cacctggct                                    29

<210> SEQ ID NO 83
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
acgctgcagg agtaggcgcg agctaagca                                    29

<210> SEQ ID NO 84
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
tagaagctta aaaaacttga gccattcacc tggct                             35

<210> SEQ ID NO 85
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
acgctgcagg agtaggcgcg agctaagca                                    29

<210> SEQ ID NO 86
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
tagaagctta aaaataagg ctttatcaac atcat                              35

<210> SEQ ID NO 87
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
acggaattcc ttgagccatt cacctggct                                    29

<210> SEQ ID NO 88
<211> LENGTH: 29
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
tagaagcttg agtaggcgcg agctaagca                                      29

<210> SEQ ID NO 89
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
acgctgcagc ttgagccatt cacctggcta gggtt                               35

<210> SEQ ID NO 90
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
tagaagctta aaaagagta ggcgcgagct aagca                                35

<210> SEQ ID NO 91
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
acgctgcagc ttgagccatt cacctggcta gggtt                               35

<210> SEQ ID NO 92
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
tagaagctta aaaagagta ggcgcgagct tccat                                35

<210> SEQ ID NO 93
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
acgctgcagc ttgagccatt cacctggcta gggtt                               35

<210> SEQ ID NO 94
<211> LENGTH: 35
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 94
tagaagctta aaaaagagta ggcgcgagct tccat                              35

<210> SEQ ID NO 95
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
acgctgcagc ttgagccatt cacctggcta gggtt                              35

<210> SEQ ID NO 96
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
tagaagctta aaaaagagta ggcgcgagct tccat                              35

<210> SEQ ID NO 97
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
acgctgcagc ttgagccatt cacctggcta gggtt                              35

<210> SEQ ID NO 98
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
tagaagctta aaaaagagta ggcgcgagct tccat                              35

<210> SEQ ID NO 99
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
acgctgcagc ttgagccatt cacctggcta gggtt                              35

<210> SEQ ID NO 100
<211> LENGTH: 35
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 100
tagaagctta aaaagagta ggcgcgagct tccat                              35

<210> SEQ ID NO 101
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
acgctgcagc ttgagccatt cacctggcta gggtt                             35

<210> SEQ ID NO 102
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
tagaagctta aaaagagta ggcgcgagct tccat                              35

<210> SEQ ID NO 103
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
acgctgcagg agacagccaa tcctgctgag ggacgcgtgg gc                     42

<210> SEQ ID NO 104
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
tagaagctta aaaagagta ggcgcgagct tccat                              35

<210> SEQ ID NO 105
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
tagaagctta aaaagagta ggcgcgagct tccat                              35

<210> SEQ ID NO 106
<211> LENGTH: 30
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 106
tagctgcagg ccgctcacct gccgcgctcc                                    30

<210> SEQ ID NO 107
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
acgaagctta aaaaggatt ggctgtctca accccca                             37

<210> SEQ ID NO 108
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
acgctgcagc ttgagccatt cacctggcta gggtt                              35

<210> SEQ ID NO 109
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
tagctgcagt ggcctgagcc ttgaagaat                                     29

<210> SEQ ID NO 110
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
acgaagctta aaaacggag gcggagggcg agggg                               35

<210> SEQ ID NO 111
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
tagctgcagt ggcctgagcc ttgaagaat                                     29

<210> SEQ ID NO 112
<211> LENGTH: 33
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 112
acgaagctta aaaaaggtga gcggcgccgg tac        33

<210> SEQ ID NO 113
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
tagctgcagt ggggagcatt tccagatgga gaaactgcaa gg        42

<210> SEQ ID NO 114
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
acgaagctta aaaacggag gcggagggcg aggg        34

<210> SEQ ID NO 115
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
tagctgcagt gagctcatgc tattcctatg a        31

<210> SEQ ID NO 116
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
acgaagctta aaaaggtcc ccaaagctgg ctcct        35

<210> SEQ ID NO 117
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
tagctgcagt gagctcatgc tattcctatg a        31

<210> SEQ ID NO 118
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
acgaagctta aaaaactggg agcaccggtg cgc                33

<210> SEQ ID NO 119
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
tagctgcagg tcctggtaac actattcatg cactaacaag tt                42

<210> SEQ ID NO 120
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
acgaagctta aaaaggtcc ccaaagctgg ctcct                35

<210> SEQ ID NO 121
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
tagctgcagg agagacagag agagagagg                29

<210> SEQ ID NO 122
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
acgaagctta aaaacgggt gtgaggagcg cggcg                35

<210> SEQ ID NO 123
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
tagctgcagg agagacagag agagagagg                29

<210> SEQ ID NO 124
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 124
acgaagctta aaaaacgctg gggccagccg ggc                                          33

<210> SEQ ID NO 125
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
tagctgcagt gaagggataa gtgtccagaa tccctggatc tg                                42

<210> SEQ ID NO 126
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
acgaagctta aaaacgggt gtgaggagcg cggcg                                         35

<210> SEQ ID NO 127
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
tagctgcaga gggtattcag tattactatt t                                            31

<210> SEQ ID NO 128
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
acgaagctta aaaatgatc aagcgaagaa tctttgtcca tg                                 42

<210> SEQ ID NO 129
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
tagctgcaga atggatgaat acataaaata a                                            31

<210> SEQ ID NO 130
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
```
acgaagctta aaaaagcacc tgggcgcttc ggtccacctc at                          42

<210> SEQ ID NO 131
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
tagctgcagt ttattcatga gaaaattctg g                                     31

<210> SEQ ID NO 132
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
acgaagctta aaaaggggt catgggagac catgctttct ag                          42

<210> SEQ ID NO 133
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
acgctgcagg agtaggcgcg agcttccat                                        29

<210> SEQ ID NO 134
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
tagaagctta aaaaacttga gccattcacc tggct                                 35

<210> SEQ ID NO 135
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
acgctgcagg agtaggcgcg agcttccat                                        29

<210> SEQ ID NO 136
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
tagaagctta aaaaacttga gccattcacc tggct                35

<210> SEQ ID NO 137
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
acgctgcagg agtaggcgcg agcttccat                29

<210> SEQ ID NO 138
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
tagaagctta aaaaacttga gccattcacc tggct                35

<210> SEQ ID NO 139
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
acgctgcagg agtaggcgcg agcttccat                29

<210> SEQ ID NO 140
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
tagaagctta aaaaacttga gccattcacc tggct                35

<210> SEQ ID NO 141
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
tagctgcagc ggaggcggag ggcgagggg                29

<210> SEQ ID NO 142
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
acgaagctta aaaaatggcc tgagccttga agaat                35

<210> SEQ ID NO 143
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
tagctgcagg gtccccaaag ctggctcct                                         29

<210> SEQ ID NO 144
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
acgaagctta aaaatgagc tcatgctctt cctat                                   35

<210> SEQ ID NO 145
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
tagctgcagc gggtgtgagg agcgcggcg                                         29

<210> SEQ ID NO 146
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
acgaagctta aaaagagag acagagagag agagg                                   35

<210> SEQ ID NO 147
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
tagctgcagt gccgcattat gtaaatcgtt ccaagttaaa gtc                         43

<210> SEQ ID NO 148
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
acgaagctta aaaaccagt tggtggaaga gagtcccccg gg                           42

<210> SEQ ID NO 149
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
tagctgcagg attcagtaat ttcaaagttt attatattta aga                    43

<210> SEQ ID NO 150
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
acgaagctta aaaacagcc cagttacaag gcatttggaa ta                      42

<210> SEQ ID NO 151
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
tagctgcagc tctgaataga aaaatagaag tccatagtat caa                    43

<210> SEQ ID NO 152
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
acgaagctta aaaacctgt cccaggagat ctgggaaggt ac                      42

<210> SEQ ID NO 153
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
tagctgcaga tataaacaaa aagtgtcagc atttgtctca act                    43

<210> SEQ ID NO 154
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
acgaagctta aaaagatgg gggttgggag tgtggcaggg ag                      42

```
<210> SEQ ID NO 155
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
tagctgcagc tctgaataga aaaatagaag tccatagtat caa              43

<210> SEQ ID NO 156
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
acgaagctta aaaaaaggaa aggtgaatgg tcaatggagt gc               42

<210> SEQ ID NO 157
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
tagctgcaga ggaggcctta agtatgattc agtgaacaca tta              43

<210> SEQ ID NO 158
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
acgaagctta aaaaaatcat tgccttggtc ccaattatta ca               42

<210> SEQ ID NO 159
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
tagctgcagt gtaattgact tagatcttga aagagttcta aaa              43

<210> SEQ ID NO 160
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
acgaagctta aaaaaggcaa cactggtctt tgttgtaggt aa               42

<210> SEQ ID NO 161
```

```
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
tagctgcagt taacaaacag cttaataaat aagctcaggg ata               43

<210> SEQ ID NO 162
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
acgaagctta aaaacaatt gcaccccatc ctcctaccca ct                42

<210> SEQ ID NO 163
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
tagctgcagc cagttggtgg aagagagt                               28

<210> SEQ ID NO 164
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
acgaagctta aaaatgccg cattatgtaa atc                          33

<210> SEQ ID NO 165
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
atgtgatatt agtgcggtta                                        20

<210> SEQ ID NO 166
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
ggctgggatg tgtccgtgga                                        20

<210> SEQ ID NO 167
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
ccataagttt tactgcgtct                                                     20

<210> SEQ ID NO 168
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
gatactgagt ggtaaattct                                                     20

<210> SEQ ID NO 169
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
tctgctcgag cacgggtcca                                                     20

<210> SEQ ID NO 170
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
aaaactgccc catgtccag                                                      19

<210> SEQ ID NO 171
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
caacctggga ggccctgcct                                                     20

<210> SEQ ID NO 172
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
cagcaacagc acaagcttgt                                                     20

<210> SEQ ID NO 173
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 173
ggctgggatg tgtccgtgga                                              20

<210> SEQ ID NO 174
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
tggtggtggt gctgtctgga                                              20

<210> SEQ ID NO 175
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
caggagaatc acttgaacct                                              20

<210> SEQ ID NO 176
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
aggccactgc actccagcct                                              20

<210> SEQ ID NO 177
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
gcaagtctcg ttgatcgcca                                              20

<210> SEQ ID NO 178
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
ttgcacacgt ttgcgaatca                                              20

<210> SEQ ID NO 179
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 179
agggagagtt gcttcccagt                                                  20

<210> SEQ ID NO 180
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
gccgatctta gcacattact                                                  20

<210> SEQ ID NO 181
<211> LENGTH: 14
<212> TYPE: DNA
<213> ORGANISM: Homo sapiens

<400> SEQUENCE: 181
ggaggggaac ctgg                                                        14

<210> SEQ ID NO 182
<211> LENGTH: 14
<212> TYPE: DNA
<213> ORGANISM: Homo sapiens

<400> SEQUENCE: 182
ccgcgtcctc ctcc                                                        14

<210> SEQ ID NO 183
<211> LENGTH: 11
<212> TYPE: DNA
<213> ORGANISM: Homo sapiens

<400> SEQUENCE: 183
gctggggagg g                                                           11

<210> SEQ ID NO 184
<211> LENGTH: 11
<212> TYPE: DNA
<213> ORGANISM: Homo sapiens

<400> SEQUENCE: 184
ccctccccag c                                                           11

<210> SEQ ID NO 185
<211> LENGTH: 12
<212> TYPE: DNA
<213> ORGANISM: Homo sapiens

<400> SEQUENCE: 185
ctgggagtgc tg                                                          12

<210> SEQ ID NO 186
<211> LENGTH: 12
<212> TYPE: DNA
<213> ORGANISM: Homo sapiens

<400> SEQUENCE: 186
```

-continued cagcactccc ag                                                           12

<210> SEQ ID NO 187
<211> LENGTH: 13
<212> TYPE: DNA
<213> ORGANISM: Homo sapiens

<400> SEQUENCE: 187
ggagagtgct ggg                                                          13

<210> SEQ ID NO 188
<211> LENGTH: 13
<212> TYPE: DNA
<213> ORGANISM: Homo sapiens

<400> SEQUENCE: 188
cccagcactc tcc                                                          13

<210> SEQ ID NO 189
<211> LENGTH: 12
<212> TYPE: DNA
<213> ORGANISM: Homo sapiens

<400> SEQUENCE: 189
tagctattat tg                                                           12

<210> SEQ ID NO 190
<211> LENGTH: 12
<212> TYPE: DNA
<213> ORGANISM: Homo sapiens

<400> SEQUENCE: 190
caataatagc ta                                                           12

<210> SEQ ID NO 191
<211> LENGTH: 107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 191
accaaaacag tgcgaggaca gctgtgtgcc attgtgagat tcaagtgggt gaccctgtag       60
tcccagctac tcgggaggct gaggcaggag aatggcgtga agttggg                    107

<210> SEQ ID NO 192
<211> LENGTH: 58
<212> TYPE: DNA
<213> ORGANISM: Homo sapiens

<400> SEQUENCE: 192
accaaaacag tgcgaggaca gctgtgtgcc attgtgagat tcaagtgggt gacactgt        58

<210> SEQ ID NO 193
<211> LENGTH: 54
<212> TYPE: DNA
<213> ORGANISM: Homo sapiens

<400> SEQUENCE: 193
cctgcagtcc cagctactcg ggaggctgag gcaggagaat ggcgtgaagt tggg            54

<210> SEQ ID NO 194

```
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 194
aagtttgttg acctgtccca ggagatctgg gaaggtactc caggaagtgg ggatgcagcc    60
agccaaaaac tttgagtgca gcagcatgga tggattttat gaccagcaag tgccttacat   120
ggtcaccaat gtgagtg                                                  137

<210> SEQ ID NO 195
<211> LENGTH: 77
<212> TYPE: DNA
<213> ORGANISM: Homo sapiens

<400> SEQUENCE: 195
aagtttgttg acctgtccca ggagatctgg gaaggtactc caggaagtgg ggatgcagcc    60
agcctcccct gaaggaa                                                   77

<210> SEQ ID NO 196
<211> LENGTH: 73
<212> TYPE: DNA
<213> ORGANISM: Homo sapiens

<400> SEQUENCE: 196
agatttgcga agagcagcag catggatgga ttttatgacc agcaagtgcc ttacatggtc    60
accaatgtga gtg                                                       73

<210> SEQ ID NO 197
<211> LENGTH: 136
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 197
aggagatctg gaaggtact ccaggaagtg gggatgcagc cagcctcccc tgaaggaagg     60 acggggttg ggattgcaga tacttatctg ctttgttgcc actgtagggc gactctgctt    120
ctataagccc agtctt                                                   136

<210> SEQ ID NO 198
<211> LENGTH: 76
<212> TYPE: DNA
<213> ORGANISM: Homo sapiens

<400> SEQUENCE: 198
aggagatctg gaaggtact ccaggaagtg gggatgcagc cagcctcccc tgaaggaagg     60 atggggttg ggagtg                                                     76

<210> SEQ ID NO 199
<211> LENGTH: 76
<212> TYPE: DNA
<213> ORGANISM: Homo sapiens

<400> SEQUENCE: 199 acggggttg ggattgcaga tacttatctg ctttgttgcc actgtagggc gactctgctt     60
ctagaagccc agtctt                                                    76
```

-continued

<210> SEQ ID NO 200
<211> LENGTH: 147
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 200
ccattgtggg attcaagtgg gtgacactgt ctgtattgaa ggaagagctc cctgccagcc     60
aaaaactttg agtcccactt gacagcccac gggggttggg attgcagata cttatctgct    120
ttgttgccac tgtagggcga ctctgct                                        147

<210> SEQ ID NO 201
<211> LENGTH: 87
<212> TYPE: DNA
<213> ORGANISM: Homo sapiens

<400> SEQUENCE: 201
ccattgtgag attcaagtgg gtgacactgt ctgtattgaa ggaagagctc cctgccagcc     60
aggaatggag cctgagtgcc acccact                                         87

<210> SEQ ID NO 202
<211> LENGTH: 86
<212> TYPE: DNA
<213> ORGANISM: Homo sapiens

<400> SEQUENCE: 202
gagggagaaa atgagaaggg aggggggcacg ggggttggga ttgcagatac ttatctgctt    60
tgttgccact gtagggcgac tctgct                                          86

<210> SEQ ID NO 203
<211> LENGTH: 46
<212> TYPE: DNA
<213> ORGANISM: Homo sapiens

<400> SEQUENCE: 203
gagtaggcgc gagctaagca ggaggcggag gcggaggcgg agggcg                    46

<210> SEQ ID NO 204
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
gagtaggcgc gagcttccat ctctcactcc tgtctggcgg agggcg                    46

<210> SEQ ID NO 205
<211> LENGTH: 40
<212> TYPE: DNA
<213> ORGANISM: Homo sapiens

<400> SEQUENCE: 205
gggtccgggc tggggagggg aacctgggcg cctgggaccc                           40

<210> SEQ ID NO 206
<211> LENGTH: 40
<212> TYPE: DNA

<213> ORGANISM: Homo sapiens

<400> SEQUENCE: 206
aagacagaga tgaccgcgtc ctcctccagc gactatggac    40

<210> SEQ ID NO 207
<211> LENGTH: 40
<212> TYPE: DNA
<213> ORGANISM: Homo sapiens

<400> SEQUENCE: 207
ggctcggggt ccgggctggg gaggggaacc tgggcgcctg    40

<210> SEQ ID NO 208
<211> LENGTH: 40
<212> TYPE: DNA
<213> ORGANISM: Homo sapiens

<400> SEQUENCE: 208
cacacatacc ctgggccctc cccagctcac gaggggtggc    40

<210> SEQ ID NO 209
<211> LENGTH: 40
<212> TYPE: DNA
<213> ORGANISM: Homo sapiens

<400> SEQUENCE: 209
tttggggagg aggactggga gtgctgtcgg ttggcttctt    40

<210> SEQ ID NO 210
<211> LENGTH: 40
<212> TYPE: DNA
<213> ORGANISM: Homo sapiens

<400> SEQUENCE: 210
ttaggttttg aggtcagcac tcccagagtc ataaaaatca    40

<210> SEQ ID NO 211
<211> LENGTH: 40
<212> TYPE: DNA
<213> ORGANISM: Homo sapiens

<400> SEQUENCE: 211
tcccggggtg ctgggagagt gctgggcgcc tgggacccct    40

<210> SEQ ID NO 212
<211> LENGTH: 40
<212> TYPE: DNA
<213> ORGANISM: Homo sapiens

<400> SEQUENCE: 212
agtccttact ggttcccagc actctccgtt taccatccag    40

<210> SEQ ID NO 213
<211> LENGTH: 40
<212> TYPE: DNA
<213> ORGANISM: Homo sapiens

<400> SEQUENCE: 213
gttgacggca tctctagcta ttattgttaa ctgttcacaa    40

<210> SEQ ID NO 214
<211> LENGTH: 40

```
<212> TYPE: DNA
<213> ORGANISM: Homo sapiens

<400> SEQUENCE: 214
tagcataaca ttttcaataa tagctacgtt tgttttttgta                    40

<210> SEQ ID NO 215
<211> LENGTH: 40
<212> TYPE: DNA
<213> ORGANISM: Homo sapiens

<400> SEQUENCE: 215
tcaagtgctc cagtctggca gtgggcgctc tgctcgagca                     40

<210> SEQ ID NO 216
<211> LENGTH: 40
<212> TYPE: DNA
<213> ORGANISM: Homo sapiens

<400> SEQUENCE: 216
gtcagtcgag atcatgccac tgcactccag cctgggcaac                     40

<210> SEQ ID NO 217
<211> LENGTH: 40
<212> TYPE: DNA
<213> ORGANISM: Homo sapiens

<400> SEQUENCE: 217
acagagaatt tgctgacatt ttcaagttca ctggtgatga                     40

<210> SEQ ID NO 218
<211> LENGTH: 40
<212> TYPE: DNA
<213> ORGANISM: Homo sapiens

<400> SEQUENCE: 218
tgagagtgac acctgatgaa aattagctaa aagcagagac                     40

<210> SEQ ID NO 219
<211> LENGTH: 13
<212> TYPE: DNA
<213> ORGANISM: Homo sapiens

<400> SEQUENCE: 219
ggagggaacc tgg                                                  13

<210> SEQ ID NO 220
<211> LENGTH: 26
<212> TYPE: DNA
<213> ORGANISM: Homo sapiens

<400> SEQUENCE: 220
gtgcgccttt tctctttggg gaggag                                    26

<210> SEQ ID NO 221
<211> LENGTH: 28
<212> TYPE: DNA
<213> ORGANISM: Homo sapiens

<400> SEQUENCE: 221
ctccaccctg ctaaaagaaa aggagcac                                  28

<210> SEQ ID NO 222
```

```
<211> LENGTH: 16
<212> TYPE: DNA
<213> ORGANISM: Homo sapiens

<400> SEQUENCE: 222
aagtggggat gcagcc                                                    16

<210> SEQ ID NO 223
<211> LENGTH: 16
<212> TYPE: DNA
<213> ORGANISM: Homo sapiens

<400> SEQUENCE: 223
ggctgaatcc ccattt                                                    16

<210> SEQ ID NO 224
<211> LENGTH: 13
<212> TYPE: DNA
<213> ORGANISM: Homo sapiens

<400> SEQUENCE: 224
ggcagggaga gtt                                                       13

<210> SEQ ID NO 225
<211> LENGTH: 13
<212> TYPE: DNA
<213> ORGANISM: Homo sapiens

<400> SEQUENCE: 225
aactctccct gcc                                                       13

<210> SEQ ID NO 226
<211> LENGTH: 11
<212> TYPE: DNA
<213> ORGANISM: Homo sapiens

<400> SEQUENCE: 226
agctgctgct g                                                         11

<210> SEQ ID NO 227
<211> LENGTH: 11
<212> TYPE: DNA
<213> ORGANISM: Homo sapiens

<400> SEQUENCE: 227
cagcagcagc t                                                         11

<210> SEQ ID NO 228
<211> LENGTH: 11
<212> TYPE: DNA
<213> ORGANISM: Homo sapiens

<400> SEQUENCE: 228
ggcagggaga g                                                         11

<210> SEQ ID NO 229
<211> LENGTH: 11
<212> TYPE: DNA
<213> ORGANISM: Homo sapiens

<400> SEQUENCE: 229
ctctccctgc c                                                         11
```

-continued

```
<210> SEQ ID NO 230
<211> LENGTH: 13
<212> TYPE: DNA
<213> ORGANISM: Homo sapiens

<400> SEQUENCE: 230
cttgaaaatt ctg                                                        13

<210> SEQ ID NO 231
<211> LENGTH: 13
<212> TYPE: DNA
<213> ORGANISM: Homo sapiens

<400> SEQUENCE: 231
cagaattttc aag                                                        13

<210> SEQ ID NO 232
<211> LENGTH: 11
<212> TYPE: DNA
<213> ORGANISM: Homo sapiens

<400> SEQUENCE: 232
atggaaatat t                                                          11

<210> SEQ ID NO 233
<211> LENGTH: 11
<212> TYPE: DNA
<213> ORGANISM: Homo sapiens

<400> SEQUENCE: 233
aatatttcca t                                                          11

<210> SEQ ID NO 234
<211> LENGTH: 11
<212> TYPE: DNA
<213> ORGANISM: Homo sapiens

<400> SEQUENCE: 234
tccttaaata t                                                          11

<210> SEQ ID NO 235
<211> LENGTH: 11
<212> TYPE: DNA
<213> ORGANISM: Homo sapiens

<400> SEQUENCE: 235
atatttaagg a                                                          11

<210> SEQ ID NO 236
<211> LENGTH: 50
<212> TYPE: DNA
<213> ORGANISM: Homo sapiens

<400> SEQUENCE: 236
gcgtattagt taccaaaggt ttatttatgt ttctgtaatg catatttata                 50

<210> SEQ ID NO 237
<211> LENGTH: 50
<212> TYPE: DNA
<213> ORGANISM: Homo sapiens

<400> SEQUENCE: 237
tcaacaaaag aactattgat tgatgccaaa caagatgaaa atttcacttt                 50
```

<210> SEQ ID NO 238
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 238
tcaacaaaag aactattgat tgatgccaaa caagatgaaa atttcacttt gcgtattagt    60
taccaaaggt ttatttatgt ttctgtaatg catatttata                         100

<210> SEQ ID NO 239
<211> LENGTH: 38
<212> TYPE: DNA
<213> ORGANISM: Homo sapiens

<400> SEQUENCE: 239
cttcactgtt ctgacagctc cagtagctgg gggagacc                            38

<210> SEQ ID NO 240
<211> LENGTH: 26
<212> TYPE: DNA
<213> ORGANISM: Homo sapiens

<400> SEQUENCE: 240
agaatatgtg taattgtgtt accagc                                         26

<210> SEQ ID NO 241
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
agaatatgtg taattgtgtt accagccttc actgttctga cagctccagt agctggggga    60
gacc                                                                 64

<210> SEQ ID NO 242
<211> LENGTH: 47
<212> TYPE: DNA
<213> ORGANISM: Homo sapiens

<400> SEQUENCE: 242
attaccagcc ttcactgttc tgacagctcc agtagctggg ggagacc                  47

<210> SEQ ID NO 243
<211> LENGTH: 45
<212> TYPE: DNA
<213> ORGANISM: Homo sapiens

<400> SEQUENCE: 243
gagatcgaga ccatcctggc taacgcagtg aaacccccgtc tctac                   45

<210> SEQ ID NO 244
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
gagatcgaga ccatcctggc taacgcagtg aaacccgtc tctacattac cagccttcac    60
tgttctgaca gctccagtag ctgggggaga cc    92

<210> SEQ ID NO 245
<211> LENGTH: 50
<212> TYPE: DNA
<213> ORGANISM: Homo sapiens

<400> SEQUENCE: 245
acttacacag tgcaactcat gtgttaccag ccttcactgt tctgacagct    50

<210> SEQ ID NO 246
<211> LENGTH: 50
<212> TYPE: DNA
<213> ORGANISM: Homo sapiens

<400> SEQUENCE: 246
agcagggggg gcggtgtcca cacatcctca ctacgctgat ttgccatttg    50

<210> SEQ ID NO 247
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 247
agcagggggg gcggtgtcca cacatcctca ctacgctgat ttgccatttg acttacacag    60
tgcaactcat gtgttaccag ccttcactgt tctgacagct    100

<210> SEQ ID NO 248
<211> LENGTH: 51
<212> TYPE: DNA
<213> ORGANISM: Homo sapiens

<400> SEQUENCE: 248
tgaaccaaag tccactagtc ccatcaaaag tgctaacagg aaggggggat c    51

<210> SEQ ID NO 249
<211> LENGTH: 50
<212> TYPE: DNA
<213> ORGANISM: Homo sapiens

<400> SEQUENCE: 249
ccaggtggag ctgcccatgc cttccccgca gggctgagcc cactcagccg    50

<210> SEQ ID NO 250
<211> LENGTH: 101
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 250
ccaggtggag ctgcccatgc cttccccgca gggctgagcc cactcagccg tgaaccaaag    60
tccactagtc ccatcaaaag tgctaacagg aaggggggat c    101